(12) United States Patent
Visnick et al.

(10) Patent No.: US 11,584,775 B2
(45) Date of Patent: Feb. 21, 2023

(54) C4-MODIFIED OLEANOLIC ACID DERIVATIVES FOR INHIBITION OF IL-17 AND OTHER USES

(71) Applicant: REATA PHARMACEUTICALS, INC., Irving, TX (US)

(72) Inventors: Melean Visnick, Irving, TX (US); Xin Jiang, Coppell, TX (US); Martha R. Hotema, Hurst, TX (US); Chitase Lee, Ann Arbor, MI (US); Bradley William Caprathe, Livonia, MI (US); William H. Roark, Ann Arbor, MI (US); Gary L. Bolton, Ann Arbor, MI (US)

(73) Assignee: REATA PHARMACEUTICALS, Inc., Irving, TX (US)

( * ) Notice: Subject to any disclaimer, the term of this patent is extended or adjusted under 35 U.S.C. 154(b) by 0 days.

(21) Appl. No.: 15/760,662

(22) PCT Filed: Sep. 23, 2016

(86) PCT No.: PCT/US2016/053545
§ 371 (c)(1),
(2) Date: Mar. 16, 2018

(87) PCT Pub. No.: WO2017/053868
PCT Pub. Date: Mar. 30, 2017

(65) Prior Publication Data
US 2019/0153022 A1    May 23, 2019

Related U.S. Application Data

(60) Provisional application No. 62/222,632, filed on Sep. 23, 2015.

(51) Int. Cl.
*C07J 63/00* (2006.01)
*C07J 71/00* (2006.01)
*A61P 29/00* (2006.01)

(52) U.S. Cl.
CPC ............ *C07J 63/008* (2013.01); *A61P 29/00* (2018.01); *C07J 71/0005* (2013.01)

(58) Field of Classification Search
CPC ....... C07J 63/008; C07J 71/0005; A61P 29/00
See application file for complete search history.

(56) References Cited

U.S. PATENT DOCUMENTS

| | | | |
|---|---|---|---|
| 4,395,423 A | 7/1983 | Neumann |
| 5,064,823 A | 11/1991 | Lee et al. |
| 6,326,507 B1 | 12/2001 | Gribble et al. |
| 6,369,101 B1 | 4/2002 | Carlson et al. |

(Continued)

FOREIGN PATENT DOCUMENTS

| | | |
|---|---|---|
| CN | 101298466 | 11/2008 |
| CN | 103665087 | 3/2014 |

(Continued)

OTHER PUBLICATIONS

"RTA 402, Therapeutic Properties I", slides/handouts presented by Reata Pharmaceuticals, Inc. at private partnering meetings at BioSquare 2006 conference, Mar. 8-10, 2006, Geneva, Switzerland.

(Continued)

*Primary Examiner* — Barbara P Badio
(74) *Attorney, Agent, or Firm* — Parker Highlander PLLC

(57) ABSTRACT

Disclosed herein are C4 modified oleanolic acid derivatives of the formula: Formula (X) or Formula (XII), as well as analogs thereof, wherein the variables are defined herein. In addition, disclosed herein are pharmaceutical compositions of these derivatives or analogs, methods for their manufacture, and methods for their use, including for the prevention and treatment of diseases or disorders associated with overproduction of IL-17.

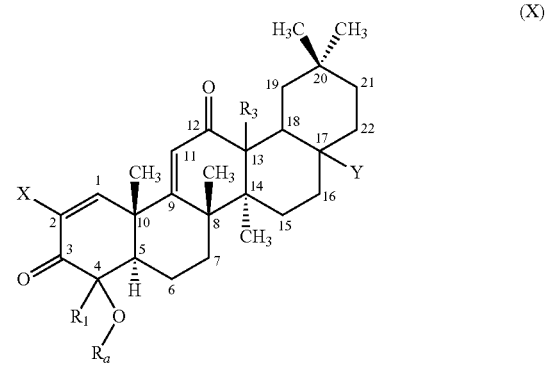

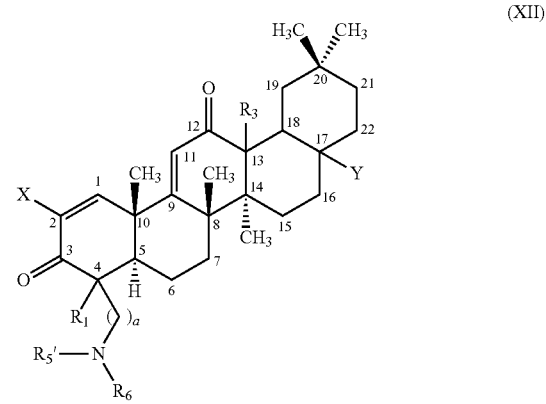

10 Claims, No Drawings

(56) References Cited

U.S. PATENT DOCUMENTS

| | | |
|---|---|---|
| 6,503,913 B1 | 1/2003 | Goldmann et al. |
| 6,552,075 B2 | 4/2003 | Gribble et al. |
| 6,642,217 B2 | 11/2003 | Krasutsky et al. |
| 6,649,654 B1 | 11/2003 | Karin et al. |
| 6,951,847 B2 | 10/2005 | Gibson et al. |
| 6,974,801 B2 | 12/2005 | Honda et al. |
| 7,053,119 B2 | 5/2006 | Karin et al. |
| 7,144,875 B2 | 12/2006 | Gibson et al. |
| 7,176,237 B2 | 2/2007 | Honda et al. |
| 7,288,568 B2 | 10/2007 | Gribble et al. |
| 7,399,606 B2 | 7/2008 | Karin et al. |
| 7,410,958 B2 | 8/2008 | Krasutsky et al. |
| 7,435,755 B2 | 10/2008 | Konopleva et al. |
| 7,678,830 B2 | 3/2010 | Honda et al. |
| 7,714,012 B2 | 5/2010 | Honda et al. |
| 7,795,305 B2 | 9/2010 | Konopleva et al. |
| 7,863,327 B2 | 1/2011 | Gribble et al. |
| 7,915,402 B2 | 3/2011 | Anderson et al. |
| 7,943,778 B2 | 5/2011 | Jiang et al. |
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,586,775 B2 | 11/2013 | Gribble et al. |
| RE45,288 E | 12/2014 | Anderson et al. |
| 8,921,419 B2 | 12/2014 | Gribble et al. |
| RE45,325 E | 1/2015 | Anderson et al. |
| 8,993,640 B2 | 3/2015 | Anderson et al. |
| 9,090,574 B2 | 7/2015 | Anderson et al. |
| 9,102,681 B2 | 8/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,278,913 B2 | 3/2016 | Gribble et al. |
| 9,290,536 B2 | 3/2016 | Anderson et al. |
| 9,512,094 B2 | 12/2016 | Jiang et al. |
| 9,556,222 B2 | 1/2017 | Anderson et al. |
| 9,593,074 B2 | 3/2017 | Bender et al. |
| 9,670,147 B2 | 6/2017 | Anderson et al. |
| 9,701,709 B2 | 7/2017 | Anderson et al. |
| 9,757,359 B2 | 9/2017 | Sporn et al. |
| 9,796,668 B2 | 10/2017 | Anderson et al. |
| 9,889,143 B2 | 2/2018 | Jiang et al. |
| 10,501,489 B2 | 12/2019 | Bender et al. |
| 10,556,858 B2 | 2/2020 | Anderson et al. |
| 2002/0042535 A1 | 4/2002 | Gribble et al. |
| 2003/0119732 A1 | 1/2003 | Konopleva et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0097436 A1 | 5/2004 | Krasutsky et al. |
| 2005/0208151 A1 | 9/2005 | Hurez et al. |
| 2005/0288363 A1 | 12/2005 | Gribble et al. |
| 2006/0258752 A1 | 11/2006 | Vander Jagt et al. |
| 2007/0155742 A1 | 7/2007 | Honda et al. |
| 2007/0232577 A1 | 10/2007 | Xu et al. |
| 2007/0244081 A1 | 10/2007 | Krasutsky et al. |
| 2007/0249561 A1 | 10/2007 | Taylor |
| 2007/0259839 A1 | 11/2007 | Krasutsky et al. |
| 2007/0259842 A1 | 11/2007 | Krasutsky et al. |
| 2008/0220057 A1 | 9/2008 | Gribble et al. |
| 2008/0233195 A1 | 9/2008 | Sporn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0071684 A1 | 3/2012 | Walling et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0283450 A1 | 11/2012 | Anderson et al. |
| 2012/0330050 A1 | 12/2012 | Walling et al. |
| 2013/0237721 A1 | 9/2013 | Gribble et al. |
| 2013/0303607 A1 | 11/2013 | Gribble et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0066408 A1 | 3/2014 | Jiang et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0259377 A1 | 9/2015 | Anderson et al. |
| 2015/0376121 A1 | 12/2015 | Anderson et al. |
| 2016/0145200 A1 | 5/2016 | Anderson et al. |
| 2017/0165278 A1 | 6/2017 | Jiang et al. |
| 2017/0260227 A1 | 9/2017 | Bender et al. |
| 2018/0002277 A1 | 1/2018 | Anderson et al. |
| 2018/0009839 A1 | 1/2018 | Anderson et al. |
| 2018/0161311 A1 | 6/2018 | Sporn et al. |
| 2018/0235981 A1 | 8/2018 | Jiang et al. |
| 2018/0237383 A1 | 8/2018 | Anderson et al. |

FOREIGN PATENT DOCUMENTS

| | | |
|---|---|---|
| CN | 104861027 | 8/2015 |
| EP | 2787002 | 10/2014 |
| JP | 2005-314381 | 11/2005 |
| WO | WO 1999/065478 | 12/1999 |
| WO | WO 2000/073253 | 12/2000 |
| WO | WO 2002/003996 | 1/2002 |
| WO | WO 2002/026761 | 4/2002 |
| WO | WO 2002/026762 | 4/2002 |
| WO | WO 2002/032410 | 4/2002 |
| WO | WO 2002/047611 | 6/2002 |
| WO | WO 2003/059339 | 7/2003 |
| WO | WO 2003/062260 | 7/2003 |
| WO | WO 2004/064723 | 8/2004 |
| WO | WO 2004/089357 | 10/2004 |
| WO | WO 2005/042002 | 5/2005 |
| WO | WO 2005/046732 | 5/2005 |
| WO | WO 2006/029221 | 3/2006 |
| WO | WO 2002/092768 | 6/2006 |
| WO | WO 2007/005879 | 1/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |

(56) References Cited

FOREIGN PATENT DOCUMENTS

| WO | WO 2009/058849 | 5/2009 |
|---|---|---|
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO2012096718 * | 7/2012 |
| WO | WO 2012/106190 | 8/2012 |
| WO | WO 2012/125488 | 9/2012 |
| WO | WO 2013/163344 | 10/2013 |
| WO | WO 2013/169740 | 11/2013 |
| WO | WO 2013/188818 | 12/2013 |
| WO | WO 2014/040056 | 3/2014 |
| WO | WO 2014/040060 | 3/2014 |
| WO | WO 2014/040073 | 3/2014 |
| WO | WO 2015/027206 | 2/2015 |
| WO | WO 2016/033132 | 3/2016 |
| WO | WO 2018/089539 | 5/2018 |

OTHER PUBLICATIONS

"RTA 402, Therapeutic Properties II", slides/handouts presented by Reata Pharmaceuticals, Inc. at private partnering meetings at BIO 2006 conference, Apr. 9-12, 2006, Chicago, Illinois.

"RTA 402, Therapeutic Properties III", slides presented by Reata Pharmaceuticals, Inc. as a podium presentation at BIO 2006 conference, Apr. 9-12, 2006, Chicago, Illinois.

"RTA 402, Therapeutic Properties IV", slides/handouts presented by Reata Pharmaceuticals, Inc. at private partnering meetings at BioPartnering Europe 2006 conference, Oct. 8-10, 2006, London, England.

"RTA 402, Therapeutic Properties IX", slides/handouts presented by Reata Pharmaceuticals, Inc. at a private partnering meeting at BIO Europe 2007 conference, Nov. 12-14, 2007, Hamburg, Germany.

"RTA 402, Therapeutic Properties V", slides/handouts presented by Reata Pharmaceuticals, Inc. at private partnering meetings at BIO 2007 conference, May 6-9, 2007, Boston Massachusetts.

"RTA 402, Therapeutic Properties VI", slides/handouts presented by Reata Pharmaceuticals, Inc. at private partnering meetings at BIO 2007 conference, May 6-9, 2007, Boston, Massachusetts.

"RTA 402, Therapeutic Properties VII", slides presented by Reata Pharmaceuticals, Inc. as a podium presentation at BIO 2007 conference, May 6-9, 2007, Boston, Massachusetts.

"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.

Ahmad et al., "Triterpenoid CDDO-Me blocks the NF-κB pathway by direct inhibition of IKKbeta on Cys-179," *J. Biol. Chem.*, 281:35764-35769, 2006.

Ahmad et al., "Triterpenoid CDDO-methyl ester inhibits the Janus-activated kinase-1 (JAK1)→signal transducer and activator of transcription-3 (STAT3) pathway by direct inhibition of JAK1 and STAT3," *Cancer Res.*, 68 (8): 2920-2926, 2008.

Akiyama et al., "Cell mediators of inflammation in the Alzheimer disease brain," *Alzheimer Dis. Assoc. Disord.*, 14 (1): S47-S53, 2000.

Albini and Sporn, "Opinion: the tumour microenvironment as a target for chemoprevention," *Nature Reviews Cancer*, 7: 139-147, 2007.

Andreef et al., "PPARγ nuclear receptor as a novel molecular target in leukemias," 2002 Keystone Symposia, Abstract 501:149, 2002.

Ballesta-Acosta et al., "A new 24-nor-oleanane triterpenoid from Salvia carduacea," *J. Nat. Prod.*, 65(10): 1513-1515, 2002.

Bore et al., "The anti-inflammatory triterpenoid methyl 2-cyano-3,12-dioxoolean 1,9(11)-dien-28-oate methanol solvate hydrate," *Acta Crystallorg C.*, 58(Pt 3):o199-o200, 2002.

Bowden et al, "Constituents of the fruit of pseudopanax arboretum (*Araliaceae*)," *Australian Journal of Chemistry*, 28(1): 91-107, 1975.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Buchanan et al., "The conversion of turraeanthin and turraeanthin A into simple melaiacins by a route involving an oxidative rearrangement of probable biogenetic importance," *J Chem. Soc C*, 17:2280-2284, 1970.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chen et al., "FOXP3 and RORγt: Transcriptional regulation of Treg and Th17," *Int. Immunopharmacol.*, 11:536-542, 2011.

Cheung et al., "Structures of triterpenes from *dryobalanops aromatic*," *Phytochemistry*, 11:1771-17780, 1972.

Chintharlapalli et al., "2-Cyano-3,12-dioxoolean-1,9-dien-28-oic acid and related compounds inhibit growth of colon cancer cells through peroxisome proliferator-activated receptor γ-dependent and -independent pathways," *Mol. Pharmacol.*, 68:119-128, 2005.

Chintharlapalli et al., "2-Cyano-lup-1-en-3-oxo-20-oic acid, a cyano derivative of betulinic acid, activates peroxisome proliferator-activated receptor γ in colon and pancreatic cancer cells.," *Carcinogenesis*, 28 (11): 2337-2346, 2007.

Chintharlapalli et al., "Structure-dependent activity of glycyrrhetinic acid derivatives as peroxisome proliferator-activated receptor γ agonists in colon cancer cells," Molecular *Cancer Therapeutics*, 6 (5): 1588-1598, 2007.

Clinical Trial NCT00322140, "CDDO to Treat Solid Tumors and Lymphomas," update of May 4, 2006.

Clinical Trial NCT00322140, "CDDO to Treat Solid Tumors and Lymphomas," update of Jun. 30, 2017.

Clinical Trial NCT00508807, "RTA 402 in Advanced Solid Tumors or Lymphoid Malignancies," update of Jul. 26, 2007.

Clinical Trial NCT00508807, "RTA 402 in Advanced Solid Tumors or Lymphoid Malignancies," update of Jul. 27, 2012.

Clinical Trial NCT00529113, "Study With Gemcitabine and RTA 402 for Patients With Unresectable Pancreatic Cancer," update of Sep. 12, 2007.

Clinical Trial NCT00529113, "Study With Gemcitabine and RTA 402 for Patients With Unresectable Pancreatic Cancer," update of Nov. 13, 2014.

Clinical Trial NCT00529438, "RTA 402 in Patients With Advanced Solid Tumors or Lymphoid Malignancies," update of Sep. 12, 2007.

Clinical Trial NCT00529438, "RTA 402 in Patients With Advanced Solid Tumors or Lymphoid Malignancies," update of Nov. 4, 2014.

Clinical Trial NCT00535314, "Study of Two Dose Levels of RTA 402 in Patients With Advanced Malignant Melanoma," update of Sep. 24, 2007.

Clinical Trial NCT00535314, "Study of Two Dose Levels of RTA 402 in Patients With Advanced Malignant Melanoma," update of Oct. 27, 2014.

Clinical Trial NCT00550849, "Study to Assess the Safety, Tolerability, and Pharmacodynamics of RTA 402 in Patients With Hepatic Dysfunction," update of Oct. 26, 2007.

Clinical Trial NCT00550849, "Study to Assess the Safety, Tolerability, and Pharmacodynamics of RTA 402 in Patients With Hepatic Dysfunction," update of Nov. 6, 2007.

Clinical Trial NCT00664027, "Phase IIa Trial to Determine the Effects of Bardoxolone Methyl on Renal Function in Patients With Diabetic Nephropathy," update of Apr. 18, 2008.

Clinical Trial NCT00664027, "Phase IIa Trial to Determine the Effects of Bardoxolone Methyl on Renal Function in Patients With Diabetic Nephropathy," update of Nov. 29, 2012.

(56) References Cited

OTHER PUBLICATIONS

Clinical Trial NCT00811889, "Trial to Determine the Effects of Bardoxolone Methyl on eGFR in Patients With Type 2 Diabetes and Chronic Kidney Disease," update of Dec. 18, 2008.
Clinical Trial NCT00811889, "Trial to Determine the Effects of Bardoxolone Methyl on eGFR in Patients With Type 2 Diabetes and Chronic Kidney Disease," update of Jun. 12, 2012.
Clinical Trial NCT01053936, "Phase II Pharmacodynamic Trial to Determine the Effects of Bardoxolone Methyl on eGFR in Patients With Type 2 Diabetes and Chronic Kidney Disease," update of Jan. 20, 2010.
Clinical Trial NCT01053936, "Phase II Pharmacodynamic Trial to Determine the Effects of Bardoxolone Methyl on eGFR in Patients With Type 2 Diabetes and Chronic Kidney Disease," update of Jun. 12, 2012.
Cohen et al., "A general method for removal of a 4-methyl group from triterpenoids. Synthesis of 4β-demethylglycyrrhetinic acid," *J Chem. Soc, Perkin Trans 1*, (19): 2076-2082, 1973.
Connolly et al., "Grandiofolione: a novel tetranortriterpenoid," *Chemical Communications*, 23:867-568, 1966.
Couch et al., "2-cyano-3,12-dioxooleana-1,9(11)-diene-28-oic acid disrupts microtubule polymerization: a possible mechanism contributing to apoptosis," *Molecular Pharmacology*, 69 (4): 1158-1165, 2006.
Couch et al., "Studies on the reactivity of CDDO, a promising new chemopreventive and chemotherapeutic agent: implications for a molecular mechanism of action," *Bioorganic and Medicinal Chemistry Letters*, 15 (9): 2215-2219, 2005.
Damsté et al., "A sedimentary tetrahydrophenanthrene derivative of tetrahymanol," *Tetrahedron Letters*, 40(20: 3949-3952, 1999.
De Mico et al., "A Versatile and Highly Selective Hypervalent Iodine (III)/2,2,6,6-Tetramethyl-1-piperidinyloxyl-Mediated Oxidation of Alcohols to Carbonyl Compounds," *J. Org. Chem.*, 62: 6974, 1997.
Dean et al., "Halogenolysis of methyl glycyrrhetate with lithium iodidedimethylformamide," *J. Chem. Soc.*, 6655-6659, 1965.
Deng and Snyder, "Preparation of a 24-Nor-1,4-dien-3-one triterpene derivative from betulin: a new route to 24-nortriterpene analogues," *J. of Organic Chemistr*, 67 (9): 2864-2873, 2002.
Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.
Dinkova-Kostova et al., "Direct evidence that sulfhydryl groups of Keap1 are the sensors regulating induction of phase 2 enzymes that protect against carcinogens and oxidants," *Proc. Natl. Acad. Sci.*, 99(18): 11908-11913, 2002.
Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.
Dirsch et al., "The triterpenoid quinonemethide pristimerin inhibits induction of inducible nitric oxide synthase in murine macrophages," *Eur J Pharmacol.*, 336(2-3): 211-217, 1997.
Dracinsky et al., "Preparation and Conformational Study of 19β,28-Epoxy-18α-olean-5-ene Derivatives," *Collection of Czechoslovak Chemical Communications*, 71(3): 387-410, 2006.
Dragnev et al., "Specific chemopreventive agents trigger proteasomal degradation of G1 cyclins: implications for combination therapy," *Clin. Cancer Research*, 10 (7): 2570-2577, 2004.
Duan et al., "Di- and triterpenoids from Triptergium hypoglaucum," *Phytochemistry*, 46(3): 535-543, 1997.
Duan et al., "Immunosuppressive terpenoids from extracts of tripterygium wilfordii," *Tetrahedron*, 57 (40): 8413-8424, 2001.
Dulubova et al., "RTA 1701 is an orally-bioavailable, potent, and selective RORγt inhibitor that suppresses Th17 differentiation in vitro and is efficacious in mouse models of autoimmune disease," *J. Immunol.*, 200 (1 Suppl.):121.14, 2018, (Abstract only).
Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.
Elsawa et al., "Preferential Inhibition of Malignant Cell Growth by CDDO in Waldenstrom Macroglobulinemia," *Blood*, 108(11):2528, 2006.
Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.
Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.
Finlay et al., "The Effect of A and C Ring Modification of Oleanolic and Ursolic Acid on the Inhibition of Nitric Oxide Formation in Mouse Macrophages," 213th American Chemical Society National Meeting, Abstract: 084, 1997.
Gao et al., "Synthetic triterpenoids inhibit growth and induce apoptosis in human glioblastoma and neuroblastoma cells through inhibition of prosurvival Akt, NF-κB and Notch1 signaling," *J. of Neuro-oncology*, 84 (2): 147-157, 2007.
Grant et al., "Boron trifluoride catalyzed rearrangements of novel epoxide derivatives of manool and manoyl oxide," *Australian Journal of Chemistry*, 46 (8): 1125-1145, 1993.
Grieco and Speake, "Synthetic Studies on Quassinoids: Total Synthesis and Biological Evaluation of (+)-Des-D-chaparrinone," *J. Org. Chem.*, 63:5929-5936, 1998.
Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.
Han et al., "CDDO-Imidazolide inhibits growth and survival of c-Myc-induced mouse B cell and plasma cell neoplasms," *Molecular Cancer*, 5:22, 2006.
Hill et al., "Synthetical approaches to the pristimerin chromophore," *J. of the Chemical Society*, 361-375, 1965.
Hirota et al., "Suppression of tumor promoter-induced inflammation of mouse ear by ursolic acid and 4,4-dimethycholestane derivatives," *Agric. Biol. Chem.*, 54:1073-1075, 1990.
Hirota et al., "Total synthesis of (±)-amarolide, a quassinoid bitter principle," *J. Org. Chem.*, 56:1119-1127, 1991.
Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.
Honda et al., "An efficient synthesis of tricyclic compounds (+)-(4aβ, 8aβ, 10aα)-1,2,3,4,4a,6,7,8,8a,9,1-,10a-Dodecahydro-1,1,4a-Trimethyl-2-Oxophenanthrene-8a-Carboxolic acid, its methyl ester, and (+)-(4aβ,8aβ,10aα)-3,4,4a,6,7,8,8a,9,10,10a-Decahydro-8a, hydroxymethyl-1,1,4a-trimethylphenanthren-2(1H)-one," *Org. Prep. Proced. Int.*, 37(6): 546-550, 2005.
Honda et al., "Design and synthesis of 23, 24-dinoroleanolic acid derivatives, novel triterpenoid-steroid hybrid molecules," *J. Org. Chem.*, 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.
Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.
Honda et al., "New enone derivatives of oleanolic acid and ursolic acid as inhibitors of nitric oxide production in mouse macrophages," *Bioorg. Med. Chem. Lett.*, 7:1623-1628, 1997.
Honda et al., "New synthetic oleanane and ursane triterpenoids as inhibitors of nitric oxide production in mouse macrophages," The

(56) References Cited

OTHER PUBLICATIONS

Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Novel tricyclic compounds having acetylene groups at C-8a and cyano enones in rings A and C: highly potent antiinflammatory and cytoprotective agents," *J. Med. Chem.*, 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.
Honda et al., "Synthesis of (±)-3,3-ethylenedioxy-14a-hydroxy-5-picrasene-11,16-dione, a 14aH-picrasane derivative," *Chem. Lett.*, 299-302, 1981.
Honda et al., "Synthesis of a novel dicyano abietane analogue: a potential antiinflammatory agent," *J. Org. Chem.*, 71:3314-3316, 2006.
Honda et al., "Synthetic oleanane and ursane triterpenoids with modified rings A and C: A series of highly active inhibitors of nitric oxide production in mouse macrophages," *J. Med. Chem.*, 43:4233-4246, 2000.
Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.
Hyer et al., "Synthetic triterpenoids cooperate with tumor necrosis factor-related apoptosis-inducing ligand to induce apoptosis of breast cancer cells," *Cancer Res.*, 65:4799-4808, 2005.
Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.
Ikeda et al., "The novel triterpenoid CDDO and its derivatives induce apoptosis by disruption of intracellular redox balance," *Cancer Res.*, 63:5551-5558, 2003.
Ikeda et al., "Triterpenoid CDDO-Im downregulates PML/RAR αexpression in acute promyelocytic leukemia cell," *Cell Death and Differentiation*, 12 (5): 523-531, 2005.
Inoue et al., "CDDO induces apoptosis via the intrinsic pathway in lymphoid cells," *Leukemia*, 18 (5): 948-952, 2004.
Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.
Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.
Ito et al., "The novel triterpenoid CDDO induces apoptosis and differentiation of human osteosarcoma cells by a caspase-8 dependent mechanism," *Mol. Pharmacol.*, 59:1094-1099, 2001.
Jang et al., "24-nor-ursane type triterpenoids from the stems of Rumex japonicus," *Chem. Pharm Bull (Tokyo)*, 53(12): 1594-1596, 2005.
Ji et al., "The synthetic triterpenoid CDDO-imidazolide induces monocytic differentiation by activating the Smad and ERK signaling pathways in HL60 leukemia cells," *Molecular Cancer Therapeutics*, 5 (6): 1452-1458, 2006.
Johansen et al., "Pharmacology and preclinical pharmacokinetics of the triterpenoid CDDO methyl ester," *Proc. Amer. Assoc. Cancer Res.*, 44:1728, 2003.
Johns et al., "Triterpenes of *Lantanta tiliaefolia*, 24-hydroxy-3-oxours-12-en-28-oic acid, a new triterpene," 36:2537-2547, 1983.

Kahne and Collum, "Kinetic cyanations of ketone enolates," *Tetrahedron Lett.*, 22:5011-5014, 1981.
Kamal et al., "23-oxoisopristimerin III: an new natural phenolic (9→8)-24-nor-D:A-friedo-oleanane triterpene," *Tetrahedron Letters*, 24(27):2799-2800, 1983.
Kamal et al., "Structures of two new phenolic 24-nor-D: A-friedoleananes related to zeylasterone: a partial synthesis of trimethylzeylasterone," *Tetrahetron Letters*, 24(19): 2025-2028, 1983.
Kamal et al., "The structure of zeylasterone, the first of a new series of phenolic 24-nor-D: A friedo-oleanane triterpenes," *Tetrahedron Letters*, 21(49): 4749-4752, 1980.
Kansanen et al., "Regulation of Nrf2-dependent gene expression by 15-deoxy-Δ12,14-prostaglandin J2," *Free Radic. Biol. Med.*, 47(9):1310-7, 2009.
Khalid et al., "Isolation and characterization of pristimerin as the antiplasmodial and antileishmanial agent of maytenus senegalensis (Lam.) Exell," *ARKIVOC*, 129-134, 2007.
Kim et al., "An inducible pathway for degradation of FLIP protein sensitizes tumor cells to TRAIL-induced apoptosis," *J. of Biological Chemistry*, 277 (25): 22320-22329, 2002.
Kim et al., "Caspase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.
Kim et al., "Identification of a novel synthetic triterpenoid, methyl-2-cyano-3,12-dioxooleana-1,9-dien-28-oate, that potently induces caspase-mediated apoptosis in human lung cancer cells," *Molecular Cancer Therapeutics*, 1:177-184, 2002.
Kincl et al., "Pituitary gonadotropin inhibitory action of neutral steroids," *Acta. Endocrinologica*, 46: 300-306, 1964.
Kircher, "Triterpenes, in organ pipe cactus," Phytochemistry, 19:2707-2712, 1980; Database CAPLUS on STN AN: 1981:550946.
Klyne et al., "The molecular rotations of polycyclic compounds. III. Polycyclic alcohols and their derivatives," *J Chem Soc.*, 1979-1988, 1954.
Kobayashi et al., "The antioxidant defense system Keap1-Nrf2 comprises a multiple sensing mechanism for responding to a wide range of chemical compounds," *Mol. Cell Biol.*, 29(2):493-502, 2009.
Kolak et al., "Antioxidant and anticholinesterase constituents of Salvia poculata," *Turkish Journal of Chemistry*, 33(6): 813-823, 2009.
Konopleva et al., "Activation of nuclear transcription factor PPARγ by the novel triterpenoid CDDO as targeted therapy in breast cancer," 2002 Keystone Symposium, Abstract No. 539, 2002.
Konopleva et al., "Mechanisms and Activity of PPARγ-Active Triterpenoids CDDO and CDDO-Me in Leukemias," *Blood*, 106:2460, 2005.
Konopleva et al., "Novel synthetic triterpenoid CDDO-Me: potent antiproliferative, proapoptotic and differentiating agent in AML," *Blood*, 96(11), Part 1: 121A, abstract #522, 2000.
Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.
Konopleva et al., "Novel triterpenoid CDDO-Me is a potent inducer of apoptosis and differentiation in acute myelogenous leukemia," *Blood*, 99(1):326-335, 2002.
Konopleva et al., "Peroxisome proliferator-activated receptor γ and retinoid X receptor ligands are potent inducers of differentiation and apoptosis in leukemias," *Mol. Cancer Ther.*, 3:1249-1262, 2004.
Konopleva et al., "PPARγ Ligand CDDO Induces Apoptosis in Leukemias Via Multiple Apoptosis Pathways," Abstracts of the 44th Annual Meeting of the American Society of Hematology, Abstract No. 2209, 2002.
Konopleva et al., "PPARγ Ligands Are Potent Inducers of Apoptosis in Leukemias and Lymphomas," American Society of Hematology 43rd Annual Meeting and Exposition, Abstract No. 501, 2001.
Konopleva et al., "PPARγ Nuclear Receptor as a Novel Molecular Target in Leukemia Therapy," *Proc. Amer. Assoc. Cancer Res.*, 43:4730, 2002.
Konopleva et al., "PPARγ nuclear receptor as a novel therapeutic target in AML," Blood, 96(11):460a, Abstract #1982, 2000.

(56) References Cited

OTHER PUBLICATIONS

Konopleva et al., "PPARγ nuclear receptor as a novel therapeutic target in AML," Proc. of the AACR, 42, Abstract #4458, 2001.
Konopleva et al., "Suppression of ERK Activation is Required for Triterpenoid Methyl-CDDO-Induced Apoptosis in AML," *Blood*, 102(11):1404, 2003.
Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.
Konopleva et al., "Synthetic triterpenoid CDDO as a novel therapy for resistant breast cancer," *Proc. Amer. Assoc. Cancer Res.*, 44:2726, 2003.
Konopleva et al., "The novel triterpenoid CDDO-Me suppresses MAPK pathways and promotes p38 activation in acute myeloid leukemia cells," *Leukemia*, 19:1350-1354, 2005.
Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.
Korovin and Tkachev, "Synthesis of quinoxalines fused with triterpenes, ursolic acid and betulin derivatives," *Russian Chemical Bulletin, (Translation of Izvestiya Akademii Nauk, Seriya Khimicheskaya)*, 20 (2): 304-310, 2001.
Koschmieder et al. "CDDO induces granulocytic differentiation of myeloid leukemic blasts through translational up-regulation of p42 CCAAT enhancer-binding protein alpha," *Blood*, 110 (10): 3695-3705, 2007.
Kress et al., "Triterpenoids display single agent activity in a mouse model of CLL/SBL," *Blood*, 108(11):2530, 2006.
Kress et al., "Triterpenoids display single agent anti-tumor activity in a transgenic mouse model of chronic lymphocytic leukemia and small B cell lymphoma," *PLOS ONE*, 6(e559):1-11, 2007.
Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.
Kutschabsky et al., "Molecular and crystal structure of a new 24-nor triperpenoid carboxylic acid from Acanthopanax trifoliatus," *Croatica Chemica Acta*, 58(4): 427-434, 1986.
Lapillonne et al., "Activation of peroxisome proliferator-activated receptor γ by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.
Larock et al., "Carbocycle synthesis via carbopalladation of nitriles," *J. of the American Chemical Society*, 121 (13): 3238-3239, 1999.
Lavie et al., "Studies on epoxides. IV. Rearrangements in triterpenoids," *Tetrahedron Letters*, 17: 2097-2100, 1968.
Lavie et al., "Tetranortriterpenoids from Melia azadirachta," *Chemical Communications*, 6:278-280, 1967.
Lei et al., "Regulatory T cell-mediated anti-inflammatory effects promote successful tissue repair in both indirect and direct manners," *Front. Pharmacol.*, 6(184):1-10, 2015.
Li et al., "Terpenoids from tripterygium wilfordii," *Phytochemistry*, 45(4): 791-796, 1997.
Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.
Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.
Liby et al., "The synthetic triterpenoids, CDDO and CDDO-imidazolide, are potent inducers of heme oxygenase-1 and Nrf2/ARE signaling," *Cancer Res.*, 65:4789-4798, 2005.
Liby et al., "Triterpenoids and rexinoids as multifunctional agents for the prevention and treatment of cancer," *Nat. Rev. Cancer*, 7 (5): 357-369, 2007.
Ling et al., "The novel triterpenoid C-28 methyl ester of 2-cyano-3,12-dioxoolen-1, 9-dien-28-oic acid inhibits metastatic murine breast tumor growth through inactivation of STAT3 signaling," *Cancer Res.*, 67:4210-4218, 2007.
Ling et al., "The novel triterpenoid CDDO-Me inhibits metastatic murine breast tumor through inhibition of Stat3 signaling," 2007 AACR Annual Meeting, Abstract No. 301, 2007.
Liu et al,. "New lupane-type triterpenoid saponins from leaves of Oplopanax horridus (Devil's Club)," *Nat Prod Comm.*, 5(7): 1019-1022, 2010.
Liu et al., "Chemical constituents from root of rubus irenaeus," *Zhongcaoyao*, 34 (5): 394-396, 2003, Abstract only.
Marples and Spilling, "Ene reactions of unsaturated acyloins," *Tetrahedron Letters*, 26(52): 6515-6518, 1985.
Marples and Spilling, "Facile intramolecular ene reactions of steroidal unsaturated acyloins," *Tetrahedron*, 48 (19): 4017-4026, 1992.
Martinez et al., "Regulation and Function of Proinflammatory TH17 Cells," *Ann. N.Y. Acad. Sci.*, 1143:188-211, 2008.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-γ expression," *Gynecologic Oncology*, 93:149-154, 2004.
Mencherini et al., "Triterpenoid constituents from the roots of the *Paeonia rockii* ssp. rockii," *J Nat Prod.*, 74(10): 2116-2121, 2011.
Minns et al., "A novel triterpenoid induces transforming growth factor β production by intraepithelial lymphocytes to prevent ileitis," *Gastroenterology*, 127:119-126, 2004.
Mix et al., "A synthetic triterpenoid selectively inhibits the induction of matrix metalloproteinases 1 and 13 by inflammatory cytokines," *Arthritis Rheum.*, 44:1096-1104, 2001.
Mix et al., "Peroxisome proliferator-activated receptor-γ-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65(2): 309-318, 2004.
Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.
Murray and Zweifel, "Preparation of Phenyl Cyanate and Its Utilization for the Synthesis of α, β-Unsaturated Nitriles," *Synthesis*, 150-151, 1980.
Muzart, "Synthesis of unsaturated carbonyl compounds via a chromium-mediated allylic oxidation by 70% tert.butylhydroperoxide," *Tetrahedron Lett.*, 28:4665-4668, 1987.
Na and Surh et al., "Transcriptional regulation via cysteine thiol modification: a novel molecular strategy for chemoprevention and cytoprotection," *Mol. Carcinog.*,45 (6): 368-380, 2006.
Nair et al., "Triterpenes. XLVII. Oxidation rates of triterpenoid secondary alcohols with chromic acid," *Collection of Czechoslovak Chemical Communications*, 41(3): 770-779, 1976.
Nanduri et al., "Biological investigation and structure-activity relationship studies on azadirone from azadirachta indica A. juss," *Bioorganic and Medicinal Chemistry*, 13 (22): 4111-4115,2003.
Nelson et al., "Oxidative demethylation at C-4 of a steroid via nitroxide photolysis," *J. of the American Chemical Society*, 97 (3): 648-649, 1975.
Niikura et al., "The effects of synthetic triterpenoids on superficial zone protein synthesis in articular chondrocytes," Abstract, *Orthopedic Research Society*, San Diego, 2007.

(56) References Cited

OTHER PUBLICATIONS

Niikura et al., "The effects of synthetic triterpenoids on szp synthesis in articular chondrocytes," Abstract P197, *Osteoarthritis and Cartilage*, 14(Suppl B):S112-S113, 2006.
Nishimura et al., "Activity-guided isolation of triterpenoid acyl CoA cholesteryl acyl transferase (ACAT) inhibitors from Ilex kudincha," *J Nat Prod.*, 62(7): 1061-1064, 1999.
Nishino et al., "Inhibition of the tumor-promoting action of 12-O tetradecanoylphorbol-13-acetate by some oleanane-type triterpenoid compounds," *Cancer Res.*, 48:5210-5215, 1988.
Osburn et al., "Genetic of pharmacologic amplification of Nrf2 signaling inhibits acute inflammatory liver injury in mice," *Toxicological Sciences*, 104:218-227, 2008.
Overnell and Whitehurts, "Reactions of steroid A-ring lactones with Grignard reagents," *J. of the Chemical Society [Section] C: Organic*, 2: 378-384, 1971.
Pappas et al., "Photoisomerization of phenalen-1-one oxide. New course of light-induced alpha beta-epoxy ketone rearrangement," *J. of the American Chemical Society*, 92 (19): 5797-5798, 1970.
Peakman et al., "Characterization of 24-nor-triterpenoids occurring in sediments and crude oils by comparison with synthesized standards," *Tetrahedron*, 47(23): 3779-3786, 1991.
Pedersen et al., "The triterpenoid CDDO induces apoptosis in refractory CLL B cells," *Blood*, 100:2965-2972, 2002.
Place et al., "The novel synthetic triterpenoid, CDDO-imidazolide, inhibits inflammatory response and tumor growth in vivo," *Clin. Cancer Res.*, 9:2798-2806, 2003.
Rasmusson et al., "Azasteroids: structure-activity relationships for inhibition of 5 α-reductase and of androgen receptor binding," *J. Med. Chem.*, 29 (11): 2298-2315, 1986.
Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor γ-independent pathway," *Exp. Hematology*, 34:1201-1210, 2006.
Reisman et., "RTA 1701 is an oral RORγt inhibitor that suppresses the IL-17A response in non-human primates," *J. Immunol.*, 200(1 Suppl.):175.22, 2018. (Abstract only).
Ribo et al., "Synthesis of methyl 1, 11-dioxooleanan-2, 12-dien-30-oate and its 24-nor derivative," *Afinidad*, 38(373): 197-200, 1981, Abstract only.
Rossi et al., "Anti-inflammatory cyclopentenone prostaglandins are direct inhibitors of IκB kinase," *Nature*, 403:103-108, 2000.
Rouquette et al., "A ring-D functionalized nor-triterpenoid of the lupane series as a key intermediate in the formation of widespread hydrocarbon derivatives of higher plant origin in petroleum," *Organic Geochemistry*, 36(9): 1227-1233, 2005.
Ruvolo et al., "The novel triterpenoid methyl-CDDO inhibits Bcl2 phosphorylation and potently kills U937 cells," *Blood*, 94(10), Suppl. 1, Part 1: 280A, abstract #1251, 1999.
Ruzicka et al., Triterpenes LXXXIX. Decomposition of hederagenin to the C26-stage, *Helvetica Chimica Acta*, 27:1185-1196, 1944. (Translation appended).
Samudio et al., "2, cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47, Abstract 4693, 2006.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.
Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46: Abstract No. 4955, 2005.
Satoh et al., "Activation of the Keap1/Nrf2 pathway for neuroprotection by electrophilic phase II inducers," *PNAS*, 103 (3): 768-773, 2006.
Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.
Sharpless et al., "Electrophilic and nucleophilic organoselenium reagents. New routes to α,β-unsaturated carbonyl compounds," *J. Am. Chem. Soc.*, 95:6137, 1973.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," *Molecular and Cellular Biology*, 27 (20): 7188-7197, 2007.
Shin et al., "Role of Nrf2 in prevention of high-fat diet-induced obesity by synthetic triterpenoid CDDO-imidazolide" *Eur. J. Pharmacol.*, 620(1-3):138-144, 2009.
Shishodia et al., "A synthetic triterpenoid, CDDO-Me, inhibits IκBα kinase and enhances apoptosis induced by TNF and chemotherapeutic agents through down-regulation of expression of nuclear factor κB-regulated gene products in human leukemic cells," *Clin Cancer Research*, 12(6):1828-1838, 2006.
Siddiqui et al., "Kanerin and 12, 13-dihydroursolic acid, two new pentacyclic triterpenes from the leaves of Nerium oleander," *J Nat Prod.*, 52(1): 57-62, 1989.
Simonsen et al., "Tetracyclic hydroxy acids," In the *Terpenes*, Cambridge University, Cambridge, 5:221-285, 1957.
Singh et al., "Anti-inflammatory activity of oleanolic acid in rats and mice," *J. Pharm.Pharmacol.*, 44:456-458, 1992.
Sporn and Roberts, "Peptide growth factors and inflammation, tissue repair, and cancer," *J. Clin. Invest.*, 78:329-332, 1986.
Sporn et al., "Prospects for prevention and treatment of cancer with selective PPARγ modulators (SPARMs)," *Trends in Molecular Medicine*, 7(9):395-400, 2001.
Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1988.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "New triterpenoids as cancer preventive and anti-inflammatory agents," Proceedings of the American Association for Cancer Research, Abstract No. 1457, 38:216, 1997.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.
Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.

(56) References Cited

OTHER PUBLICATIONS

Sultana et al., "Phytochemical studies on Alstonia scholaris," *Zeitschrift für Naturforschung. B, A Journal of Chemical Sciences*, 65(2): 203-210, 2010.
Sun et al., "Stracture-activity relationships of oleanan- and ursane-type triterpenoids," *Botanical Studies*, 47:339-368, 2006.
Sun et al., "The Synthetic Triterpenoid, CDDO, Suppresses Alloreactive T Cell Responses and Reduces Murine Early Acute Graft-versus-Host Disease Mortality," *Biology of Blood and Marrow Transplantation*, 13 (5): 521-529, 2007.
Tabe et al., "Chromatin-Mediated Transcriptional Activation with Novel Peroxisome Proliferator—Activated Receptor gamma(PPARγ) Ligand 2-cyano-1,9-dien-28-oic Acid (CDDO) in Acute Promyelocytic Leukemia Cells," Abstracts of the 44th Annual Meeting of the American Society of Hematology, Abstract 2191, 2002.
Thimmulappa et al., "Nrf2 is a critical regulator of the innate immune response and survival during experimental sepsis," *J. Clinical Investigation*, 116 (4): 984-995, 2006.
Thimmulappa et al., "Nrf2 -dependent protection from LPS induced inflammatory response and mortality by CDDO-imidazolide," *Biochem. Biophys. Res. Commun.*, 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants and Redox Signalling*, 9:1-8, 2007.
Tran et al., "The synthetic triterpenoid CDDO-methyl ester modulates microglial activities, inhibits TNF production, and provides dopaminergic neuroprotection," Journal of Neuroinflammation, 5:1-14, 2008.
Tsao et al., "DRIP205 co-activator overexpression enhances PPARγ-mediated differentiation of leukemia cells by CDDO," *Proc. Amer. Assoc. Cancer Res.*, 46: Abstract No. 1855, 2005.
Tsao et al., "Targeted Induction of Apoptosis in Leukemias by PPARα Ligation," American Society of Hematology 43rd Annual Meeting and Exposition, Abstract No. 2381, 2001.
Urban et al., "Influence of esterification and modification of A-ring in a group of lupane acids on their cytotoxicity," *Bioorganic and Medicinal Chemistry*, 13 (19): 5527-5535, 2005.
Urban et al., "Synthesis of A-seco derivatives of betulinic acid with cytotoxic activity," *J. of Natural Products*, 67 (7): 1100-1105, 2004.
Uskoković et al., "D-Homosteroids. I. 3β-Hydroxy-17a,17a-dimethyl-D-homoandrostane-17-one and related compounds," *J. of the American Chemical Society*, 81: 4561-4566, 1959.
Vannini et al., "The synthetic oleanane triterpenoid, CDDO-methyl ester, is a potent antiangiogenic agent," *Molecular Cancer Therapeutics*, 6 (12 Part 1), 3139-3146, 2007.
Vilayur and Harris, "Emerging therapies for chronic kidney disease: what is their role?" *Nature Reviews*, 5:375-383, 2009.
Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.
Wada and Tanaka, "Synthetic lanostane-type triterpenoids as inhibitors of DNA topoisomerase II," *Bioorganic and Medicinal Chemistry Letters*, 15(12):2966-2969, 2005.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.
Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.

Wen et al., "Pentacyclic triterpenes. Part 2: Synthesis and biological evaluation of maslinic acid derivatives as glycogen phosphorylase inhibitors," *Bioorganic and Medicinal Chemistry Letters*, 16 (3): 722-726, 2006.
Wolff et al., "Novel monoaromatic triterpenoid hydrocarbons occurring in sediments," *Tetrahedron*, 45(21): 6721-6728, 1989.
Yates et al., "Pharmacodynamic characterization of chemopreventive triterpenoids as exceptionally potent inducers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-, 12-dioxooleana-1,9(11)-dien-28-oyl]imidazole," *Cancer Res.*, 66 (4): 2488-2494, 2007.
Yore et al., "The synthetic triterpenoid 1-[2-cyano-3,12-dioxooleana-1,9(11)-dien-28-oyl] imidazole blocks nuclear factor-κB activation through direct inhibition of IkappaB kinase β," *Mol. Cancer Ther.*, 5 (12): 3232-3239, 2006.
You et al., "Synthesis and cytotoxic activity of a-ring modified betulinic acid derivatives," *Bioorganic and Medicinal Chemistry Letters*, 13 (19): 3137-3140, 2003.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me)," *Cancer & Biology Ther.*, 5(5):492-497, 2006.
Zapata et al., "CDDO and CDDO-Im Reduce Tumor Burden in a Transgenic Mouse Model of CLL," *Blood*, 104:3477, 2004.
Zapata et al., "Triterpenoids show activity against leukemic cells in a transgenic mouse model of CLL," *Proc. Amer. Assoc. Cancer Res.*, 46: Abstract No. 5179, 2005.
Zhang et al., "Synthetic triterpenoid CDDO as effective therapy for HER2-expressing resistant breast cancer," *Proc. Amer. Assoc. Cancer Res.*, Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.
Zhou et al., "A new triterpenoid from the roots of Tripterygium wildfordii," *Chinese Chemical Letters*, 21(5): 600-602, 2010.
Ziegler et al., "Isolation and Structure of Eucosterol and 16 β-Hydroxyeucosterol, Two Novel Spirocyclic Nortriterpenes, and of a New 24-Nor-5α-chola-8,16-diene-23-oic Acid from Bulbs of Several Eucomis Species," *Helv Chim Acta*, 59(6):1997-2011, 1976.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.
International Preliminary Report on Patentability issued in corresponding PCT Application No. PCT/US2016/053545, dated Jan. 25, 2018.
International Search Report and Written Opinion issued in corresponding PCT Application No. PCT/US2016/053545, dated Dec. 2, 2016.
Office Communication issued in corresponding European Application No. 16781915.0, dated Jun. 25, 2019.
Subba Rao et al., "Chemical modifications of natural triterpenes—glycyrrhetinic and boswellic acids: evaluation of their biological activity," Tetrahedron, 64(51):11541-11548, 2008.
U.S. Appl. No. 15/433,100, filed Feb. 15, 2017.
U.S. Appl. No. 16/115,028, filed Aug. 28, 2018.
Gaffen et al., "IL-23-IL-17 immune axis: discovery, mechanistic understanding, and clinical testing", *Nat. Rev. Immunol.*, 14(9):585-600, 2014.
Guix et al., "The physiology and pathophysiology of nitric oxide in the brain", *Prog. Neurobiol.*, 76:126-152, 2005.
Hu et al., "The IL-17 pathway as a major therapeutic target in autoimmune diseases", *Ann. N.Y. Acad. Sci.*, 1217:60-76, 2011.
Ivanov et al., "The orphan nuclear receptor RORγt directs the differentiation program of proinflammatory IL-17+ T helper cells", *Cell*, 126:1121-1133, 2006.
Iwakura and Ishigame, "The IL-23/IL-17 axis in inflammation", 116(5):1218-1222, 2006.

(56) References Cited

OTHER PUBLICATIONS

Li and Förstermann, "Nitric oxide in the pathogenesis of vascular disease", *J. Pathol.*, 190:244-254, 2000.
Ricciardolo et al., "Nitric oxide in health and disease of the respiratory system", *Physiol. Rev.*, 84:731-765, 2004.
Written Opinion of the International Preliminary Examination Authority issued in corresponding PCT Application No. PCT/US2016/053545, dated Sep. 6, 2017.
Yan et al., "CNS-specific therapy for ongoing EAE by silencing IL-17 pathway in astrocytes", *Mol. Ther.*, 20(7):1338-1348, 2012.
Office Action issued in corresponding Eurasian Application No. 201890767, dated Mar. 27, 2020. English translation appended.
U.S. Appl. No. 16/786,429, filed Feb. 10, 2020.
U.S. Appl. No. 15/622,568, filed Jun. 14, 2017.
U.S. Appl. No. 16/527,171, filed Jul. 31, 2019.
Office Communication issued in corresponding Indian Patent Application No. 201817015090, dated Aug. 27, 2020.
U.S. Appl. No. 17/135,128, filed Dec. 28, 2020.
Auletta et al., "The Synthetic Triterpenoid, CDDO-Me, Modulates the Proinflammatory Response to In Vivo Lipopolysaccharide Challenge", *J. Interferon Cytokine Res.*, 30(7):497-508, 2010.
Banerjee et al., "JAK-STAT Signaling as a Target for Inflammatory and Autoimmune Diseases: Cunent and Future Prospects", *Drugs*, 77:521-546, 2017.
Feehan and Gilroy, "Is Resolution the End of Inflammation?", *Trends Mol. Med.*, 25(3):198-214, 2019.
Fitzpatrick et al., "The synthetic triterpenoid (CDDO-Im) inhibits STAT3, as well as IL-17, and improves DSS-induced colitis in mice", *Inflammopharmacology*, 22:341-349, 2014.
Huerta et al., "Characterization of novel small-molecule NRF2 activators: Structural and biochemical validation of stereospecific KEAP1 binding," *Biochim. Biophys. Acta*, 1860:2537-2552, 2016.
Iizuka et al., "Nrf2-deficient mice are highly susceptible to cigarette smoke-induced emphysema", *Genes Cells*, 10:1113-1125, 2005.
Ishii et al. "Transcription factor Nrf2 plays a pivotal role in protection against elastase-induced pulmonary inflammation and emphysema", *J. Immunol.*, 175, 6968-6975, 2005.

Kobayashi et al., "Nrf2 suppresses macrophage inflammatory response by blocking proinflaimnatory cytokine transcription", *Nat. Commun.*, 7:11624, 2016.
Lawrence, "The Nuclear Factor NF-κB Pathway in Inflammation", *Cold Spring Harb. Perspect. Biol.*, 1:a001651, 2009.
Li et al., "Nrf2 Lowers the Risk of Lung Injury via Modulating the Airway Innate Immune Response Induced by Diesel Exhaust in Mice", *Biomedicines*, 8, 2020.
Noel et al., "KEAP1 Editing Using CRISPR/Cas9 for Therapeutic NRF2 Activation in Primary Human T Lymphocytes", *J. Immunol.*, 200:1929-1936, 2018.
Office Communication issued in corresponding Chinese Patent Application No. 201680067912.8, dated Nov. 13, 2020.
Pareek et al., "Triterpenoid modulation of IL-17 and Nrf-2 expression ameliorates neuroinflammation and promotes remyelination in autoimmune encephalomyelitis", *Sci. Rep.*, 1, 201, 2011.
Segal et al., "NADPH oxidase limits innate immune responses in the lungs in mice", *PLoS One*, 5:e9631, 2010.
Walsh et al., "Identification and quantification of the basal and inducible Nrf2-dependent proteomes in mouse liver: Biochemical, pharmacological and toxicological implications", *J. Proteom.*, 108:171-187, 2014.
Yang et al., "Keap1-Nrf2 signaling activation by Bardoxolone-methyl ameliorates high glucose-induced oxidative injury in human umbilical vein endothelial cells", *Aging*, 12(11):10370-10380, 2020.
Zhang et al., "Nrf2 Activator RTA-408 Protects Against Ozone-Induced Acute Asthma Exacerbation by Suppressing ROS and γδ17 Cells", *Inflammation*, 42:1843-1856, 2019.
Zhao et al., "γδ T cells as a major source of IL-17 production during age-dependent RPE degeneration", *Invest. Ophthalmol. Vis. Sci.*, 55:6580-6589, 2014.
Laufer, Stefan, and Jeremy Ian Levin, eds. *Anti-Inflammatory Drug Discovery*, Royal Society of Chemistry, 2012.
Schenone, Monica, et al. "Target identification and mechanism of action in chemical biology and drug discovery." *Nature Chemical Biology* 9.4 (2013): 232-240.
Tabarkiewicz, Jacek, et al. "The role of IL-17 and Th17 lymphocytes in autoimmune diseases." *Archivum Immunologiae et Therapiae Experimentalis* 63.6 (2015): 435-449.

\* cited by examiner

C4-MODIFIED OLEANOLIC ACID DERIVATIVES FOR INHIBITION OF IL-17 AND OTHER USES

The present application is a national phase application under 35 U.S.C. § 371 of International Application No. PCT/US2016/053545, filed Sep. 23, 2016, which claims the benefit of U.S. Provisional Patent Application No. 62/222,632, filed on Sep. 23, 2015, the entirety of each of which is incorporated herein by reference.

BACKGROUND OF THE INVENTION

I. Field of the Invention

The present invention relates generally to the fields of biology and medicine. More particularly, it concerns compounds, compositions, and methods for the treatment and prevention of diseases or disorders, such as those associated with excess production of IL-17.

II. Description of Related Art

Inflammatory diseases, particularly autoimmune diseases, such as rheumatoid arthritis, osteoarthritis, psoriasis, and multiple sclerosis, frequently have severe and long-term adverse effects on physical well-being and quality of life. In many patients these diseases cause significant disability, and in some cases (e.g., lupus and multiple sclerosis) may be life-threatening. Recent advances in therapeutic options, such as the development of therapeutic antibodies against tumor necrosis factor (TNF), have improved outcomes and quality of life for many patients. However, significant numbers of patients do not achieve adequate relief of symptoms from these therapies or cannot tolerate them. Even in patients who do respond, side effects can be significant and may be life-threatening due to immune suppression or other complications.

Recent research on chronic inflammation and autoimmunity has revealed an important role played by a subpopulation of T lymphocytes known as Th17 cells. These cells produce the inflammatory cytokine interleukin 17 (IL-17). Excessive levels of IL-17 have been reported in a variety of autoimmune diseases including multiple sclerosis, rheumatoid arthritis, psoriasis, inflammatory bowel diseases, vitiligo, Sjögren syndrome, and ankylosing spondylitis (Miossec and Kolls, 2012; Yang et al., 2014; Gaffen et al., 2014). Evidence suggests that IL-17 also plays a significant role in the pathology of vasculitis, atherosclerosis, and inflammatory lung diseases, such as cystic fibrosis and chronic obstructive pulmonary disorder (COPD). IL-17 is also implicated in the pathophysiology of epilepsy and neurodegenerative diseases including Alzheimer's disease, Parkinson's disease, and ALS. Elevated levels of IL-17 or Th17 cells have been reported in patients with psychiatric and neuropsychiatric conditions including schizophrenia, obsessive-compulsive disorder, bipolar disorder, post-traumatic stress disorder, major depression, and autism. Elevations in IL-17 have been implicated in other conditions involving dysregulated inflammatory signaling, including obesity, insulin resistance, and fatty liver disease.

Although Th17 cells are not the only source of IL-17, it has been reported that these cells are a major source of this cytokine in tissues undergoing damage from autoimmune disease, such as arthritic joints. And elevated levels of IL-17 have been reported to promote tissue degradation, e.g. by stimulating the production of matrix metalloproteinases (a source of damage to connective tissue and cartilage) and increasing the expression of receptor activator of NF-κd ligand (RANKL), which stimulates osteoclast activity and promotes bone damage.

Inappropriate activity of Th17 cells, including overproduction of IL-17, has also been implicated in the pathologies associated with certain viral and parasitic infections. For example, IL-17 has been implicated in the development of severe neuroinflammation associated with *Toxoplasma gondii* infection and increased severity of lesions associated with *Leishmania* infection. In these and other cases, IL-17 appears to play a role in perpetuating the infection, promoting an excessive inflammatory response, and inhibiting clearance of the infectious agent (Waite and Skokos, 2012). Accordingly, therapies that prevent or inhibit excess production of IL-17, or otherwise reduce circulating levels of IL-17, would have significant potential in a wide range of diseases or disorders, including those with inflammatory and autoimmune-related components.

SUMMARY OF THE INVENTION

The present disclosure provides novel compounds, including C4 modified oleanolic acid derivatives, pharmaceutical compositions thereof, methods for their manufacture, and methods for their use, including for the prevention and treatment of diseases or disorders associated with overproduction of IL-17.

In some aspects, the present disclosure provides compounds of the formula:

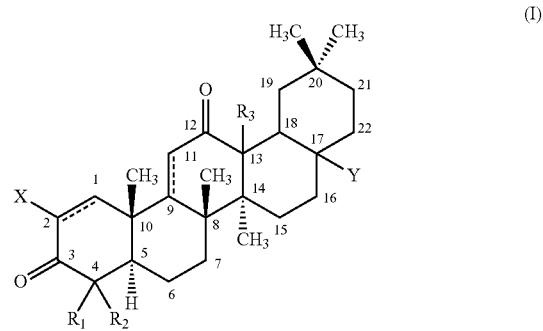

(I)

wherein:
  the bond between atoms 1 and 2 is a single bond, an epoxidized double bond, or a double bond;
  the bond between atoms 9 and 11 is a single bond or a double bond; X is cyano, heteroaryl$_{(C\leq 8)}$, substituted heteroaryl$_{(C\leq 8)}$, —CF$_3$, or —C(O)—R$_4$; wherein
    R$_4$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;
  R$_1$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;
  R$_3$ is hydrogen, hydroxy, or alkoxy$_{(C\leq 8)}$, acyloxy$_{(C\leq 8)}$, or substituted version of either of these groups; or R$_3$ is taken together with Y as described below; and
wherein variables R$_2$ and Y are defined according to either Group A or B, wherein for Group A:
  R$_2$ is amino, cyano, halo, or hydroxy, substituted alkyl$_{(C\leq 8)}$, substituted cycloalkyl$_{(C\leq 8)}$, heteroaryl$_{(C\leq 8)}$, substituted heteroaryl$_{(C\leq 8)}$, acyl$_{(C\leq 8)}$, substituted acyl$_{(C\leq 8)}$, amido$_{(C\leq 8)}$, substituted amido$_{(C\leq 8)}$, alkylamino$_{(C\leq 8)}$, substituted alkylamino$_{(C\leq 8)}$, dialkylamino$_{(C\leq 8)}$, or dialkylamino$_{(C\leq 8)}$;

—OR$_a$, wherein:
  R$_a$ is hydrogen or alkyl$_{(C\leq 8)}$, alkenyl$_{(C\leq 8)}$, alkynyl$_{(C\leq 8)}$, aryl$_{(C\leq 12)}$, aralkyl$_{(C\leq 12)}$, heteroaryl$_{(C\leq 12)}$, heterocycloalkyl$_{(C\leq 8)}$, acyl$_{(C\leq 8)}$, or a substituted version of any of these groups;

—(CH$_2$)$_m$—(OCH$_2$)$_n$—R$_5$, wherein:
  R$_5$ is hydroxy or acyl$_{(C\leq 8)}$, alkoxy$_{(C\leq 8)}$, acyloxy$_{(C\leq 8)}$, alkylsilyloxy$_{(C\leq 8)}$, or a substituted version of any of these groups;
  m is 0, 1, 2, 3, or 4; and
  n is 0, 1, 2, or 3;

—(CH$_2$)$_s$NR$_5$'(R$_6$), wherein:
  s is 0, 1, 2, 3, or 4;
  R$_5$' is hydrogen, alkyl$_{(C\leq 8)}$, alkoxy$_{(C\leq 8)}$, substituted alkoxy$_{(C\leq 8)}$, acyl$_{(C\leq 8)}$, substituted acyl$_{(C\leq 8)}$, —C(O)-alkoxy$_{(C\leq 8)}$, substituted —C(O)-alkoxy$_{(C\leq 8)}$, acyloxy$_{(C\leq 8)}$, substituted acyloxy$_{(C\leq 8)}$, alkylsilyloxy$_{(C\leq 8)}$, or substituted alkylsilyloxy$_{(C\leq 8)}$; and
  R$_6$ is hydrogen, alkyl$_{(C\leq 8)}$, or substituted alkyl$_{(C\leq 8)}$; or —(CH$_2$)$_q$—C(O)—R$_5$", wherein:
  R$_5$" is amino, hydroxy, or mercapto; or
    alkoxy$_{(C\leq 8)}$, alkylthio$_{(C\leq 8)}$, alkylamino$_{(C\leq 8)}$, dialkylamino$_{(C\leq 8)}$, or a substituted version of any of these groups; and
  q is 0, 1, 2, 3, or 4; and Y is hydrogen, hydroxy, halo, amino, cyano, isocyanate, or mercapto;
  alkyl$_{(C\leq 8)}$, cycloalkyl$_{(C\leq 8)}$, alkenyl$_{(C\leq 8)}$, alkynyl$_{(C\leq 8)}$, aryl$_{(C\leq 12)}$, heteroaryl$_{(C\leq 8)}$, heterocycloalkyl$_{(C\leq 12)}$, alkoxy$_{(C\leq 8)}$, cycloalkoxy$_{(C\leq 8)}$, aryloxy$_{(C\leq 12)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, alkylthio$_{(C\leq 8)}$, acylthio$_{(C\leq 8)}$, alkylsulfonylamino$_{(C\leq 8)}$, or substituted versions of any of these groups;
  alkanediyl$_{(C\leq 8)}$-R$_b$, -alkenediyl$_{(C\leq 8)}$-R$_b$, or a substituted version of any of these groups, wherein R$_b$ is:
    hydrogen, hydroxy, halo, amino or mercapto; or
    aryl$_{(C\leq 8)}$, heteroaryl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, heteroarylamino$_{(C\leq 8)}$, alkylsulfonylamino$_{(C\leq 8)}$, amido$_{(C\leq 8)}$, —OC(O)NH-alkyl$_{(C\leq 8)}$, —OC(O)CH$_2$NHC(O)O-t-butyl, —OCH$_2$-alkylthio$_{(C\leq 8)}$, or a substituted version of any of these groups;

—(CH$_2$)$_p$C(O)R$_c$, wherein p is 0-6 and R$_c$ is:
  hydrogen, halo, amino, —NHOH, or mercapto; or
  alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkylamino$_{(C\leq 8)}$, dialkylamino$_{(C\leq 8)}$, arylamino$_{(C\leq 8)}$, alkyl-sulfonylamino$_{(C\leq 8)}$, amido$_{(C\leq 8)}$, alkoxyamino$_{(C\leq 8)}$, heterocycloalkylamino$_{(C\leq 8)}$, —NHC(NOH)-alkyl$_{(C\leq 8)}$, —NH-amido$_{(C\leq 8)}$, or a substituted version of any of these groups;

—NR$_d$C(O)R$_e$, wherein
  R$_d$ is hydrogen, alkyl$_{(C\leq 8)}$, or substituted alkyl$_{(C\leq 8)}$;
  R$_e$ is hydrogen, hydroxy, amino; or
    alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, cycloalkoxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, arylamino$_{(C\leq 8)}$, or a substituted version of any of these groups; or Y is taken together with R$_3$ and is —(CH$_2$)$_p$C(O)R$_f$—, wherein
  p is 0-6; and
  R$_f$ is —O— or —NR$_7$—; wherein:
    R$_7$ is hydrogen, alkyl$_{(C\leq 8)}$, substituted alkyl$_{(C\leq 8)}$, acyl$_{(C\leq 8)}$, or substituted acyl$_{(C\leq 8)}$; or for Group B:

R$_2$ is amino, cyano, halo, or hydroxy,
  haloalkyl$_{(C\leq 8)}$, substituted cycloalkyl$_{(C\leq 8)}$, heteroaryl$_{(C\leq 8)}$, substituted heteroaryl$_{(C\leq 8)}$, acyl$_{(C\leq 8)}$, substituted acyl$_{(C\leq 8)}$, amido$_{(C\leq 8)}$, substituted amido$_{(C\leq 8)}$, alkylamino$_{(C\leq 8)}$, substituted alkylamino$_{(C\leq 8)}$, dialkylamino$_{(C\leq 8)}$, or dialkylamino$_{(C\leq 8)}$; or —OR$_a$, wherein:
  R$_a$ is hydrogen or alkyl$_{(C\leq 8)}$, alkenyl$_{(C\leq 8)}$, alkynyl$_{(C\leq 8)}$, aryl$_{(C\leq 12)}$, aralkyl$_{(C\leq 12)}$, heteroaryl$_{(C\leq 12)}$, heterocycloalkyl$_{(C\leq 8)}$, acyl$_{(C\leq 8)}$, or a substituted version of any of these groups;

—(CH$_2$)$_m$—R$_5$''', wherein:
  R$_5$''' is alkoxy$_{(C\leq 8)}$, acyloxy$_{(C\leq 8)}$, substituted acyloxy$_{(C\leq 8)}$, alkylsilyloxy$_{(C\leq 8)}$, or substituted alkylsilyloxy$_{(C\leq 8)}$; and
  m is 0, 1, 2, 3, or 4;

—(CH$_2$)$_{m2}$—R$_5$''', wherein:
  R$_5$''' is hydroxy; and
  m$_2$ is 2, 3, or 4;

—(CH$_2$)$_s$NR$_5$'(R$_6$), wherein:
  s is 0, 1, 2, 3, or 4;
  R$_5$' is hydrogen, alkyl$_{(C\leq 8)}$, alkoxy$_{(C\leq 8)}$, substituted alkoxy$_{(C\leq 8)}$, acyl$_{(C\leq 8)}$, substituted acyl$_{(C\leq 8)}$, —C(O)-alkoxy$_{(C\leq 8)}$, substituted —C(O)-alkoxy$_{(C\leq 8)}$, acyloxy$_{(C\leq 8)}$, substituted acyloxy$_{(C\leq 8)}$, alkylsilyloxy$_{(C\leq 8)}$, or substituted alkylsilyloxy$_{(C\leq 8)}$; and
  R$_6$ is hydrogen, alkyl$_{(C\leq 8)}$, or substituted alkyl$_{(C\leq 8)}$; or —(CH$_2$)$_q$—C(O)—R$_5$", wherein:
  R$_5$" is amino, hydroxy, or mercapto; or
    alkoxy$_{(C\leq 8)}$, alkylthio$_{(C\leq 8)}$, alkylamino$_{(C\leq 8)}$, dialkylamino$_{(C\leq 8)}$, or a substituted version of any of these groups; and
  q is 0, 1, 2, 3, or 4; and Y is —(CH$_2$)$_o$C(O)R$_c$, wherein o is 0-6 and R$_c$ is:
  hydroxy; or
  alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, or a substituted version of any of these groups;

or a pharmaceutically acceptable salt, acetal, or hemiacetal thereof.

In some embodiments, the compounds are further defined as:

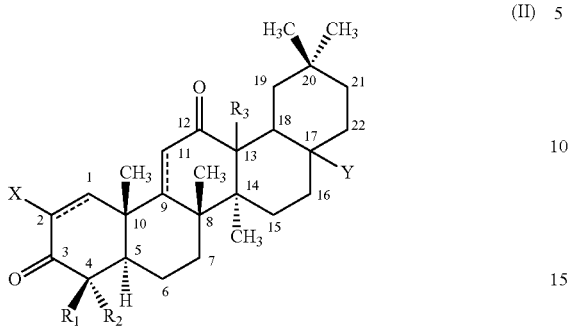

wherein:
the bond between atoms 1 and 2 is a single bond, an epoxidized double bond, or a double bond;
the bond between atoms 9 and 11 is a single bond or a double bond;
X is cyano, heteroaryl$_{(C≤8)}$, substituted heteroaryl$_{(C≤8)}$, —CF$_3$, or —C(O)—R$_4$; wherein
  R$_4$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
R$_1$ is hydrogen, alkyl$_{(C≤8)}$, cycloalkyl$_{(C≤8)}$, substituted alkyl$_{(C≤8)}$, or substituted cycloalkyl$_{(C≤8)}$;
R$_2$ is amino,
  heteroaryl$_{(C≤8)}$, substituted heteroaryl$_{(C≤8)}$, acyl$_{(C≤8)}$, substituted acyl$_{(C≤8)}$, amido$_{(C≤8)}$, substituted amido$_{(C≤8)}$, alkylamino$_{(C≤8)}$, substituted alkylamino$_{(C≤8)}$, dialkylamino$_{(C≤8)}$, or dialkylamino$_{(C≤8)}$;
  —OR$_a$, wherein:
    R$_a$ is hydrogen or alkyl$_{(C≤8)}$, acyl$_{(C≤8)}$, or a substituted version of either of these groups;
  —(CH$_2$)$_s$NR$_5$'(R$_6$), wherein:
    s is 0, 1, 2, 3, or 4;
    R$_5$' is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)-alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
    R$_6$ is hydrogen, alkyl$_{(C≤8)}$, or substituted alkyl$_{(C≤8)}$; or
  —(CH$_2$)$_q$—C(O)—R$_5$", wherein:
    R$_5$" is amino, hydroxy, or mercapto; or
      alkoxy$_{(C≤8)}$, alkylthio$_{(C≤8)}$, alkylamino$_{(C≤8)}$, dialkylamino$_{(C≤8)}$, or a substituted version of any of these groups; and
    q is 0, 1, 2, 3, or 4;
R$_3$ is hydrogen, hydroxy, or alkoxy$_{(C≤8)}$, acyloxy$_{(C≤8)}$, or substituted version of either of these groups; or R$_3$ is taken together with Y as described below; and
Y is hydrogen, hydroxy, halo, amino, cyano, isocyanate, or mercapto;
  alkyl$_{(C≤8)}$, cycloalkyl$_{(C≤8)}$, alkenyl$_{(C≤8)}$, alkynyl$_{(C≤8)}$, aryl$_{(C≤12)}$, heteroaryl$_{(C≤8)}$, heterocycloalkyl$_{(C≤12)}$, alkoxy$_{(C≤8)}$, cycloalkoxy$_{(C≤8)}$, aryloxy$_{(C≤12)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, alkylthio$_{(C≤8)}$, acylthio$_{(C≤8)}$, alkylsulfonylamino$_{(C≤8)}$, or substituted versions of any of these groups;
  alkanediyl$_{(C≤8)}$-R$_b$, -alkenediyl$_{(C≤8)}$-R$_b$, or a substituted version of any of these groups, wherein R$_b$ is: hydrogen, hydroxy, halo, amino or mercapto; or
  aryl$_{(C≤8)}$, heteroaryl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, heteroarylamino$_{(C≤8)}$, alkylsulfonylamino$_{(C≤8)}$, amido$_{(C≤8)}$, —OC(O)NH-alkyl$_{(C≤8)}$, —OC(O)CH$_2$NHC(O)O-t-butyl, —OCH$_2$-alkylthio$_{(C≤8)}$, or a substituted version of any of these groups;
  —(CH$_2$)$_p$C(O)R$_c$, wherein p is 0-6 and R$_c$ is: hydrogen, halo, hydroxy, amino, —NHOH, or mercapto; or
    alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, arylamino$_{(C≤8)}$, alkylsulfonylamino$_{(C≤8)}$, amido$_{(C≤8)}$, alkoxyamino$_{(C≤8)}$, heterocycloalkylamino$_{(C≤8)}$, —NHC(NOH)-alkyl$_{(C≤8)}$, —NH-amido$_{(C≤8)}$, or a substituted version of any of these groups;
  —NR$_d$C(O)R$_e$, wherein
    R$_d$ is hydrogen, alkyl$_{(C≤8)}$, or substituted alkyl$_{(C≤8)}$;
    R$_e$ is hydrogen, hydroxy, amino; or
      alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, arylamino$_{(C≤8)}$, or a substituted version of any of these groups; or
  Y is taken together with R$_3$ and is —(CH$_2$)$_p$C(O)R$_f$—, wherein
    p is 0-6; and
    R$_f$ is —O— or —NR$_7$—; wherein:
      R$_7$ is hydrogen, alkyl$_{(C≤8)}$, substituted alkyl$_{(C≤8)}$, acyl$_{(C≤8)}$, or substituted acyl$_{(C≤8)}$;
or a pharmaceutically acceptable salt thereof.

In some embodiments, the compounds are further defined as:

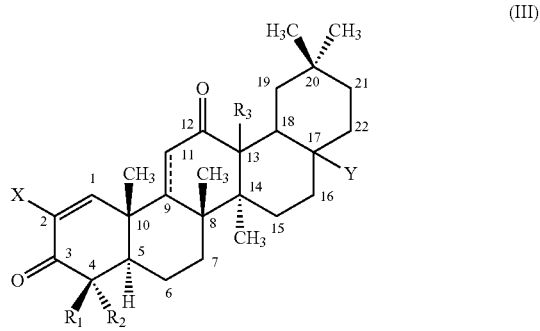

wherein:
the bond between atoms 9 and 11 is a single bond or a double bond;
X is cyano, heteroaryl$_{(C≤8)}$, substituted heteroaryl$_{(C≤8)}$, —CF$_3$, or —C(O)—R$_4$; wherein
  R$_4$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;

$R_1$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;

$R_2$ is amino, heteroaryl$_{(C\leq 8)}$, substituted heteroaryl$_{(C\leq 8)}$, acyl$_{(C\leq 8)}$, substituted acyl$_{(C\leq 8)}$, amido$_{(C\leq 8)}$, substituted amido$_{(C\leq 8)}$, alkylamino$_{(C\leq 8)}$, substituted alkylamino$_{(C\leq 8)}$, dialkylamino$_{(C\leq 8)}$, or dialkylamino$_{(C\leq 8)}$;

—OR$_a$, wherein:

$R_a$ is hydrogen or alkyl$_{(C\leq 8)}$, acyl$_{(C\leq 8)}$, or a substituted version of either of these groups;

—(CH$_2$)$_s$NR$_5'$(R$_6$), wherein:

s is 0, 1, 2, 3, or 4;

$R_5'$ is hydrogen, alkyl$_{(C\leq 8)}$, alkoxy$_{(C\leq 8)}$, substituted alkoxy$_{(C\leq 8)}$, acyl$_{(C\leq 8)}$, substituted acyl$_{(C\leq 8)}$, —C(O)-alkoxy$_{(C\leq 8)}$, substituted —C(O)-alkoxy$_{(C\leq 8)}$, acyloxy$_{(C\leq 8)}$, substituted acyloxy$_{(C\leq 8)}$, alkylsilyloxy$_{(C\leq 8)}$, or substituted alkylsilyloxy$_{(C\leq 8)}$; and $R_6$ is hydrogen, alkyl$_{(C\leq 8)}$, or substituted alkyl$_{(C\leq 8)}$; or —(CH$_2$)$_q$—C(O)—R$_5''$, wherein:

$R_5''$ is amino, hydroxy, or mercapto; or alkoxy$_{(C\leq 8)}$, alkylthio$_{(C\leq 8)}$, alkylamino$_{(C\leq 8)}$, dialkylamino$_{(C\leq 8)}$, or a substituted version of any of these groups; and q is 0, 1, 2, 3, or 4;

$R_3$ is hydrogen, hydroxy, or alkoxy$_{(C\leq 8)}$, acyloxy$_{(C\leq 8)}$, or substituted version of either of these groups; or $R_3$ is taken together with Y as described below; and Y is hydrogen, hydroxy, halo, amino, cyano, isocyanate, or mercapto;

alkyl$_{(C\leq 8)}$, cycloalkyl$_{(C\leq 8)}$, alkenyl$_{(C\leq 8)}$, alkynyl$_{(C\leq 8)}$, aryl$_{(C\leq 12)}$, heteroaryl$_{(C\leq 8)}$, heterocycloalkyl$_{(C\leq 12)}$, alkoxy$_{(C\leq 8)}$, cycloalkoxy$_{(C\leq 8)}$, aryloxy$_{(C\leq 12)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, alkylthio$_{(C\leq 8)}$, acylthio$_{(C\leq 8)}$, alkylsulfonylamino$_{(C\leq 8)}$, or substituted versions of any of these groups;

alkanediyl$_{(C\leq 8)}$-R$_b$, -alkenediyl$_{(C\leq 8)}$-R$_b$, or a substituted version of any of these groups, wherein R$_b$ is:

hydrogen, hydroxy, halo, amino or mercapto; or aryl$_{(C\leq 8)}$, heteroaryl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, heteroarylamino$_{(C\leq 8)}$, alkylsulfonylamino$_{(C\leq 8)}$, amido$_{(C\leq 8)}$, —OC(O)NH-alkyl$_{(C\leq 8)}$, —OC(O)CH$_2$NHC(O)O-t-butyl, —OCH$_2$-alkylthio$_{(C\leq 8)}$, or a substituted version of any of these groups;

—(CH$_2$)$_p$C(O)R$_c$, wherein p is 0-6 and R$_c$ is:

hydrogen, halo, hydroxy, amino, —NHOH, or mercapto; or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, arylamino$_{(C\leq 8)}$, alkylsulfonylamino$_{(C\leq 8)}$, amido$_{(C\leq 8)}$, alkoxyamino$_{(C\leq 8)}$, heterocycloalkylamino$_{(C\leq 8)}$, —NHC(NOH)-alkyl$_{(C\leq 8)}$, —NH-amido$_{(C\leq 8)}$, or a substituted version of any of these groups;

—NR$_d$C(O)R$_e$, wherein

R$_d$ is hydrogen, alkyl$_{(C\leq 8)}$, or substituted alkyl$_{(C\leq 8)}$;

R$_e$ is hydrogen, hydroxy, amino; or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, cycloalkoxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, arylamino$_{(C\leq 8)}$, or a substituted version of any of these groups; or Y is taken together with $R_3$ and is —(CH$_2$)$_p$C(O)R$_f$—, wherein p is 0-6; and R$_f$ is —O— or —NR$_7$—; wherein:

$R_7$ is hydrogen, alkyl$_{(C\leq 8)}$, substituted alkyl$_{(C\leq 8)}$, acyl$_{(C\leq 8)}$, or substituted acyl$_{(C\leq 8)}$;

or a pharmaceutically acceptable salt thereof.

In some embodiments, the compounds are further defined as:

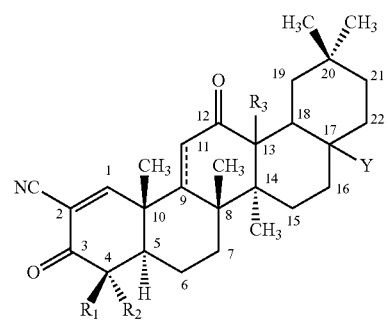

(IV)

wherein:

the bond between atoms 9 and 11 is a single bond or a double bond;

$R_1$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;

$R_2$ is amino, heteroaryl$_{(C\leq 8)}$, substituted heteroaryl$_{(C\leq 8)}$, acyl$_{(C\leq 8)}$, substituted acyl$_{(C\leq 8)}$, amido$_{(C\leq 8)}$, substituted amido$_{(C\leq 8)}$, alkylamino$_{(C\leq 8)}$, substituted alkylamino$_{(C\leq 8)}$, dialkylamino$_{(C\leq 8)}$, or dialkylamino$_{(C\leq 8)}$;

—OR$_a$, wherein:

$R_a$ is hydrogen or alkyl$_{(C\leq 8)}$, acyl$_{(C\leq 8)}$, or a substituted version of either of these groups;

—(CH$_2$)$_s$NR$_5'$(R$_6$), wherein:

s is 0, 1, 2, 3, or 4;

$R_5'$ is hydrogen, alkyl$_{(C\leq 8)}$, alkoxy$_{(C\leq 8)}$, substituted alkoxy$_{(C\leq 8)}$, acyl$_{(C\leq 8)}$, substituted acyl$_{(C\leq 8)}$, —C(O)-alkoxy$_{(C\leq 8)}$, substituted —C(O)-alkoxy$_{(C\leq 8)}$, acyloxy$_{(C\leq 8)}$, substituted acyloxy$_{(C\leq 8)}$, alkylsilyloxy$_{(C\leq 8)}$, or substituted alkylsilyloxy$_{(C\leq 8)}$; and $R_6$ is hydrogen, alkyl$_{(C\leq 8)}$, or substituted alkyl$_{(C\leq 8)}$; or —(CH$_2$)$_q$—C(O)—R$_5''$, wherein:

$R_5''$ is amino, hydroxy, or mercapto; or alkoxy$_{(C\leq 8)}$, alkylthio$_{(C\leq 8)}$, alkylamino$_{(C\leq 8)}$, dialkylamino$_{(C\leq 8)}$, or a substituted version of any of these groups; and q is 0, 1, 2, 3, or 4;

$R_3$ is hydrogen, hydroxy, or alkoxy$_{(C\leq 8)}$, acyloxy$_{(C\leq 8)}$, or substituted version of either of these groups; or $R_3$ is taken together with Y as described below; and Y is hydrogen, hydroxy, halo, amino, cyano, isocyanate, or mercapto;

alkyl$_{(C\leq8)}$, cycloalkyl$_{(C\leq8)}$, alkenyl$_{(C\leq8)}$, alkynyl$_{(C\leq8)}$, aryl$_{(C\leq12)}$, heteroaryl$_{(C\leq8)}$, heterocycloalkyl$_{(C\leq12)}$, alkoxy$_{(C\leq8)}$, cycloalkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

-alkanediyl$_{(C\leq8)}$-R$_b$, -alkenediyl$_{(C\leq8)}$-R$_b$, or a substituted version of any of these groups, wherein R$_b$ is: hydrogen, hydroxy, halo, amino or mercapto; or aryl$_{(C\leq8)}$, heteroaryl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)CH$_2$NHC(O)O-t-butyl, —OCH$_2$-alkylthio$_{(C\leq8)}$, or a substituted version of any of these groups;

—(CH$_2$)$_p$C(O)R$_c$, wherein p is 0-6 and R$_c$ is:
hydrogen, halo, hydroxy, amino, —NHOH, or mercapto; or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, alkylsulfonylamino$_{(C\leq8)}$, amido$_{(C\leq8)}$, alkoxyamino$_{(C\leq8)}$, heterocycloalkylamino$_{(C\leq8)}$, —NHC(NOH)-alkyl$_{(C\leq8)}$, —NH-amido$_{(C\leq8)}$, or a substituted version of any of these groups;

—NR$_d$C(O)R$_e$, wherein
R$_d$ is hydrogen, alkyl$_{(C\leq8)}$, or substituted alkyl$_{(C\leq8)}$;
R$_e$ is hydrogen, hydroxy, amino; or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, cycloalkoxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, or a substituted version of any of these groups; or Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C\leq8)}$, substituted alkyl$_{(C\leq8)}$, acyl$_{(C\leq8)}$, or substituted acyl$_{(C\leq8)}$;

or a pharmaceutically acceptable salt thereof.

In some embodiments, the compounds are further defined as:

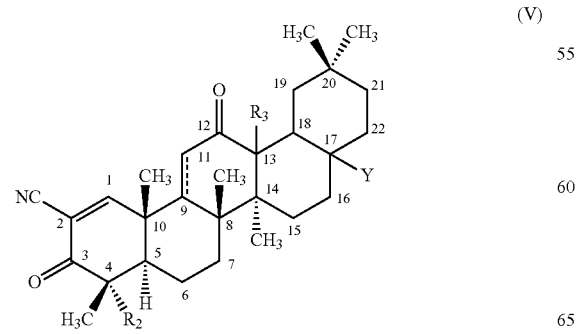

(V)

wherein:
the bond between atoms 9 and 11 is a single bond or a double bond;
R$_2$ is amino,
heteroaryl$_{(C\leq8)}$, substituted heteroaryl$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or dialkylamino$_{(C\leq8)}$;
—OR$_a$, wherein:
R$_a$ is hydrogen or alkyl$_{(C\leq8)}$, acyl$_{(C\leq8)}$, or a substituted version of either of these groups;
—(CH$_2$)$_s$NR$_5$'(R$_6$), wherein:
s is 0, 1, 2, 3, or 4;
R$_5$' is hydrogen, alkyl$_{(C\leq8)}$, alkoxy$_{(C\leq8)}$, substituted alkoxy$_{(C\leq8)}$, acyl$_{(C\leq8)}$, substituted acyl$_{(C\leq8)}$, —C(O)-alkoxy$_{(C\leq8)}$, substituted —C(O)-alkoxy$_{(C\leq8)}$, acyloxy$_{(C\leq8)}$, substituted acyloxy$_{(C\leq8)}$, alkylsilyloxy$_{(C\leq8)}$, or substituted alkylsilyloxy$_{(C\leq8)}$; and
R$_6$ is hydrogen, alkyl$_{(C\leq8)}$, or substituted alkyl$_{(C\leq8)}$; or
—(CH$_2$)$_q$—C(O)—R$_5$'', wherein:
R$_5$'' is amino, hydroxy, or mercapto; or
alkoxy$_{(C\leq8)}$, alkylthio$_{(C\leq8)}$, alkylamino$_{(C\leq8)}$, dialkylamino$_{(C\leq8)}$, or a substituted version of any of these groups; and
q is 0, 1, 2, 3, or 4;
R$_3$ is hydrogen, hydroxy, or alkoxy$_{(C\leq8)}$, acyloxy$_{(C\leq8)}$, or substituted version of either of these groups; or R$_3$ is taken together with Y as described below; and
Y is hydrogen, hydroxy, halo, amino, cyano, isocyanate, or mercapto;

alkyl$_{(C\leq8)}$, cycloalkyl$_{(C\leq8)}$, alkenyl$_{(C\leq8)}$, alkynyl$_{(C\leq8)}$, aryl$_{(C\leq12)}$, heteroaryl$_{(C\leq8)}$, heterocycloalkyl$_{(C\leq12)}$, alkoxy$_{(C\leq8)}$, cycloalkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

-alkanediyl$_{(C\leq8)}$-R$_b$, -alkenediyl$_{(C\leq8)}$-R$_b$, or a substituted version of any of these groups, wherein R$_b$ is: hydrogen, hydroxy, halo, amino or mercapto; or aryl$_{(C\leq8)}$, heteroaryl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)CH$_2$NHC(O)O-t-butyl, —OCH$_2$-alkylthio$_{(C\leq8)}$, or a substituted version of any of these groups;

—(CH$_2$)$_p$C(O)R$_c$, wherein p is 0-6 and R$_c$ is:
hydrogen, halo, hydroxy, amino, —NHOH, or mercapto; or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, alkylsulfonylamino$_{(C\leq8)}$, amido$_{(C\leq8)}$, alkoxyamino$_{(C\leq8)}$, heterocycloalkylamino$_{(C\leq8)}$, —NHC(NOH)-alkyl$_{(C\leq8)}$, —NH-amido$_{(C\leq8)}$, or a substituted version of any of these groups;

—NR$_d$C(O)R$_e$, wherein
R$_d$ is hydrogen, alkyl$_{(C≤8)}$, or substituted alkyl$_{(C≤8)}$;
R$_e$ is hydrogen, hydroxy, amino; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, arylamino$_{(C≤8)}$, or a substituted version of any of these groups; or
Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C≤8)}$, substituted alkyl$_{(C≤8)}$, acyl$_{(C≤8)}$, or substituted acyl$_{(C≤8)}$;
or a pharmaceutically acceptable salt thereof.

In some embodiments, the compounds are further defined as:

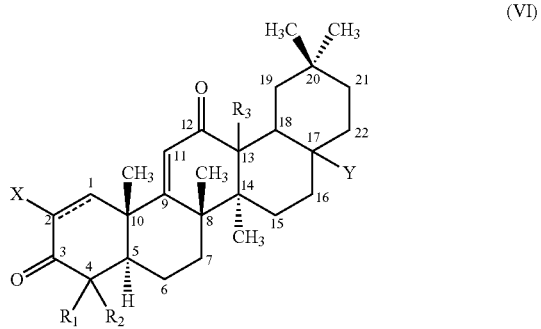

(VI)

wherein:
the bond between atoms 1 and 2 is a single bond, an epoxidized double bond, or a double bond;
X is cyano, heteroaryl$_{(C≤8)}$, substituted heteroaryl$_{(C≤8)}$, —CF$_3$, or —C(O)—R$_4$; wherein
R$_4$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
R$_1$ is hydrogen, alkyl$_{(C≤8)}$, cycloalkyl$_{(C≤8)}$, substituted alkyl$_{(C≤8)}$, or substituted cycloalkyl$_{(C≤8)}$;
R$_2$ is amino, cyano, halo, or hydroxy,
substituted alkyl$_{(C≤8)}$, heteroaryl$_{(C≤8)}$, substituted heteroaryl$_{(C≤8)}$, acyl$_{(C≤8)}$, substituted acyl$_{(C≤8)}$, amido$_{(C≤8)}$, substituted amido$_{(C≤8)}$, alkylamino$_{(C≤8)}$, substituted alkylamino$_{(C≤8)}$, dialkylamino$_{(C≤8)}$, or dialkylamino$_{(C≤8)}$; or
—OR$_a$, wherein:
R$_a$ is hydrogen or alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤12)}$, heterocycloalkyl$_{(C≤8)}$, acyl$_{(C≤8)}$, or a substituted version of any of these groups;
—(CH$_2$)$_m$—(OCH$_2$)$_n$—R$_5$, wherein:
R$_5$ is hydroxy or acyl$_{(C≤8)}$, alkoxy$_{(C≤8)}$, acyloxy$_{(C≤8)}$, alkylsilyloxy$_{(C≤8)}$, or a substituted version of any of these groups;
m is 0, 1, 2, 3, or 4; and
n is 0, 1, 2, or 3;
—(CH$_2$)$_s$NR$_5$'(R$_6$), wherein:
s is 0, 1, 2, 3, or 4;
R$_5$' is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)-alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
R$_6$ is hydrogen, alkyl$_{(C≤8)}$, or substituted alkyl$_{(C≤8)}$; or
—(CH$_2$)$_q$—C(O)—R$_5$'', wherein:
R$_5$'' is amino, hydroxy, or mercapto; or
alkoxy$_{(C≤8)}$, alkylthio$_{(C≤8)}$, alkylamino$_{(C≤8)}$, dialkylamino$_{(C≤8)}$, or a substituted version of any of these groups; and
q is 0, 1, 2, 3, or 4;
R$_3$ is hydrogen, hydroxy, or alkoxy$_{(C≤8)}$, acyloxy$_{(C≤8)}$, or substituted version of either of these groups; or R$_3$ is taken together with Y as described below; and
Y is hydrogen, hydroxy, halo, amino, cyano, isocyanate, or mercapto;
alkyl$_{(C≤8)}$, cycloalkyl$_{(C≤8)}$, alkenyl$_{(C≤8)}$, alkynyl$_{(C≤8)}$, aryl$_{(C≤12)}$, aralkyl$_{(C≤12)}$,
heteroaryl$_{(C≤8)}$, heterocycloalkyl$_{(C≤12)}$, alkoxy$_{(C≤8)}$, cycloalkoxy$_{(C≤8)}$, aryloxy$_{(C≤12)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, alkylthio$_{(C≤8)}$, acylthio$_{(C≤8)}$, alkylsulfonylamino$_{(C≤8)}$, or substituted versions of any of these groups;
-alkanediyl$_{(C≤8)}$-R$_b$, -alkenediyl$_{(C≤8)}$-R$_b$, or a substituted version of any of these groups, wherein R$_b$ is:
hydrogen, hydroxy, halo, amino or mercapto; or
heteroaryl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, heteroarylamino$_{(C≤8)}$, alkylsulfonylamino$_{(C≤8)}$, amido$_{(C≤8)}$, —OC(O)NH-alkyl$_{(C≤8)}$, —OC(O)CH$_2$NHC(O)O-t-butyl, —OCH$_2$-alkylthio$_{(C≤8)}$, or a substituted version of any of these groups;
—(CH$_2$)$_o$C(O)R$_c$, wherein o is 0-6 and R$_c$ is:
hydrogen, halo, amino, —NHOH, or mercapto; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkylamino$_{(C≤8)}$, dialkylamino$_{(C≤8)}$, arylamino$_{(C≤8)}$, alkylsulfonylamino$_{(C≤8)}$, amido$_{(C≤8)}$, alkoxyamino$_{(C≤8)}$, heterocycloalkylamino$_{(C≤8)}$, —NHC(NOH)-alkyl$_{(C≤8)}$, —NH-amido$_{(C≤8)}$, or a substituted version of any of these groups;
—NR$_d$C(O)R$_e$, wherein
R$_d$ is hydrogen, alkyl$_{(C≤8)}$, or substituted alkyl$_{(C≤8)}$;
R$_e$ is hydrogen, hydroxy, amino; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkyl-amino$_{(C≤8)}$, dialkylamino$_{(C≤8)}$, arylamino$_{(C≤8)}$, or a substituted version of any of these groups; or
Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C≤8)}$, substituted alkyl$_{(C≤8)}$, acyl$_{(C≤8)}$, or substituted acyl$_{(C≤8)}$;
or a pharmaceutically acceptable salt, acetal, or hemiacetal thereof.

In some embodiments, the compounds are further defined as:

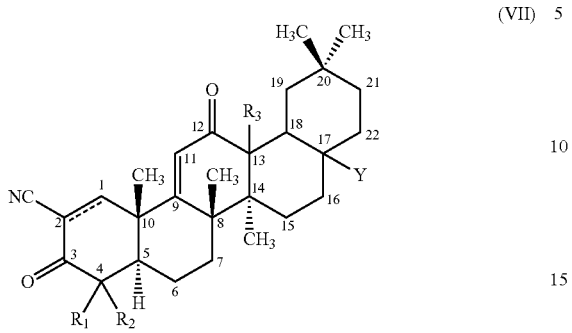

(VII)

wherein:
the bond between atoms 1 and 2 is a single bond, an epoxidized double bond, or a double bond;
$R_1$ is hydrogen, alkyl$_{(C\le 8)}$, cycloalkyl$_{(C\le 8)}$, substituted alkyl$_{(C\le 8)}$, or substituted cycloalkyl$_{(C\le 8)}$;
$R_2$ is amino, cyano, halo, or hydroxy,
substituted alkyl$_{(C\le 8)}$, heteroaryl$_{(C\le 8)}$, substituted heteroaryl$_{(C\le 8)}$, acyl$_{(C\le 8)}$, substituted acyl$_{(C\le 8)}$, amido$_{(C\le 8)}$, substituted amido$_{(C\le 8)}$, alkylamino$_{(C\le 8)}$, substituted alkylamino$_{(C\le 8)}$, dialkylamino$_{(C\le 8)}$, or dialkylamino$_{(C\le 8)}$; or
—OR$_a$, wherein:
$R_a$ is hydrogen or alkyl$_{(C\le 8)}$, alkenyl$_{(C\le 8)}$, alkynyl$_{(C\le 8)}$, aryl$_{(C\le 12)}$, aralkyl$_{(C\le 12)}$, heteroaryl$_{(C\le 12)}$, heterocycloalkyl$_{(C\le 8)}$, acyl$_{(C\le 8)}$, or a substituted version of any of these groups;
—(CH$_2$)$_m$—(OCH$_2$)$_n$—R$_5$, wherein:
$R_5$ is hydroxy or acyl$_{(C\le 8)}$, alkoxy$_{(C\le 8)}$, acyloxy$_{(C\le 8)}$, alkylsilyloxy$_{(C\le 8)}$, or a substituted version of any of these groups;
m is 0, 1, 2, 3, or 4; and
n is 0, 1, 2, or 3;
—(CH$_2$)$_s$NR$_5$'(R$_6$), wherein:
s is 0, 1, 2, 3, or 4;
$R_5$' is hydrogen, alkyl$_{(C\le 8)}$, alkoxy$_{(C\le 8)}$, substituted alkoxy$_{(C\le 8)}$, acyl$_{(C\le 8)}$, substituted acyl$_{(C\le 8)}$, —C(O)-alkoxy$_{(C\le 8)}$, substituted —C(O)-alkoxy$_{(C\le 8)}$, acyloxy$_{(C\le 8)}$, substituted acyloxy$_{(C\le 8)}$, alkylsilyloxy$_{(C\le 8)}$, or substituted alkylsilyloxy$_{(C\le 8)}$; and
$R_6$ is hydrogen, alkyl$_{(C\le 8)}$, or substituted alkyl$_{(C\le 8)}$; or
—(CH$_2$)$_q$—C(O)—R$_5$", wherein:
$R_5$" is amino, hydroxy, or mercapto; or
alkoxy$_{(C\le 8)}$, alkylthio$_{(C\le 8)}$, alkylamino$_{(C\le 8)}$, dialkylamino$_{(C\le 8)}$, or a substituted version of any of these groups; and
q is 0, 1, 2, 3, or 4;
$R_3$ is hydrogen, hydroxy, or alkoxy$_{(C\le 8)}$, acyloxy$_{(C\le 8)}$, or substituted version of either of these groups; or $R_3$ is taken together with Y as described below; and
Y is hydrogen, hydroxy, halo, amino, cyano, isocyanate, or mercapto;
alkyl$_{(C\le 8)}$, cycloalkyl$_{(C\le 8)}$, alkenyl$_{(C\le 8)}$, alkynyl$_{(C\le 8)}$, aryl$_{(C\le 12)}$, aralkyl$_{(C\le 12)}$, heteroaryl$_{(C\le 8)}$, heterocycloalkyl$_{(C\le 12)}$, alkoxy$_{(C\le 8)}$, cycloalkoxy$_{(C\le 8)}$, aryloxy$_{(C\le 12)}$, acyloxy$_{(C\le 8)}$, alkylamino$_{(C\le 8)}$, dialkylamino$_{(C\le 8)}$, alkenylamino$_{(C\le 8)}$, arylamino$_{(C\le 8)}$, aralkylamino$_{(C\le 8)}$, alkylthio$_{(C\le 8)}$, acylthio$_{(C\le 8)}$, alkylsulfonylamino$_{(C\le 8)}$, or substituted versions of any of these groups;
-alkanediyl$_{(C\le 8)}$-R$_b$, -alkenediyl$_{(C\le 8)}$-R$_b$, or a substituted version of any of these groups, wherein R$_b$ is:
hydrogen, hydroxy, halo, amino or mercapto; or
heteroaryl$_{(C\le 8)}$, alkoxy$_{(C\le 8)}$, cycloalkoxy$_{(C\le 8)}$, alkenyloxy$_{(C\le 8)}$, aryloxy$_{(C\le 8)}$, aralkoxy$_{(C\le 8)}$, heteroaryloxy$_{(C\le 8)}$, acyloxy$_{(C\le 8)}$, alkylamino$_{(C\le 8)}$, dialkylamino$_{(C\le 8)}$, alkenylamino$_{(C\le 8)}$, arylamino$_{(C\le 8)}$, aralkylamino$_{(C\le 8)}$, heteroarylamino$_{(C\le 8)}$, alkylsulfonylamino$_{(C\le 8)}$, amido$_{(C\le 8)}$, —OC(O)NH-alkyl$_{(C\le 8)}$, —OC(O)CH$_2$NHC(O)O-t-butyl, —OCH$_2$-alkylthio$_{(C\le 8)}$, or a substituted version of any of these groups;
—(CH$_2$)$_o$C(O)R$_c$, wherein o is 0-6 and R$_c$ is:
hydrogen, halo, amino, —NHOH, or mercapto; or
alkyl$_{(C\le 8)}$, cycloalkyl$_{(C\le 8)}$, alkenyl$_{(C\le 8)}$, alkynyl$_{(C\le 8)}$, aryl$_{(C\le 8)}$, aralkyl$_{(C\le 8)}$, heteroaryl$_{(C\le 8)}$, heterocycloalkyl$_{(C\le 8)}$, alkylamino$_{(C\le 8)}$, dialkylamino$_{(C\le 8)}$, arylamino$_{(C\le 8)}$, alkylsulfonylamino$_{(C\le 8)}$, amido$_{(C\le 8)}$, alkoxyamino$_{(C\le 8)}$, heterocycloalkylamino$_{(C\le 8)}$, —NHC(NOH)-alkyl$_{(C\le 8)}$, —NH-amido$_{(C\le 8)}$, or a substituted version of any of these groups;
—NR$_d$C(O)R$_e$, wherein
$R_d$ is hydrogen, alkyl$_{(C\le 8)}$, or substituted alkyl$_{(C\le 8)}$;
$R_e$ is hydrogen, hydroxy, amino; or
alkyl$_{(C\le 8)}$, cycloalkyl$_{(C\le 8)}$, alkenyl$_{(C\le 8)}$, alkynyl$_{(C\le 8)}$, aryl$_{(C\le 8)}$, aralkyl$_{(C\le 8)}$, heteroaryl$_{(C\le 8)}$, heterocycloalkyl$_{(C\le 8)}$, alkoxy$_{(C\le 8)}$, cycloalkoxy$_{(C\le 8)}$, aryloxy$_{(C\le 8)}$, aralkoxy$_{(C\le 8)}$, heteroaryloxy$_{(C\le 8)}$, acyloxy$_{(C\le 8)}$, alkyl-amino$_{(C\le 8)}$, dialkylamino$_{(C\le 8)}$, arylamino$_{(C\le 8)}$, or a substituted version of any of these groups; or
Y is taken together with $R_3$ and is —(CH$_2$)$_p$C(O)R$_f$—, wherein
p is 0-6; and
$R_f$ is —O— or —NR$_7$—; wherein:
$R_7$ is hydrogen, alkyl$_{(C\le 8)}$, substituted alkyl$_{(C\le 8)}$, acyl$_{(C\le 8)}$, or substituted acyl$_{(C\le 8)}$;
or a pharmaceutically acceptable salt, acetal, or hemiacetal thereof.

In some embodiments, the compounds are further defined as:

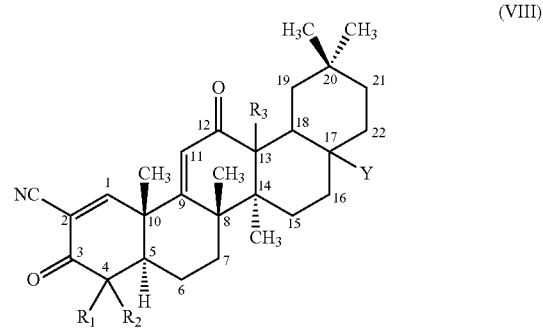

(VIII)

wherein:
$R_1$ is hydrogen, alkyl$_{(C\le 8)}$, cycloalkyl$_{(C\le 8)}$, substituted alkyl$_{(C\le 8)}$, or substituted cycloalkyl$_{(C\le 8)}$;
$R_2$ is amino, cyano, halo, or hydroxy,
substituted alkyl$_{(C\le 8)}$, heteroaryl$_{(C\le 8)}$, substituted heteroaryl$_{(C\le 8)}$, acyl$_{(C\le 8)}$, substituted acyl$_{(C\le 8)}$, amido$_{(C\le 8)}$, substituted amido$_{(C\le 8)}$, alkylamino$_{(C\le 8)}$, substituted alkylamino$_{(C\le 8)}$, dialkylamino$_{(C\le 8)}$, or dialkylamino$_{(C\le 8)}$; or

15

—OR$_a$, wherein:
R$_a$ is hydrogen or alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq12)}$, heterocycloalkyl$_{(C\leq8)}$, acyl$_{(C\leq8)}$, or a substituted version of any of these groups;

—(CH$_2$)$_m$—(OCH$_2$)$_n$—R$_5$, wherein:
R$_5$ is hydroxy or acyl$_{(C\leq8)}$, alkoxy$_{(C\leq8)}$, acyloxy$_{(C\leq8)}$, alkylsilyloxy$_{(C\leq8)}$, or a substituted version of any of these groups;
m is 0, 1, 2, 3, or 4; and
n is 0, 1, 2, or 3;

—(CH$_2$)$_s$NR$_5'$(R$_6$), wherein:
s is 0, 1, 2, 3, or 4;
R$_5'$ is hydrogen, alkyl$_{(C\leq8)}$, alkoxy$_{(C\leq8)}$, substituted alkoxy$_{(C\leq8)}$, acyl$_{(C\leq8)}$, substituted acyl$_{(C\leq8)}$, —C(O)-alkoxy$_{(C\leq8)}$, substituted —C(O)-alkoxy$_{(C\leq8)}$, acyloxy$_{(C\leq8)}$, substituted acyloxy$_{(C\leq8)}$, alkylsilyloxy$_{(C\leq8)}$, or substituted alkylsilyloxy$_{(C\leq8)}$; and
R$_6$ is hydrogen, alkyl$_{(C\leq8)}$, or substituted alkyl$_{(C\leq8)}$; or —(CH$_2$)$_q$—C(O)—R$_5''$, wherein:
R$_5''$ is amino, hydroxy, or mercapto; or
alkoxy$_{(C\leq8)}$, alkylthio$_{(C\leq8)}$, alkylamino$_{(C\leq8)}$, dialkylamino$_{(C\leq8)}$, or a substituted version of any of these groups; and
q is 0, 1, 2, 3, or 4;

R$_3$ is hydrogen, hydroxy, or alkoxy$_{(C\leq8)}$, acyloxy$_{(C\leq8)}$, or substituted version of either of these groups; or R$_3$ is taken together with Y as described below; and
Y is hydrogen, hydroxy, halo, amino, cyano, isocyanate, or mercapto;
alkyl$_{(C\leq8)}$, cycloalkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, cycloalkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

-alkanediyl$_{(C\leq8)}$-R$_b$, -alkenediyl$_{(C\leq8)}$-R$_b$, or a substituted version of any of these groups, wherein R$_b$ is:
hydrogen, hydroxy, halo, amino or mercapto; or
heteroaryl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)CH$_2$NHC(O)O-t-butyl, —OCH$_2$-alkylthio$_{(C\leq8)}$, or a substituted version of any of these groups;

—(CH$_2$)$_o$C(O)R$_c$, wherein o is 0-6 and R$_c$ is:
hydrogen, halo, amino, —NHOH, or mercapto; or
alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkylamino$_{(C\leq8)}$, dialkylamino$_{(C\leq8)}$, arylamino$_{(C\leq8)}$, alkylsulfonylamino$_{(C\leq8)}$, amido$_{(C\leq8)}$, alkoxyamino$_{(C\leq8)}$, heterocycloalkylamino$_{(C\leq8)}$, —NHC(NOH)-alkyl$_{(C\leq8)}$, —NH-amido$_{(C\leq8)}$, or a substituted version of any of these groups;

—NR$_d$C(O)R$_e$, wherein
R$_d$ is hydrogen, alkyl$_{(C\leq8)}$, or substituted alkyl$_{(C\leq8)}$;
R$_e$ is hydrogen, hydroxy, amino; or
alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, cycloalkoxy$_{(C\leq8)}$,

16 aryloxy$_{(C\leq8)}$, aralkoxy$_{(C\leq8)}$, heteroaryloxy$_{(C\leq8)}$, acyloxy$_{(C\leq8)}$, alkyl-amino$_{(C\leq8)}$, dialkylamino$_{(C\leq8)}$, arylamino$_{(C\leq8)}$, or a substituted version of any of these groups; or
Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C\leq8)}$, substituted alkyl$_{(C\leq8)}$, acyl$_{(C\leq8)}$, or substituted acyl$_{(C\leq8)}$;

or a pharmaceutically acceptable salt, acetal, or hemiacetal thereof.

In some embodiments, the compounds are further defined as:

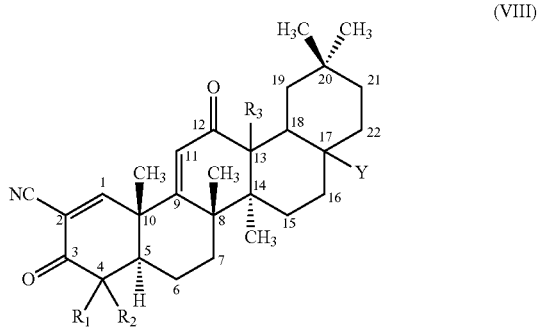

(VIII)

wherein:
R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;
R$_2$ is amino, cyano, halo, hydroxy, substituted alkyl$_{(C\leq8)}$, heteroaryl$_{(C\leq8)}$, substituted heteroaryl$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or dialkylamino$_{(C\leq8)}$;
R$_3$ is hydrogen, hydroxy, or alkoxy$_{(C\leq8)}$, acyloxy$_{(C\leq8)}$, or substituted version of either of these groups; or R$_3$ is taken together with Y as described below; and
Y is hydrogen, hydroxy, halo, amino, cyano, isocyanate, or mercapto;
alkyl$_{(C\leq8)}$, cycloalkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, cycloalkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;
-alkanediyl$_{(C\leq8)}$-R$_b$, -alkenediyl$_{(C\leq8)}$-R$_b$, or a substituted version of any of these groups, wherein R$_b$ is:
hydrogen, hydroxy, halo, amino or mercapto; or
heteroaryl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)CH$_2$NHC(O)O-t-butyl, —OCH$_2$-alkylthio$_{(C\leq8)}$, or a substituted version of any of these groups;
—(CH$_2$)$_o$C(O)R$_c$, wherein o is 0-6 and R$_c$ is:
hydrogen, halo, amino, —NHOH, or mercapto; or
alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkylamino$_{(C\leq8)}$, dialkylamino$_{(C\leq8)}$, arylamino$_{(C \leq 8)}$, alkylsulfonylamino$_{(C \leq 8)}$, amido$_{(C \leq 8)}$, alkoxyamino$_{(C \leq 8)}$, heterocycloalkylamino$_{(C \leq 8)}$, —NHC(NOH)-alkyl$_{(C \leq 8)}$, —NH-amido$_{(C \leq 8)}$, or a substituted version of any of these groups;

—NR$_d$C(O)R$_e$, wherein

R$_d$ is hydrogen, alkyl$_{(C \leq 8)}$, or substituted alkyl$_{(C \leq 8)}$;

R$_e$ is hydrogen, hydroxy, amino; or alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkoxy$_{(C \leq 8)}$, cycloalkoxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkyl-amino$_{(C \leq 8)}$, dialkylamino$_{(C \leq 8)}$, arylamino$_{(C \leq 8)}$, or a substituted version of any of these groups; or Y is taken together with R$_3$ and is —(CH$_2$)$_p$C(O)R$_f$—, wherein p is 0-6; and R$_f$ is —O— or —NR$_7$—; wherein:

R$_7$ is hydrogen, alkyl$_{(C \leq 8)}$, substituted alkyl$_{(C \leq 8)}$, acyl$_{(C \leq 8)}$, or substituted acyl$_{(C \leq 8)}$;

or a pharmaceutically acceptable salt, acetal, or hemiacetal thereof.

In some embodiments, the compounds are further defined as:

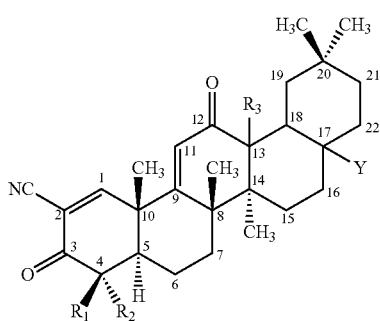

(IX)

wherein:

R$_1$ is hydrogen, alkyl$_{(C \leq 8)}$, cycloalkyl$_{(C \leq 8)}$, substituted alkyl$_{(C \leq 8)}$, or substituted cycloalkyl$_{(C \leq 8)}$;

R$_2$ is amino, cyano, halo, hydroxy, substituted alkyl$_{(C \leq 8)}$, heteroaryl$_{(C \leq 8)}$, substituted heteroaryl$_{(C \leq 8)}$, acyl$_{(C \leq 8)}$, substituted acyl$_{(C \leq 8)}$, amido$_{(C \leq 8)}$, substituted amido$_{(C \leq 8)}$, alkylamino$_{(C \leq 8)}$, substituted alkylamino$_{(C \leq 8)}$, dialkylamino$_{(C \leq 8)}$, or dialkylamino$_{(C \leq 8)}$;

R$_3$ is hydrogen, hydroxy, or alkoxy$_{(C \leq 8)}$, acyloxy$_{(C \leq 8)}$, or substituted version of either of these groups; or R$_3$ is taken together with Y as described below; and Y is hydrogen, hydroxy, halo, amino, cyano, isocyanate, or mercapto;

alkyl$_{(C \leq 8)}$, cycloalkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, alkoxy$_{(C \leq 8)}$, cycloalkoxy$_{(C \leq 8)}$, aryloxy$_{(C \leq 12)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, alkylthio$_{(C \leq 8)}$, acylthio$_{(C \leq 8)}$, alkylsulfonylamino$_{(C \leq 8)}$, or substituted versions of any of these groups;

-alkanediyl$_{(C \leq 8)}$-R$_b$, -alkenediyl$_{(C \leq 8)}$-R$_b$, or a substituted version of any of these groups, wherein R$_b$ is:

hydrogen, hydroxy, halo, amino or mercapto; or heteroaryl$_{(C \leq 8)}$, alkoxy$_{(C \leq 8)}$, cycloalkoxy$_{(C \leq 8)}$, alkenyloxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, heteroarylamino$_{(C \leq 8)}$, alkylsulfonylamino$_{(C \leq 8)}$, amido$_{(C \leq 8)}$, —OC(O)NH-alkyl$_{(C \leq 8)}$, —OC(O)CH$_2$NHC(O)O-t-butyl, —OCH$_2$-alkylthio$_{(C \leq 8)}$, or a substituted version of any of these groups;

—(CH$_2$)$_o$C(O)R$_c$, wherein o is 0-6 and R$_c$ is:

hydrogen, halo, amino, —NHOH, or mercapto; or alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkylamino$_{(C \leq 8)}$, dialkylamino$_{(C \leq 8)}$, arylamino$_{(C \leq 8)}$, alkylsulfonylamino$_{(C \leq 8)}$, amido$_{(C \leq 8)}$, alkoxyamino$_{(C \leq 8)}$, heterocycloalkylamino$_{(C \leq 8)}$, —NHC(NOH)-alkyl$_{(C \leq 8)}$, —NH-amido$_{(C \leq 8)}$, or a substituted version of any of these groups;

—NR$_d$C(O)R$_e$, wherein

R$_d$ is hydrogen, alkyl$_{(C \leq 8)}$, or substituted alkyl$_{(C \leq 8)}$;

R$_e$ is hydrogen, hydroxy, amino; or alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkoxy$_{(C \leq 8)}$, cycloalkoxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkyl-amino$_{(C \leq 8)}$, dialkylamino$_{(C \leq 8)}$, arylamino$_{(C \leq 8)}$, or a substituted version of any of these groups; or Y is taken together with R$_3$ and is —(CH$_2$)$_p$C(O)R$_f$—, wherein p is 0-6; and R$_f$ is —O— or —NR$_7$—; wherein:

R$_7$ is hydrogen, alkyl$_{(C \leq 8)}$, substituted alkyl$_{(C \leq 8)}$, acyl$_{(C \leq 8)}$, or substituted acyl$_{(C \leq 8)}$;

or a pharmaceutically acceptable salt, acetal, or hemiacetal thereof.

In other embodiments, the compounds are further defined as:

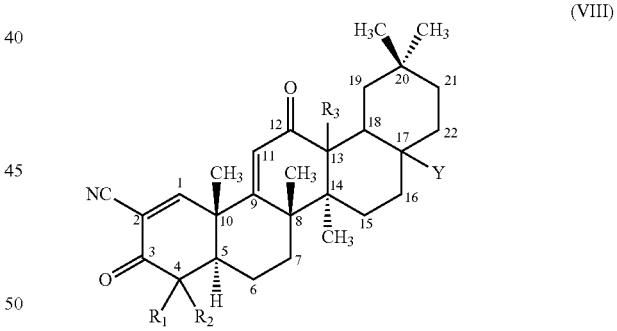

(VIII)

wherein:

R$_1$ is hydrogen, alkyl$_{(C \leq 8)}$, cycloalkyl$_{(C \leq 8)}$, substituted alkyl$_{(C \leq 8)}$, or substituted cycloalkyl$_{(C \leq 8)}$;

R$_2$ is —OR$_a$, wherein:

R$_a$ is hydrogen or alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 12)}$, heterocycloalkyl$_{(C \leq 8)}$, acyl$_{(C \leq 8)}$, or a substituted version of any of these groups;

R$_3$ is hydrogen, hydroxy, or alkoxy$_{(C \leq 8)}$, acyloxy$_{(C \leq 8)}$, or substituted version of either of these groups; or R$_3$ is taken together with Y as described below; and Y is hydrogen, hydroxy, halo, amino, cyano, isocyanate, or mercapto;

alkyl$_{(C \leq 8)}$, cycloalkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C≤12)}$, alkoxy$_{(C≤8)}$, cycloalkoxy$_{(C≤8)}$, aryloxy$_{(C≤12)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, alkylthio$_{(C≤8)}$, acylthio$_{(C≤8)}$, alkylsulfonylamino$_{(C≤8)}$, or substituted versions of any of these groups;

-alkanediyl$_{(C≤8)}$-R$_b$, -alkenediyl$_{(C≤8)}$-R$_b$, or a substituted version of any of these groups, wherein R$_b$ is:
hydrogen, hydroxy, halo, amino or mercapto; or
heteroaryl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, heteroarylamino$_{(C≤8)}$, alkylsulfonylamino$_{(C≤8)}$, amido$_{(C≤8)}$, —OC(O)NH-alkyl$_{(C≤8)}$, —OC(O)CH$_2$NHC(O)O-t-butyl, —OCH$_2$-alkylthio$_{(C≤8)}$, or a substituted version of any of these groups;

—(CH$_2$)$_o$C(O)R$_c$, wherein o is 0-6 and R$_c$ is:
hydrogen, halo, amino, —NHOH, or mercapto; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkylamino$_{(C≤8)}$, dialkylamino$_{(C≤8)}$, arylamino$_{(C≤8)}$, alkylsulfonylamino$_{(C≤8)}$, amido$_{(C≤8)}$, alkoxyamino$_{(C≤8)}$, heterocycloalkylamino$_{(C≤8)}$, —NHC(NOH)-alkyl$_{(C≤8)}$, —NH-amido$_{(C≤8)}$, or a substituted version of any of these groups;

—NR$_d$C(O)R$_e$, wherein
R$_d$ is hydrogen, alkyl$_{(C≤8)}$, or substituted alkyl$_{(C≤8)}$;
R$_e$ is hydrogen, hydroxy, amino; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkyl-amino$_{(C≤8)}$, dialkylamino$_{(C≤8)}$, arylamino$_{(C≤8)}$, or a substituted version of any of these groups; or Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C≤8)}$, substituted alkyl$_{(C≤8)}$, acyl$_{(C≤8)}$, or substituted acyl$_{(C≤8)}$;

or a pharmaceutically acceptable salt, acetal, or hemiacetal thereof.

In some embodiments, the compounds are further defined as:

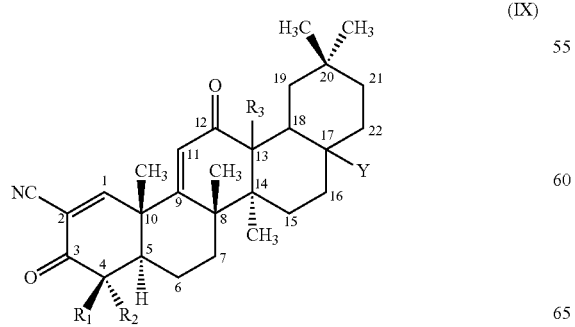

(IX)

wherein:
R$_1$ is hydrogen, alkyl$_{(C≤8)}$, cycloalkyl$_{(C≤8)}$, substituted alkyl$_{(C≤8)}$, or substituted cycloalkyl$_{(C≤8)}$;
R$_2$ is —OR$_a$, wherein:
R$_a$ is hydrogen or alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤12)}$, heterocycloalkyl$_{(C≤8)}$, acyl$_{(C≤8)}$, or a substituted version of any of these groups;

R$_3$ is hydrogen, hydroxy, or alkoxy$_{(C≤8)}$, acyloxy$_{(C≤8)}$, or substituted version of either of these groups; or R$_3$ is taken together with Y as described below; and Y is hydrogen, hydroxy, halo, amino, cyano, isocyanate, or mercapto;

alkyl$_{(C≤8)}$, cycloalkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤8)}$, heterocycloalkyl$_{(C≤12)}$, alkoxy$_{(C≤8)}$, cycloalkoxy$_{(C≤8)}$, aryloxy$_{(C≤12)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, alkylthio$_{(C≤8)}$, acylthio$_{(C≤8)}$, alkylsulfonylamino$_{(C≤8)}$, or substituted versions of any of these groups;

-alkanediyl$_{(C≤8)}$-R$_b$, -alkenediyl$_{(C≤8)}$-R$_b$, or a substituted version of any of these groups, wherein R$_b$ is:
hydrogen, hydroxy, halo, amino or mercapto; or
heteroaryl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, alkenylamino$_{(C≤8)}$, arylamino$_{(C≤8)}$, aralkylamino$_{(C≤8)}$, heteroarylamino$_{(C≤8)}$, alkylsulfonylamino$_{(C≤8)}$, amido$_{(C≤8)}$, —OC(O)NH-alkyl$_{(C≤8)}$, —OC(O)CH$_2$NHC(O)O-t-butyl, —OCH$_2$-alkylthio$_{(C≤8)}$, or a substituted version of any of these groups;

—(CH$_2$)$_o$C(O)R$_c$, wherein o is 0-6 and R$_c$ is:
hydrogen, halo, amino, —NHOH, or mercapto; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkylamino$_{(C≤8)}$, dialkylamino$_{(C≤8)}$, arylamino$_{(C≤8)}$, alkylsulfonylamino$_{(C≤8)}$, amido$_{(C≤8)}$, alkoxyamino$_{(C≤8)}$, heterocycloalkylamino$_{(C≤8)}$, —NHC(NOH)-alkyl$_{(C≤8)}$, —NH-amido$_{(C≤8)}$, or a substituted version of any of these groups;

—NR$_d$C(O)R$_e$, wherein
R$_d$ is hydrogen, alkyl$_{(C≤8)}$, or substituted alkyl$_{(C≤8)}$;
R$_e$ is hydrogen, hydroxy, amino; or
alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, cycloalkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkyl-amino$_{(C≤8)}$, dialkylamino$_{(C≤8)}$, arylamino$_{(C≤8)}$, or a substituted version of any of these groups; or Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C≤8)}$, substituted alkyl$_{(C≤8)}$, acyl$_{(C≤8)}$, or substituted acyl$_{(C≤8)}$;

or a pharmaceutically acceptable salt, acetal, or hemiacetal thereof.

In other embodiments, the compounds are further defined as:

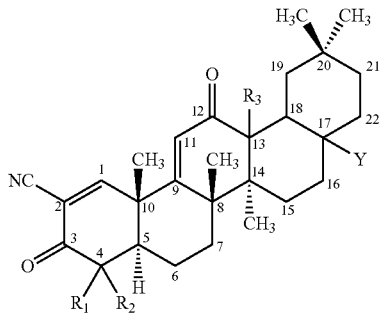

(VIII)

wherein:
R$_1$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;
R$_2$ is —(CH$_2$)$_m$—(OCH$_2$)$_n$—R$_5$, wherein:
R$_5$ is hydroxy or acyl$_{(C\leq 8)}$, alkoxy$_{(C\leq 8)}$, acyloxy$_{(C\leq 8)}$, alkylsilyloxy$_{(C\leq 8)}$, or a substituted version of any of these groups;
m is 0, 1, 2, 3, or 4; and
n is 0, 1, 2, or 3;
R$_3$ is hydrogen, hydroxy, or alkoxy$_{(C\leq 8)}$, acyloxy$_{(C\leq 8)}$, or substituted version of either of these groups; or R$_3$ is taken together with Y as described below; and
Y is hydrogen, hydroxy, halo, amino, cyano, isocyanate, or mercapto;
alkyl$_{(C\leq 8)}$, cycloalkyl$_{(C\leq 8)}$, alkenyl$_{(C\leq 8)}$, alkynyl$_{(C\leq 8)}$, aryl$_{(C\leq 12)}$, aralkyl$_{(C\leq 12)}$, heteroaryl$_{(C\leq 8)}$, heterocycloalkyl$_{(C\leq 12)}$, alkoxy$_{(C\leq 8)}$, cycloalkoxy$_{(C\leq 8)}$, aryloxy$_{(C\leq 12)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, alkylthio$_{(C\leq 8)}$, acylthio$_{(C\leq 8)}$, alkylsulfonylamino$_{(C\leq 8)}$, or substituted versions of any of these groups;
-alkanediyl$_{(C\leq 8)}$-R$_b$, -alkenediyl$_{(C\leq 8)}$-R$_b$, or a substituted version of any of these groups, wherein R$_b$ is:
hydrogen, hydroxy, halo, amino or mercapto; or
heteroaryl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, heteroarylamino$_{(C\leq 8)}$, alkylsulfonylamino$_{(C\leq 8)}$, amido$_{(C\leq 8)}$, —OC(O)NH-alkyl$_{(C\leq 8)}$, —OC(O)CH$_2$NHC(O)O-t-butyl, —OCH$_2$-alkylthio$_{(C\leq 8)}$, or a substituted version of any of these groups;
—(CH$_2$)$_o$C(O)R$_c$, wherein o is 0-6 and R$_c$ is:
hydrogen, halo, amino, —NHOH, or mercapto; or
alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkylamino$_{(C\leq 8)}$, dialkylamino$_{(C\leq 8)}$, arylamino$_{(C\leq 8)}$, alkylsulfonylamino$_{(C\leq 8)}$, amido$_{(C\leq 8)}$, alkoxyamino$_{(C\leq 8)}$, heterocycloalkylamino$_{(C\leq 8)}$, —NHC(NOH)-alkyl$_{(C\leq 8)}$, —NH-amido$_{(C\leq 8)}$, or a substituted version of any of these groups;
—NR$_d$C(O)R$_e$, wherein
R$_d$ is hydrogen, alkyl$_{(C\leq 8)}$, or substituted alkyl$_{(C\leq 8)}$;
R$_e$ is hydrogen, hydroxy, amino; or
alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, cycloalkoxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkyl-amino$_{(C\leq 8)}$, dialkylamino$_{(C\leq 8)}$, arylamino$_{(C\leq 8)}$, or a substituted version of any of these groups; or
Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C\leq 8)}$, substituted alkyl$_{(C\leq 8)}$, acyl$_{(C\leq 8)}$, or substituted acyl$_{(C\leq 8)}$;
or a pharmaceutically acceptable salt, acetal, or hemiacetal thereof.

In some embodiments, the compounds are further defined as:

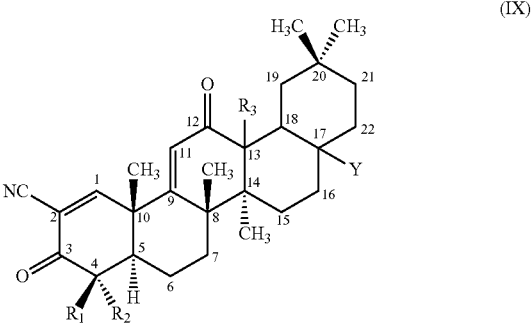

(IX)

wherein:
R$_1$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;
R$_2$ is —(CH$_2$)$_m$—(OCH$_2$)$_n$—R$_5$, wherein:
R$_5$ is hydroxy or acyl$_{(C\leq 8)}$, alkoxy$_{(C\leq 8)}$, acyloxy$_{(C\leq 8)}$, alkylsilyloxy$_{(C\leq 8)}$, or a substituted version of any of these groups;
m is 0, 1, 2, 3, or 4; and
n is 0, 1, 2, or 3;
R$_3$ is hydrogen, hydroxy, or alkoxy$_{(C\leq 8)}$, acyloxy$_{(C\leq 8)}$, or substituted version of either of these groups; or R$_3$ is taken together with Y as described below; and
Y is hydrogen, hydroxy, halo, amino, cyano, isocyanate, or mercapto;
alkyl$_{(C\leq 8)}$, cycloalkyl$_{(C\leq 8)}$, alkenyl$_{(C\leq 8)}$, alkynyl$_{(C\leq 8)}$, aryl$_{(C\leq 12)}$, aralkyl$_{(C\leq 12)}$, heteroaryl$_{(C\leq 8)}$, heterocycloalkyl$_{(C\leq 12)}$, alkoxy$_{(C\leq 8)}$, cycloalkoxy$_{(C\leq 8)}$, aryloxy$_{(C\leq 12)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, alkylthio$_{(C\leq 8)}$, acylthio$_{(C\leq 8)}$, alkylsulfonylamino$_{(C\leq 8)}$, or substituted versions of any of these groups;
-alkanediyl$_{(C\leq 8)}$-R$_b$, -alkenediyl$_{(C\leq 8)}$-R$_b$, or a substituted version of any of these groups, wherein R$_b$ is:
hydrogen, hydroxy, halo, amino or mercapto; or heteroaryl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, alkenylamino$_{(C\leq 8)}$, arylamino$_{(C\leq 8)}$, aralkylamino$_{(C\leq 8)}$, heteroarylamino$_{(C\leq 8)}$, alkylsulfonylamino$_{(C\leq 8)}$, amido$_{(C\leq 8)}$, —OC(O)NH-alkyl$_{(C\leq 8)}$, —OC(O)CH$_2$NHC(O)O-t-butyl, —OCH$_2$-alkylthio$_{(C\leq 8)}$, or a substituted version of any of these groups;
—(CH$_2$)$_o$C(O)R$_c$, wherein o is 0-6 and R$_c$ is:
hydrogen, halo, amino, —NHOH, or mercapto; or
alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, alkoxyamino$_{(C\le8)}$, heterocycloalkylamino$_{(C\le8)}$, —NHC(NOH)-alkyl$_{(C\le8)}$, —NH-amido$_{(C\le8)}$, or a substituted version of any of these groups;

—NR$_d$C(O)R$_e$, wherein

R$_d$ is hydrogen, alkyl$_{(C\le8)}$, or substituted alkyl$_{(C\le8)}$;

R$_e$ is hydrogen, hydroxy, amino; or alkyl$_{(C\le8)}$, cycloalkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, cycloalkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkyl-amino$_{(C\le8)}$, dialkylamino$_{(C\le8)}$, arylamino$_{(C\le8)}$, or a substituted version of any of these groups; or Y is taken together with R$_3$ and is —(CH$_2$)$_p$C(O)R$_f$—, wherein p is 0-6; and R$_f$ is —O— or —NR$_7$—; wherein:

R$_7$ is hydrogen, alkyl$_{(C\le8)}$, substituted alkyl$_{(C\le8)}$, acyl$_{(C\le8)}$, or substituted acyl$_{(C\le8)}$;

or a pharmaceutically acceptable salt, acetal, or hemiacetal thereof.

In other embodiments, the compounds are further defined as:

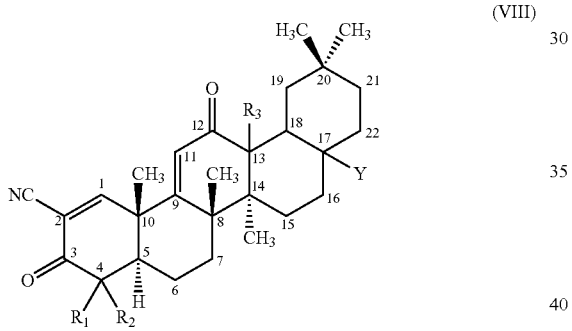

(VIII)

wherein:

R$_1$ is hydrogen, alkyl$_{(C\le8)}$, cycloalkyl$_{(C\le8)}$, substituted alkyl$_{(C\le8)}$, or substituted cycloalkyl$_{(C\le8)}$;

R$_2$ is —(CH$_2$)$_s$NR$_5$'(R$_6$), wherein:

s is, 1, 2, 3, or 4;

R$_5$' is hydrogen, alkyl$_{(C\le8)}$, alkoxy$_{(C\le8)}$, substituted alkoxy$_{(C\le8)}$, acyl$_{(C\le8)}$, substituted acyl$_{(C\le8)}$, —C(O)-alkoxy$_{(C\le8)}$, substituted —C(O)-alkoxy$_{(C\le8)}$, acyloxy$_{(C\le8)}$, substituted acyloxy$_{(C\le8)}$, alkylsilyloxy$_{(C\le8)}$, or substituted alkylsilyloxy$_{(C\le8)}$; and R$_6$ is hydrogen, alkyl$_{(C\le8)}$, or substituted alkyl$_{(C\le8)}$;

R$_3$ is hydrogen, hydroxy, or alkoxy$_{(C\le8)}$, acyloxy$_{(C\le8)}$, or substituted version of either of these groups; or R$_3$ is taken together with Y as described below; and Y is hydrogen, hydroxy, halo, amino, cyano, isocyanate, or mercapto;

alkyl$_{(C\le8)}$, cycloalkyl$_{(C\le8)}$, alkenyl$_{(C\le8)}$, alkynyl$_{(C\le8)}$, aryl$_{(C\le12)}$, aralkyl$_{(C\le12)}$, heteroaryl$_{(C\le8)}$, heterocycloalkyl$_{(C\le12)}$, alkoxy$_{(C\le8)}$, cycloalkoxy$_{(C\le8)}$, aryloxy$_{(C\le12)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, alkylthio$_{(C\le8)}$, acylthio$_{(C\le8)}$, alkylsulfonylamino$_{(C\le8)}$, or substituted versions of any of these groups;

-alkanediyl$_{(C\le8)}$-R$_b$, -alkenediyl$_{(C\le8)}$-R$_b$, or a substituted version of any of these groups, wherein R$_b$ is:

hydrogen, hydroxy, halo, amino or mercapto; or heteroaryl$_{(C\le8)}$, alkoxy$_{(C\le8)}$, cycloalkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, heteroarylamino$_{(C\le8)}$, alkylsulfonylamino$_{(C\le8)}$, amido$_{(C\le8)}$, —OC(O)NH-alkyl$_{(C\le8)}$, —OC(O)CH$_2$NHC(O)O-t-butyl, —OCH$_2$-alkylthio$_{(C\le8)}$, or a substituted version of any of these groups;

—(CH$_2$)$_o$C(O)R$_c$, wherein o is 0-6 and R$_c$ is:

hydrogen, halo, amino, —NHOH, or mercapto; or alkyl$_{(C\le8)}$, cycloalkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, alkoxyamino$_{(C\le8)}$, heterocycloalkylamino$_{(C\le8)}$, —NHC(NOH)-alkyl$_{(C\le8)}$, —NH-amido$_{(C\le8)}$, or a substituted version of any of these groups;

—NR$_d$C(O)R$_e$, wherein

R$_d$ is hydrogen, alkyl$_{(C\le8)}$, or substituted alkyl$_{(C\le8)}$;

R$_e$ is hydrogen, hydroxy, amino; or alkyl$_{(C\le8)}$, cycloalkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, cycloalkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkyl-amino$_{(C\le8)}$, dialkylamino$_{(C\le8)}$, arylamino$_{(C\le8)}$, or a substituted version of any of these groups; or Y is taken together with R$_3$ and is —(CH$_2$)$_p$C(O)R$_f$—, wherein p is 0-6; and R$_f$ is —O— or —NR$_7$—; wherein:

R$_7$ is hydrogen, alkyl$_{(C\le8)}$, substituted alkyl$_{(C\le8)}$, acyl$_{(C\le8)}$, or substituted acyl$_{(C\le8)}$;

or a pharmaceutically acceptable salt, acetal, or hemiacetal thereof.

In some embodiments, the compounds are further defined as:

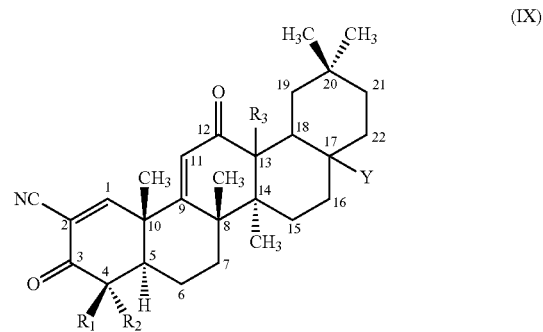

(IX)

wherein:

R$_1$ is hydrogen, alkyl$_{(C\le8)}$, cycloalkyl$_{(C\le8)}$, substituted alkyl$_{(C\le8)}$, or substituted cycloalkyl$_{(C\le8)}$;

R$_2$ is —(CH$_2$)$_s$NR$_5$'(R$_6$), wherein:

s is 0, 1, 2, 3, or 4;

R$_5$' is hydrogen, alkyl$_{(C\le8)}$, alkoxy$_{(C\le8)}$, substituted alkoxy$_{(C\le8)}$, acyl$_{(C\le8)}$, substituted acyl$_{(C\le8)}$, —C(O)-alkoxy$_{(C\le8)}$, substituted —C(O)-alkoxy$_{(C\le8)}$, acyloxy$_{(C\le8)}$, substituted acyloxy$_{(C\le8)}$, alkylsilyloxy$_{(C\le8)}$, or substituted alkylsilyloxy$_{(C\le8)}$; and R$_6$ is hydrogen, alkyl$_{(C\le8)}$, or substituted alkyl$_{(C\le8)}$;

R$_3$ is hydrogen, hydroxy, or alkoxy$_{(C\leq 8)}$, acyloxy$_{(C\leq 8)}$, or substituted version of either of these groups; or R$_3$ is taken together with Y as described below; and Y is hydrogen, hydroxy, halo, amino, cyano, isocyanate, or mercapto;

alkyl$_{(C\leq 8)}$, cycloalkyl$_{(C\leq 8)}$, alkenyl$_{(C\leq 8)}$, alkynyl$_{(C\leq 8)}$, aryl$_{(C\leq 12)}$, aralkyl$_{(C\leq 12)}$, heteroaryl$_{(C\leq 8)}$, heterocycloalkyl$_{(C\leq 12)}$, alkoxy$_{(C\leq 8)}$, cycloalkoxy$_{(C\leq 8)}$, aryloxy$_{(C\leq 12)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, alkylthio$_{(C\leq 8)}$, acylthio$_{(C\leq 8)}$, alkylsulfonylamino$_{(C\leq 8)}$, or substituted versions of any of these groups;

-alkanediyl$_{(C\leq 8)}$-R$_b$, -alkenediyl$_{(C\leq 8)}$-R$_b$, or a substituted version of any of these groups, wherein R$_b$ is:

hydrogen, hydroxy, halo, amino or mercapto; or heteroaryl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, heteroarylamino$_{(C\leq 8)}$, alkylsulfonylamino$_{(C\leq 8)}$, amido$_{(C\leq 8)}$, —OC(O)NH-alkyl$_{(C\leq 8)}$, —OC(O)CH$_2$NHC(O)O-t-butyl, —OCH$_2$-alkylthio$_{(C\leq 8)}$, or a substituted version of any of these groups;

—(CH$_2$)$_o$C(O)R$_c$, wherein o is 0-6 and R$_c$ is:

hydrogen, halo, amino, —NHOH, or mercapto; or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkylamino$_{(C\leq 8)}$, dialkylamino$_{(C\leq 8)}$, arylamino$_{(C\leq 8)}$, alkylsulfonylamino$_{(C\leq 8)}$, amido$_{(C\leq 8)}$, alkoxyamino$_{(C\leq 8)}$, heterocycloalkylamino$_{(C\leq 8)}$, —NHC(NOH)-alkyl$_{(C\leq 8)}$, —NH-amido$_{(C\leq 8)}$, or a substituted version of any of these groups;

—NR$_d$C(O)R$_e$, wherein

R$_d$ is hydrogen, alkyl$_{(C\leq 8)}$, or substituted alkyl$_{(C\leq 8)}$;

R$_e$ is hydrogen, hydroxy, amino; or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, cycloalkoxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkyl-amino$_{(C\leq 8)}$, dialkylamino$_{(C\leq 8)}$, arylamino$_{(C\leq 8)}$, or a substituted version of any of these groups; or Y is taken together with R$_3$ and is —(CH$_2$)$_p$C(O)R$_f$—, wherein p is 0-6; and R$_f$ is —O— or —NR$_7$—; wherein:

R$_7$ is hydrogen, alkyl$_{(C\leq 8)}$, substituted alkyl$_{(C\leq 8)}$, acyl$_{(C\leq 8)}$, or substituted acyl$_{(C\leq 8)}$;

or a pharmaceutically acceptable salt, acetal, or hemiacetal thereof.

In other embodiments, the compounds are further defined as:

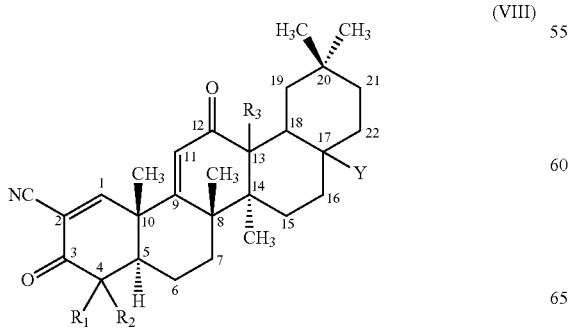

(VIII)

wherein:

R$_1$ is hydrogen, alkyl$_{(C\leq 8)}$, cycloalkyl$_{(C\leq 8)}$, substituted alkyl$_{(C\leq 8)}$, or substituted cycloalkyl$_{(C\leq 8)}$;

R$_2$ is —(CH$_2$)$_q$C(O)—R$_5$", wherein:

R$_5$" is amino, hydroxy, or mercapto; or alkoxy$_{(C\leq 8)}$, alkylthio$_{(C\leq 8)}$, alkylamino$_{(C\leq 8)}$, dialkylamino$_{(C\leq 8)}$, or a substituted version of any of these groups; and q is 0, 1, 2, 3, or 4;

R$_3$ is hydrogen, hydroxy, or alkoxy$_{(C\leq 8)}$, acyloxy$_{(C\leq 8)}$, or substituted version of either of these groups; or R$_3$ is taken together with Y as described below; and Y is hydrogen, hydroxy, halo, amino, cyano, isocyanate, or mercapto;

alkyl$_{(C\leq 8)}$, cycloalkyl$_{(C\leq 8)}$, alkenyl$_{(C\leq 8)}$, alkynyl$_{(C\leq 8)}$, aryl$_{(C\leq 12)}$, aralkyl$_{(C\leq 12)}$, heteroaryl$_{(C\leq 8)}$, heterocycloalkyl$_{(C\leq 12)}$, alkoxy$_{(C\leq 8)}$, cycloalkoxy$_{(C\leq 8)}$, aryloxy$_{(C\leq 12)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, alkylthio$_{(C\leq 8)}$, acylthio$_{(C\leq 8)}$, alkylsulfonylamino$_{(C\leq 8)}$, or substituted versions of any of these groups;

-alkanediyl$_{(C\leq 8)}$-R$_b$, -alkenediyl$_{(C\leq 8)}$-R$_b$, or a substituted version of any of these groups, wherein R$_b$ is:

hydrogen, hydroxy, halo, amino or mercapto; or heteroaryl$_{(C\leq 8)}$, alkoxy$_{(C\leq 8)}$, cycloalkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkylamino$_{(C\leq 8)}$, dialkylamino$_{(C\leq 8)}$, alkenylamino$_{(C\leq 8)}$, arylamino$_{(C\leq 8)}$, aralkylamino$_{(C\leq 8)}$, heteroarylamino$_{(C\leq 8)}$, alkylsulfonylamino$_{(C\leq 8)}$, amido$_{(C\leq 8)}$, —OC(O)NH-alkyl$_{(C\leq 8)}$, —OC(O)CH$_2$NHC(O)O-t-butyl, —OCH$_2$-alkylthio$_{(C\leq 8)}$, or a substituted version of any of these groups;

—(CH$_2$)$_o$C(O)R$_c$, wherein o is 0-6 and R$_c$ is:

hydrogen, halo, amino, —NHOH, or mercapto; or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkylamino$_{(C\leq 8)}$, dialkylamino$_{(C\leq 8)}$, arylamino$_{(C\leq 8)}$, alkylsulfonylamino$_{(C\leq 8)}$, amido$_{(C\leq 8)}$, alkoxyamino$_{(C\leq 8)}$, heterocycloalkylamino$_{(C\leq 8)}$, —NHC(NOH)-alkyl$_{(C\leq 8)}$, —NH-amido$_{(C\leq 8)}$, or a substituted version of any of these groups;

—NR$_d$C(O)R$_e$, wherein

R$_d$ is hydrogen, alkyl$_{(C\leq 8)}$, or substituted alkyl$_{(C\leq 8)}$;

R$_e$ is hydrogen, hydroxy, amino; or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, cycloalkoxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, alkyl-amino$_{(C\leq 8)}$, dialkylamino$_{(C\leq 8)}$, arylamino$_{(C\leq 8)}$, or a substituted version of any of these groups; or Y is taken together with R$_3$ and is —(CH$_2$)$_p$C(O)R$_f$—, wherein p is 0-6; and R$_f$ is —O— or —NR$_7$—; wherein:

R$_7$ is hydrogen, alkyl$_{(C\leq 8)}$, substituted alkyl$_{(C\leq 8)}$, acyl$_{(C\leq 8)}$, or substituted acyl$_{(C\leq 8)}$;

or a pharmaceutically acceptable salt, acetal, or hemiacetal thereof.

In some embodiments, the compounds are further defined as:

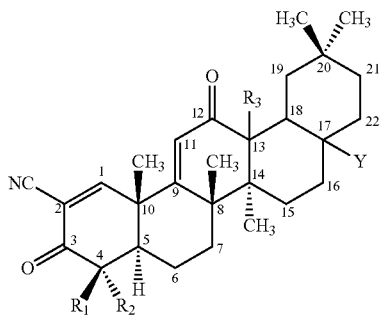

(IX)

wherein:
R$_1$ is hydrogen, alkyl$_{(C\le8)}$, cycloalkyl$_{(C\le8)}$, substituted alkyl$_{(C\le8)}$, or substituted cycloalkyl$_{(C\le8)}$;
R$_2$ is —(CH$_2$)$_q$C(O)—R$_5$'', wherein:
R$_5$'' is amino, hydroxy, or mercapto; or
alkoxy$_{(C\le8)}$, alkylthio$_{(C\le8)}$, alkylamino$_{(C\le8)}$, dialkylamino$_{(C\le8)}$, or a substituted version of any of these groups; and
q is 0, 1, 2, 3, or 4;
R$_3$ is hydrogen, hydroxy, or alkoxy$_{(C\le8)}$, acyloxy$_{(C\le8)}$, or substituted version of either of these groups; or R$_3$ is taken together with Y as described below; and
Y is hydrogen, hydroxy, halo, amino, cyano, isocyanate, or mercapto;
alkyl$_{(C\le8)}$, cycloalkyl$_{(C\le8)}$, alkenyl$_{(C\le8)}$, alkynyl$_{(C\le8)}$, aryl$_{(C\le12)}$, aralkyl$_{(C\le12)}$, heteroaryl$_{(C\le8)}$, heterocycloalkyl$_{(C\le12)}$, alkoxy$_{(C\le8)}$, cycloalkoxy$_{(C\le8)}$, aryloxy$_{(C\le12)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, alkylthio$_{(C\le8)}$, acylthio$_{(C\le8)}$, alkylsulfonylamino$_{(C\le8)}$, or substituted versions of any of these groups;
-alkanediyl$_{(C\le8)}$-R$_b$, -alkenediyl$_{(C\le8)}$-R$_b$, or a substituted version of any of these groups, wherein R$_b$ is:
hydrogen, hydroxy, halo, amino or mercapto; or
heteroaryl$_{(C\le8)}$, alkoxy$_{(C\le8)}$, cycloalkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, heteroarylamino$_{(C\le8)}$, alkylsulfonylamino$_{(C\le8)}$, amido$_{(C\le8)}$, —OC(O)NH-alkyl$_{(C\le8)}$, —OC(O)CH$_2$NHC(O)O-t-butyl, —OCH$_2$-alkylthio$_{(C\le8)}$, or a substituted version of any of these groups;
—(CH$_2$)$_o$C(O)R$_c$, wherein o is 0-6 and R$_c$ is:
hydrogen, halo, amino, —NHOH, or mercapto; or
alkyl$_{(C\le8)}$, cycloalkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, alkoxyamino$_{(C\le8)}$, heterocycloalkylamino$_{(C\le8)}$, —NHC(NOH)-alkyl$_{(C\le8)}$, —NH-amido$_{(C\le8)}$, or a substituted version of any of these groups;
—NR$_d$C(O)R$_e$, wherein
R$_d$ is hydrogen, alkyl$_{(C\le8)}$, or substituted alkyl$_{(C\le8)}$;
R$_e$ is hydrogen, hydroxy, amino; or
alkyl$_{(C\le8)}$, cycloalkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, cycloalkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkyl-amino$_{(C\le8)}$, dialkylamino$_{(C\le8)}$, arylamino$_{(C\le8)}$, or a substituted version of any of these groups; or
Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C\le8)}$, substituted alkyl$_{(C\le8)}$, acyl$_{(C\le8)}$, or substituted acyl$_{(C\le8)}$;
or a pharmaceutically acceptable salt, acetal, or hemiacetal thereof.

In other embodiments, the compounds are further defined as:

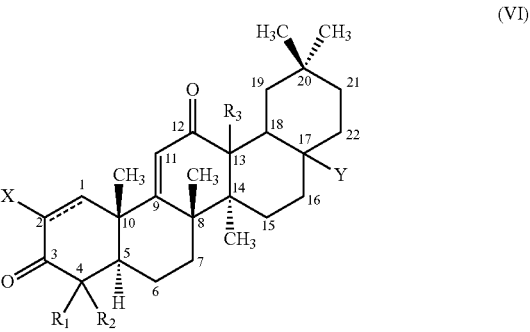

(VI)

wherein:
the bond between atoms 1 and 2 is a single bond, an epoxidized double bond, or a double bond;
X is cyano, heteroaryl$_{(C\le8)}$, substituted heteroaryl$_{(C\le8)}$, —CF$_3$, or —C(O)—R$_4$; wherein
R$_4$ is hydroxy, amino, or alkoxy$_{(C\le8)}$, alkylamino$_{(C\le8)}$, dialkylamino$_{(C\le8)}$, alkylsulfonylamino$_{(C\le8)}$, or a substituted version of any of these groups;
R$_1$ is hydrogen, alkyl$_{(C\le8)}$, cycloalkyl$_{(C\le8)}$, substituted alkyl$_{(C\le8)}$, or substituted cycloalkyl$_{(C\le8)}$;
R$_2$ is amino, cyano, halo, or hydroxy,
haloalkyl$_{(C\le8)}$, substituted cycloalkyl$_{(C\le8)}$, heteroaryl$_{(C\le8)}$, substituted heteroaryl$_{(C\le8)}$, acyl$_{(C\le8)}$, substituted acyl$_{(C\le8)}$, amido$_{(C\le8)}$, substituted amido$_{(C\le8)}$, alkylamino$_{(C\le8)}$, substituted alkylamino$_{(C\le8)}$, dialkylamino$_{(C\le8)}$, or dialkylamino$_{(C\le8)}$; or
—OR$_a$, wherein:
R$_a$ is hydrogen or alkyl$_{(C\le8)}$, alkenyl$_{(C\le8)}$, alkynyl$_{(C\le8)}$, aryl$_{(C\le12)}$, aralkyl$_{(C\le12)}$, heteroaryl$_{(C\le12)}$, heterocycloalkyl$_{(C\le8)}$, acyl$_{(C\le8)}$, or a substituted version of any of these groups;
—(CH$_2$)$_m$—R$_5$''', wherein:
R$_5$''' is alkoxy$_{(C\le8)}$, acyloxy$_{(C\le8)}$, substituted acyloxy$_{(C\le8)}$, alkylsilyloxy$_{(C\le8)}$, or substituted alkylsilyloxy$_{(C\le8)}$; and
m is 0, 1, 2, 3, or 4;
—(CH$_2$)$_{m2}$—R$_5$''', wherein:
R$_5$''' is hydroxy; and
m$_2$ is 2, 3, or 4;
—(CH$_2$)$_s$NR$_5$'(R$_6$), wherein:
s is 0, 1, 2, 3, or 4;
R$_5$' is hydrogen, alkyl$_{(C\le8)}$, alkoxy$_{(C\le8)}$, substituted alkoxy$_{(C\le8)}$, acyl$_{(C\le8)}$, substituted acyl$_{(C\le8)}$, —C(O)-alkoxy$_{(C\le8)}$, substituted —C(O)-alkoxy$_{(C\le8)}$, acyloxy$_{(C\le8)}$, substituted acyloxy$_{(C\le8)}$, alkylsilyloxy$_{(C\le8)}$, or substituted alkylsilyloxy$_{(C\le8)}$; and $R_6$ is hydrogen, alkyl$_{(C≤8)}$, or substituted alkyl$_{(C≤8)}$; or
—(CH$_2$)$_q$—C(O)—R$_5$", wherein:
  R$_5$" is amino, hydroxy, or mercapto; or
    alkoxy$_{(C≤8)}$, alkylthio$_{(C≤8)}$, alkylamino$_{(C≤8)}$, dialkylamino$_{(C≤8)}$, or a substituted version of any of these groups; and
  q is 0, 1, 2, 3, or 4;
R$_3$ is hydrogen, hydroxy, or alkoxy$_{(C≤8)}$, acyloxy$_{(C≤8)}$, or substituted version of either of these groups; and
Y is —(CH$_2$)$_o$C(O)R$_c$, wherein o is 0-6 and R$_c$ is:
  hydroxy; or
  alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups;
or a pharmaceutically acceptable salt, acetal, or hemiacetal thereof.

In some embodiments, the compounds are further defined as:

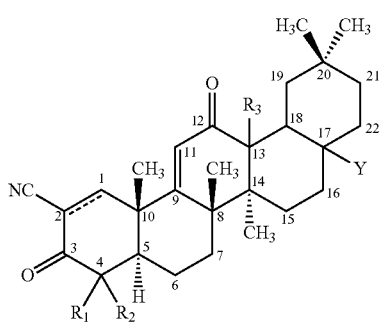

(VII)

wherein:
  the bond between atoms 1 and 2 is a single bond, an epoxidized double bond, or a double bond;
  R$_1$ is hydrogen, alkyl$_{(C≤8)}$, cycloalkyl$_{(C≤8)}$, substituted alkyl$_{(C≤8)}$, or substituted cycloalkyl$_{(C≤8)}$;
  R$_2$ is amino, cyano, halo, or hydroxy,
    haloalkyl$_{(C≤8)}$, substituted cycloalkyl$_{(C≤8)}$, heteroaryl$_{(C≤8)}$, substituted heteroaryl$_{(C≤8)}$, acyl$_{(C≤8)}$, substituted acyl$_{(C≤8)}$, amido$_{(C≤8)}$, substituted amido$_{(C≤8)}$, alkylamino$_{(C≤8)}$, substituted alkylamino$_{(C≤8)}$, dialkylamino$_{(C≤8)}$, or dialkylamino$_{(C≤8)}$; or
    —OR$_a$, wherein:
      R$_a$ is hydrogen or alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤12)}$, heterocycloalkyl$_{(C≤8)}$, acyl$_{(C≤8)}$, or a substituted version of any of these groups;
    —(CH$_2$)$_m$—R$_5$''', wherein:
      R$_5$''' is alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
    m is 0, 1, 2, 3, or 4; or
    —(CH$_2$)$_{m2}$—R$_5$''', wherein:
      R$_5$''' is hydroxy; and
      m$_2$ is 2, 3, or 4;
    —(CH$_2$)$_s$NR$_5$'(R$_6$), wherein:
      s is 0, 1, 2, 3, or 4;
      R$_5$' is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)- alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
  R$_6$ is hydrogen, alkyl$_{(C≤8)}$, or substituted alkyl$_{(C≤8)}$; or
—(CH$_2$)$_q$—C(O)—R$_5$", wherein:
  R$_5$" is amino, hydroxy, or mercapto; or
    alkoxy$_{(C≤8)}$, alkylthio$_{(C≤8)}$, alkylamino$_{(C≤8)}$, dialkylamino$_{(C≤8)}$, or a substituted version of any of these groups; and
  q is 0, 1, 2, 3, or 4;
R$_3$ is hydrogen, hydroxy, or alkoxy$_{(C≤8)}$, acyloxy$_{(C≤8)}$, or substituted version of either of these groups; and
Y is —(CH$_2$)$_o$C(O)R$_c$, wherein o is 0-6 and R$_c$ is:
  hydroxy; or
  alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups;
or a pharmaceutically acceptable salt, acetal, or hemiacetal thereof.

In some embodiments, the compounds are further defined as:

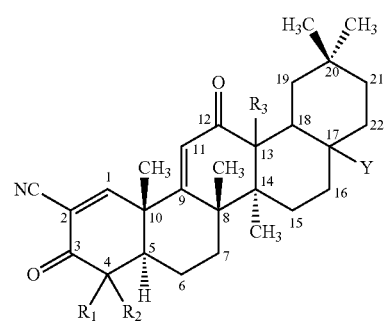

(VIII)

wherein:
  R$_1$ is hydrogen, alkyl$_{(C≤8)}$, cycloalkyl$_{(C≤8)}$, substituted alkyl$_{(C≤8)}$, or substituted cycloalkyl$_{(C≤8)}$;
  R$_2$ is amino, cyano, halo, or hydroxy,
    haloalkyl$_{(C≤8)}$, substituted cycloalkyl$_{(C≤8)}$, heteroaryl$_{(C≤8)}$, substituted heteroaryl$_{(C≤8)}$, acyl$_{(C≤8)}$, substituted acyl$_{(C≤8)}$, amido$_{(C≤8)}$, substituted amido$_{(C≤8)}$, alkylamino$_{(C≤8)}$, substituted alkylamino$_{(C≤8)}$, dialkylamino$_{(C≤8)}$, or dialkylamino$_{(C≤8)}$; or
    —OR$_a$, wherein:
      R$_a$ is hydrogen or alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤12)}$, heterocycloalkyl$_{(C≤8)}$, acyl$_{(C≤8)}$, or a substituted version of any of these groups;
    —(CH$_2$)$_m$—R$_5$''', wherein:
      R$_5$''' is alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
    m is 0, 1, 2, 3, or 4; or
    —(CH$_2$)$_{m2}$—R$_5$''', wherein:
      R$_5$''' is hydroxy; and
      m$_2$ is 2, 3, or 4;
    —(CH$_2$)$_s$NR$_5$'(R$_6$), wherein:
      s is 0, 1, 2, 3, or 4;
      R$_5$' is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)- alkoxy$_{(C\leq8)}$, acyloxy$_{(C\leq8)}$, substituted acyloxy$_{(C\leq8)}$, alkylsilyloxy$_{(C\leq8)}$, or substituted alkylsilyloxy$_{(C\leq8)}$; and R$_6$ is hydrogen, alkyl$_{(C\leq8)}$, or substituted alkyl$_{(C\leq8)}$; or —(CH$_2$)$_q$—C(O)—R$_5$″, wherein:

R$_5$″ is amino, hydroxy, or mercapto; or alkoxy$_{(C\leq8)}$, alkylthio$_{(C\leq8)}$, alkylamino$_{(C\leq8)}$, dialkylamino$_{(C\leq8)}$, or a substituted version of any of these groups; and q is 0, 1, 2, 3, or 4;

R$_3$ is hydrogen, hydroxy, or alkoxy$_{(C\leq8)}$, acyloxy$_{(C\leq8)}$, or substituted version of either of these groups; and Y is —(CH$_2$)$_o$C(O)R$_c$, wherein o is 0-6 and R$_c$ is:

hydroxy; or alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;

or a pharmaceutically acceptable salt, acetal, or hemiacetal thereof.

In other embodiments, the compounds are further defined as:

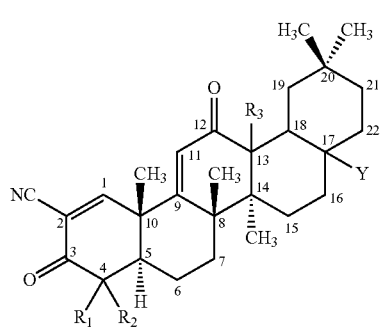

(VIII)

wherein:

R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;

R$_2$ is amino, cyano, halo, or hydroxy, haloalkyl$_{(C\leq8)}$, heteroaryl$_{(C\leq8)}$, substituted heteroaryl$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or dialkylamino$_{(C\leq8)}$;

R$_3$ is hydrogen, hydroxy, or alkoxy$_{(C\leq8)}$, acyloxy$_{(C\leq8)}$, or substituted version of either of these groups; and Y is —(CH$_2$)$_o$C(O)R$_c$, wherein o is 0-6 and R$_c$ is:

hydroxy; or alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;

or a pharmaceutically acceptable salt, acetal, or hemiacetal thereof.

In some embodiments, the compounds are further defined as:

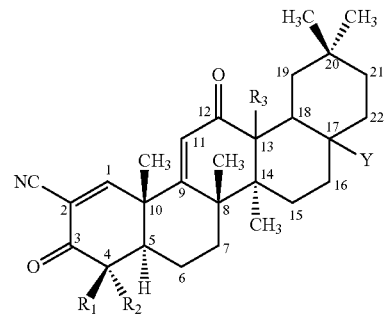

(IX)

wherein:

R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;

R$_2$ is amino, cyano, halo, or hydroxy, haloalkyl$_{(C\leq8)}$, heteroaryl$_{(C\leq8)}$, substituted heteroaryl$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or dialkylamino$_{(C\leq8)}$;

R$_3$ is hydrogen, hydroxy, or alkoxy$_{(C\leq8)}$, acyloxy$_{(C\leq8)}$, or substituted version of either of these groups; and Y is —(CH$_2$)$_o$C(O)R$_c$, wherein o is 0-6 and R$_c$ is:

hydroxy; or alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;

or a pharmaceutically acceptable salt, acetal, or hemiacetal thereof.

In other embodiments, the compounds are further defined as:

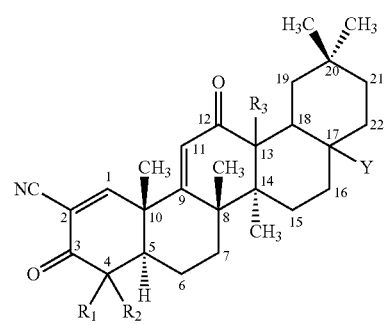

(VIII)

wherein:

R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;

R$_2$ is —(CH$_2$)$_m$—R$_5$‴, wherein:

R$_5$‴ is alkoxy$_{(C\leq8)}$, acyloxy$_{(C\leq8)}$, substituted acyloxy$_{(C\leq8)}$, alkylsilyloxy$_{(C\leq8)}$, or substituted alkylsilyloxy$_{(C\leq8)}$; and m is 0, 1, 2, 3, or 4; or R$_2$ is —(CH$_2$)$_{m2}$—R$_5$‴, wherein:

R$_5$‴ is hydroxy; and m$_2$ is 2, 3, or 4;

R$_3$ is hydrogen, hydroxy, or alkoxy$_{(C\leq8)}$, acyloxy$_{(C\leq8)}$, or substituted version of either of these groups; and Y is —(CH$_2$)$_o$C(O)R$_c$, wherein o is 0-6 and R$_c$ is:
  hydrogen; or
  alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;
or a pharmaceutically acceptable salt, acetal, or hemiacetal thereof.

In some embodiments, the compounds are further defined as:

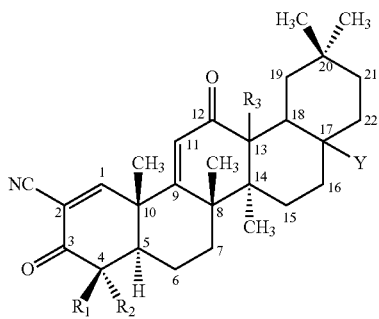

(IX)

wherein:
  R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;
  R$_2$ is —(CH$_2$)$_m$—R$_5'''$, wherein:
    R$_5'''$ is alkoxy$_{(C\leq8)}$, acyloxy$_{(C\leq8)}$, substituted acyloxy$_{(C\leq8)}$, alkylsilyloxy$_{(C\leq8)}$, or substituted alkylsilyloxy$_{(C\leq8)}$; and
    m is 0, 1, 2, 3, or 4; or
  R$_2$ is —(CH$_2$)$_{m2}$—R$_5'''$, wherein:
    R$_5'''$ is hydroxy; and
    m$_2$ is 2, 3, or 4;
  R$_3$ is hydrogen, hydroxy, or alkoxy$_{(C\leq8)}$, acyloxy$_{(C\leq8)}$, or substituted version of either of these groups; and
  Y is —(CH$_2$)$_o$C(O)R$_c$, wherein o is 0-6 and R$_c$ is:
    hydroxy; or
    alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;
or a pharmaceutically acceptable salt, acetal, or hemiacetal thereof.

In other embodiments, the compounds are further defined as:

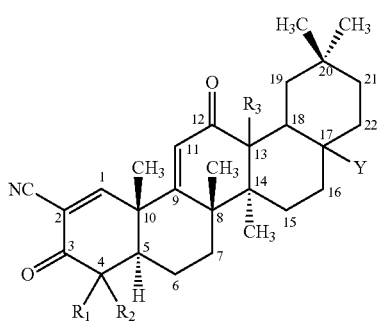

(VIII)

wherein:
  R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;
  R$_2$ is —OR$_a$, wherein:
    R$_a$ is hydrogen or alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq12)}$, heterocycloalkyl$_{(C\leq8)}$, acyl$_{(C\leq8)}$, or a substituted version of any of these groups;
  R$_3$ is hydrogen, hydroxy, or alkoxy$_{(C\leq8)}$, acyloxy$_{(C\leq8)}$, or substituted version of either of these groups; and
  Y is —(CH$_2$)$_o$C(O)R$_c$, wherein o is 0-6 and R$_c$ is:
    hydroxy; or
    alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;
or a pharmaceutically acceptable salt, acetal, or hemiacetal thereof.

In some embodiments, the compounds are further defined as:

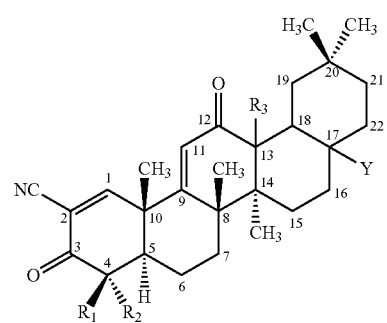

(IX)

wherein:
  R$_1$ is hydrogen, alkyl$_{(C\leq8)}$, cycloalkyl$_{(C\leq8)}$, substituted alkyl$_{(C\leq8)}$, or substituted cycloalkyl$_{(C\leq8)}$;
  R$_2$ is —OR$_a$, wherein:
    R$_a$ is hydrogen or alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq12)}$, heterocycloalkyl$_{(C\leq8)}$, acyl$_{(C\leq8)}$, or a substituted version of any of these groups;
  R$_3$ is hydrogen, hydroxy, or alkoxy$_{(C\leq8)}$, acyloxy$_{(C\leq8)}$, or substituted version of either of these groups; and
  Y is —(CH$_2$)$_o$C(O)R$_c$, wherein o is 0-6 and R$_c$ is:
    hydroxy; or
    alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, or a substituted version of any of these groups;
or a pharmaceutically acceptable salt, acetal, or hemiacetal thereof.

In some embodiments, the compounds are further defined as:

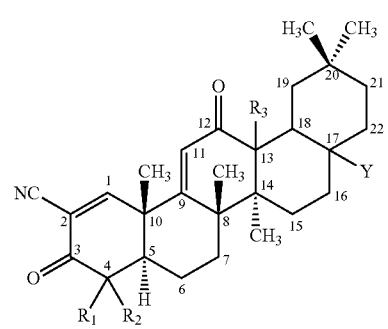

(VIII)

wherein:
- $R_1$ is hydrogen, alkyl$_{(C≤8)}$, cycloalkyl$_{(C≤8)}$, substituted alkyl$_{(C≤8)}$, or substituted cycloalkyl$_{(C≤8)}$;
- $R_2$ is —(CH$_2$)$_s$NR$_5$'(R$_6$), wherein:
  - s is 0, 1, 2, 3, or 4;
  - $R_5$' is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)-alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
  - $R_6$ is hydrogen, alkyl$_{(C≤8)}$, or substituted alkyl$_{(C≤8)}$;
- $R_3$ is hydrogen, hydroxy, or alkoxy$_{(C≤8)}$, acyloxy$_{(C≤8)}$, or substituted version of either of these groups; and
- Y is —(CH$_2$)$_o$C(O)R$_c$, wherein o is 0-6 and R$_c$ is:
  - hydroxy; or
  - alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups;

or a pharmaceutically acceptable salt, acetal, or hemiacetal thereof.

In some embodiments, the compounds are further defined as:

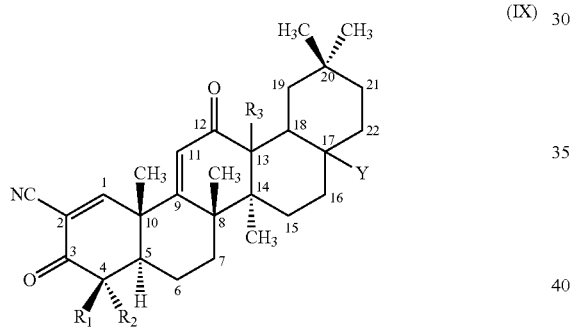

(IX)

wherein:
- $R_1$ is hydrogen, alkyl$_{(C≤8)}$, cycloalkyl$_{(C≤8)}$, substituted alkyloxy(c), or substituted cycloalkyl$_{(C≤8)}$;
- $R_2$ is —(CH$_2$)$_s$NR$_5$'(R$_6$), wherein:
  - s is 0, 1, 2, 3, or 4;
  - $R_5$' is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)-alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and
  - $R_6$ is hydrogen, alkyl$_{(C≤8)}$, or substituted alkyl$_{(C≤8)}$;
- $R_3$ is hydrogen, hydroxy, or alkoxy$_{(C≤8)}$, acyloxy$_{(C≤8)}$, or substituted version of either of these groups; and
- Y is —(CH$_2$)$_o$C(O)R$_c$, wherein o is 0-6 and R$_c$ is:
  - hydroxy; or
  - alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups;

or a pharmaceutically acceptable salt, acetal, or hemiacetal thereof.

In other embodiments, the compounds are further defined as:

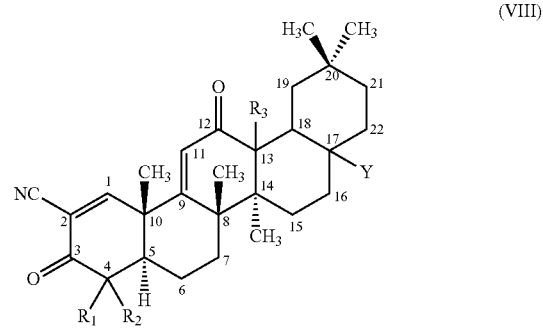

(VIII)

wherein:
- $R_1$ is hydrogen, alkyl$_{(C≤8)}$, cycloalkyl$_{(C≤8)}$, substituted alkyl$_{(C≤8)}$, or substituted cycloalkyl$_{(C≤8)}$;
- $R_2$ is —(CH$_2$)$_q$C(O)—R$_5$", wherein:
  - $R_5$" is amino, hydroxy, or mercapto; or alkoxy$_{(C≤8)}$, alkylthio$_{(C≤8)}$, alkylamino$_{(C≤8)}$, dialkylamino$_{(C≤8)}$, or a substituted version of any of these groups; and
  - q is 0, 1, 2, 3, or 4;
- $R_3$ is hydrogen, hydroxy, or alkoxy$_{(C≤8)}$, acyloxy$_{(C≤8)}$, or substituted version of either of these groups; and
- Y is —(CH$_2$)$_o$C(O)R$_c$, wherein o is 0-6 and R$_c$ is:
  - hydroxy; or
  - alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups;

or a pharmaceutically acceptable salt, acetal, or hemiacetal thereof.

In some embodiments, the compounds are further defined as:

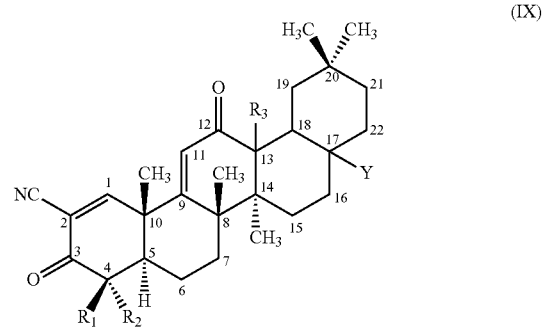

(IX)

wherein:
- $R_1$ is hydrogen, alkyl$_{(C≤8)}$, cycloalkyl$_{(C≤8)}$, substituted alkyl$_{(C≤8)}$, or substituted cycloalkyl$_{(C≤8)}$;
- $R_2$ is —(CH$_2$)$_q$—C(O)—R$_5$", wherein:
  - $R_5$" is amino, hydroxy, or mercapto; or alkoxy$_{(C≤8)}$, alkylthio$_{(C≤8)}$, alkylamino$_{(C≤8)}$, dialkylamino$_{(C≤8)}$, or a substituted version of any of these groups; and
  - q is 0, 1, 2, 3, or 4;
- $R_3$ is hydrogen, hydroxy, or alkoxy$_{(C≤8)}$, acyloxy$_{(C≤8)}$, or substituted version of either of these groups; and
- Y is —(CH$_2$)$_o$C(O)R$_c$, wherein o is 0-6 and R$_c$ is:
  - hydroxy; or alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups;

or a pharmaceutically acceptable salt, acetal, or hemiacetal thereof.

In some embodiments, X is cyano. In some embodiments, the bond between atoms 1 and 2 are an epoxidized double bond. In other embodiments, the bond between atoms 1 and 2 are a double bond. In some embodiments, $R_1$ is hydrogen. In other embodiments, $R_1$ is alkyl$_{(C≤8)}$ or substituted alkyl$_{(C≤8)}$. In some embodiments, $R_1$ is alkyl$_{(C≤8)}$, for example, $R_1$ is methyl.

In some embodiments, $R_2$ is amino. In other embodiments, $R_2$ is substituted alkyl$_{(C≤8)}$, for example, $R_2$ is hydroxymethyl, difluoromethyl, acetoxymethyl, methoxyethyl, methoxymethyl, methyl carboxymethyl, 2-hydroxyethyl, or 1-hydroxyethyl. In some embodiments, $R_2$ is haloalkyl$_{(C≤8)}$, for example, $R_2$ is difluoromethyl. In other embodiments, $R_2$ is heteroaryl$_{(C≤8)}$ or substituted heteroaryl$_{(C≤8)}$, for example, $R_2$ is 2-methyloxadiazole. In other embodiments, $R_2$ is amido$_{(C≤8)}$ or substituted amido$_{(C≤8)}$, for example, $R_2$ is N-acetamide.

In other embodiments, $R_2$ is —(CH$_2$)$_m$—(OCH$_2$)$_n$—$R_5$, wherein: $R_5$ is hydroxy or acyl$_{(C≤8)}$, alkoxy$_{(C≤8)}$, acyloxy$_{(C≤8)}$, alkylsilyloxy$_{(C≤8)}$, or a substituted version of any of these groups; m is 0, 1, 2, 3, or 4; and n is 0, 1, 2, or 3. In some embodiments, $R_5$ is alkoxy$_{(C≤8)}$ or substituted alkoxy$_{(C≤8)}$, for example, $R_5$ is methoxy. In other embodiments, $R_5$ is acyloxy$_{(C≤8)}$ or substituted acyloxy$_{(C≤8)}$, for example, $R_5$ is —OC(O)C$_6$H$_5$. In other embodiments, $R_5$ is alkylsilyloxy$_{(C≤8)}$ or alkylsilyloxy$_{(C≤8)}$, for example, $R_5$ is t-butyldimethylsiloxy. In some embodiments, m is 1 or 2. In some embodiments, m is 1. In other embodiments, m is 2. In some embodiments, n is 0 or 1. In some embodiments, n is 0. In other embodiments, n is 1.

In other embodiments, $R_2$ is —(CH$_2$)$_m$—$R_5'''$, wherein: $R_5'''$ is alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and m is 0, 1, 2, 3, or 4. In other embodiments, $R_2$ is —(CH$_2$)$_{m2}$—$R_5'''$, wherein: $R_5'''$ is hydroxy; and $m_2$ is 2, 3, or 4. In some embodiments, $R_5'''$ is alkoxy$_{(C≤8)}$ or substituted alkoxy$_{(C≤8)}$, for example, $R_5'''$ is methoxy. In other embodiments, $R_5'''$ is acyloxy$_{(C≤8)}$ or substituted acyloxy$_{(C≤8)}$, for example, $R_5'''$ is —OC(O)C$_6$H$_5$. In other embodiments, $R_5'''$ is alkylsilyloxy$_{(C≤8)}$ or alkylsilyloxy$_{(C≤8)}$, for example, $R_5'''$ is t-butyldimethylsiloxy. In some embodiments, m is 1 or 2. In some embodiments, m is 1. In other embodiments, m is 2. In some embodiments, $m_2$ is 2 or 3.

In other embodiments, $R_2$ is —(CH$_2$)$_s$NR$_5'$(R$_6$), wherein: s is 0, 1, 2, 3, or 4; $R_5'$ is hydrogen, alkyl$_{(C≤8)}$, alkoxy$_{(C≤8)}$, substituted alkoxy$_{(C≤8)}$, acyl$_{(C≤8)}$, substituted acyl$_{(C≤8)}$, —C(O)-alkoxy$_{(C≤8)}$, substituted —C(O)-alkoxy$_{(C≤8)}$, acyloxy$_{(C≤8)}$, substituted acyloxy$_{(C≤8)}$, alkylsilyloxy$_{(C≤8)}$, or substituted alkylsilyloxy$_{(C≤8)}$; and $R_6$ is hydrogen, alkyl$_{(C≤8)}$, or substituted alkyl$_{(C≤8)}$. In some embodiments, s is 0 or 1. In some embodiments, s is 0. In other embodiments, s is 1. In some embodiments, $R_5'$ is hydrogen. In other embodiments, $R_5'$ is acyl$_{(C≤8)}$, for example, $R_5'$ is acetyl. In other embodiments, $R_5'$ is —C(O)-alkoxy$_{(C≤8)}$, for example, $R_5'$ is tert-butyloxycarbonyl. In some embodiments, $R_6$ is hydrogen.

In other embodiments, $R_2$ is —(CH$_2$)$_q$—C(O)—$R_5''$, wherein: $R_5''$ is amino, hydroxy, or mercapto; or alkoxy$_{(C≤8)}$, alkylthio$_{(C≤8)}$, alkylamino$_{(C≤8)}$, dialkylamino$_{(C≤8)}$, or a substituted version of any of these groups; and q is 0, 1, 2, 3, or 4. In some embodiments, $R_5''$ is amino. In other embodiments, $R_5''$ is alkylamino$_{(C≤8)}$, for example, $R_5''$ is methylamino. In other embodiments, $R_5''$ is dialkylamino$_{(C≤8)}$, for example, $R_5''$ is dimethylamino. In other embodiments, $R_5''$ is hydroxy. In other embodiments, $R_5''$ is alkoxy$_{(C≤8)}$, for example, $R_5''$ is methoxy. In some embodiments, q is 0.

In other embodiments, $R_2$ is —OR$_a$, wherein: $R_a$ is hydrogen or alkyl$_{(C≤8)}$, acyl$_{(C≤8)}$, or a substituted version of either of these groups. In some embodiments, $R_a$ is hydrogen. In other embodiments, $R_a$ is alkyl$_{(C≤8)}$ or substituted alkyl$_{(C≤8)}$. In other embodiments, $R_a$ is acyl$_{(C≤8)}$ or substituted acyl$_{(C≤8)}$.

In some embodiments, Y is heteroaryl$_{(C≤8)}$ or substituted heteroaryl$_{(C≤8)}$, for example, Y is 3-methyl-1,2,4-oxadiazole or 2-methyl-1,3,4-oxadiazole. In other embodiments, Y is —(CH$_2$)$_o$C(O)R$_c$, wherein o is 0-6 and $R_c$ is: hydrogen, halo, amino, —NHOH, or mercapto; or alkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkylamino$_{(C≤8)}$, dialkylamino$_{(C≤8)}$, arylamino$_{(C≤8)}$, alkylsulfonylamino$_{(C≤8)}$, amido$_{(C≤8)}$, alkoxyamino$_{(C≤8)}$, heterocycloalkylamino$_{(C≤8)}$, —NHC(NOH)-alkyl$_{(C≤8)}$, —NH-amido$_{(C≤8)}$, or a substituted version of any of these groups. In some embodiments, o is 0, 1, or 2. In some embodiments, o is 0. In some embodiments, $R_c$ is alkylamino$_{(C≤8)}$ or substituted alkylamino$_{(C≤8)}$. In some embodiments, $R_c$ is alkylamino$_{(C≤8)}$, for example, $R_c$ is ethylamino. In other embodiments, $R_c$ is substituted alkylamino$_{(C≤8)}$, for example, $R_c$ is 2,2,2-trifluoroethylamino. In some embodiments, $R_c$ is dialkylamino$_{(C≤8)}$ or substituted dialkylamino$_{(C≤8)}$. In some embodiments, $R_c$ is dialkylamino$_{(C≤8)}$, for example, $R_c$ is dimethylamino.

In other embodiments, Y is —(CH$_2$)$_o$C(O)R$_c$, wherein o is 0-6 and $R_c$ is: hydroxy; or alkoxy$_{(C≤8)}$, alkenyloxy$_{(C≤8)}$, aryloxy$_{(C≤8)}$, aralkoxy$_{(C≤8)}$, heteroaryloxy$_{(C≤8)}$, acyloxy$_{(C≤8)}$, or a substituted version of any of these groups. In some embodiments, o is 0, 1, or 2. In some embodiments, o is 0. In some embodiments, $R_c$ is alkoxy$_{(C≤8)}$ or substituted alkoxy$_{(C≤8)}$. In some embodiments, $R_c$ is alkoxy$_{(C≤8)}$, for example, $R_c$ is methoxy.

In other embodiments, Y is —NR$_d$C(O)R$_e$, wherein $R_d$ is hydrogen, alkyl$_{(C≤8)}$, or substituted alkyl$_{(C≤8)}$; $R_e$ is hydrogen, hydroxy, amino; or alkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, alkoxy$_{(C≤8)}$, aryloxy$_{(C≤8)}$, aralkoxy$_{(C≤8)}$, heteroaryloxy$_{(C≤8)}$, acyloxy$_{(C≤8)}$, alkylamino$_{(C≤8)}$, dialkylamino$_{(C≤8)}$, arylamino$_{(C≤8)}$, or a substituted version of any of these groups. In some embodiments, $R_d$ is hydrogen. In some embodiments, $R_e$ is alkyl$_{(C≤8)}$ or substituted alkyl$_{(C≤8)}$. In some embodiments, $R_e$ is substituted alkyl$_{(C≤8)}$, for example, $R_e$ is 1,1-difluoroethyl. In some embodiments, $R_e$ is alkoxy$_{(C≤8)}$ or substituted alkoxy$_{(C≤8)}$. In some embodiments, $R_e$ is alkoxy$_{(C≤8)}$, for example, $R_e$ is methoxy.

In other embodiments, Y is taken together with $R_3$ and is —(CH$_2$)$_p$C(O)R$_f$—, wherein p is 0-6; and $R_f$ is —O— or —NR$_7$—; wherein: $R_7$ is hydrogen, alkyl$_{(C≤8)}$, substituted alkyl$_{(C≤8)}$, acyl$_{(C≤8)}$, or substituted acyl$_{(C≤8)}$. In some embodiments, p is 0 or 1. In some embodiments, p is 0. In some embodiments, $R_f$ is —O—. In some embodiments, $R_3$ is hydrogen. In other embodiments, $R_3$ is hydroxy.

In some embodiments, the carbon atom 4 is in the α orientation. In other embodiments, the carbon atom 4 is in the β orientation. In some embodiments, the carbon atom 4 is in the S configuration. In other embodiments, the carbon atom 4 is in the R configuration. In some embodiments, the compounds are further defined as:

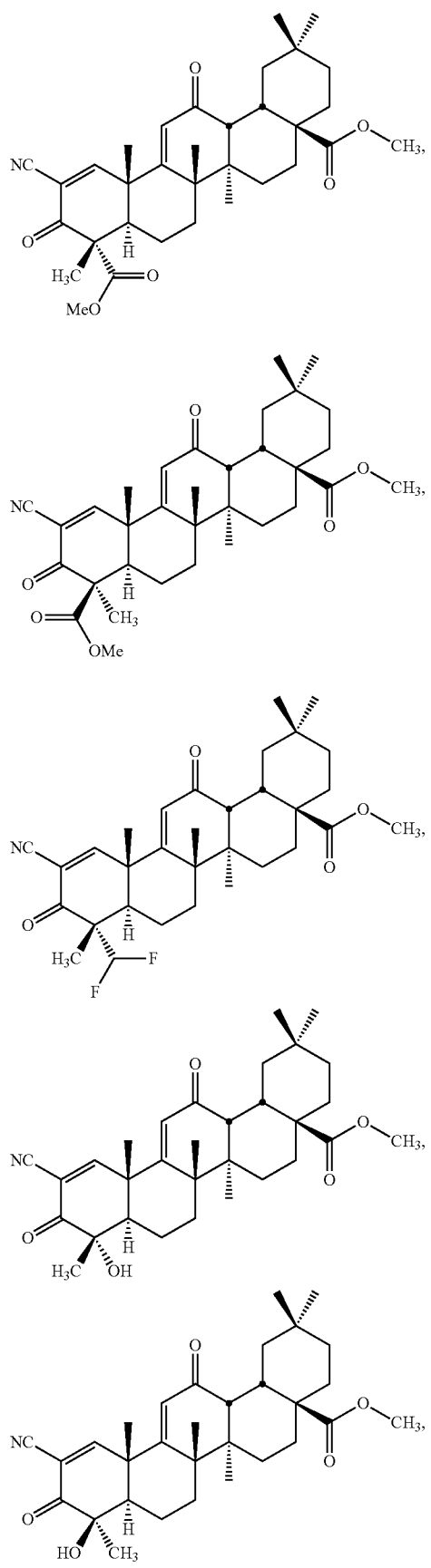
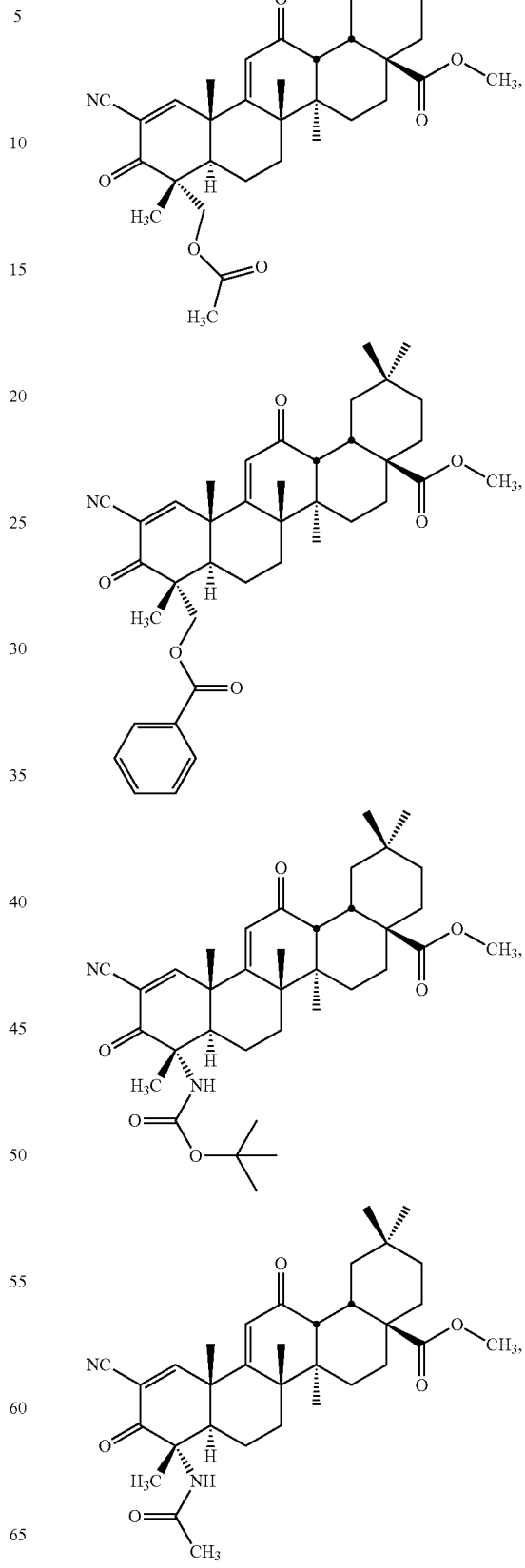

41
-continued
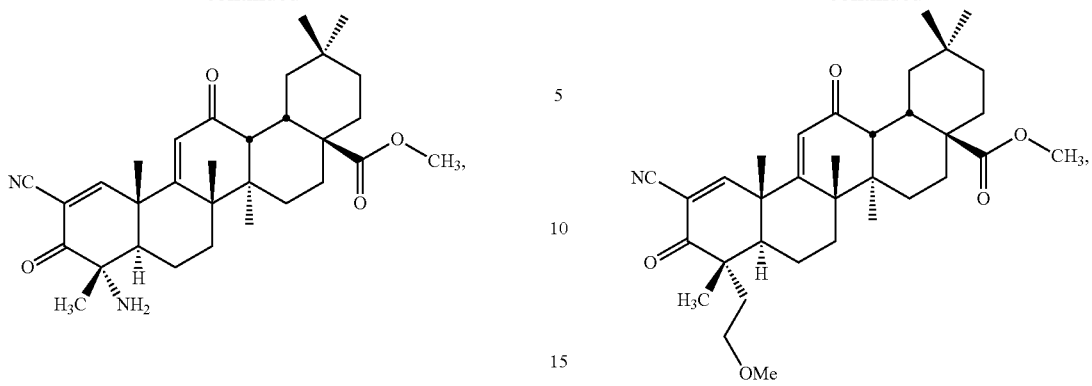
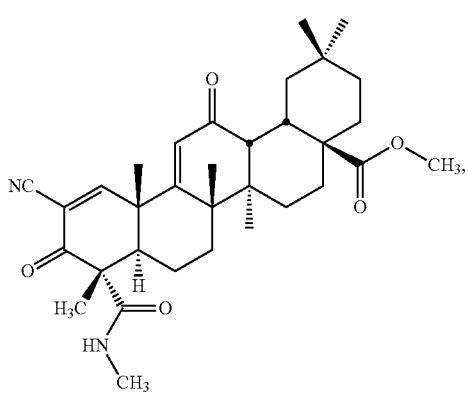
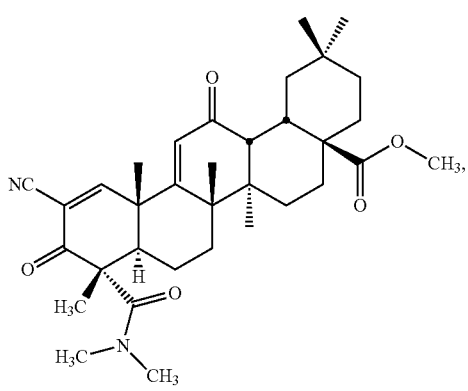
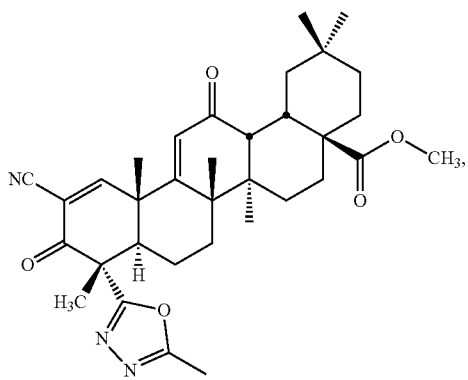
42
-continued
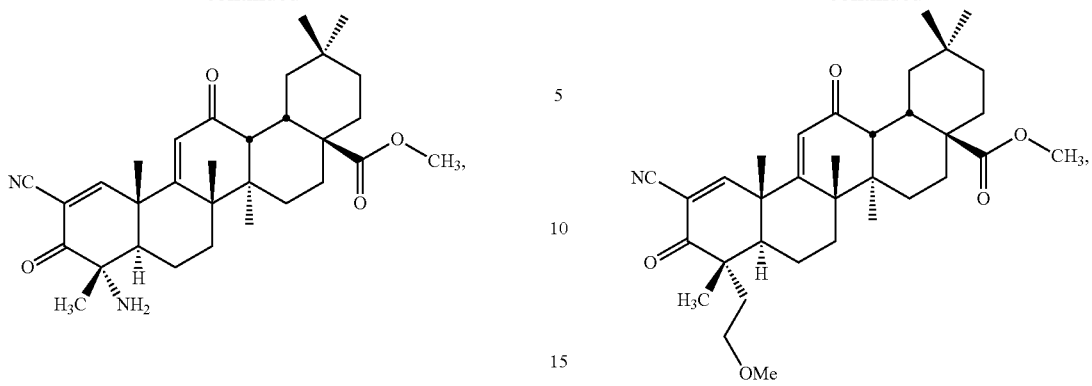
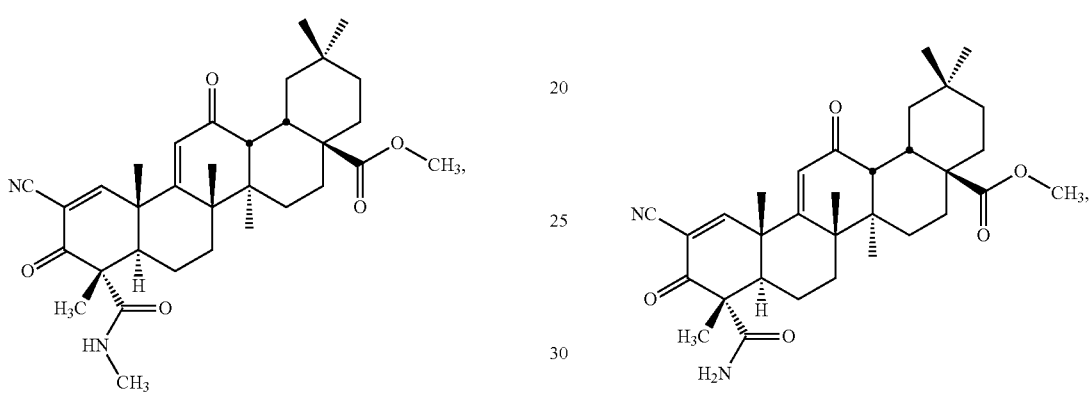
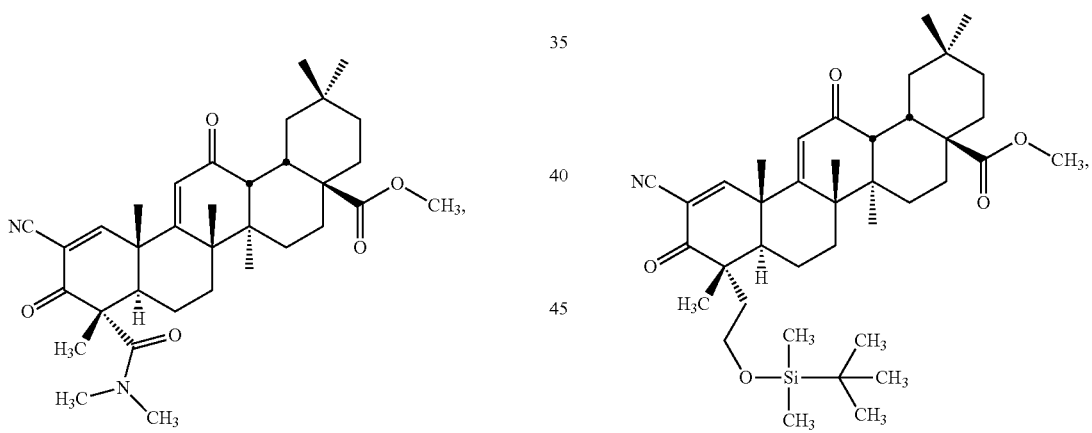
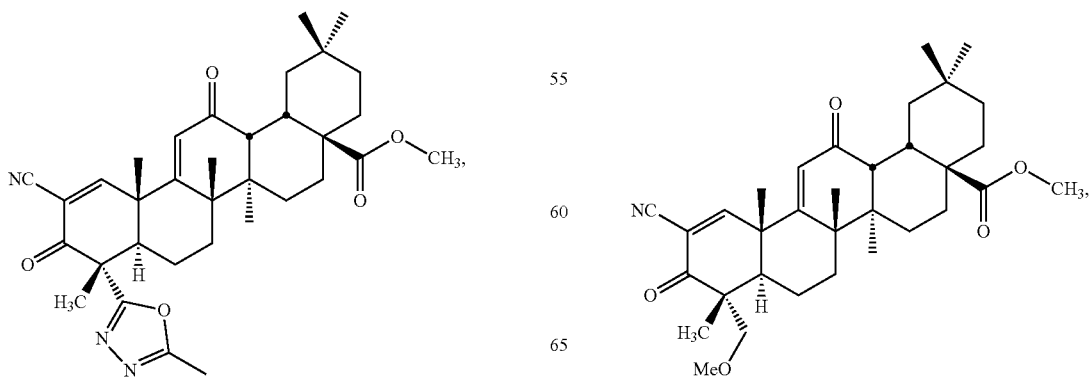

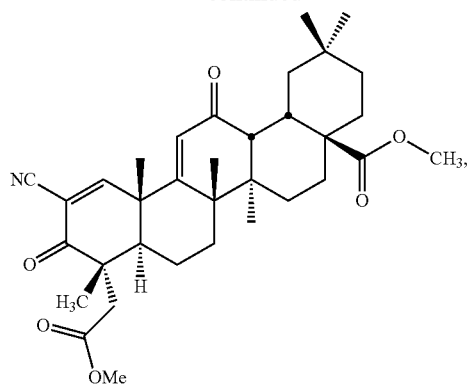
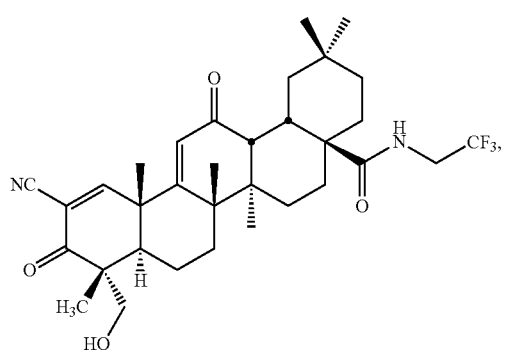
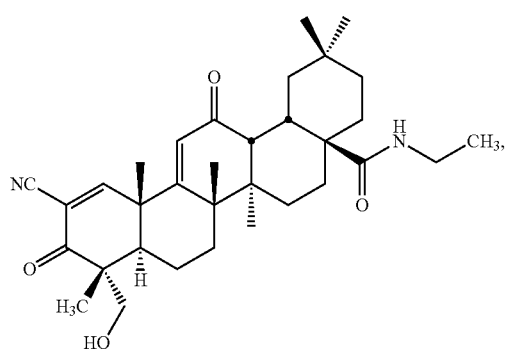
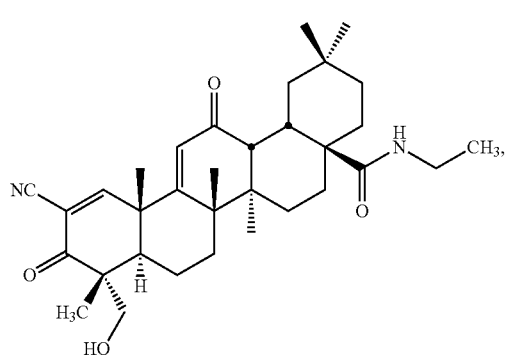
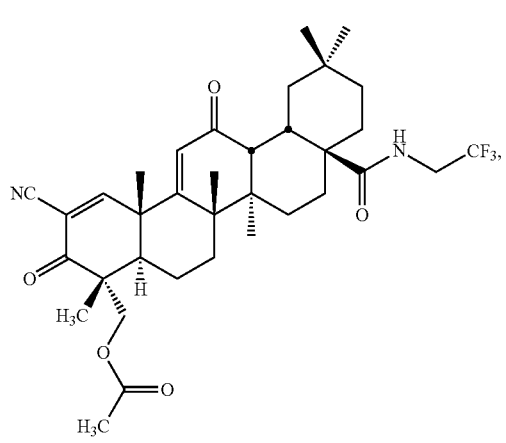
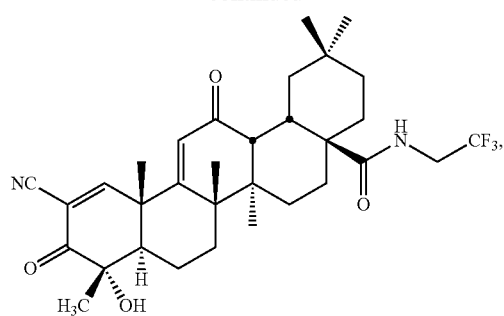
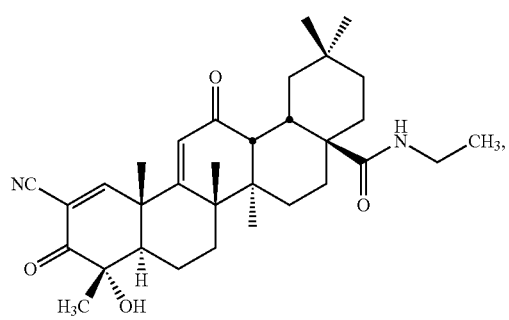
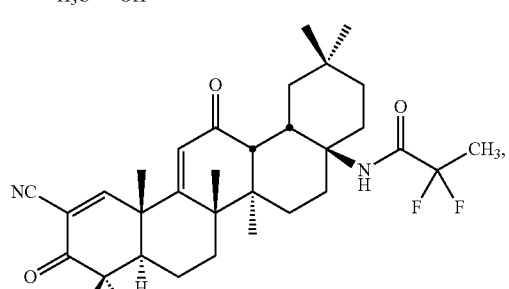
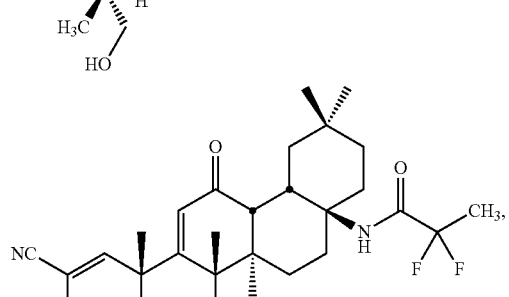
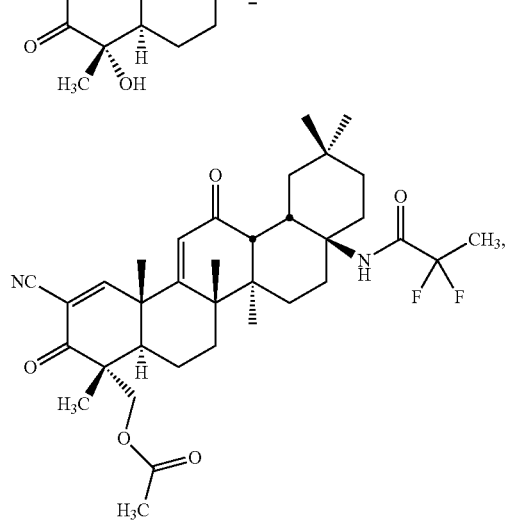

-continued
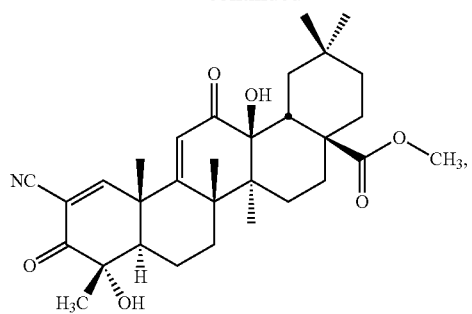
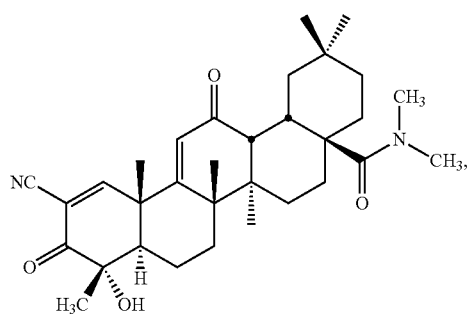
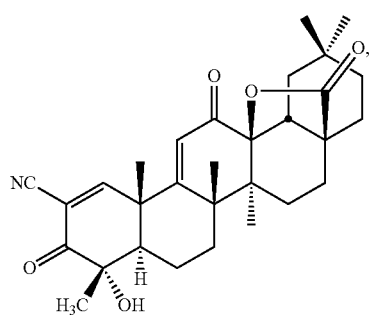
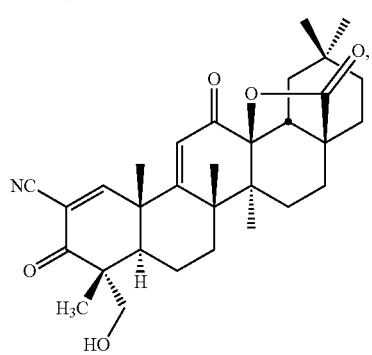
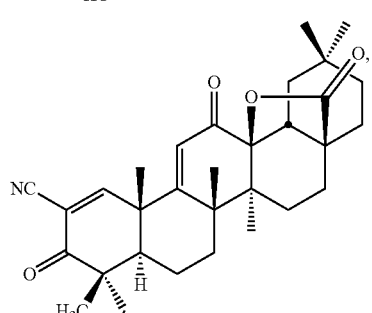
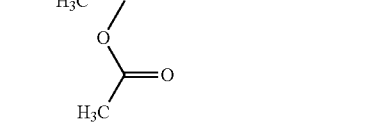
-continued
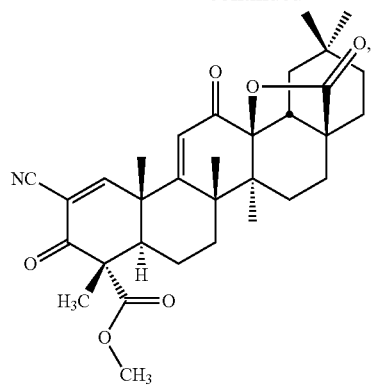
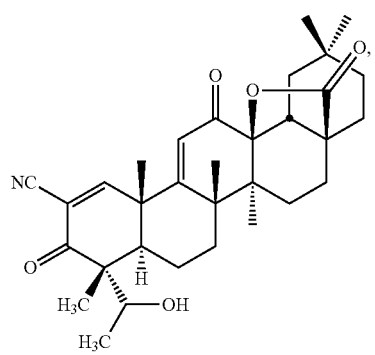
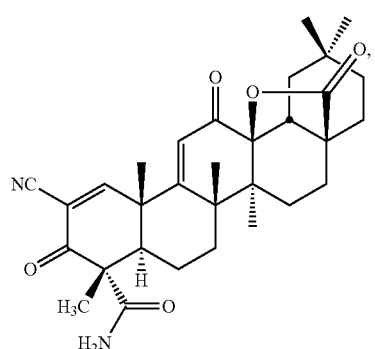
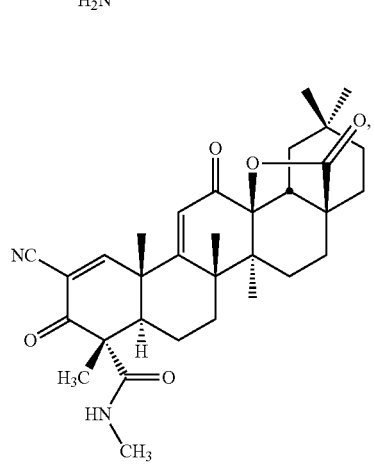

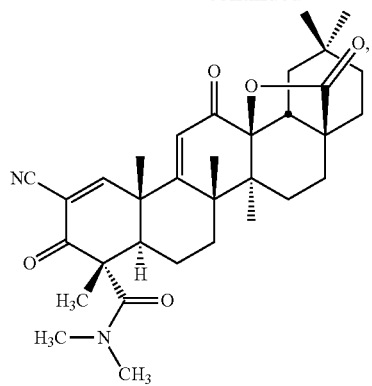
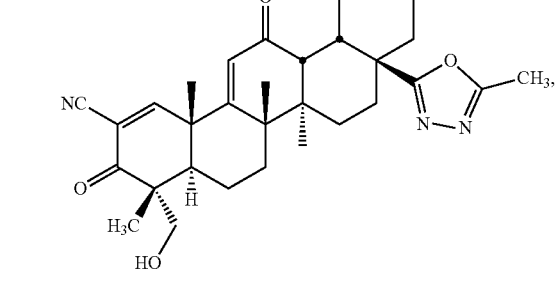
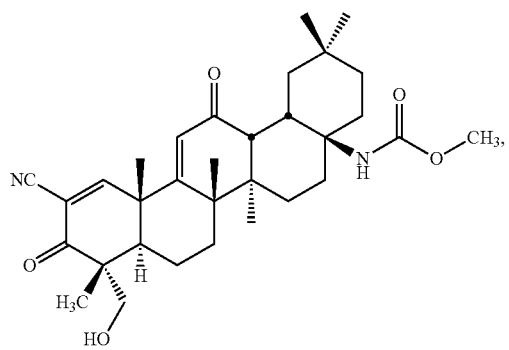
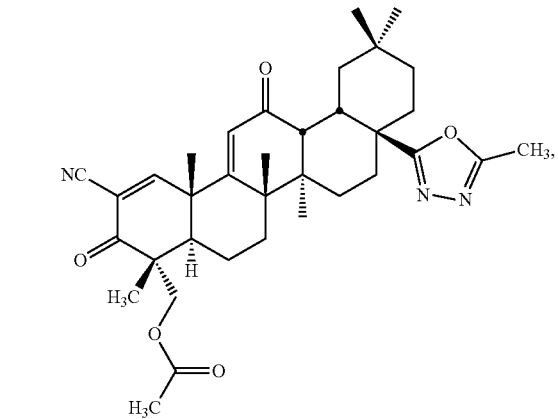
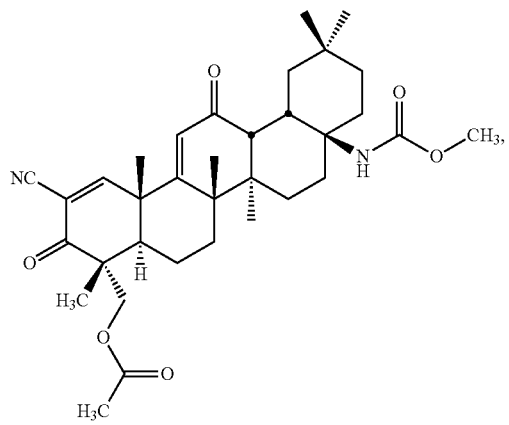
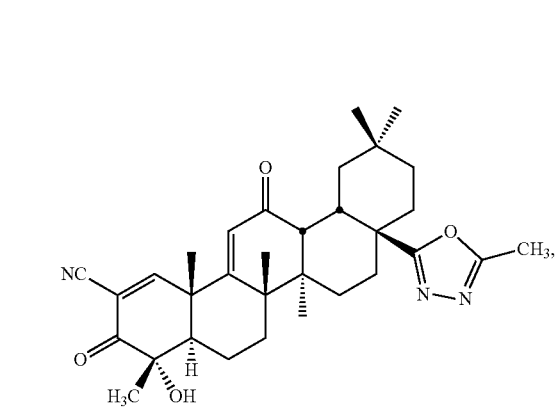
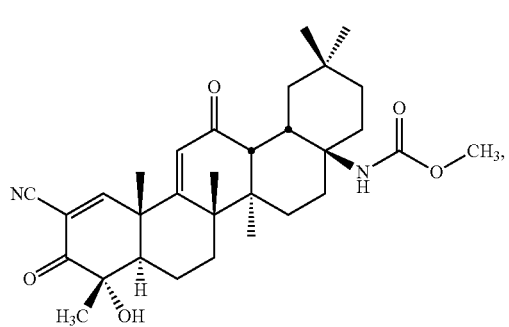
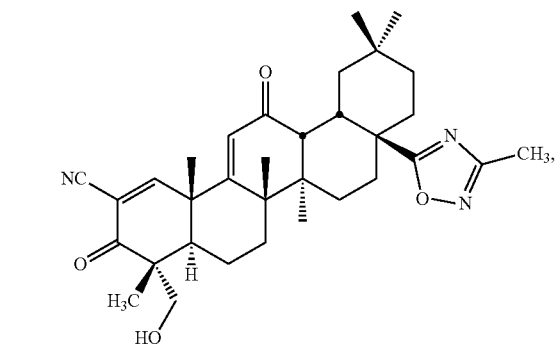

-continued
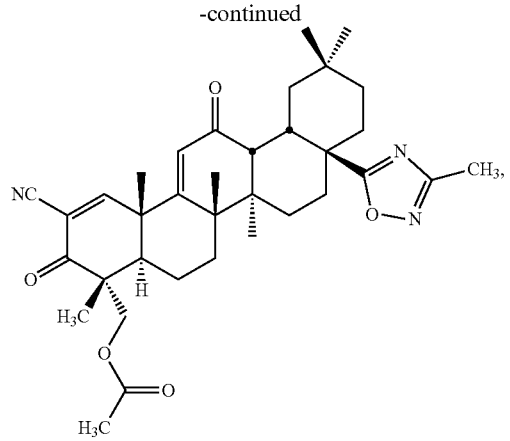
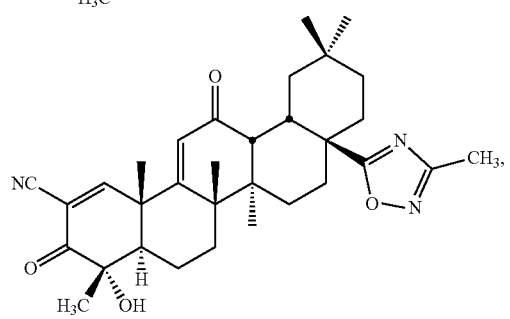
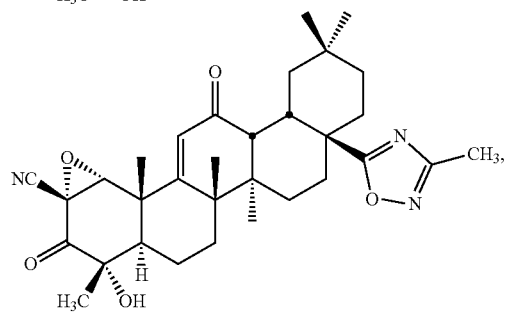
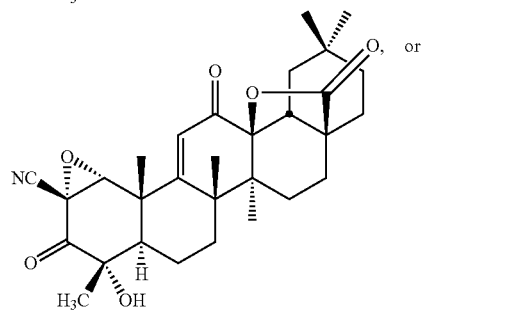
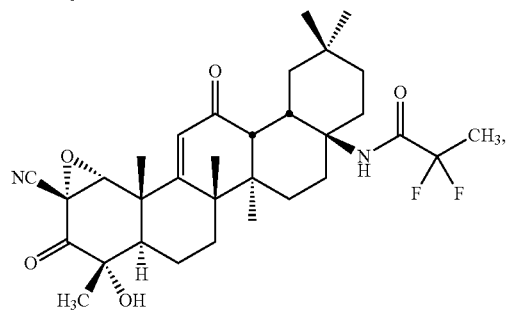
or a pharmaceutically acceptable salt, acetal, or hemiacetal thereof.
In some embodiments, the compounds are further defined as:
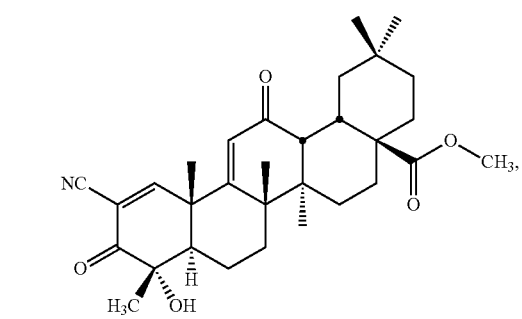
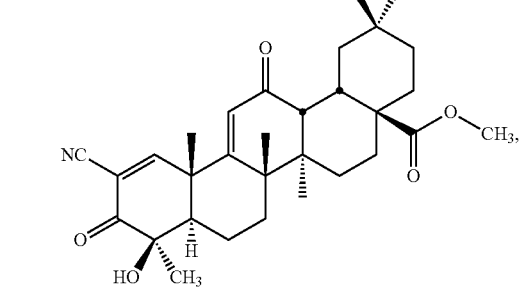
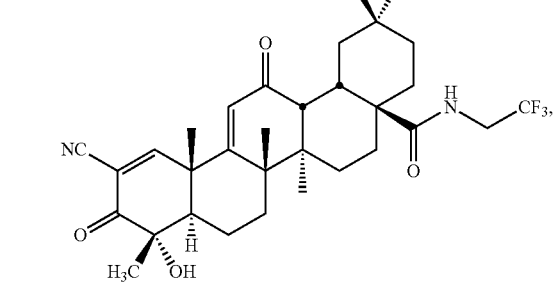
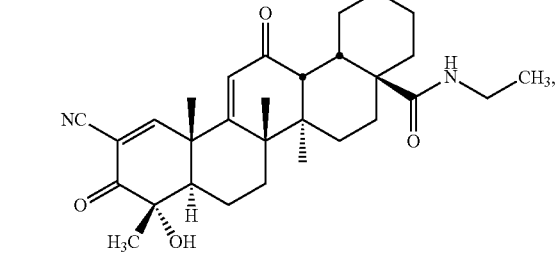
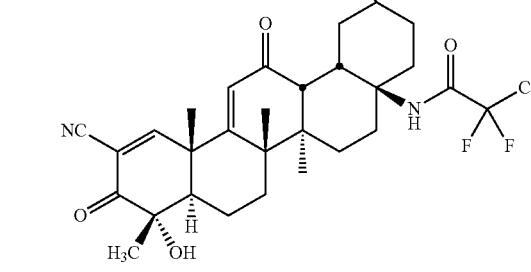

51
-continued
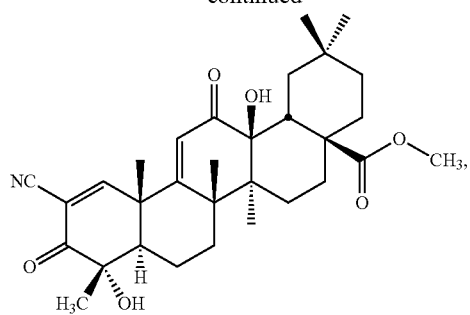
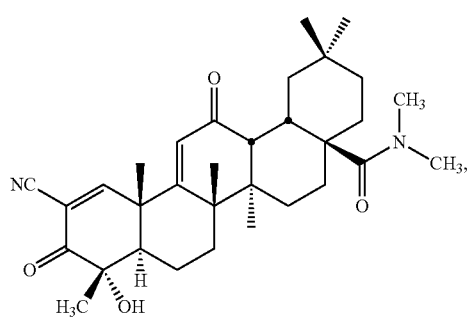
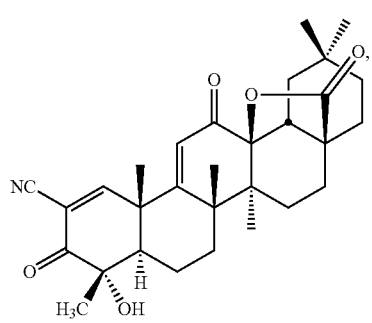
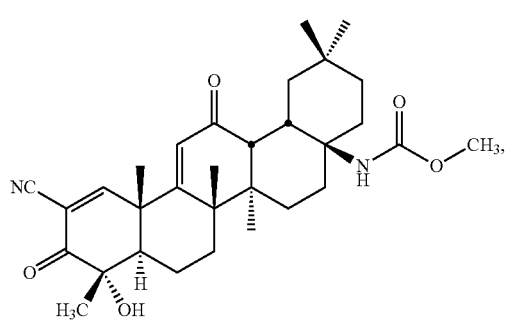
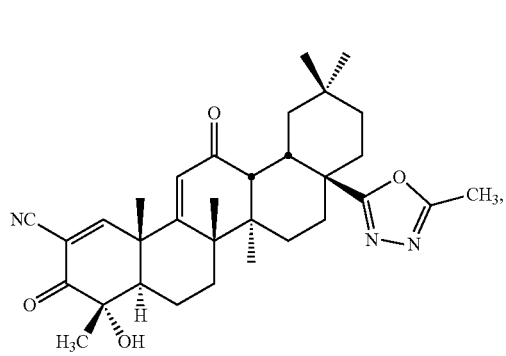
52
-continued
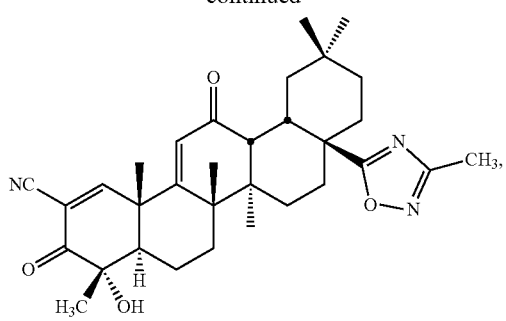
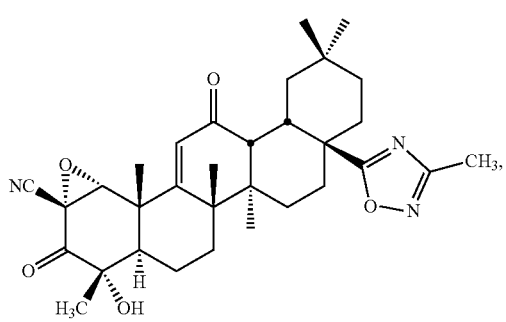
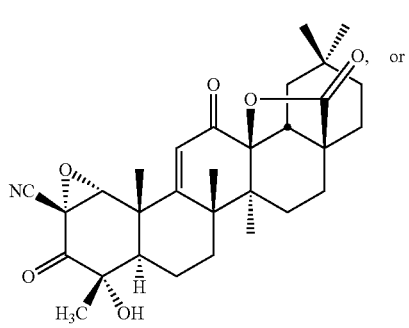
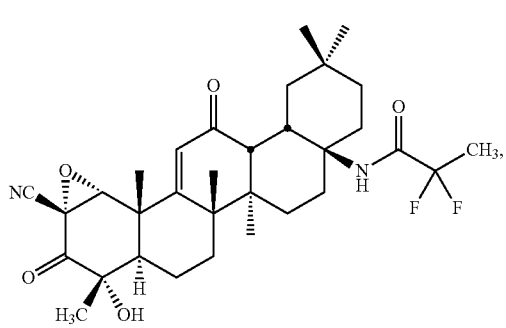
or a pharmaceutically acceptable salt, acetal, or hemiacetal thereof.

In other embodiments, the compounds are further defined as:
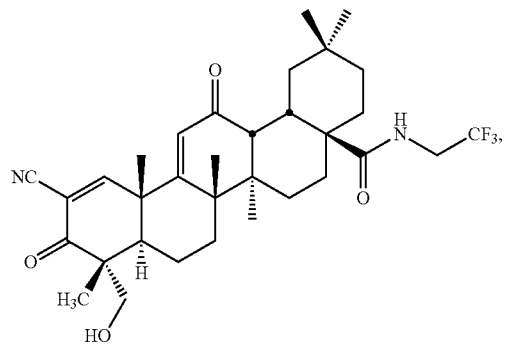
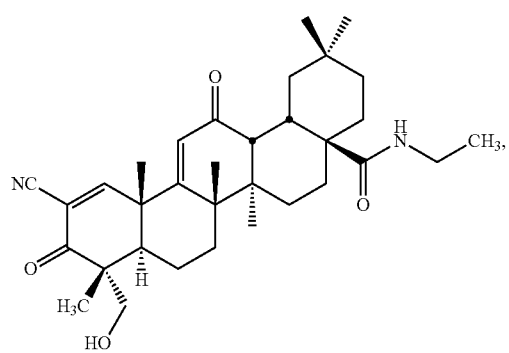
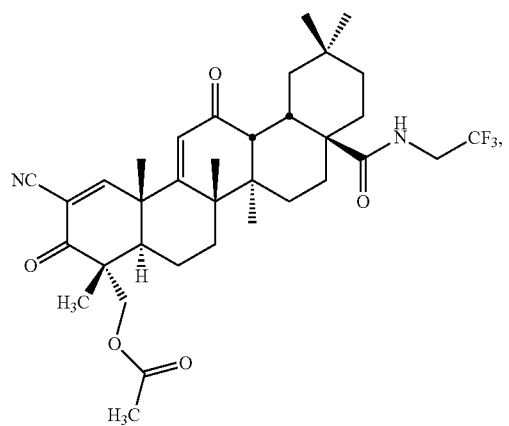
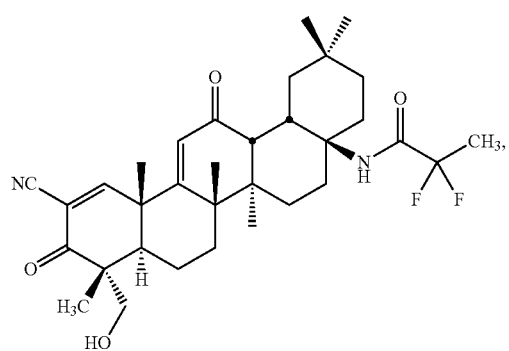
-continued
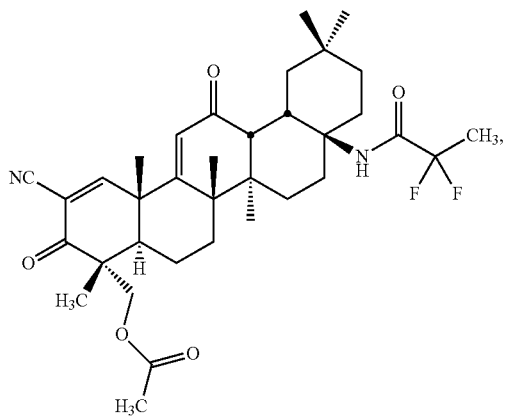
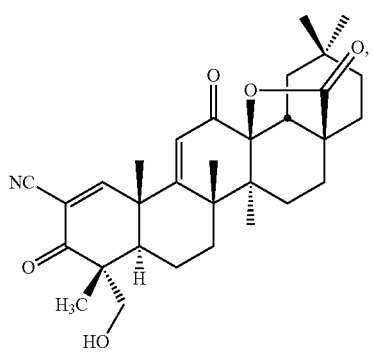
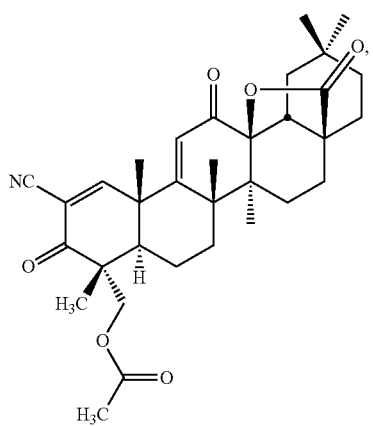
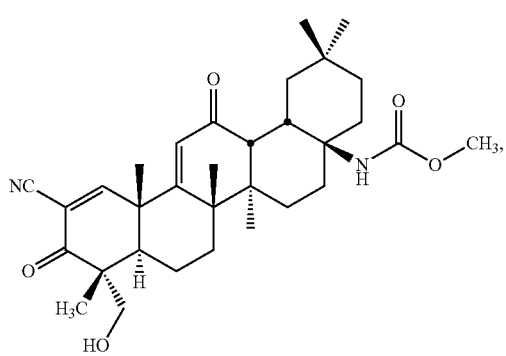

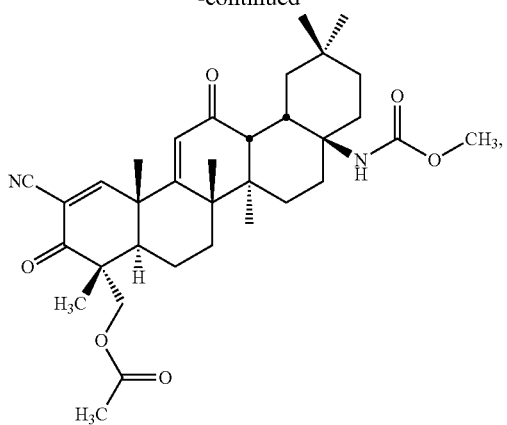
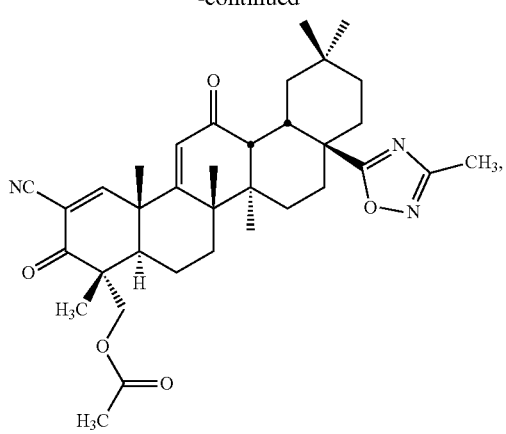
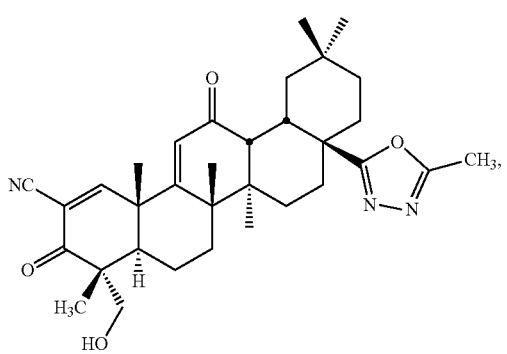
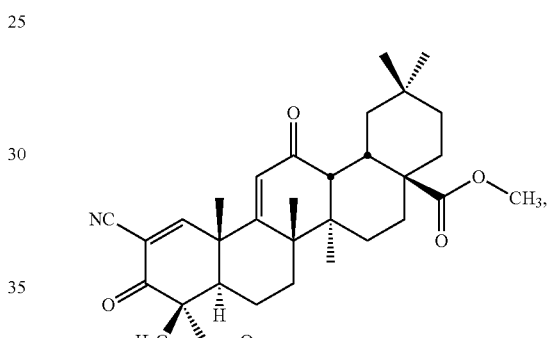
or a pharmaceutically acceptable salt, acetal, or hemiacetal thereof.
In other embodiments, the compounds are further defined as:
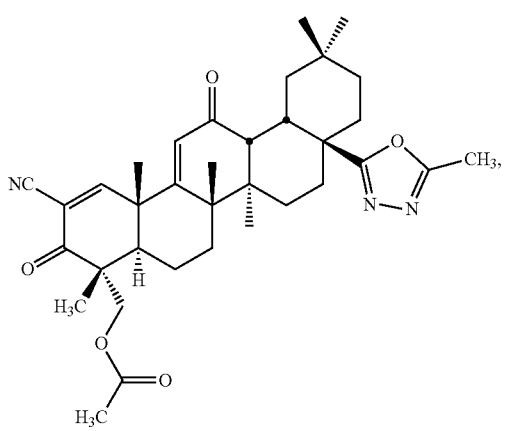
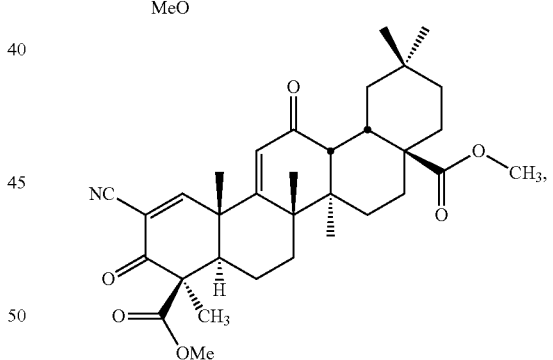
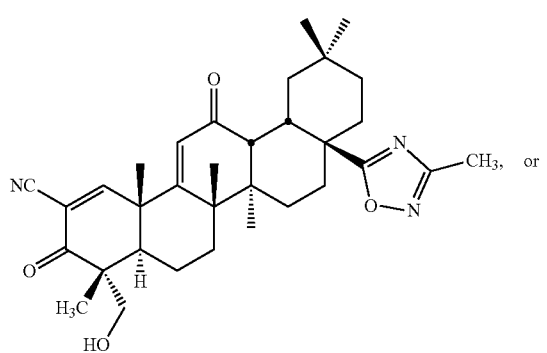
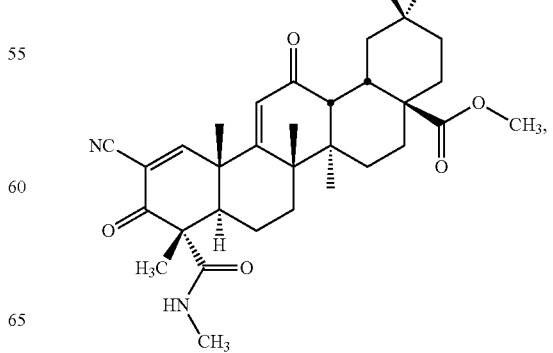

57
-continued
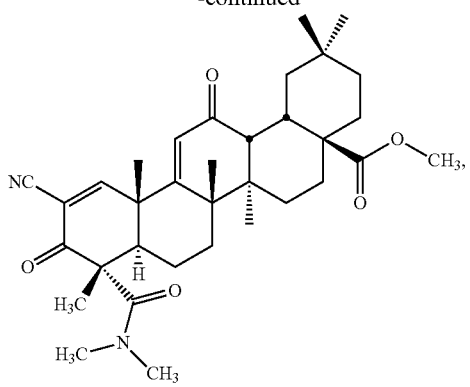
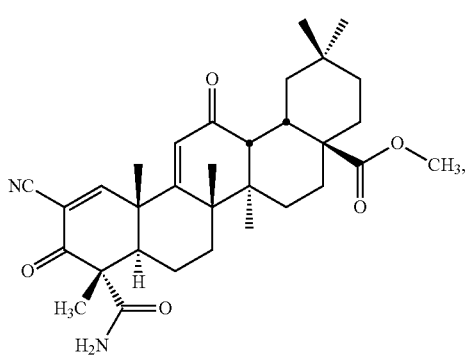
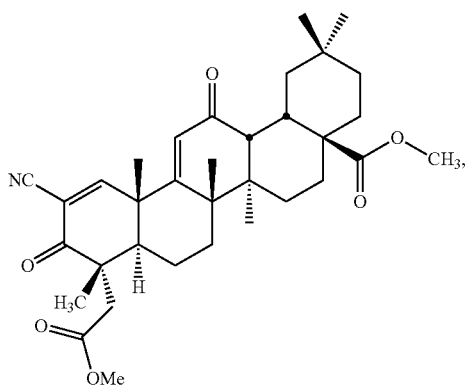
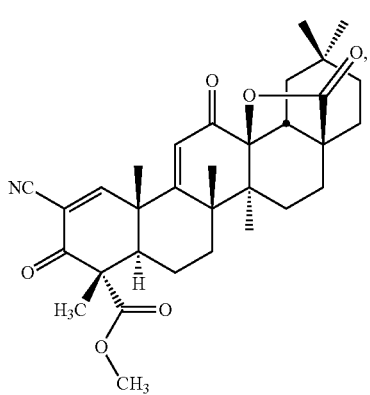
58
-continued
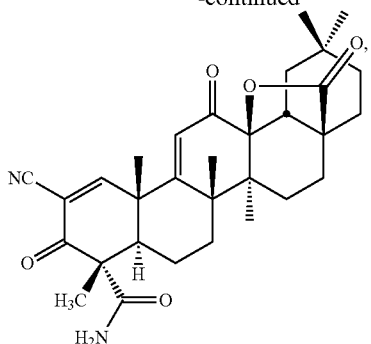
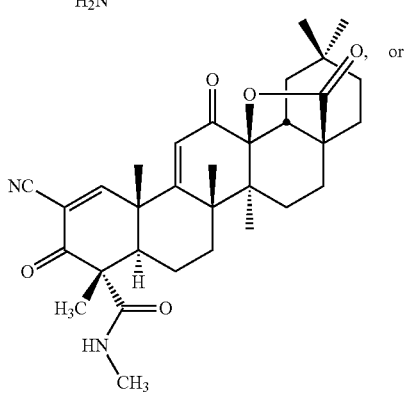
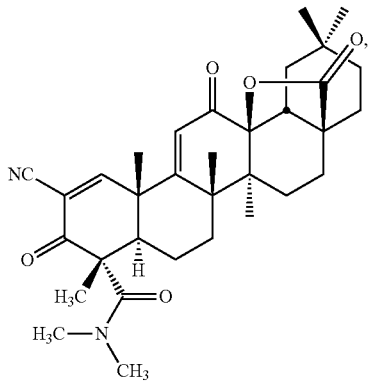
or a pharmaceutically acceptable salt, acetal, or hemiacetal thereof.
In other embodiments, the compounds are further defined as:
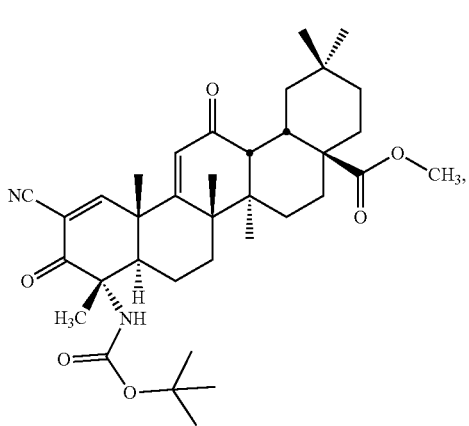

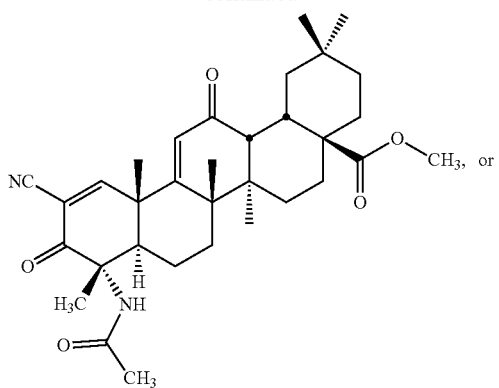
or a pharmaceutically acceptable salt, acetal, or hemiacetal thereof.
In other embodiments, the compounds are further defined as:
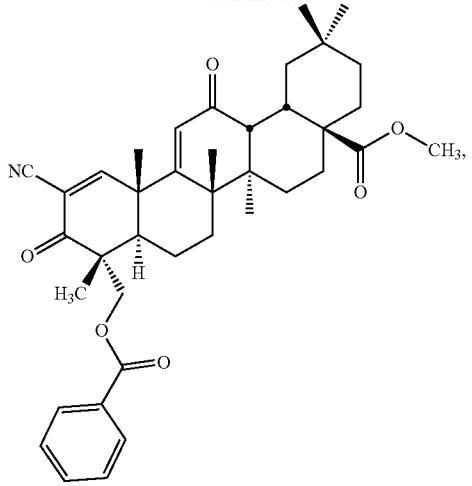
or a pharmaceutically acceptable salt, acetal, or hemiacetal thereof.
In another aspect, the present disclosure provides compounds of the formula:

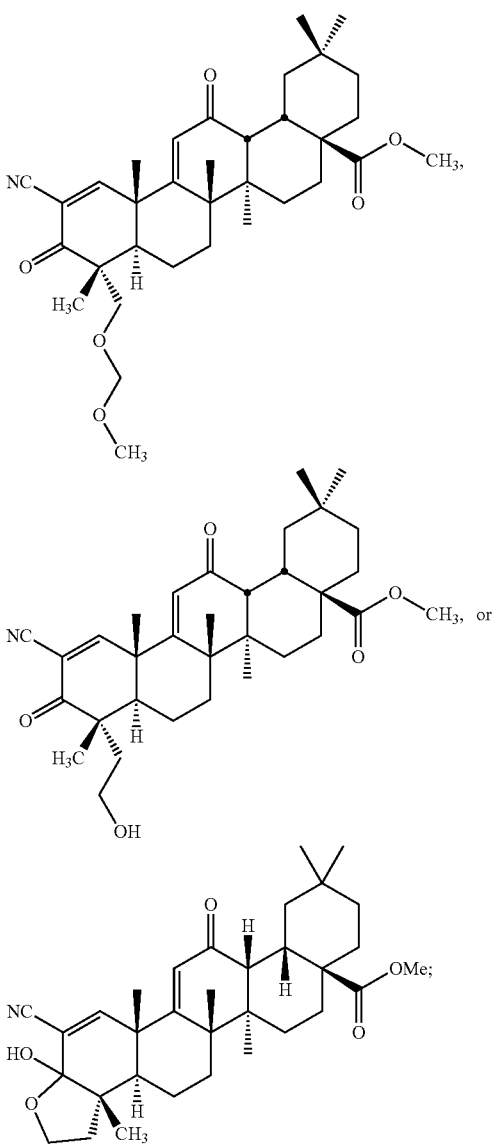

or a pharmaceutically acceptable salt, acetal, or hemiacetal thereof.

In still yet another aspect, the present disclosure provides compounds further defined as:

dimethyl (4S,4aR,6aS,6bR,8aS,12aS,12bR,14bS)-2-cyano-4,6a,6b,11,11,14b-hexamethyl-3,13-dioxo-4,4a,5,6,6a,6b,7,8,9,10,11,12,12a,12b,13,14b-hexadecahydropicene-4,8a(3H)-dicarboxylate;

dimethyl (4R,4aR,6aS,6bR,8aS,12aS,12bR,14bS)-2-cyano-4,6a,6b, 11,11,14b-hexamethyl-3,13-dioxo-4,4a,5,6,6a,6b,7,8,9,10,11,12,12a,12b,13,14b-hexadecahydropicene-4,8a(3H)-dicarboxylate;

methyl (4aS,6aR,6bS,8aR,9S,12aS,14aR,14bS)-11-cyano-9-(difluoromethyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-1-cyano-9-hydroxy-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9R,12aS,14aR,14bS)-11-cyano-9-hydroxy-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9R,12aS,14aR,14bS)-9-(acetoxymethyl)-11-cyano-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9R,12aS,14aR,14bS)-9-((benzoyloxy)methyl)-11-cyano-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-9-((tert-butoxycarbonyl)amino)-1-cyano-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-9-acetamido-11-cyano-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-9-amino-11-cyano-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-11-cyano-2,2,6a,6b,9,12a-hexamethyl-9-(methylcarbamoyl)-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-1-cyano-9-(dimethylcarbamoyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9R,12aS,14aR,14bS)-11-cyano-2,2,6a,6b,9,12a-hexamethyl-9-(5-methyl-1,3,4-oxadiazol-2-yl)-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-11-cyano-9-(2-methoxyethyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-9-carbamoyl-11-cyano-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-9-(2-((tert-butyldimethylsilyl)oxy)ethyl)-11-cyano-2,2,6a,6b,9,12a-hexamethyl-10,14-dioxo-1,3,4,5,6,6a,6b,7,8,8a,9,10,12a,14,14a, 14b-hexadecahydropicene-4a(2H)-carboxylate;

methyl (4aS,6aR,6bS,8aR,9R,12aS,14aR,14bS)-1-cyano-9-(methoxymethyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-11-cyano-9-(2-methoxy-2-oxoethyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

(4aS,6aR,6bS,8aR,9R,12aS,14aR,14bS)-11-cyano-9-(hydroxymethyl)-2,2,6a,6b,9,12a-hexamethyl-10,14-dioxo-N-(2,2,2-trifluoroethyl)-1,3,4,5,6,6a,6b,7,8,8a,9,10,12a,14,14a,14b-hexadecahydropicene-4a(2H)-carboxamide;

(4aS,6aR,6bS,8aR,9R,12aS,14aR,14bS)-11-cyano-N-ethyl-9-(hydroxymethyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxamide;

((4R,4aR,6aS,6bR,8aS,12aS,12bR,14bS)-2-cyano-4,6a,6b, 11,11,14b-hexamethyl-3,13-dioxo-8a-((2,2,2-trifluoroethyl)carbamoyl)-3,4,4a,5,6,6a,6b,7,8,8a,9,10,11,12,12a,12b,13,14b-octadecahydropicen-4-yl)methyl acetate;

(4aS,6aR,6bS,8aR,9S,12aS,14aR,14bS)-11-cyano-9-hydroxy-2,2,6a,6b,9,12a-hexamethyl-10,14-dioxo-N-(2,2,2-trifluoroethyl)-1,3,4,5,6,6a,6b,7,8,8a,9,10,12a,14,14a,14b-hexadecahydropicene-4a(2H)-carboxamide;

(4aS,6aR,6bS,8aR,9S,12aS,14aR,14bS)-11-cyano-N-ethyl-9-hydroxy-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxamide;

N-((4aS,6aR,6bS,8aR,9R,12aS,14aR,14bS)-11-cyano-9-(hydroxymethyl)-2,2,6a,6b,9,12a-hexamethyl-10,14-dioxo-1,3,4,5,6,6a,6b,7,8,8a,9,10,12a,14,14a,14b-hexadecahydropicen-4a(2H)-yl)-2,2-difluoropropanamide;

N-((4aS,6aR,6bS,8aR,9S,12aS,14aR,14bS)-11-cyano-9-hydroxy-2,2,6a,6b,9,12a-hexamethyl-10,14-dioxo-1,3,4,5,6,6a,6b,7,8,8a,9,10,12a,14,14a,14b-hexadecahydropicen-4a(2H)-yl)-2,2-difluoropropanamide;

((4R,4aR,6aS,6bR,8aS,12aS,12bR,14bS)-2-cyano-8a-(2,2-difluoropropanamido)-4,6a,6b,11,11,14b-hexamethyl-3,13-dioxo-3,4,4a,5,6,6a,6b,7,8,8a,9,10,11,12,12a,12b,13,14b-octadecahydropicen-4-yl)methyl acetate;

methyl (4aS,6aS,6bR,8aR,9S,12aS,14aS,14bR)-11-cyano-9,14a-dihydroxy-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

(4aS,6aR,6bS,8aR,9S,12aS,14aR,14bS)-11-cyano-9-hydroxy-N,N,2,2,6a,6b,9,12a-octamethyl-10,14-dioxo-1,3,4,5,6,6a,6b,7,8,8a,9,10,12a,14,14a,14b-hexadecahydropicene-4a(2H)-carboxamide;

(4S,4aR,6aR,6bS,8aS,12aR,12bS,14bS)-4-hydroxy-4,6a,6b,11,11,14b-hexamethyl-3,13,16-trioxo-4,4a,5,6,6a,6b,7,8,10,11,12,12a,13,14b-tetradecahydro-3H,9H-12b,8a-(epoxymethano)picene-2-carbonitrile;

(4R,4aR,6aR,6bS,8aS,12aR,12bS,14bS)-4-(hydroxymethyl)-4,6a,6b,11,11,14b-hexamethyl-3,13,16-trioxo-4,4a,5,6,6a,6b,7,8,10,11,12,12a,13,14b-tetradecahydro-3H,9H-12b,8a-(epoxymethano)picene-2-carbonitrile;

((4R,4aR,6aR,6bS,8aS,12aR,12bS,14bS)-2-cyano-4,6a,6b,11,11,14b-hexamethyl-3,13,16-trioxo-4,4a,5,6,6a,6b,7,8,10,11,12,12a,13,14b-tetradecahydro-3H,9H-12b,8a-(epoxymethano)picen-4-yl)methyl acetate;

methyl (4S,4aR,6aR,6bS,8aS,12aR,12bS,14bS)-2-cyano-4,6a,6b,11,11,14b-hexamethyl-3,13,16-trioxo-4,4a,5,6,6a,6b,7,8,10,11,12,12a,13,14b-tetradecahydro-3H,9H-12b,8a-(epoxymethano)picene-4-carboxylate;

(4R,4aR,6aR,6bS,8aS,12aR,12bS,14bS)-4-((S)-1-hydroxyethyl)-4,6a,6b,11,11,14b-hexamethyl-3,13,16-trioxo-4,4a,5,6,6a,6b,7,8,10,11,12,12a,13,14b-tetradecahydro-3H,9H-12b,8a-(epoxymethano)picene-2-carbonitrile;

(4S,4aR,6aR,6bS,8aS,12aR,12bS,14bS)-2-cyano-4,6a,6b,11,11,14b-hexamethyl-3,13,16-trioxo-4,4a,5,6,6a,6b,7,8,10,11,12,12a,13,14b-tetradecahydro-3H,9H-12b,8a-(epoxymethano)picene-4-carboxamide;

(4S,4aR,6aR,6bS,8aS,12aR,12bS,14bS)-2-cyano-N,4,6a,6b,11,11,14b-heptamethyl-3,13,16-trioxo-4,4a,5,6,6a,6b,7,8,10,11,12,12a,13,14b-tetradecahydro-3H,9H-12b,8a-(epoxymethano)picene-4-carboxamide;

(4S,4aR,6aR,6bS,8aS,12aR,12bS,14bS)-2-cyano-N,N,4,6a,6b,11,11,14b-octamethyl-3,13,16-trioxo-4,4a,5,6,6a,6b,7,8,10,11,12,12a,13,14b-tetradecahydro-3H,9H-12b,8a-(epoxymethano)picene-4-carboxamide;

methyl ((4aS,6aR,6bS,8aR,9R,12aS,14aR,14bS)-11-cyano-9-(hydroxymethyl)-2,2,6a,6b,9,12a-hexamethyl-10,14-dioxo-1,3,4,5,6,6a,6b,7,8,8a,9,10,12a,14,14a,14b-hexadecahydropicen-4a(2H)-yl)carbamate;

((4R,4aR,6aS,6bR,8aS,12aS,12bR,14bS)-2-cyano-8a-((methoxycarbonyl)amino)-4,6a,6b, 11,11,14b-hexamethyl-3,13-dioxo-3,4,4a,5,6,6a,6b,7,8,8a,9,10,11,12,12a,12b,13,14b-octadecahydropicen-4-yl)methyl acetate;

methyl ((4aS,6aR,6bS,8aR,9S,12aS,14aR,14bS)-11-cyano-9-hydroxy-2,2,6a,6b,9,12a-hexamethyl-10,14-dioxo-1,3,4,5,6,6a,6b,7,8,8a,9,10,12a,14,14a,14b-hexadecahydropicen-4a(2H)-yl)carbamate;

(4R,4aR,6aS,6bR,8aS,12aS,12bR,14bS)-4-(hydroxymethyl)-4,6a,6b, 11,11,14b-hexamethyl-8a-(5-methyl-1,3,4-oxadiazol-2-yl)-3,13-dioxo-3,4,4a,5,6,6a,6b,7,8,8a,9,10,11,12,12a,12b,13,14b-octadecahydropicene-2-carbonitrile;

((4R,4aR,6aS,6bR,8aS,12aS,12bR,14bS)-2-cyano-4,6a,6b,11,11,14b-hexamethyl-8a-(5-methyl-1,3,4-oxadiazol-2-yl)-3,13-dioxo-3,4,4a,5,6,6a,6b,7,8,8a,9,10,11,12,12a,12b,13,14b-octadecahydropicen-4-yl)methyl acetate;

(4S,4aR,6aS,6bR,8aS,12aS,12bR,14bS)-4-hydroxy-4,6a,6b,11,11,14b-hexamethyl-8a-(5-methyl-1,3,4-oxadiazol-2-yl)-3,13-dioxo-3,4,4a,5,6,6a,6b,7,8,8a,9,10,11,12,12a,12b,13,14b-octadecahydropicene-2-carbonitrile;

(4R,4aR,6aS,6bR,8aS,12aS,12bR,14bS)-4-(hydroxymethyl)-4,6a,6b, 11,11,14b-hexamethyl-8a-(3-methyl-1,2,4-oxadiazol-5-yl)-3,13-dioxo-3,4,4a,5,6,6a,6b,7,8,8a,9,10,11,12,12a,12b,13,14b-octadecahydropicene-2-carbonitrile;

((4R,4aR,6aS,6bR,8aS,12aS,12bR,14bS)-2-cyano-4,6a,6b,11,11,14b-hexamethyl-8a-(3-methyl-1,2,4-oxadiazol-5-yl)-3,13-dioxo-3,4,4a,5,6,6a,6b,7,8,8a,9,10,11,12,12a,12b,13,14b-octadecahydropicen-4-yl)methyl acetate;

(4S,4aR,6aS,6bR,8aS,12aS,12bR,14bS)-4-hydroxy-4,6a,6b,11,11,14b-hexamethyl-8a-(3-methyl-1,2,4-oxadiazol-5-yl)-3,13-dioxo-3,4,4a,5,6,6a,6b,7,8,8a,9,10,11,12,12a,12b,13,14b-octadecahydropicene-2-carbonitrile;

(1aR,3S,3aR,5aS,5bR,7aS,11aS,11bR,13bS,13cR)-3-hydroxy-3,5a,5b, 10,10,13b-hexamethyl-7a-(3-methyl-1,2,4-oxadiazol-5-yl)-2,12-dioxo-3,3a,4,5,5a,5b,6,7,7a,8,9,10,11,11a,11b,12,13b,13c-octadecahydropiceno[1,2-b]oxirene-1a(2H)-carbonitrile;

(1aR,3S,3aR,5aR,5bS,7aS,11aR,11bS,13bS,13cR)-3-hydroxy-3,5a,5b,10,10,13b-hexamethyl-2,12,15-trioxo-3,3a,4,5,5a,6,7,9,10,11,11a,12,13b,13c-tetradecahydro-2H,8H-11b,7a-(epoxymethano)piceno[1,2-b]oxirene-1a(5bH)-carbonitrile; and N-((1aR,3S,3aR,5aS,5bR,7aS,11aS,11bR,13bS,13cR)-1a-cyano-3-hydroxy-3,5a,5b,10,10,13b-hexamethyl-2,12-dioxo-1a,3,3a,4,5,5a,5b,6,7,8,9,10,11,11a,11b,12,13b,13c-octadecahydropiceno[1,2-b]oxiren-7a(2H)-yl)-2,2-difluoropropanamide.

In yet another aspect, the present disclosure provides compounds further defined as:

methyl (4aS,6aR,6bS,8aR,9R,12aS,14aR,14bS)-11-cyano-9-((methoxymethoxy)methyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate;

methyl (4aS,6aR,6bS,8aR,9S,12aS,14aR,14bS)-1-cyano-9-(2-hydroxyethyl)-2,2,6a,6b,9,12a-hexamethyl-10,14-dioxo-1,3,4,5,6,6a,6b,7,8,8a,9,10,12a,14,14a,14b-hexadecahydropicene-4a(2H)-carboxylate; and methyl (3aS,3bR,5aS,5bR,7aS,11aS,11bR,13bS)-15-cyano-15a-hydroxy-3a,5a,5b,10,10,13b-hexamethyl-12-oxo-2,3,3a,4,5,5a,5b,6,7,8,9,10,11,11a,11b,12,13b, 15a-octadecahydropiceno[3,4-b]furan-7a(3bH)-carboxylate.

In another aspect, the present disclosure provides pharmaceutical compositions comprising:

(A) a compound described herein; and
(B) an excipient or a pharmaceutically acceptable carrier.

In some embodiments, the compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In still yet another aspect, the present disclosure provides methods of treating or preventing a disease or disorder in a patient in need thereof comprising administering to the patient a therapeutically effective amount of a compound or composition described herein. In some embodiments, the patient is a mammal, for example, the patient is a human. In some embodiments, the disease or disorder is associated with increased production of cytokine IL-17. In some embodiments, the disease or disorder is associated with dysregulated angiogenesis.

In some embodiments, the disease or disorder is an autoimmune disease, organ rejection, asthma, cancer, a neurological disorder, a psychiatric disorder, a neuropsychiatric disorder, chronic pain syndrome, an inflammatory condition, or a cardiovascular disease. In some embodiments, the autoimmune disease is psoriasis, multiple sclerosis, scleroderma, rheumatoid arthritis, lupus, psoriatic arthritis, ankylosing spondylitis, Sjögren syndrome, vitiligo, uveitis, systemic sclerosis, type 1 diabetes, myasthenia gravis, and inflammatory bowel disease. In some embodiments, the cardiovascular disease is vasculitis, atherosclerosis, myocardial infarction, myocarditis, heart failure, pulmonary hypertension, or stroke. In some embodiments, the neurological disorder is epilepsy, multiple sclerosis, spinal cord injury, Guillain-Barre syndrome, or a neurological disorder. In some embodiments, the neurodegenerative disorder is Alzheimer's disease, Parkinson's disease, amyotrophic lateral sclerosis, or Huntington's disease. In some embodiments, the inflammatory condition is pancreatitis, hepatitis, pulmonary fibrosis, cystic fibrosis, chronic obstructive pulmonary disease, asthma, dermatitis, gastritis, esophagitis, irritable bowel syndrome, inflammatory bowel disease, nephritis, muscle wasting, or osteoarthritis. In some embodiments, the chronic pain syndrome is fibromyalgia or neuropathic pain. In other embodiments, the disease or disorder is a severe inflammatory response to a pathogen. In some embodiments, the severe inflammatory response to a pathogen is from encephalitis, meningitis, *H. pylori*, *Toxoplasma gondii*, or *Leishmania* spp. In other embodiments, the disease or disorder is obesity or a condition associated with obesity. In some embodiments, the condition associated with obesity are insulin resistance or fatty liver disease.

In some embodiments, the method comprises administering the compound once. In other embodiments, the method comprises administering the compound two or more times.

In still yet another aspect, the present disclosure provides methods of inhibiting the activity of an interleukin 17 comprising contacting the interleukin 17 with an effective amount of a compound or composition described herein. In some embodiments, the methods comprise inhibiting the activity of interleukin 17 in vivo. In some embodiments, the methods comprise contacting the interleukin comprises administering the compound to a patient in need thereof. In some embodiments, the compounds also inhibit the production of nitric oxide in vivo. In some embodiments, the inhibition of interleukin 17 activity is sufficient to treat a disease or disorder. In some embodiments, the disease or disorder is associated with the misregulation of interleukin 17. In other embodiments, the disease or disorder is associated with inflammation. In other embodiments, the disease or disorder is associated with the misregulation of nitric oxide production.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions that may be used to prevent or inhibit excessive production of IL-17, reduce circulating levels of IL-17, and/or prevent or treat wide range of diseases or disorders, including those with inflammatory and autoimmune-related components.

I. COMPOUNDS AND SYNTHETIC METHODS

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in March's *Advanced Organic Chemistry: Reactions, Mechanisms, and Structure* (2007), which is incorporated by reference herein.

In some embodiments, the present disclosure provides compounds of the formula:

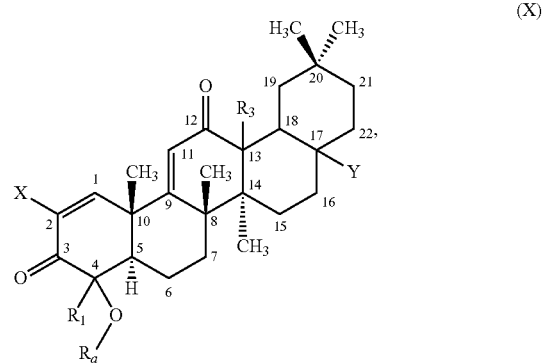

(X)

-continued

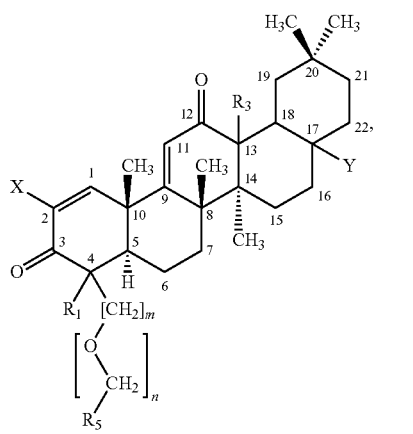

(XI)

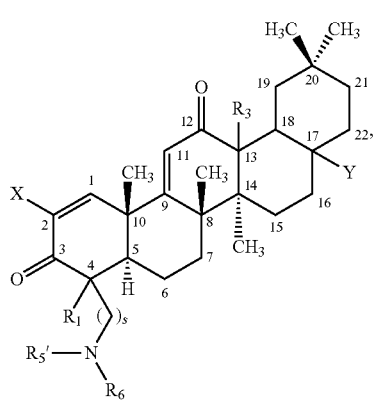

(XII)

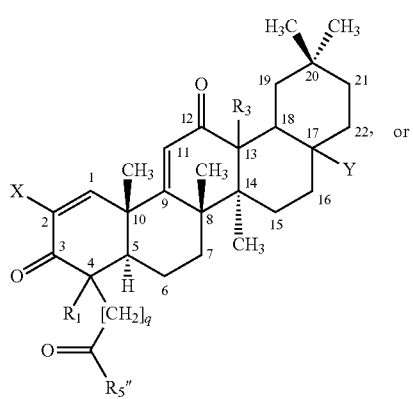

(XIII) or

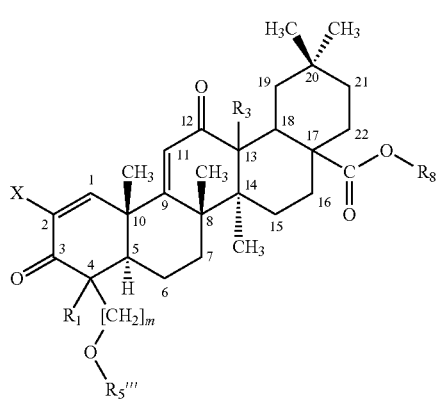

(XIV)

wherein:
X is cyano, heteroaryl$_{(C \leq 8)}$, substituted heteroaryl$_{(C \leq 8)}$, —CF$_3$, or —C(O)—R$_4$; wherein
   R$_4$ is hydroxy, amino, or alkoxy$_{(C \leq 8)}$, alkylamino$_{(C \leq 8)}$, dialkylamino$_{(C \leq 8)}$, alkylsulfonylamino$_{(C \leq 8)}$, or a substituted version of any of these groups;
R$_1$ is hydrogen, alkyl$_{(C \leq 8)}$, cycloalkyl$_{(C \leq 8)}$, substituted alkyl$_{(C \leq 8)}$, or substituted cycloalkyl$_{(C \leq 8)}$;
R$_3$ is hydrogen, hydroxy, or alkoxy$_{(C \leq 8)}$, acyloxy$_{(C \leq 8)}$, or substituted version of either of these groups; or R$_3$ is taken together with Y as described below;
R$_a$ is hydrogen or alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 12)}$, heterocycloalkyl$_{(C \leq 8)}$, acyl$_{(C \leq 8)}$, or a substituted version of any of these groups;
R$_5$ is hydroxy or acyl$_{(C \leq 8)}$, alkoxy$_{(C \leq 8)}$, acyloxy$_{(C \leq 8)}$, alkylsilyloxy$_{(C \leq 8)}$, or a substituted version of any of these groups;
R$_5$' is hydrogen, alkyl$_{(C \leq 8)}$, alkoxy$_{(C \leq 8)}$, substituted alkoxy$_{(C \leq 8)}$, acyl$_{(C \leq 8)}$, substituted acyl$_{(C \leq 8)}$, —C(O)-alkoxy$_{(C \leq 8)}$, substituted —C(O)-alkoxy$_{(C \leq 8)}$, acyloxy$_{(C \leq 8)}$, substituted acyloxy$_{(C \leq 8)}$, alkylsilyloxy$_{(C \leq 8)}$, or substituted alkylsilyloxy$_{(C \leq 8)}$;
R$_5$" is hydrogen, amino, hydroxy, or mercapto; or
   alkyl$_{(C \leq 8)}$, cycloalkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, alkoxy$_{(C \leq 8)}$, alkylthio$_{(C \leq 8)}$, alkylamino$_{(C \leq 8)}$, dialkylamino$_{(C \leq 8)}$, or a substituted version of any of these groups;
R$_5$''' is alkyl$_{(C \leq 8)}$, acyl$_{(C \leq 8)}$, substituted acyl$_{(C \leq 8)}$, alkylsilyl$_{(C \leq 8)}$, or substituted alkylsilyl$_{(C \leq 8)}$;
R$_6$ is hydrogen, alkyl$_{(C \leq 8)}$, or substituted alkyl$_{(C \leq 8)}$;
R$_8$ is hydrogen, alkyl$_{(C \leq 8)}$, cycloalkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, or a substituted version of any of these groups;
m is 1, 2, 3, or 4;
n is 0, 1, 2, or 3;
q is 0, 1, 2, 3, or 4;
s is 0, 1, 2, 3, or 4; and
provided that if the compound is further defined by formulas I, III, and IV then Y is hydrogen, hydroxy, halo, amino, cyano, isocyanate, or mercapto;
   alkyl$_{(C \leq 8)}$, cycloalkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, alkoxy$_{(C \leq 8)}$, cycloalkoxy$_{(C \leq 8)}$, aryloxy$_{(C \leq 12)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, alkylthio$_{(C \leq 8)}$, acylthio$_{(C \leq 8)}$, alkylsulfonylamino$_{(C \leq 8)}$, or substituted versions of any of these groups;
   -alkanediyl$_{(C \leq 8)}$-R$_b$, -alkenediyl$_{(C \leq 8)}$-R$_b$, or a substituted version of any of these groups, wherein R$_b$ is: hydrogen, hydroxy, halo, amino or mercapto; or
   heteroaryl$_{(C \leq 8)}$, alkoxy$_{(C \leq 8)}$, cycloalkoxy$_{(C \leq 8)}$, alkenyloxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, heteroarylamino$_{(C \leq 8)}$, alkylsulfonylamino$_{(C \leq 8)}$, amido$_{(C \leq 8)}$, —OC(O)NH-alkyl$_{(C \leq 8)}$, —OC(O)CH$_2$NHC(O)O-t-butyl, —OCH$_2$-alkylthio$_{(C \leq 8)}$, or a substituted version of any of these groups;
   —(CH$_2$)$_o$C(O)R$_c$, wherein o is 0-6 and R$_c$ is:
   hydrogen, halo, hydroxy, amino, —NHOH, or mercapto; or
   alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkoxy$_{(C \leq 8)}$, cycloalkoxy$_{(C \leq 8)}$, alkenyloxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkylamino$_{(C \leq 8)}$, dialkylamino$_{(C \leq 8)}$, arylamino$_{(C \leq 8)}$, alkylsulfonylamino$_{(C \leq 8)}$, amido$_{(C \leq 8)}$, alkoxyamino$_{(C \leq 8)}$, heterocycloalkylamino$_{(C \leq 8)}$, —NHC(NOH)-alkyl$_{(C \leq 8)}$, —NH-amido$_{(C \leq 8)}$, or a substituted version of any of these groups;

—NR$_d$C(O)R$_e$, wherein
R$_d$ is hydrogen, alkyl$_{(C \leq 8)}$, or substituted alkyl$_{(C \leq 8)}$;
R$_e$ is hydrogen, hydroxy, amino; or
alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkoxy$_{(C \leq 8)}$, cycloalkoxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkylamino$_{(C \leq 8)}$, dialkylamino$_{(C \leq 8)}$, arylamino$_{(C \leq 8)}$, or a substituted version of any of these groups; or Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C \leq 8)}$, substituted alkyl$_{(C \leq 8)}$, acyl$_{(C \leq 8)}$, or substituted acyl$_{(C \leq 8)}$; or if the compound is further defined by formulas II, then Y is hydrogen, hydroxy, halo, amino, cyano, isocyanate, or mercapto;
alkyl$_{(C \leq 8)}$, cycloalkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, alkoxy$_{(C \leq 8)}$, cycloalkoxy$_{(C \leq 8)}$, aryloxy$_{(C \leq 12)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, alkylthio$_{(C \leq 8)}$, acylthio$_{(C \leq 8)}$, alkylsulfonylamino$_{(C \leq 8)}$, or substituted versions of any of these groups;

-alkanediyl$_{(C \leq 8)}$-R$_b$, -alkenediyl$_{(C \leq 8)}$—R$_b$, or a substituted version of any of these groups, wherein R$_b$ is:
hydrogen, hydroxy, halo, amino or mercapto; or
heteroaryl$_{(C \leq 8)}$, alkoxy$_{(C \leq 8)}$, cycloalkoxy$_{(C \leq 8)}$, alkenyloxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, heteroarylamino$_{(C \leq 8)}$, alkylsulfonylamino$_{(C \leq 8)}$, amido$_{(C \leq 8)}$, —OC(O)NH-alkyl$_{(C \leq 8)}$, —OC(O)CH$_2$NHC(O)O-t-butyl, —OCH$_2$-alkylthio$_{(C \leq 8)}$, or a substituted version of any of these groups;

—(CH$_2$)$_o$C(O)R$_c$, wherein o is 0-6 and R$_c$ is:
hydrogen, halo, amino, —NHOH, or mercapto; or
alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkylamino$_{(C \leq 8)}$, dialkylamino$_{(C \leq 8)}$, arylamino$_{(C \leq 8)}$, alkyl-sulfonylamino$_{(C \leq 8)}$, amido$_{(C \leq 8)}$, alkoxyamino$_{(C \leq 8)}$, heterocycloalkylamino$_{(C \leq 8)}$, —NHC(NOH)-alkyl$_{(C \leq 8)}$, —NH-amido$_{(C \leq 8)}$, or a substituted version of any of these groups;

—NR$_d$C(O)R$_e$, wherein
R$_d$ is hydrogen, alkyl$_{(C \leq 8)}$, or substituted alkyl$_{(C \leq 8)}$;
R$_e$ is hydrogen, hydroxy, amino; or
alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, alkoxy$_{(C \leq 8)}$, cycloalkoxy$_{(C \leq 8)}$, aryloxy$_{(C \leq 8)}$, aralkoxy$_{(C \leq 8)}$, heteroaryloxy$_{(C \leq 8)}$, acyloxy$_{(C \leq 8)}$, alkylamino$_{(C \leq 8)}$, dialkylamino$_{(C \leq 8)}$, arylamino$_{(C \leq 8)}$, or a substituted version of any of these groups; or Y is taken together with R$_3$ and is —(CH$_2$)$_p$C(O)R$_f$—, wherein
p is 0-6; and
R$_f$ is —O— or —NR$_7$—; wherein:
R$_7$ is hydrogen, alkyl$_{(C \leq 8)}$, substituted alkyl$_{(C \leq 8)}$, acyl$_{(C \leq 8)}$, or substituted acyl$_{(C \leq 8)}$;

or a pharmaceutically acceptable salt, acetal, or hemiacetal thereof.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. In some embodiments of the present disclosure, the heteroatom containing group on carbon atom 4 of the formulas I and X-XIV is oriented away from the viewer such that the group appears on the opposite face of the ring system from the viewer and on the same face of the ring system as the hydrogen atom at carbon atom 5. As would be obvious to a person of skill in the art, the specific stereochemical configuration of this carbon atom depends on the identity of the particular substituents at R$_1$ and R$_2$ and is either the R or the S configuration.

Without being bound by theory, in some embodiments, the compounds provided herein having an S-configuration at carbon atom 4 exhibit retained inhibition of hIL17 while exhibiting reduced NRF2 activation and/or reduced suppression of IFNγ-induced NO production compared with their respective diastereomers having an R-configuration at carbon atom 4. In some embodiments, the present disclosure provides compounds exhibiting an IC$_{50}$<100 nM for inhibition of hIL17 as measure by determining the concentration required to inhibit using fluorescently tagged anti-IL17 antibodies, for example, as described in Example 2. In some of these embodiments, the IC$_{50}$ is less than 90 nM, 80 nM, 70 nM, 60 nM, or 50 nM. In some embodiments, the present disclosure provides compounds exhibiting an EC$_{2x}$>50 nM for the activation of NRF2 as measured by determining the concentration requirement to increase GST ARE Luciferase reporter activity by 2-fold in AREc32 cells relative to DMSO treated cells, for example, as described in Example 2. In some of these embodiments, the EC$_{2x}$ is greater than 60 nM, 70 nM, 80 nM, 90 nM, or 100 nM. In some embodiments, the present disclosure provides compounds exhibiting an IC$_{50}$>20 nM for the suppression of IFNγ-induced NO production, as measured by the concentration required to suppress 50% of IFNγ-induced nitric oxide production normalized to cell viability measured using the WST-1 reagent, for example, as described in Example 2. In some of these embodiments, the IC$_{50}$ is greater than 30 nM, 40 nM, 50 nM, 60 nM, or 70 nM.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof, are within the scope of the present invention.

II. DISEASES ASSOCIATED WITH INFLAMMATORY CYTOKINE IL-17

Various reports have implicated the inflammatory cytokine IL-17 in the pathogenesis of many autoimmune diseases, including rheumatoid arthritis, psoriasis and psoriatic arthritis, inflammatory bowel diseases (including but not limited to Crohn's disease), multiple sclerosis, autoimmune nephritis, autoimmune uveitis, Type 1 diabetes, and ankylosing spondylitis. A type of T lymphocyte known as a Th17 cell is a primary source of IL-17. There are multiple members of the IL-17 family. The first identified member, IL-17A, is commonly referred to as IL-17. IL-17 is composed of two monomers linked by disulfide bonds to form a homodimer (Miossec and Kolls, 2012). Aside from IL-17A, the other principal family member is IL-17F. Some evidence suggests that IL-17F and IL-17A, though they have many effects in common, may have different effects in certain settings such as lung inflammation. The IL-17 cytokines bind to IL-17 receptors (IL-17R) located in the membrane of select cell types. Although there are multiple subtypes of the IL-17 receptor, the IL-17RA/IL-17RC complex is required for the activity of IL-17A and IL-17F. IL-17RA has the unusual property of signaling through a pathway that involves an adaptor protein (ACT1) rather than the Janus kinase/signal transducer and activator of transcription (JAK/STAT) pathway employed by most interleukin receptors. Binding of IL-17A to IL-17RA activates the pro-inflammatory nuclear factor-kappa B (NF-κB) pathway and pro-inflammatory elements of the mitogen-activated protein kinase (MAPK) pathway such as JUN N-terminal kinase (JNK), p38 and extracellular signal-related kinase (ERK). IL-17 activity stimulates secretion of IL-6 and IL-8 from mesenchymal cells and leads to fever along with the accumulation of neutrophils in blood and tissue.

Aside from its contribution to acute inflammation, IL-17 also contributes to chronic inflammation (Miossec and Kolls, 2012). IL-17 stimulates the production of matrix metalloproteinases (MMPs), which among other effects can degrade cartilage in joints. IL-17 also increases the expression of receptor activator of NF-κB ligand (RANKL) in osteoblasts, leading to differentiation and activation of osteoclasts and bone degradation. Depending on the target cell that is exposed to it, IL-17 may stimulate the production of IL-6, IL-8, IL-1, tumor necrosis factor (TNF), MMPs, nitric oxide, or several other proteins that are implicated in inflammatory conditions (e.g., tissue factor, CCL20, G-CSF and GM-CSF).

Although IL-17 plays a role in the immune response to invading pathogens, excessive IL-17 activity has been implicated in pathologies associated with an excessive immune response to an infection. For example, IL-17 has been implicated in the severe neuroinflammation associated with *Toxoplasma gondii* infection and increased severity of lesions associated with *Leishmania* infection. In these and other cases, IL-17 appears to play a role in perpetuating the infection, promoting an excessive inflammatory response, and inhibiting clearance of the infectious agent (Waite and Skokos, 2012).

Drugs targeting IL-17 have entered clinical trials for a wide variety of inflammatory conditions, including psoriasis, rheumatoid arthritis, ankylosing spondylitis, uveitis, Behcet's disease, psoriatic arthritis, Crohn's disease, polymyalgia rheumatica, dry eye syndrome, multiple sclerosis, graft-versus-host disease, and asthma. Preclinical evidence also implicates IL-17 in the pathology of type 1 diabetes, and Th117 cells are elevated in patients with adult onset Still's disorder, another autoimmune disease. Activity of Th17 cells has been implicated in the development of graft-versus-host disease following allogeneic stem cell (i.e., bone marrow) transplantation (Fujiwara, et al., 2014). Given the large body of evidence to date, it is likely that therapies reducing the expression of IL-17 or otherwise reducing its levels in circulation or target tissues (e.g., anti-IL17 monoclonal antibodies) could have broad applications in the treatment of autoimmune diseases and other inflammatory conditions.

Overproduction of IL-17 or elevated numbers of Th17 cells have been reported in patient studies or animal models of a large number of conditions, including autoimmune diseases, neurological disorders, cardiovascular diseases, cancer, psychiatric and neuropsychiatric disorders, acute and chronic inflammatory conditions, chronic pain syndromes, organ rejection or graft-versus-host disease, or asthma and other allergic conditions.

Both the differentiation of Th17 cells and their production of IL-17 are regulated to a significant degree by the retinoid orphan receptor RORγt, a member of the nuclear hormone receptor family. Expression of RORγt is common to all types of Th17 cells, and plays a significant role in their differentiation as well as their activity. RORγ also regulates the production of IL-17 in other cell types, including gamma delta T cells, innate lymphoid cells, and lymphoid tissue inducer cells (Bronner et al., 2016). Inhibition of RORγt activity results in reduced expression of IL-17, and the identification of small molecule inhibitors of RORγt is currently an area of great interest in the pharmaceutical industry.

Compounds and compositions provided herein may be used to suppress IL-17 production in cultures of human T cells that are exposed to a mixture of cytokines known to induce differentiation into Th17 cells. In some embodiments, the ability to act as inverse agonists of RORγt is also demonstrated. Without wishing to be bound by any theory, it is believed that for examples RORγt-independent mechanisms appear to contribute to the suppression of IL-17 production. Thus, the compounds and compositions provided herein may be used for inhibiting differentiation of T cells into Th17 cells, as well as inhibiting production of IL-17 by mature Th17 cells. In both cases, the net result is a reduction in IL-17 levels. In some embodiments, the compounds provided herein may be used for the treatment or prevention of any of the disordered discussed in this section.

III. PHARMACEUTICAL FORMULATIONS AND ROUTES OF ADMINISTRATION

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound of the present invention formulated with one or more excipients and/or drug carriers appropriate to the indicated route of administration. In some embodiments, the compounds of the present invention are formulated in a manner amenable for the treatment of human and/or veterinary patients. In some embodiments, formulation comprises admixing or combining one or more of the compounds of the present invention with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

Pharmaceutical formulations may be administered by a variety of methods, e.g., orally or by injection (e.g. subcutaneous, intravenous, intraperitoneal, etc.). Depending on the route of administration, the compounds of the present invention may be coated in a material to protect the compound from the action of acids and other natural conditions which may inactivate the compound. To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds of the present invention may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds of the present invention can be administered orally, for example, with an inert diluent or an assimilable edible carrier. The compounds and other ingredients may also be enclosed in a hard or soft shell gelatin capsule, compressed into tablets, or incorporated directly into the subject's diet. For oral therapeutic administration, the compounds of the present invention may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

In some embodiments, the therapeutic compound may also be administered topically to the skin, eye, or mucosa. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., *FASEB J*, 22(3):659-661, 2008, which is incorporated herein by reference):

$$\text{HED (mg/kg)} = \text{Animal dose (mg/kg)} \times (\text{Animal } K_m/\text{Human } K_m) \quad (a)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

IV. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders.

Compounds of the invention may be combined with agents designed to improve a patient's immune response to cancer, including (but not limited to) cancer vaccines. See Lu et al. (2011), which is incorporated herein by reference.

V. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "—" means a single bond, "=" means a double bond, and "≡" means triple bond. An "epoxidized double bond" represents the group:

The symbol "- - -" represents an optional bond, that is either no bond or a single bond. The symbol "====" represents a single bond or a double bond. The symbol "====" may also be used to represent an epoxidized double bond. Thus, for example, the formula

includes

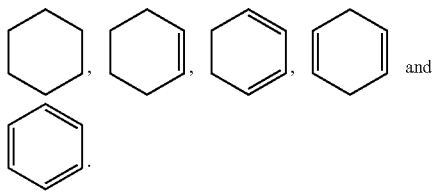

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀⦀⦀" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

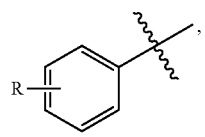

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

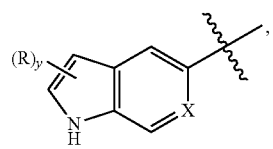

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "$C_5$ olefin", "$C_5$-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic).

Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

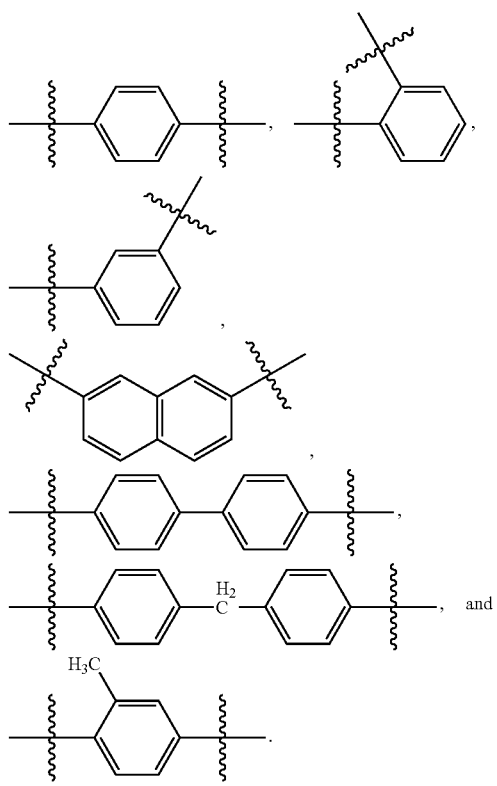

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refer to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC (O)CH₃, —S(O)₂OH, or —S(O)₂NH₂. The groups —NHC(O)OCH₃ and —NHC(O)NHCH₃ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The term "acetal" is used to describe a carbonyl group which have reacted with two hydroxy or a dihydroxy containing compounds to form a diether of a germinal diol of the structure $R_2C(OR')_2$ arising from the carbonyl group of the structure: $R_2C(O)$, wherein neither R' is not hydrogen and each R' may be the same, different, or may be taken together to form a ring. A "mixed acetal" is an acetal wherein R' are both different. "Acetal" may be used to describe the carbonyl group, which is an aldehyde, wherein one or both R groups are hydrogen atoms, or a ketone, wherein neither R group is a hydrogen atom. "Ketal" is a subgroup of "acetal" wherein the carbonyl group is a ketone. The term "hemiacetal" is used to describe a carbonyl group which has been reacted with one hydroxy containing compound to form a monoether of a germinal diol forming a group of the structure: $R_2C(OH)OR'$, wherein R' is not hydrogen. "Hemiacetal" may be used to describe the carbonyl group that is an aldehyde, wherein one or both R groups are hydrogen atoms, or a ketone, wherein neither R group is a hydrogen atom. Analogous to "ketal", a "hemiketal" is a subgroup of "hemiacetal" wherein the carbonyl group is a ketone.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "normal" or "normality" refers to the concentration of a solution wherein the molar concentration is divided by the equivalence factor. The equivalence factor is the number of ions which are obtained from a compound when it has dissociated in a solution. For a solution such as HCl, the solution is 1 N in both protons and 1 N concentration of chloride ions, whereas a solution of $CaCl_2$) is 1 N in calcium ions and 2 N in chloride ions.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: NO, nitric oxide; iNOS, inducible nitric oxide synthase; COX-2, cyclooxygenase-2; FBS, fetal bovine serum; IFNγ or IFN-γ, interferon-γ; TNFα or TNF-α, tumor necrosis factor-α; IL-1β, interleukin-1β; IL17 or IL-17, interleukin 17; HO-1, inducible heme oxygenase; Me, methyl; Bn, benzyl; Et, ethyl; Ph, phenyl; Ac, acetyl; Bz, benzoyl; Ts, tosyl; Boc, t-butyloxycarbonyl; quant., quantitative; aq., aqueous; w/w, weight per weight; ° C., degrees Celsius; N, normal or normality; h or hr, hours; rt, room temperature; TLC, thin layer chromatography; DMSO, dimethyl sulfoxide; EtOAc, ethyl acetate; DMF, N,N-dimethylformamide; DMA, dimethylacetamide; MeCN, acetonitrile; MTBE, methyl t-butylether; Et$_2$O, diethyl ether; THF, tetrahydrofuran; MeOH, methanol, EtOH, ethanol; iPrOH, isopropanol; Pd/C, palladium on carbon; Py, pyridine; DIPEA, diisopropylethylamine; DMAP, dimethylaminopyridine; mCPBA, m-chloroperoxybenzoic acid; MOMCl, methoxymethyl chloride; TBSCl, t-butyldimethylsilyl chloride; SEMCl, 2-(trimethylsilyl)ethoxymethyl chloride; DMP, Dess Martin periodinane; T$_3$P®, propylphosphonic anhydride; DPPA, diphenylphosphoryl azide; PPTS, pyridinium p-toluenesulfonate; DDQ, 2,3-dichloro-5,6-dicyano-1,4-benzoquinone; DAST, diethylaminosulfur trifluoride; TMSCHN$_2$, trimethylsilyldiazomethane; DBDMH, 1,3-dibromo-5,5-dimethylhydantoin.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis and Characterization

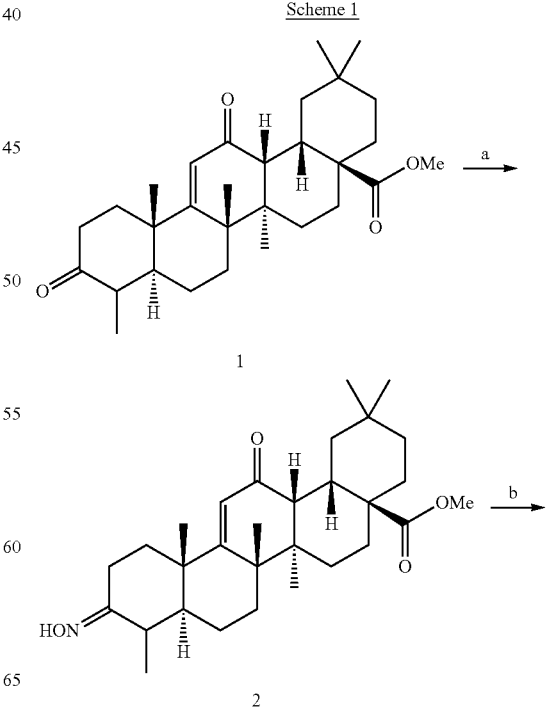

Scheme 1

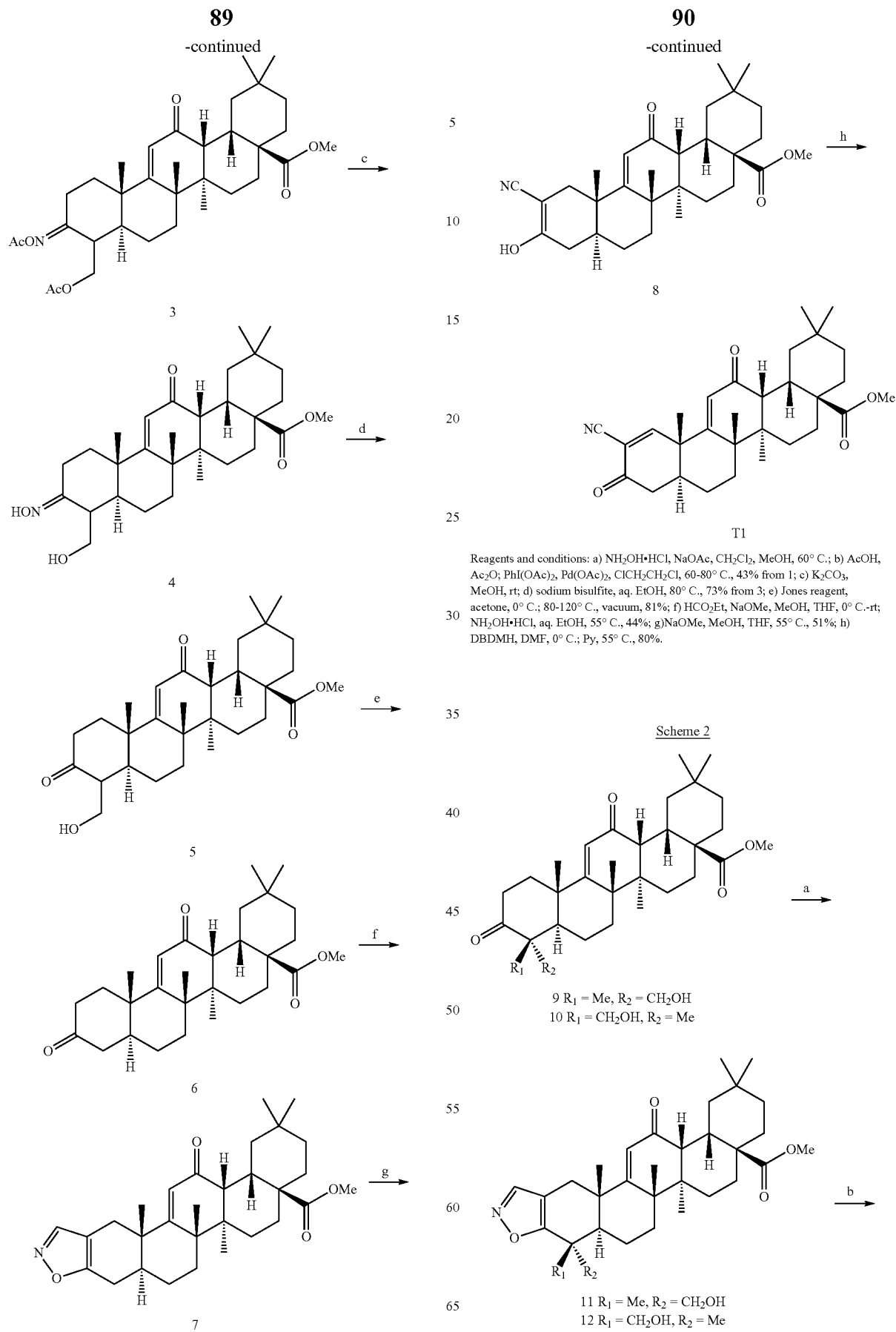
Reagents and conditions: a) NH₂OH•HCl, NaOAc, CH₂Cl₂, MeOH, 60° C.; b) AcOH, Ac₂O; PhI(OAc)₂, Pd(OAc)₂, ClCH₂CH₂Cl, 60-80° C., 43% from 1; c) K₂CO₃, MeOH, rt; d) sodium bisulfite, aq. EtOH, 80° C., 73% from 3; e) Jones reagent, acetone, 0° C.; 80-120° C., vacuum, 81%; f) HCO₂Et, NaOMe, MeOH, THF, 0° C.-rt; NH₂OH•HCl, aq. EtOH, 55° C., 44%; g) NaOMe, MeOH, THF, 55° C., 51%; h) DBDMH, DMF, 0° C.; Py, 55° C., 80%.
Scheme 2

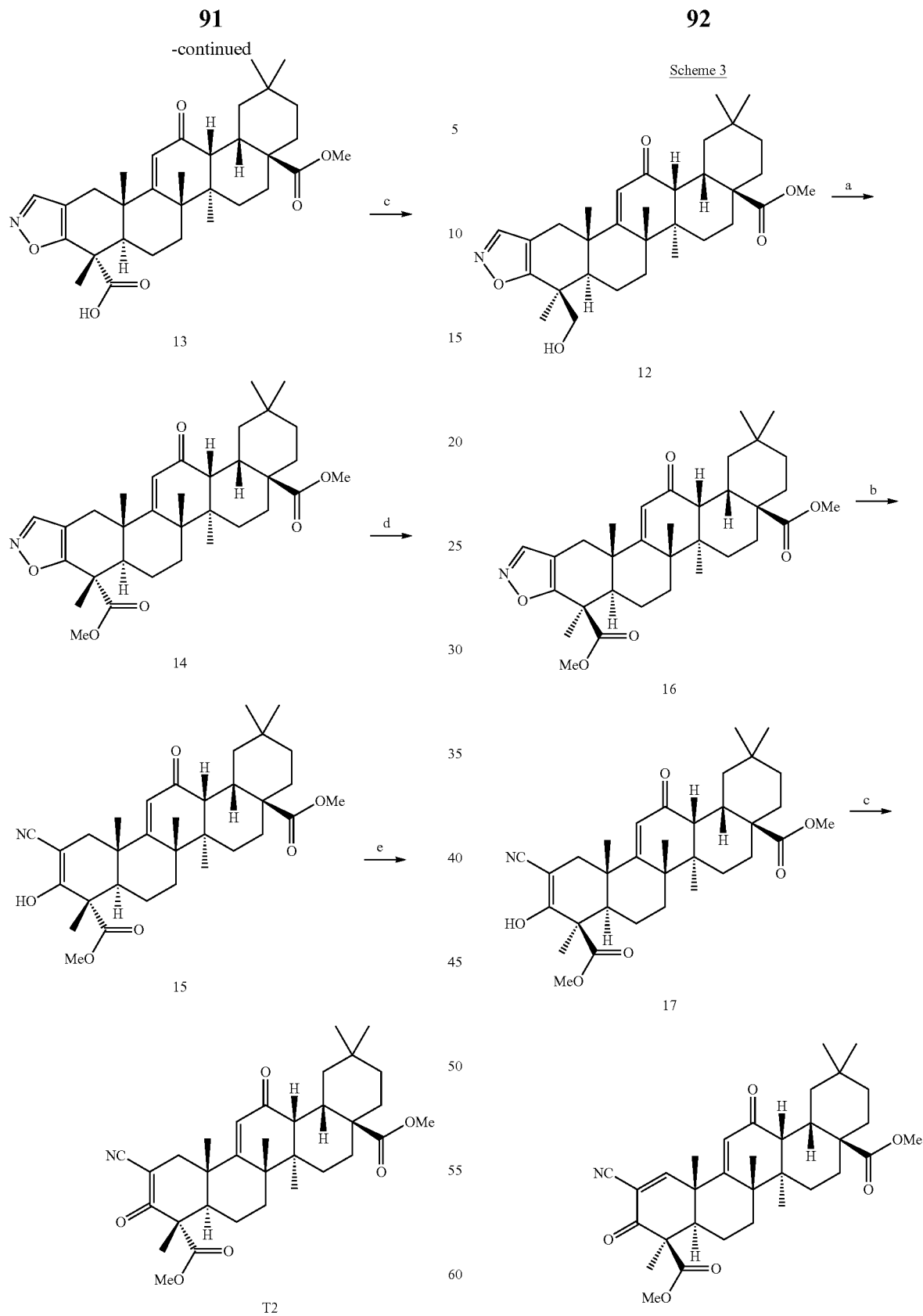
Scheme 3
Reagents and conditions: a) HCO₂Et, NaOMe, MeOH, 0° C.; NH₂OH•HCl, aq. EtOH, 55° C., 57% b) Jones reagent, acetone, 0° C.-rt, 88%; c) TMSCHN₂, Et₂O, toluene, MeOH, 0° C., 84%; d) NaOME, MeOH, 55° C., quantitative yield; e) DBDMH, DMF, 0° C.; Py, 55° C., 77%.
Reagents and conditions: a) i) Jones reagent, acetone, 0° C.-rt; ii) TMSCHN₂, Et₂O, toluene, MeOH, 0° C., 49% from 12; b) NaOMe, MeOH, 55° C., 75%; c) DBDMH, DMF, 0° C.; Py, 55° C., 74%.

Scheme 4
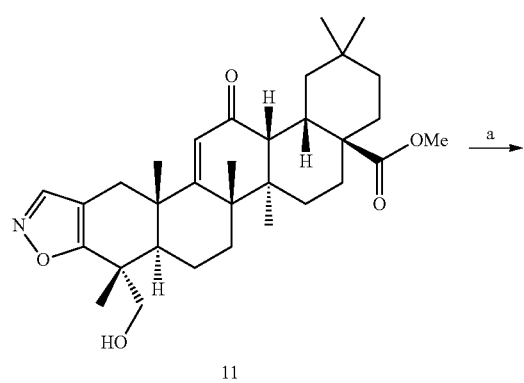
11
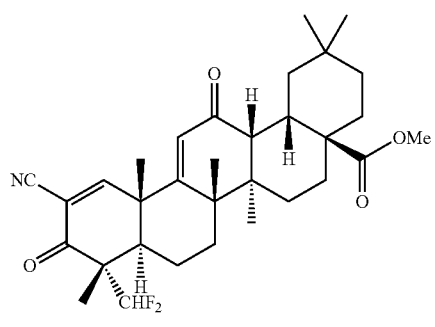
T4
Reagents and conditions: a) (COCl)$_2$, DMSO, CH$_2$Cl$_2$, -78° C.; Et$_3$N, -78° C.-rt, 86%; b) i) DAST, CH$_2$Cl$_2$, rt; ii) NaBH$_4$, MeOH, 0° C., 32%; c) NaOMe, MeOH, 55° C., 82%; d) DBDMH, DMF, 0° C.; Py, 55° C., 86%.
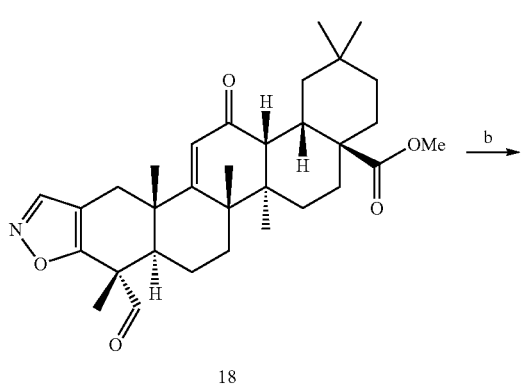
18
Scheme 5
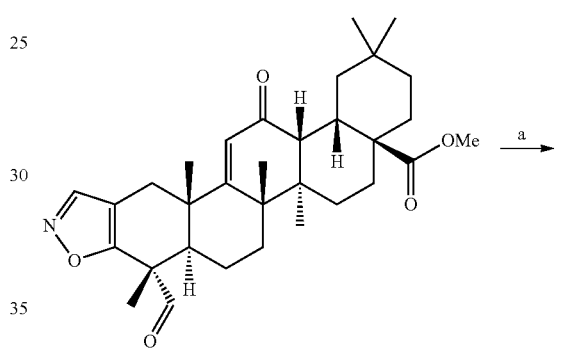
18
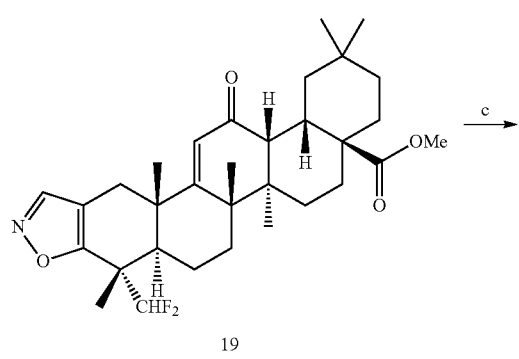
19
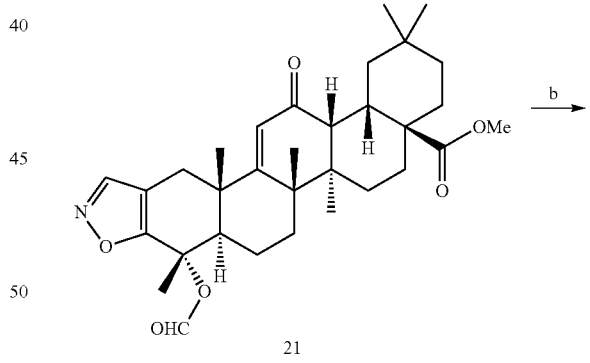
21
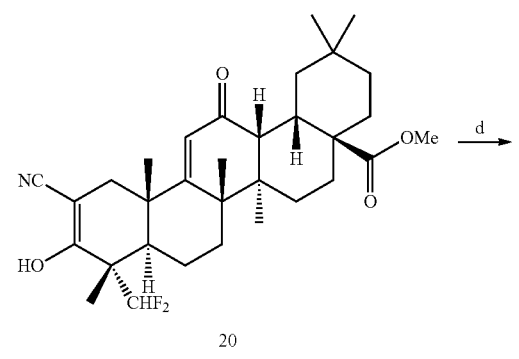
20
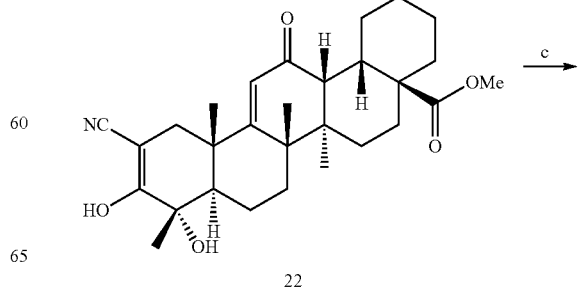
22

95
-continued
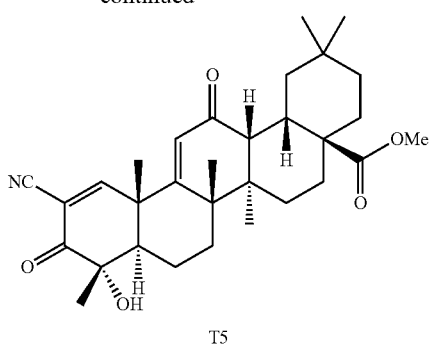
T5
Reagents and conditions: a) Na₂HPO₄, m-CPBA, CH₂Cl₂, rt, 86%; b) NaOMe, MeOH, 55° C., 98%; c) DBDMH, DMF, 0° C.; Py, 55° C., 80%
Scheme 6
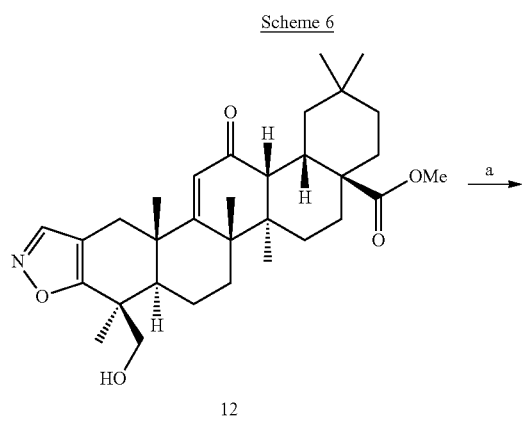
12
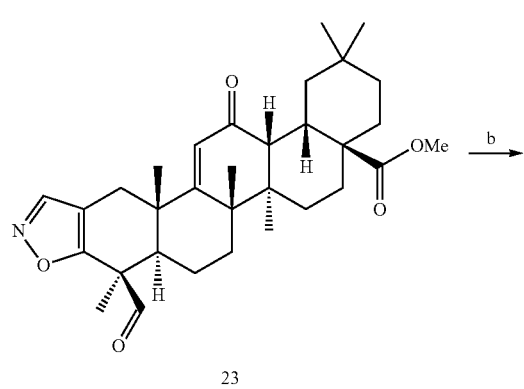
23
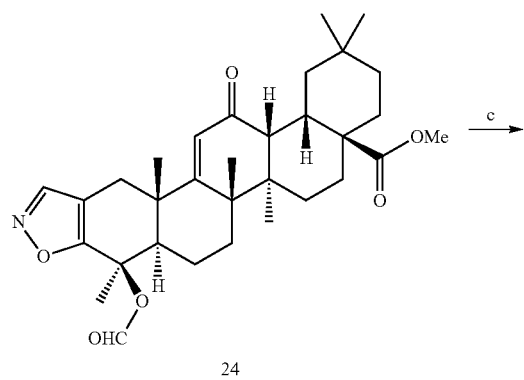
24
96
-continued
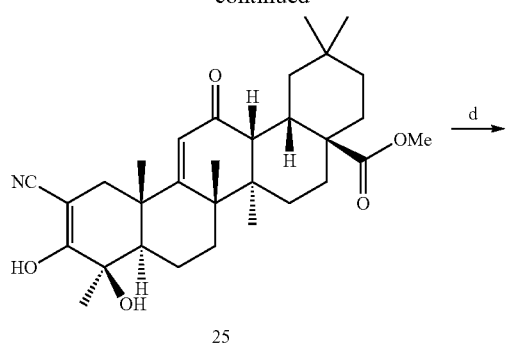
25
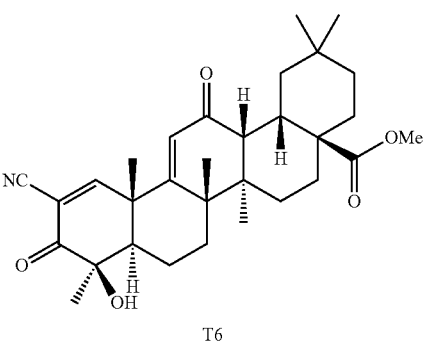
T6
Reagents and conditions: a) (COCl)₂, DMSO, CH₂Cl₂, -78° C.; Et₃N, -78° C.-rt, 72%; b) Na₂HPO₄, m-CPBA, CH₂Cl₂, rt, 63%; c) NaOMe, MeOH, 55° C., 68%; d) DBDMH, DMF, 0° C.; Py, 55° C., 63%.
Scheme 7
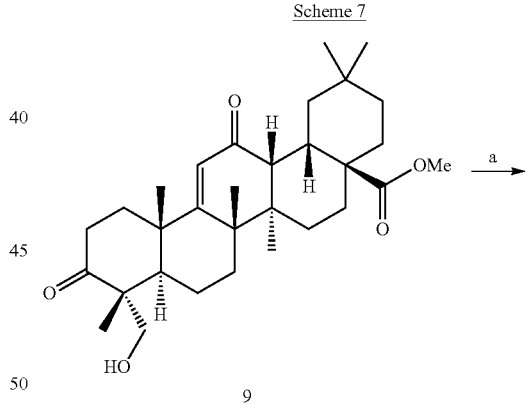
9
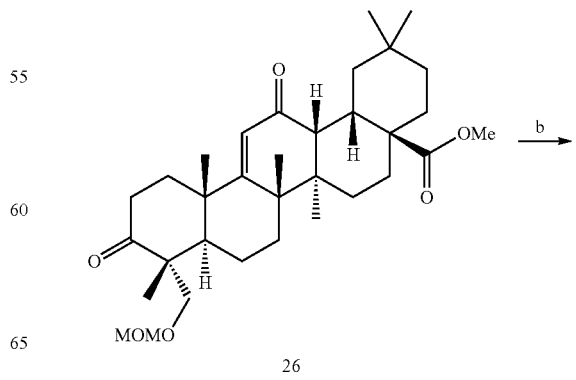
26

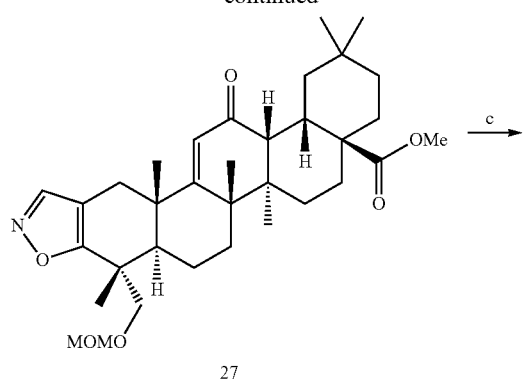
27
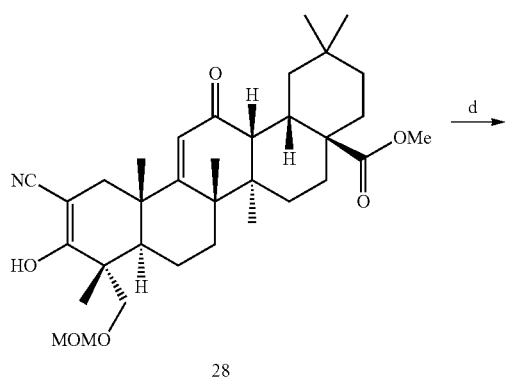
28
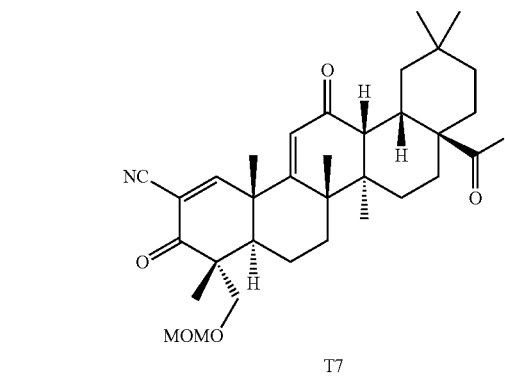
T7
Reagents and conditions: a) MOMCl, DIPEA, 0° C.-rt, 90%; b) i) HCO$_2$Et, NaOMe, MeOH, 0° C.-rt; ii) NH$_2$OH•HCl, aq. EtOH, 55° C., 61%; c) NaOMe, MeOH, THF, 55° C., quant.; d) DBDMH, DMF, 0° C.; Py, 55° C., 85%.
Scheme 8
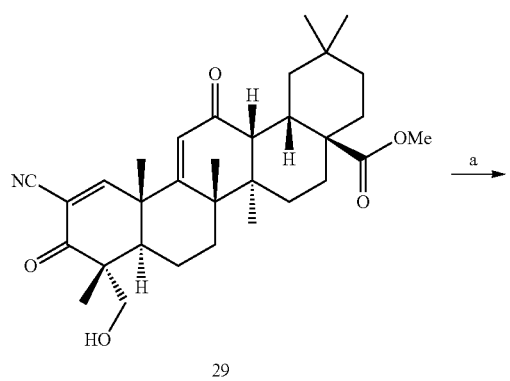
29
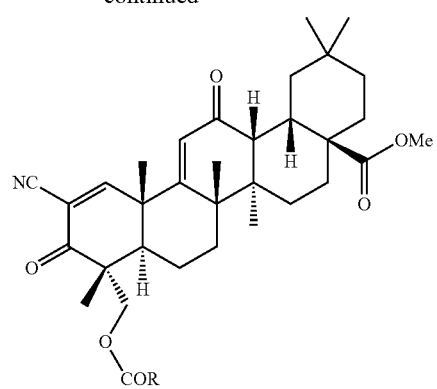
T8 R = CH$_2$
T9 R = Ph
Reagents and conditions: a) Ac$_2$O, DMAP, Py, rt, 32% for T8; a) BzCl, DMAP, Py, CH$_2$Cl$_2$, rt, 70% for T9.
Scheme 9
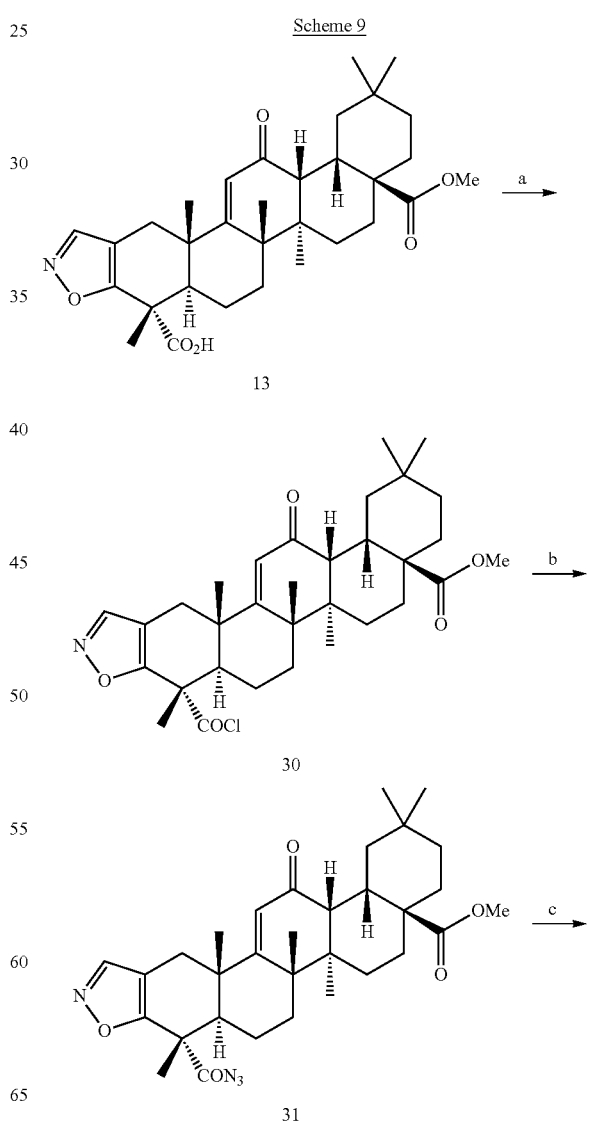

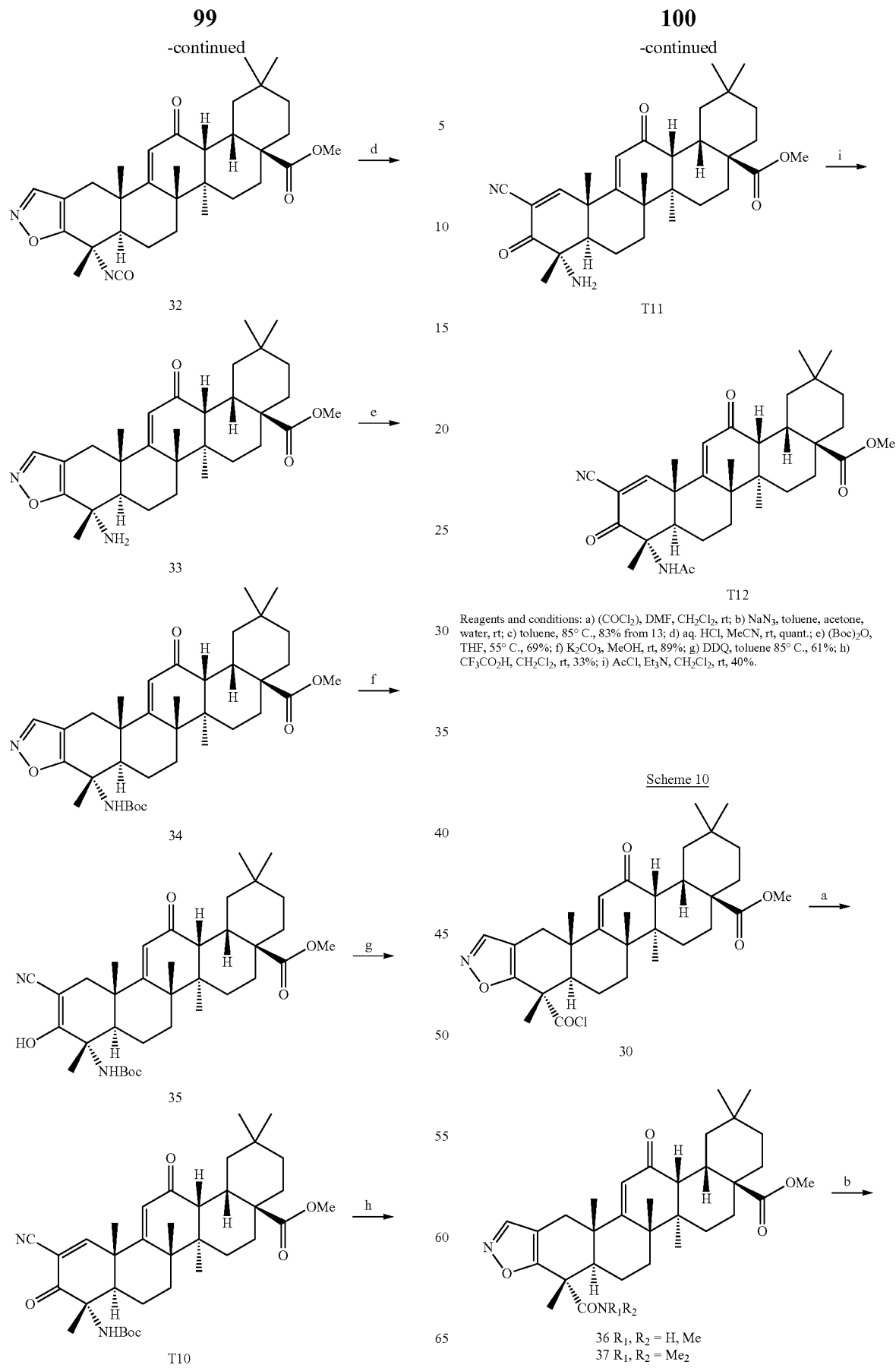

101
-continued
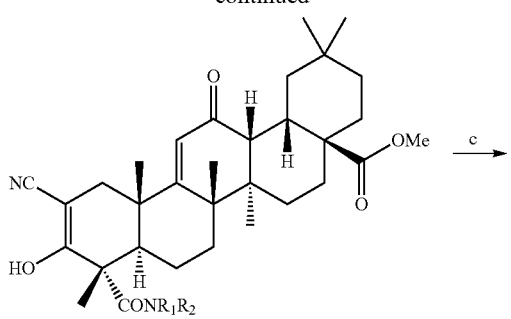
38 R$_1$, R$_2$ = H, Me
39 R$_1$, R$_2$ = Me$_2$
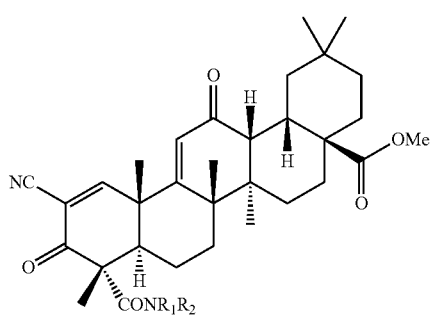
T13 R$_1$, R$_2$ = H, Me
T14 R$_1$, R$_2$ = Me$_2$
Reagents and conditions: a) R$_1$R$_2$NH·HCl, Et$_3$N, CH$_2$Cl$_2$, 0° C., 84% for 36; 88% for 37; b) K$_2$CO$_3$, MeOH, rt; c) DDQ, benzene, reflux, T13: 51% from 36; T14: 20% from 37.
102
-continued
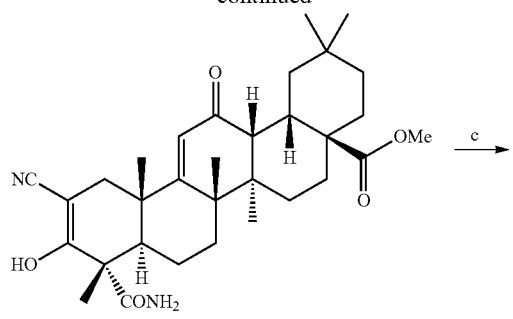
41
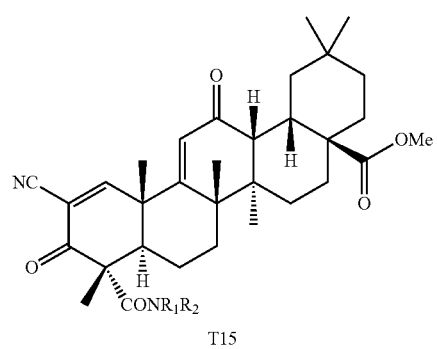
T15
Reagents and conditions: a) NH$_3$, MeOH, CH$_2$Cl$_2$, rt, 52%; b) K$_2$CO$_3$, MeOH, rt, 66%; c) DBDMH, DMF, 0° C.; Py, 55° C., 65%.
Scheme 11
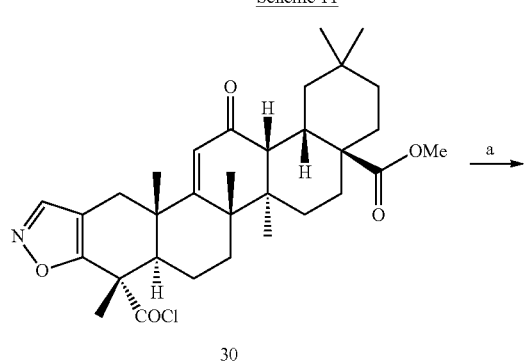
30
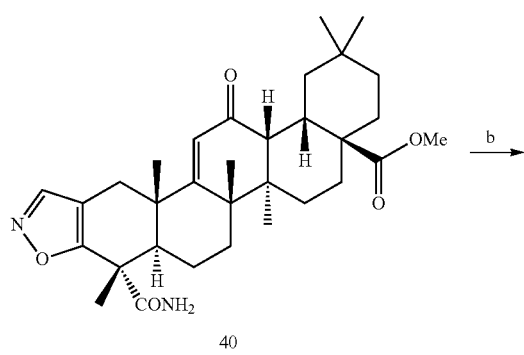
40
Scheme 12
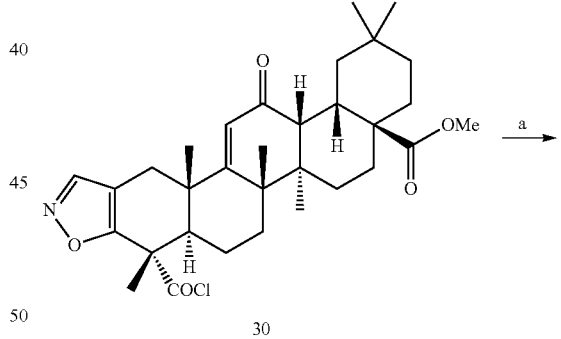
30
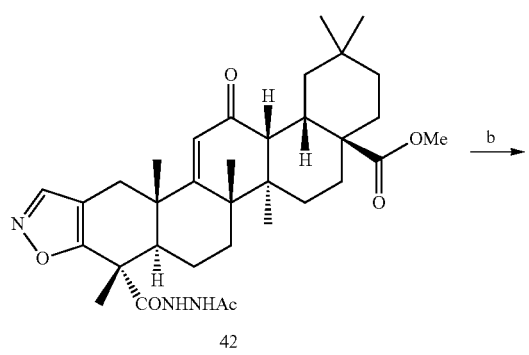
42

Scheme 13
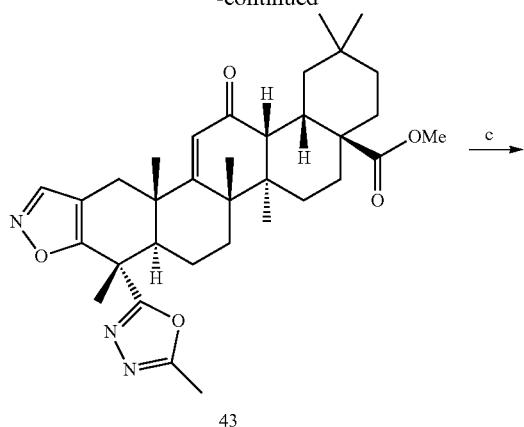
43
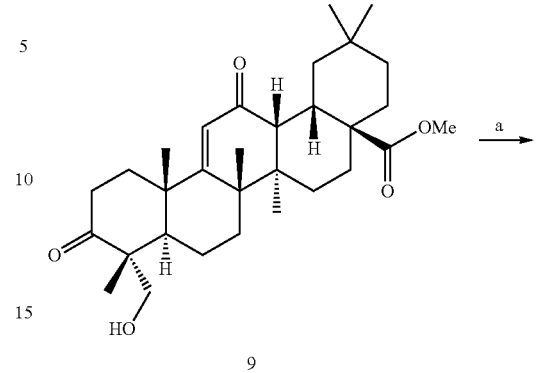
9
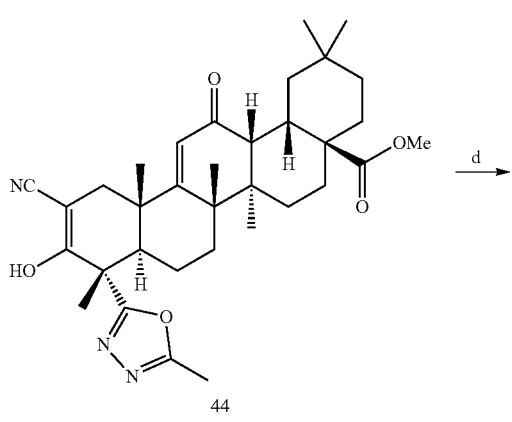
44
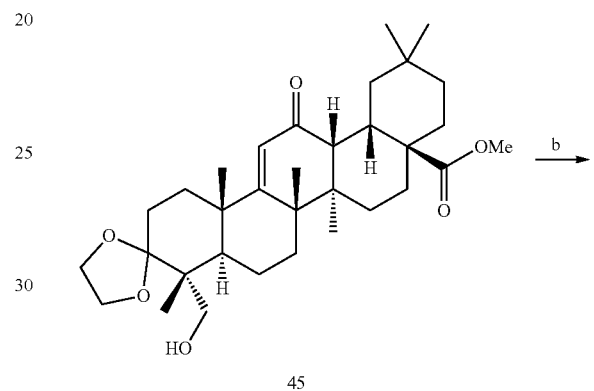
45
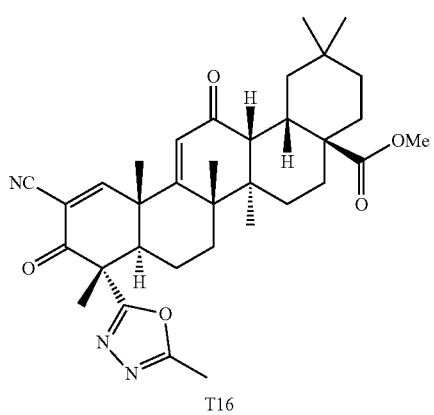
T16
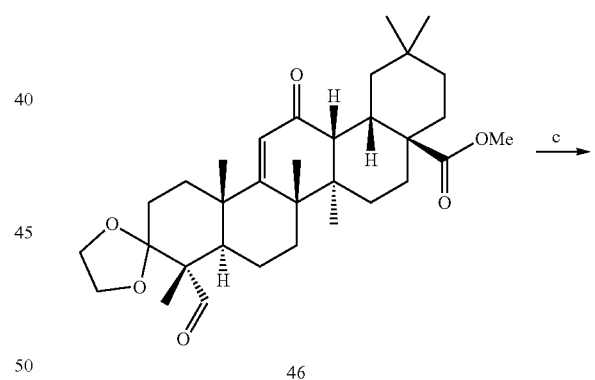
46
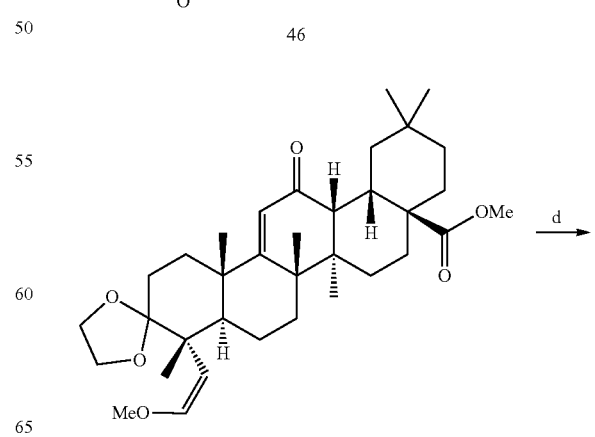
47
Reagents and conditions: a) AcNHNH$_2$, Et$_3$N, Et$_2$O, CH$_2$Cl$_2$, rt, 78%; b) TsOH·H$_2$O, toluene, reflux, 86%; c) K$_2$CO$_3$, MeOH, rt, quant.; d) DDQ, benzene, reflux, 60%.

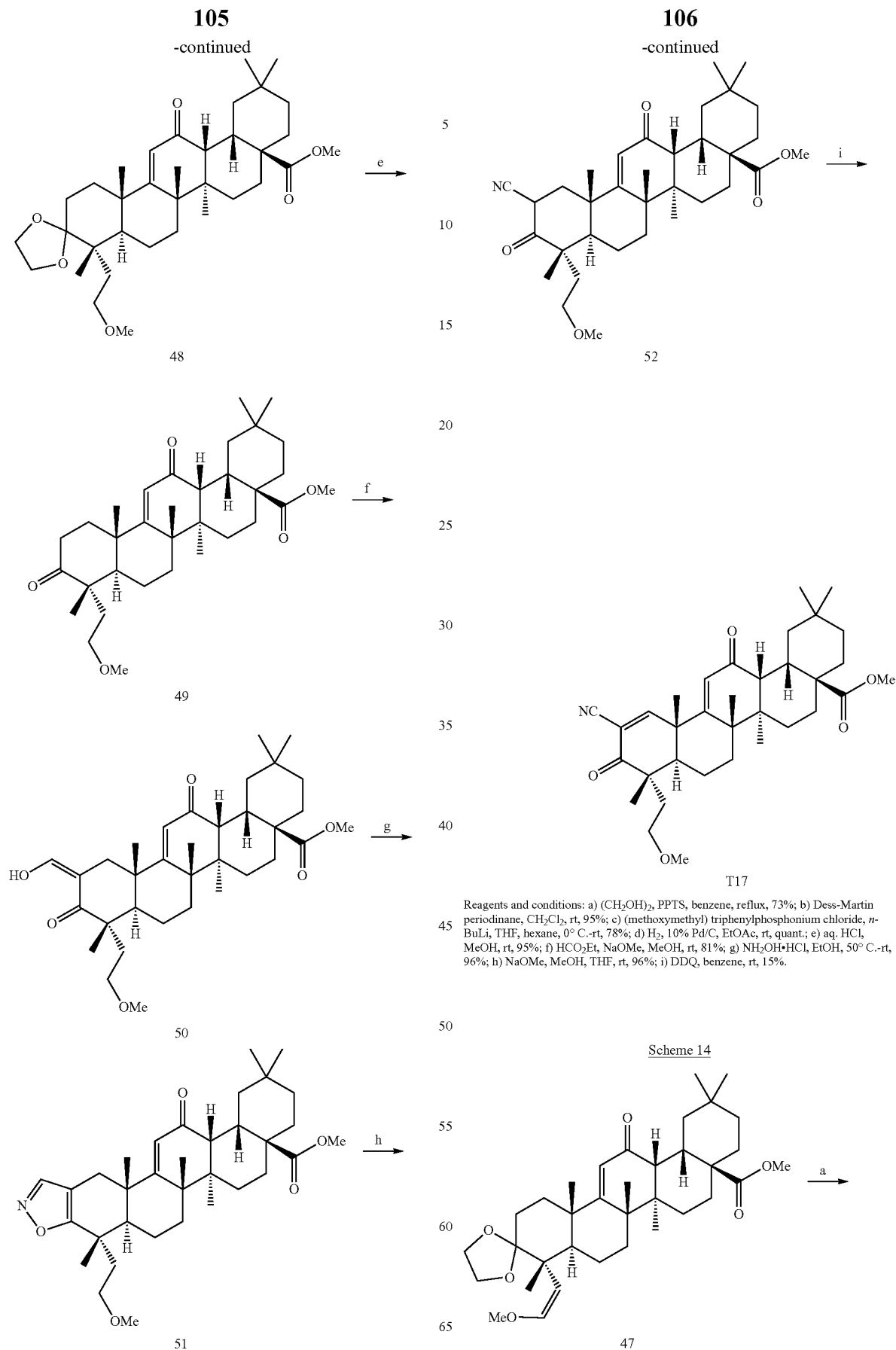

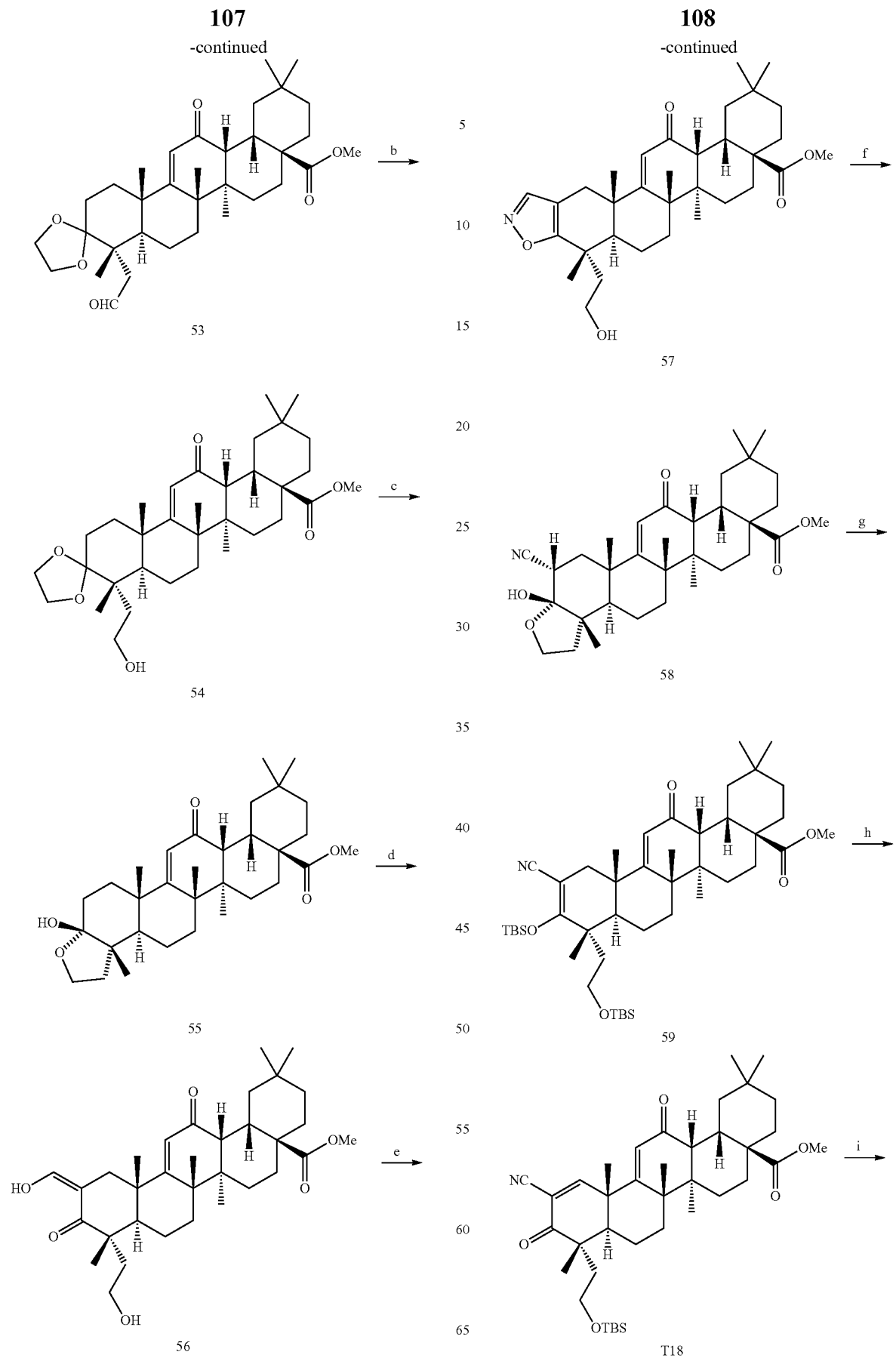

109
-continued

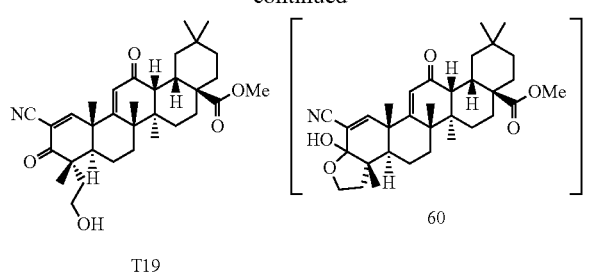

T19

Reagents and conditions: a) aq. HCl, THF, rt, 92%; b) NaBH₄, THF, EtOH, 0° C., quant.; c) aq. HCl, THF, rt, quant.; d) HCO₂Et, NaOMe, MeOH, 0° C.-rt, quant.; e) NH₂OH·HCl, aq. EtOH, 50° C., quant.; f) K₂CO₃, MeOH, rt, 65%; g) TBSCl, Et₃N, DMAP, CH₂Cl₂, rt, 98%; h) DBDMH, DMF, 0° C.-rt; Py, 60° C., 47%; i) HF·Py, MeCN, water, rt, 57%.

Scheme 15

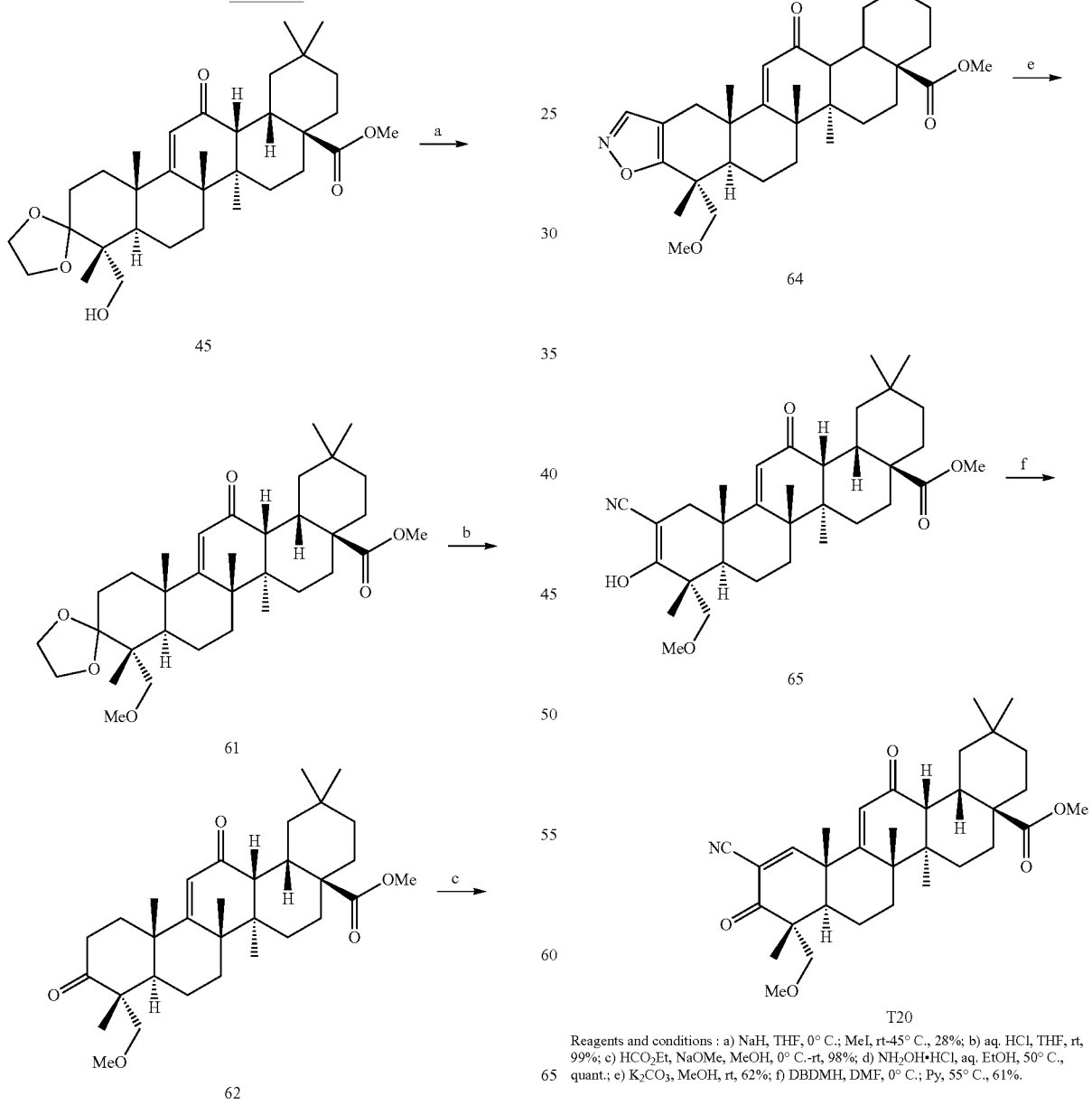

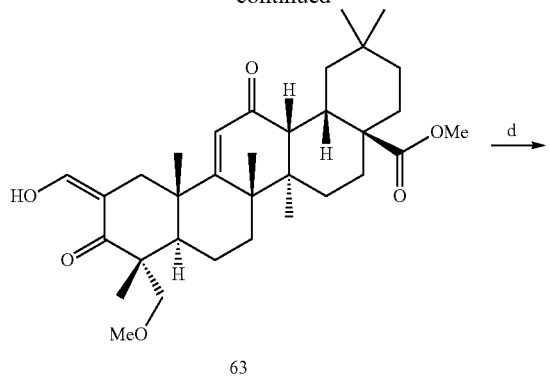

T20

Reagents and conditions: a) NaH, THF, 0° C.; MeI, rt-45° C., 28%; b) aq. HCl, THF, rt, 99%; c) HCO₂Et, NaOMe, MeOH, 0° C.-rt, 98%; d) NH₂OH·HCl, aq. EtOH, 50° C., quant.; e) K₂CO₃, MeOH, rt, 62%; f) DBDMH, DMF, 0° C.; Py, 55° C., 61%.

Scheme 16
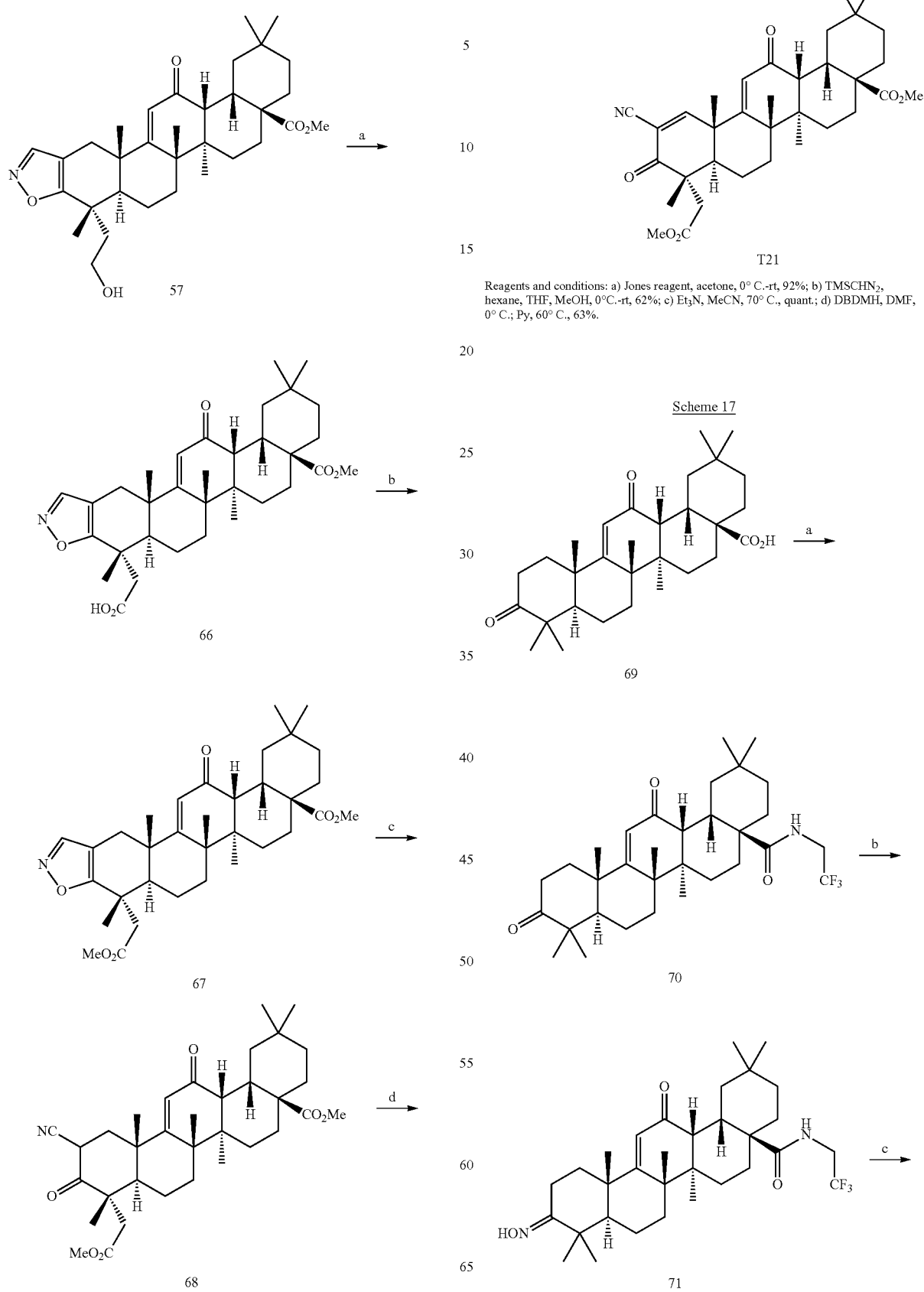
Reagents and conditions: a) Jones reagent, acetone, 0° C.-rt, 92%; b) TMSCHN$_2$, hexane, THF, MeOH, 0°C.-rt, 62%; c) Et$_3$N, MeCN, 70° C., quant.; d) DBDMH, DMF, 0° C.; Py, 60° C., 63%.
Scheme 17
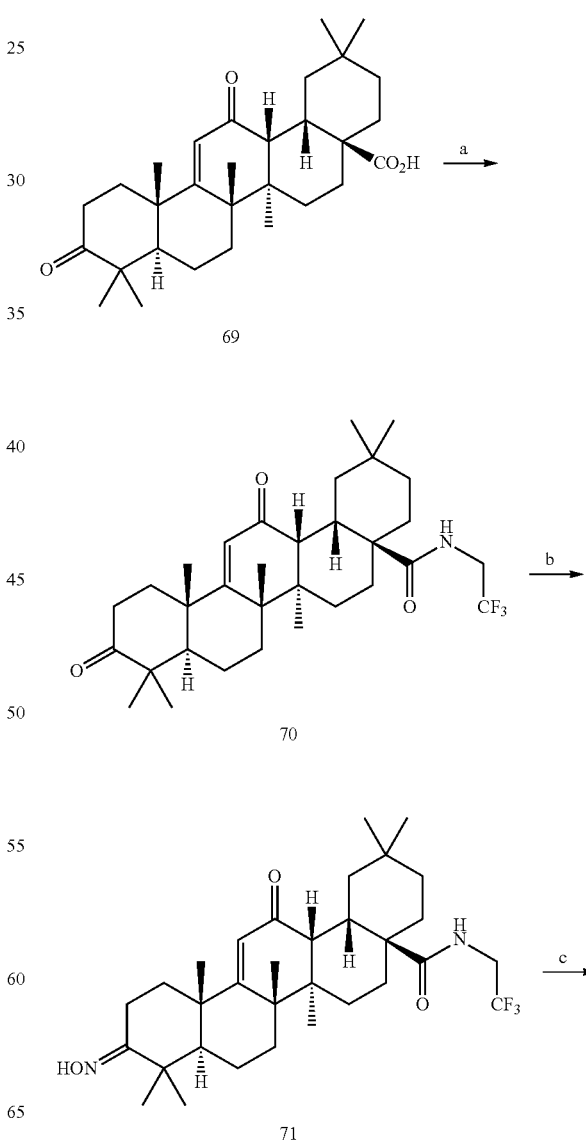

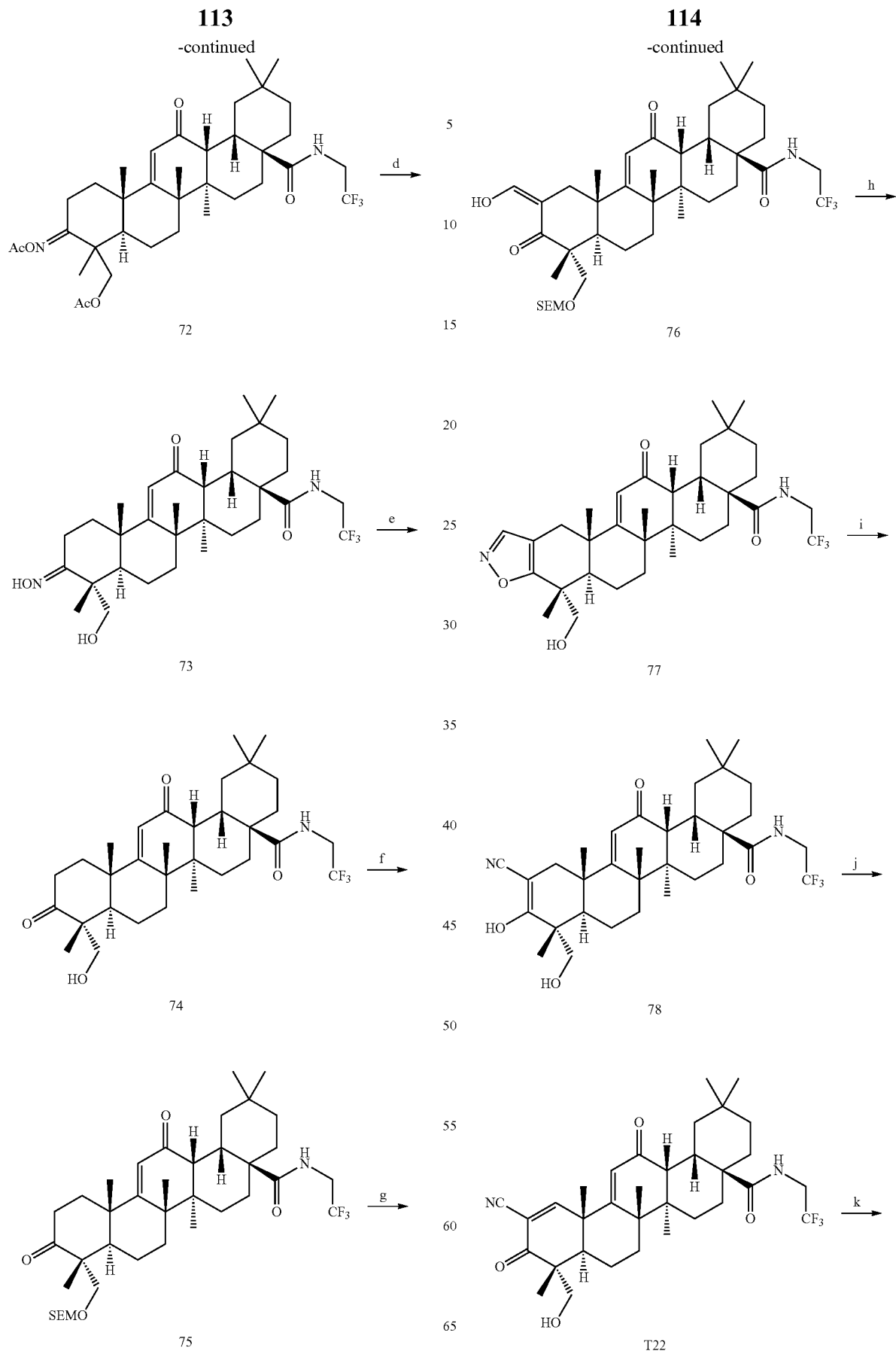

115
-continued

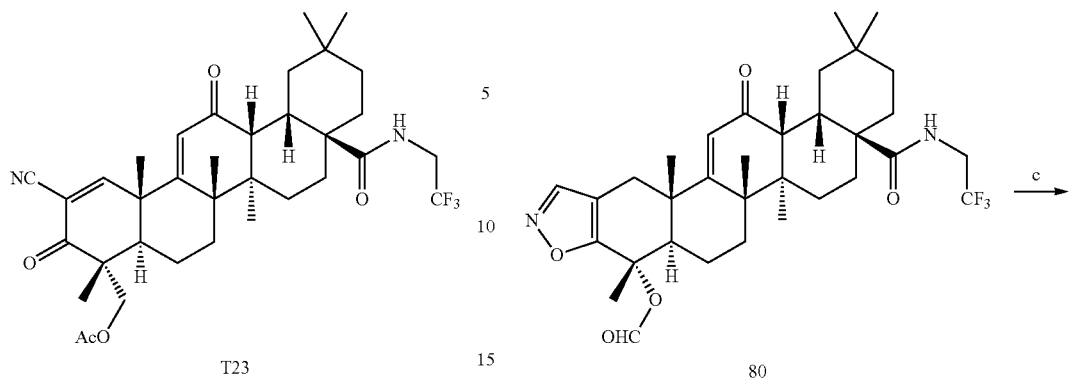

T23

Reagents and conditions: a) i) (COCl)₂, DMF, CH₂Cl₂, rt; ii) CF₃CH₂NH₂•HCl, Et₃N, CH₂Cl₂, rt, 81%; b) NH₂OH•HCl, NaOAc, CH₂Cl₂, EtOH, 60° C., quant.; c) AcOH, Ac₂O; PhI(OAc)₂, Pd(OAc)₂, ClCH₂CH₂Cl, 70° C., 38%; d) K₂CO₃, MeOH, rt, 67%; e) sodium bisulfite, aq. EtOH, 80° C., 85%; f) SEMCl, DIPEA, CH₂Cl₂, 0° C.-rt, 51% g) HCO₂Et, NaOMe, MeOH, rt, 97%; h) NH₂OH•HCl, EtOH, 50° C., 92%; i) K₂CO₃, MeOH, rt, 92%; j) DDQ, benzene, dioxane, 85° C., 32%; k) Ac₂O, NaOAc, rt, 52%.

Scheme 18

116
-continued

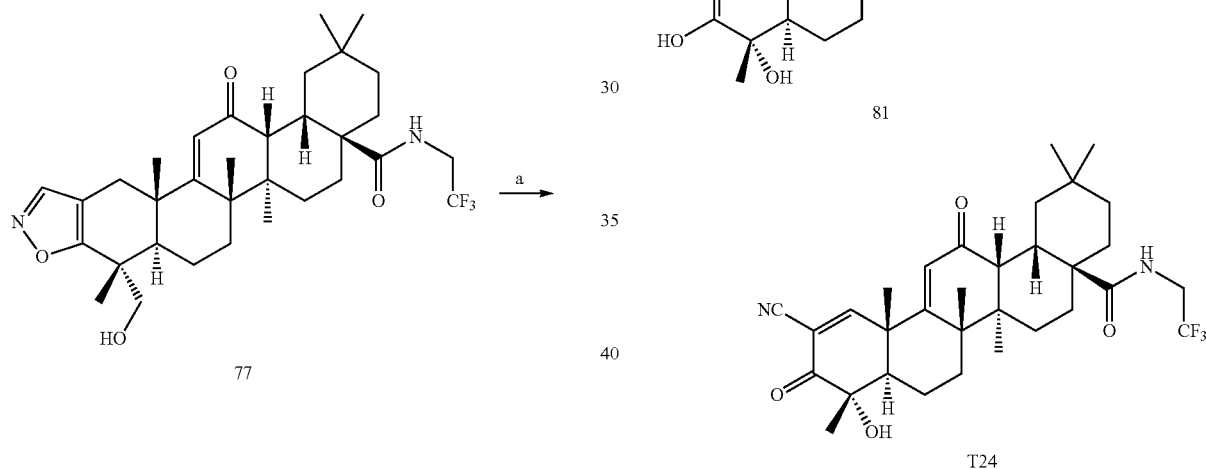

80

81

T24

Reagents and conditions: a) Dess-Martin periodinane, CH₂Cl₂, rt, quant.; b) m-CPBA, Na₂HPO₄, CH₂Cl₂, rt, 81%; c) NaOMe, MeOH, rt, 89% d) DBDMH, DMF, 0° C.; Py, 60° C., 59%.

Scheme 19

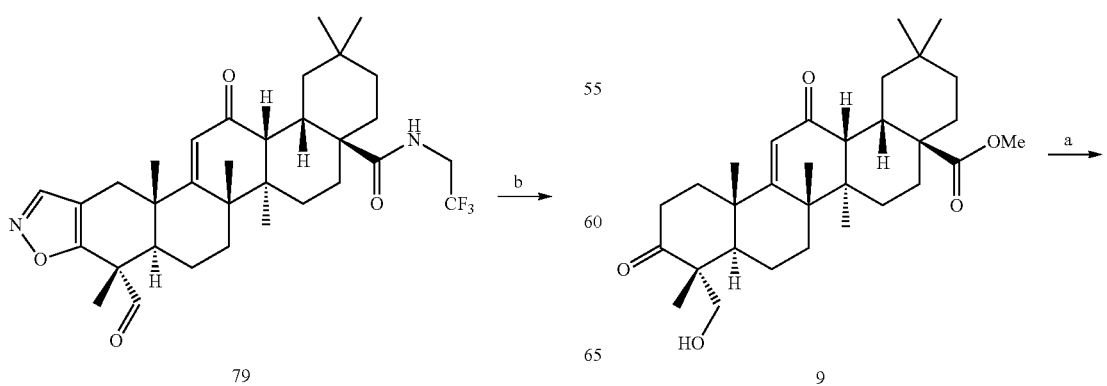

77

79

9

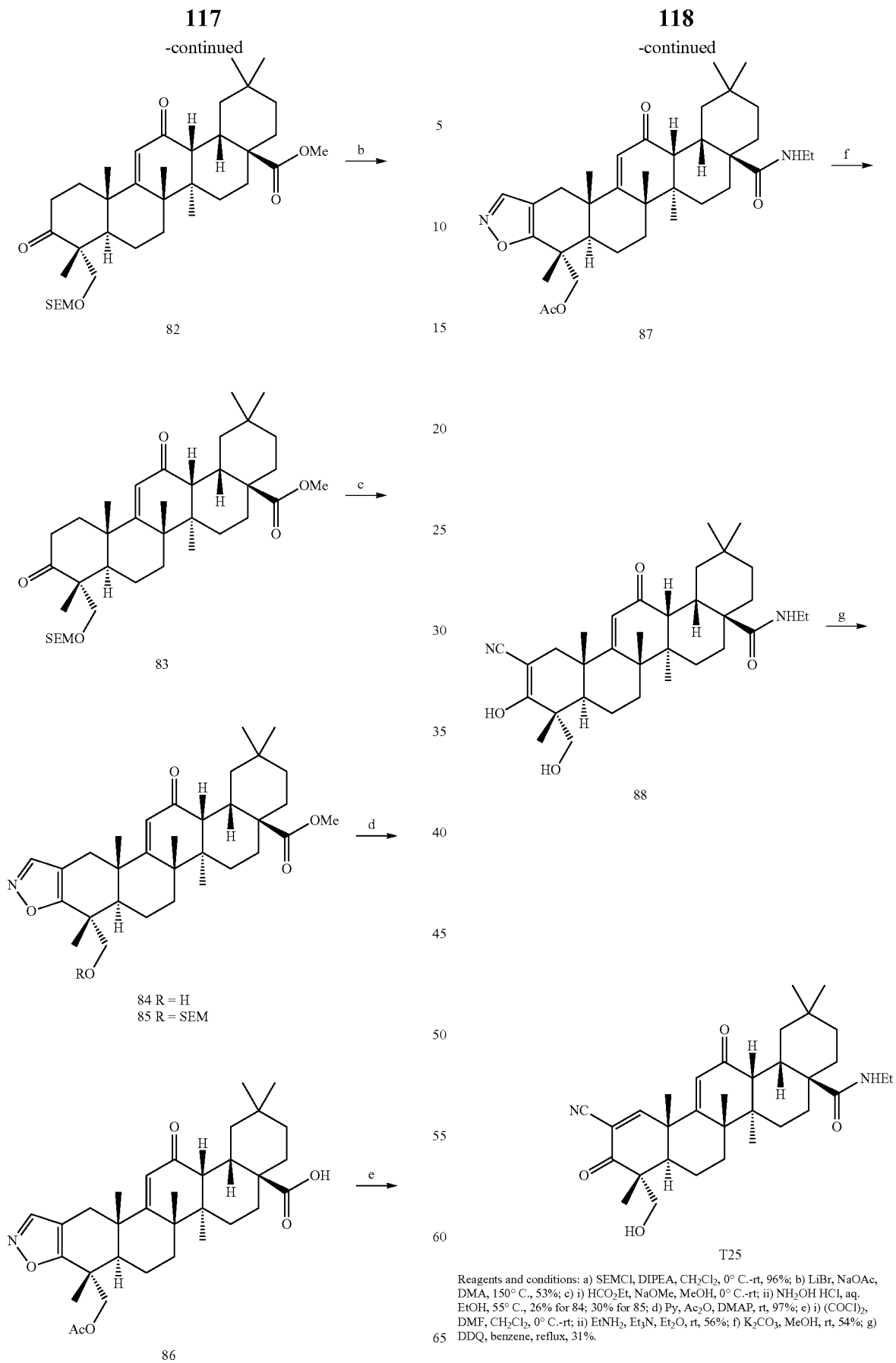
Reagents and conditions: a) SEMCl, DIPEA, CH$_2$Cl$_2$, 0° C.-rt, 96%; b) LiBr, NaOAc, DMA, 150° C., 53%; c) HCO$_2$Et, NaOMe, MeOH, 0° C.-rt; ii) NH$_2$OH HCl, aq. EtOH, 55° C., 26% for 84; 30% for 85; d) Py, Ac$_2$O, DMAP, rt, 97%; e) i) (COCl)$_2$, DMF, CH$_2$Cl$_2$, 0° C.-rt; ii) EtNH$_2$, Et$_3$N, Et$_2$O, rt, 56%; f) K$_2$CO$_3$, MeOH, rt, 54%; g) DDQ, benzene, reflux, 31%.

Scheme 20
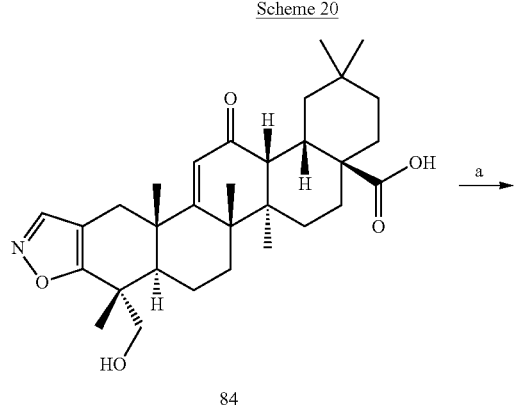
84
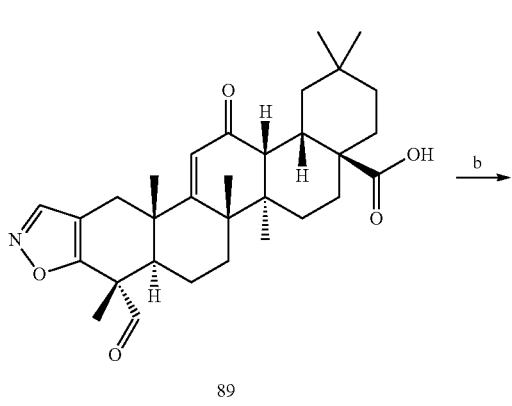
89
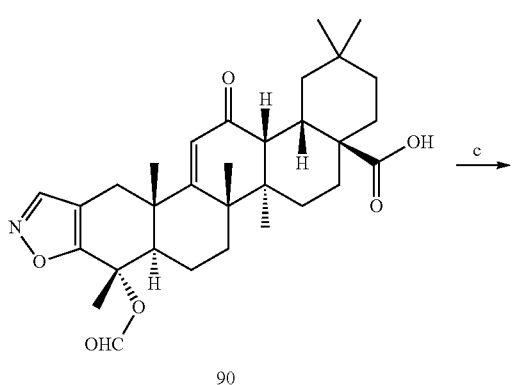
90
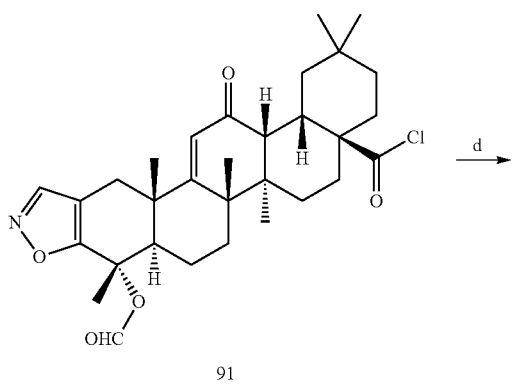
91
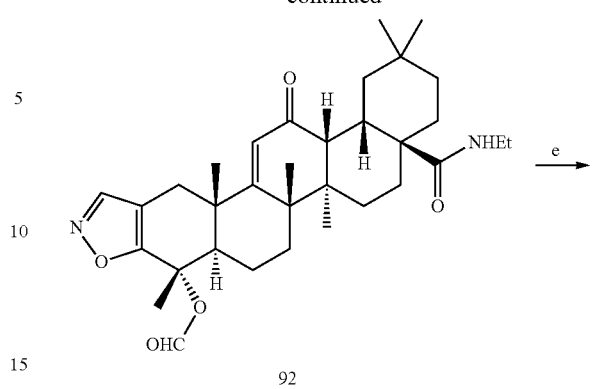
92
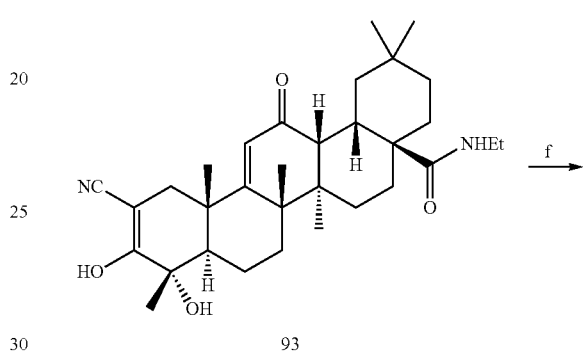
93
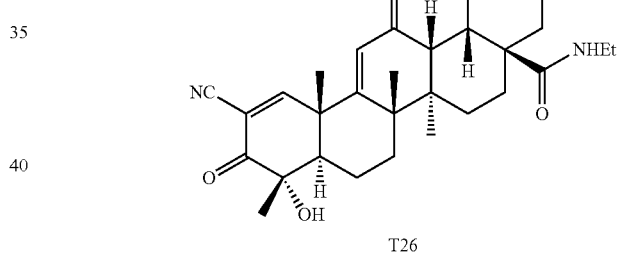
T26
Reagents and conditions: a) Dess-Martin periodinane, Na₂HPO₄, CH₂Cl₂, rt; b) m-CPBA, Na₂HPO₄, CH₂Cl₂, rt, 50% from 84; c) (COCl)₂, DMF, CH₂Cl₂, 0° C.-rt; d) EtNH₂, THF, CH₂Cl₂, rt, 60% from 90; e) K₂CO₃, MeOH, rt, 83%; f) DBDMH, DMF, 0° C.; Py, 55° C., 77%.
Scheme 21
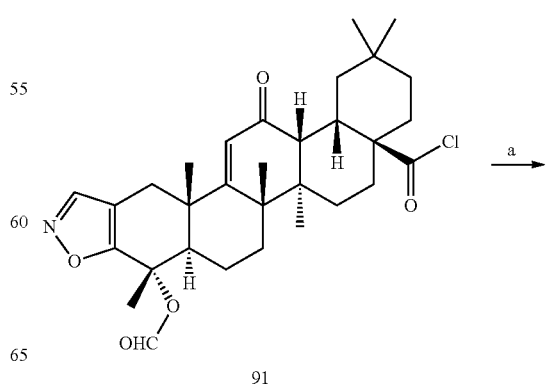
91

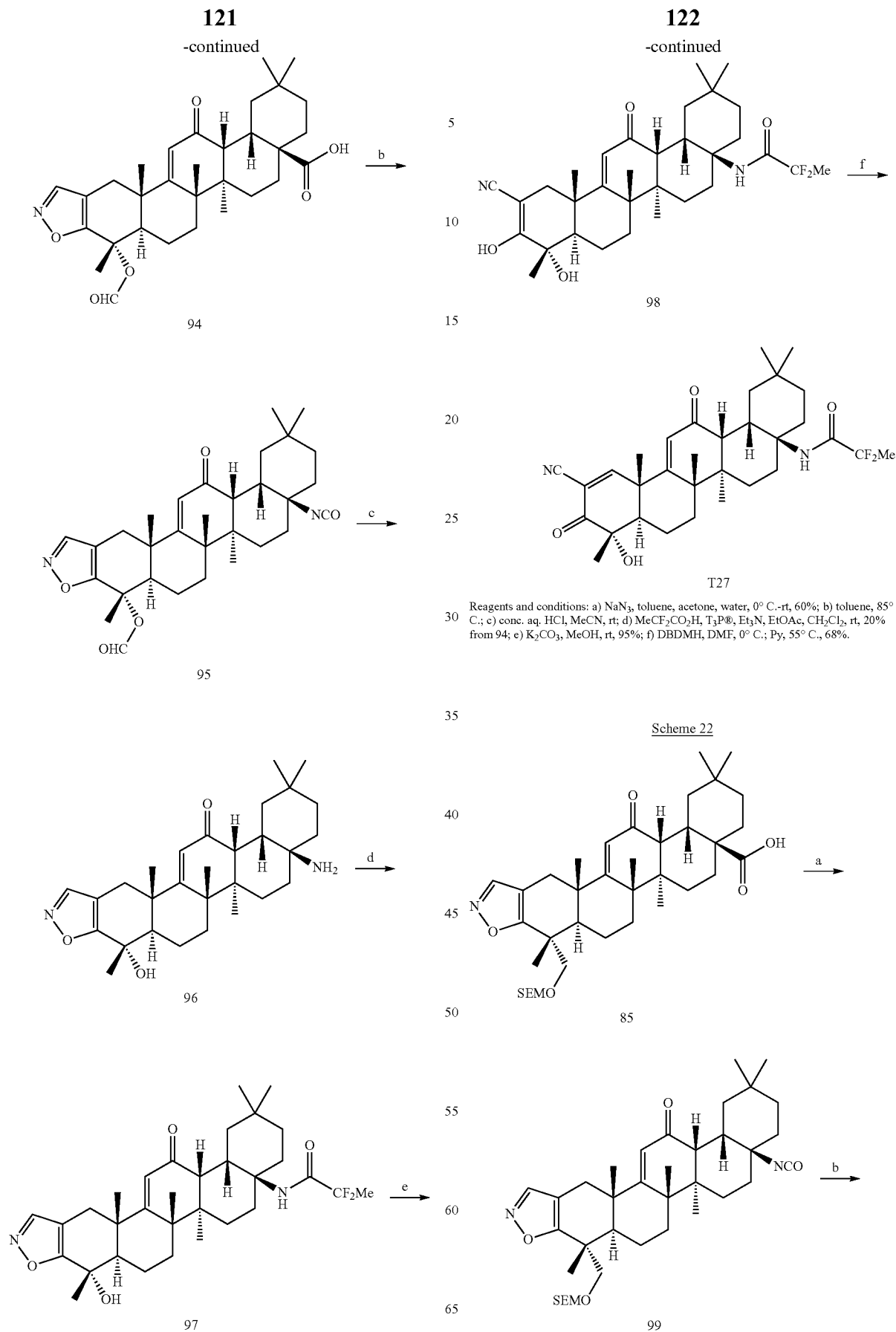

123
-continued
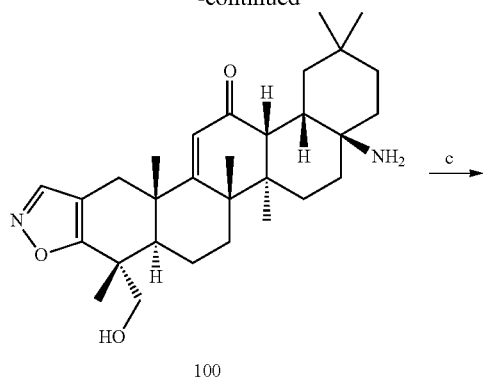
100
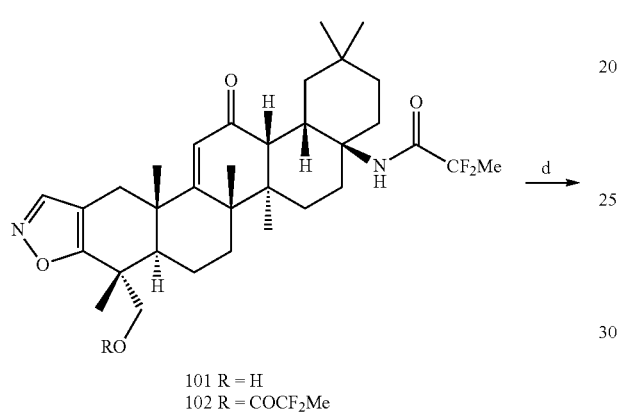
101 R = H
102 R = COCF₂Me
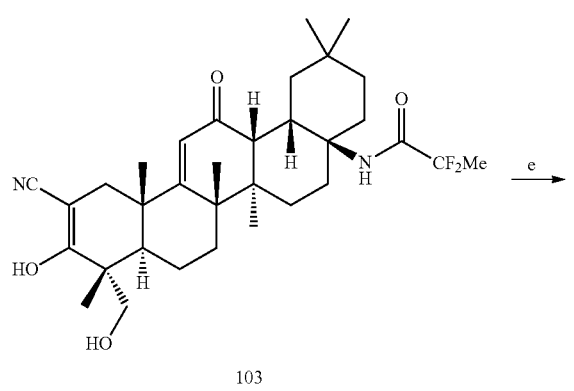
103
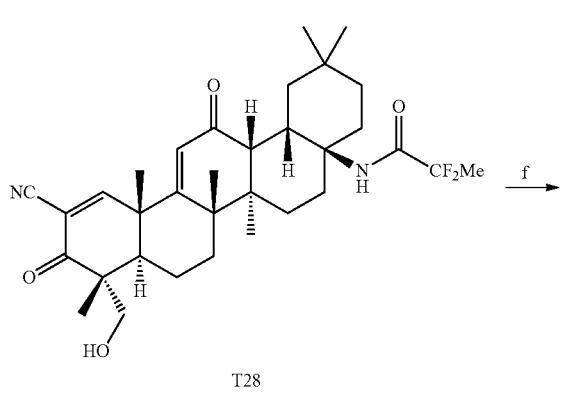
T28
124
-continued
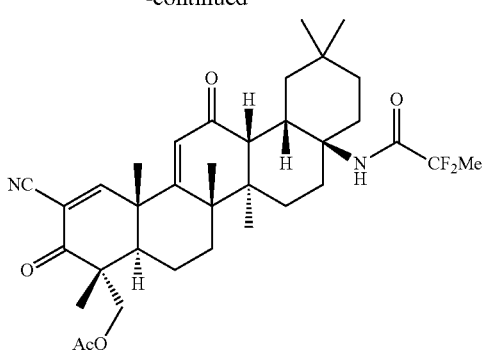
T29
Reagents and conditions: a) i) DPPA, Et₃N, benzene, 0° C.-rt; ii) benzene, reflux, quant.; b) conc. aq. HCl, MeCN, rt, quant.; c) MeCF₂CO₂H, T₃P®, Et₃N, EtOAc, CH₂Cl₂, rt; d) K₂CO₃, MeOH, rt, 31% yield from 100; e) DBDMH, DMF, 0° C.; Py, 60° C., 43%; f) Ac₂O, NaOAc, rt, 58%.
Scheme 23
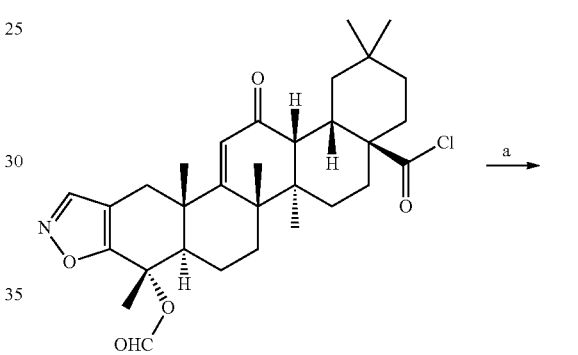
91
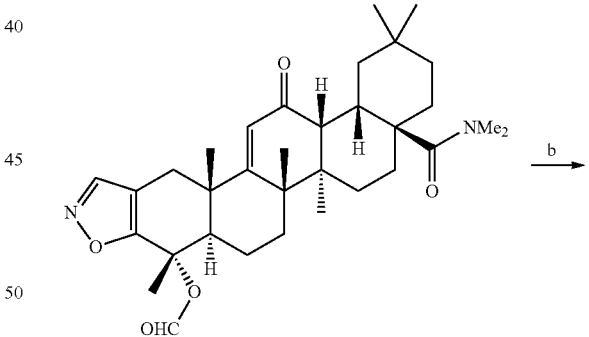
104
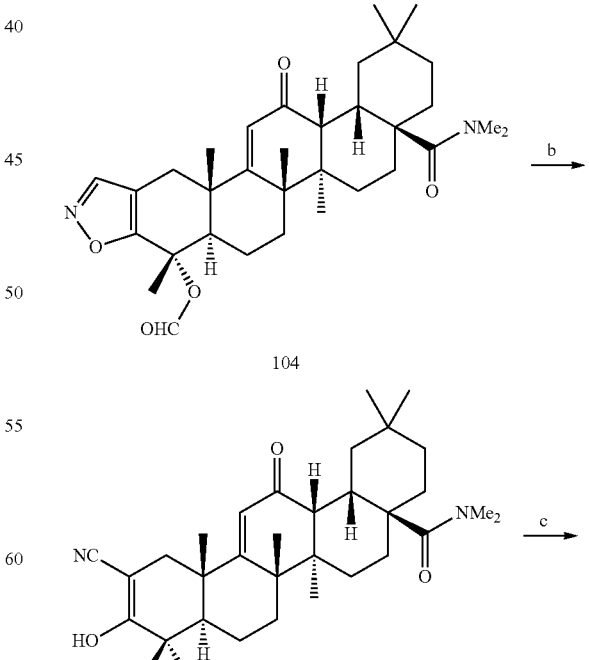
105

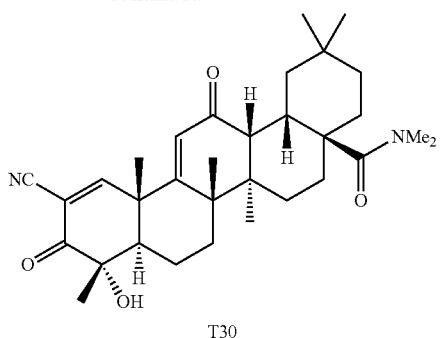
T30
Reagents and conditions: a) Me₂NH•HCl, Et₃N, rt, 86%; b) K₂CO₃, MeOH, rt, quant.; c) DDQ, benzene, reflux, 31%.
Scheme 24
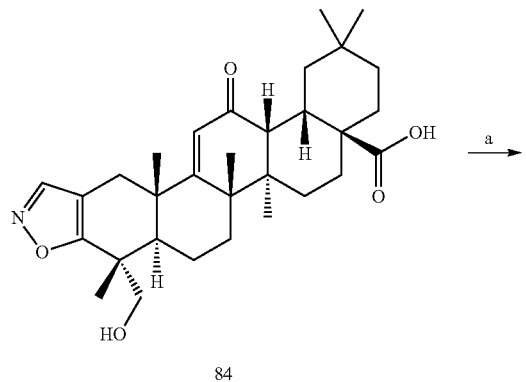
84
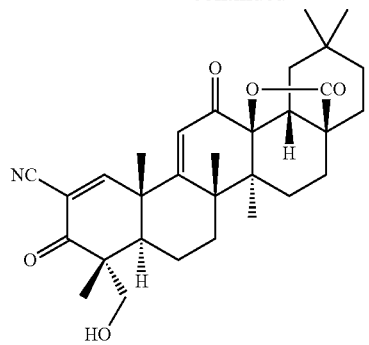
T31
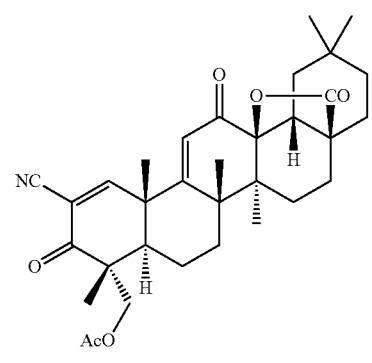
T32
Reagents and conditions: a) PhI(OH)(OTs), CH₂Cl₂, 55° C., 35%; b) K₂CO₃, MeOH, rt, 87%; c) DDQ, benzene, reflux to rt, 52%; d) AcCl, Et₃N, CH₂Cl₂, rt, 99%.
Scheme 25
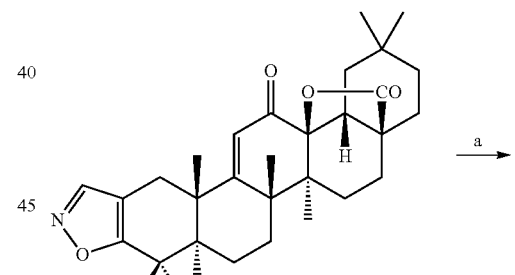
106
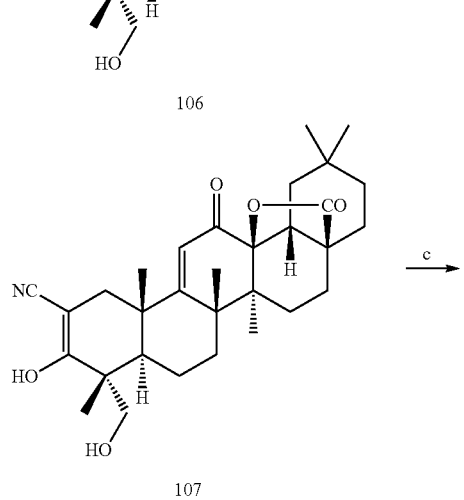
107
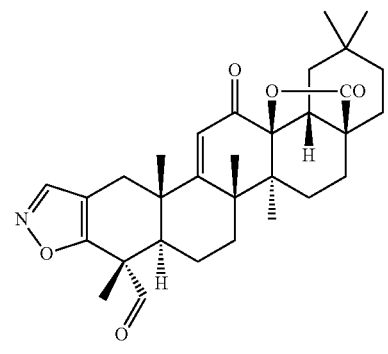
108

127
-continued
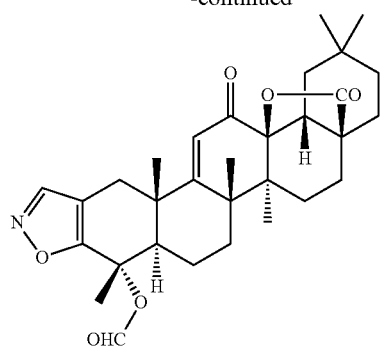
109
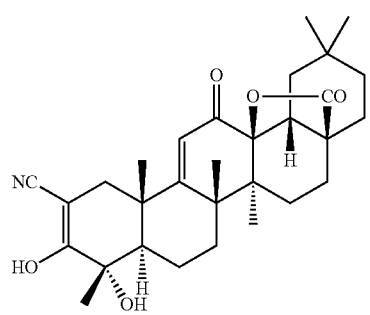
110
T33
Reagents and conditions: a) (COCl)$_2$, DMSO, CH$_2$Cl$_2$, -78° C.; Et$_3$N, -78° C. - rt; b) m-CPBA, Na$_2$HPO$_4$, CH$_2$Cl$_2$, rt, 65% from 106; c) K$_2$CO$_3$, MeOH, rt, quant.; d) DBDMH, DMF, 0° C.; Py, 55° C., 66%.
Scheme 26
106
128
-continued
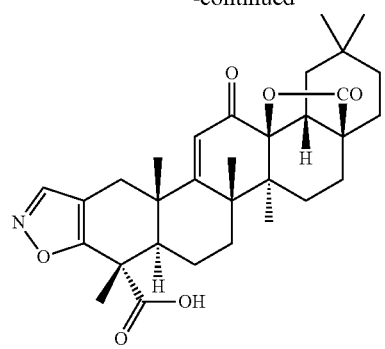
111
112
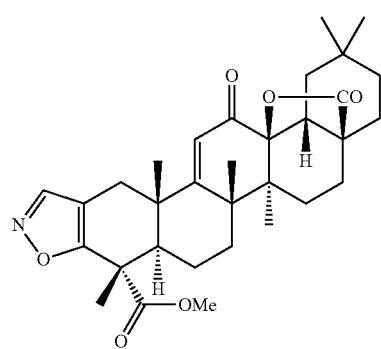
113
T34
Reagents and conditions: a) Jones reagent, acetone, 0° C. - rt, 61%; b) TMSCHN$_2$, Et$_2$O, toluene, MeOH, 0° C., 77%; c) K$_2$CO$_3$, MeOH, rt, quantitative yield; d) DBDMH, DMF, 0° C.; Py, 55° C., 83%.

Scheme 27
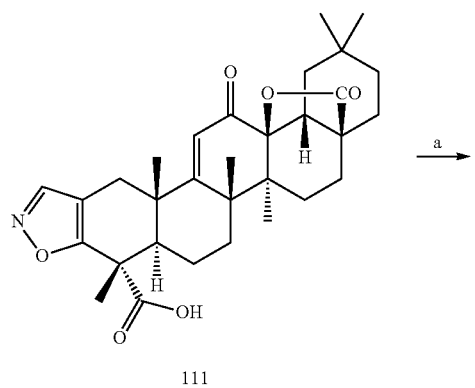
111
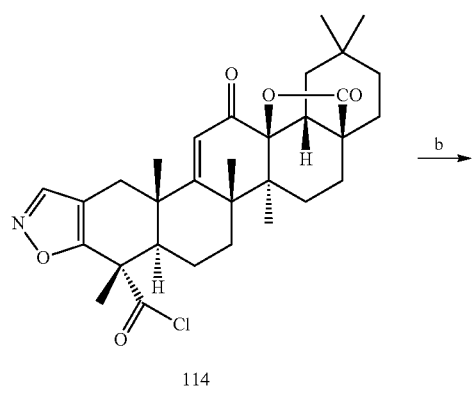
114
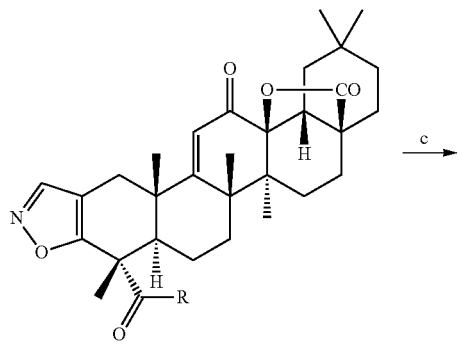
115 R = NHMe
117 R = NMe₂
119 R = NH₂
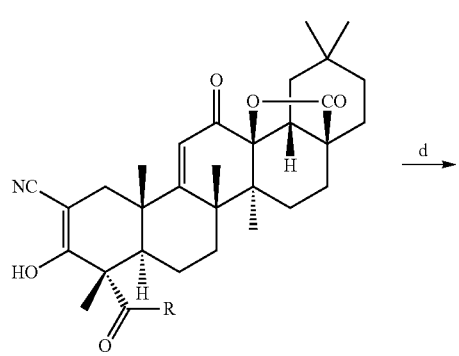
116 R = NHMe
118 R = NMe₂
120 R = NH₂
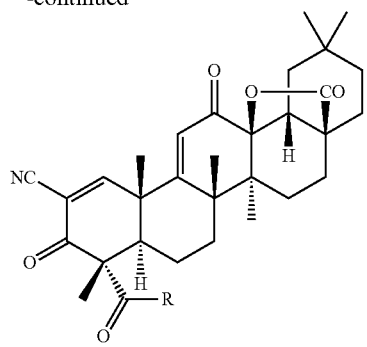
T35 R = NHMe
T36 R = NMe₂
T37 R = NH₂
Reagents and conditions: a) (COCl)₂, DMF, CH₂Cl₂, 0° C. - rt, quant.; b) 115 and 117: RH·HCl, Et₃N, CH₂Cl₂, rt, 75% for 115; 73% for 117; 119: NH₃, MeOH, CH₂Cl₂, 0° C., 74%; c) K₂CO₃, MeOH, rt, 97% for 116; quant. for 118; quant. for 120; d) DBDMH, DMF, Py, 55° C., 70% for T35; 65% for T36; 66% for T37.
Scheme 28
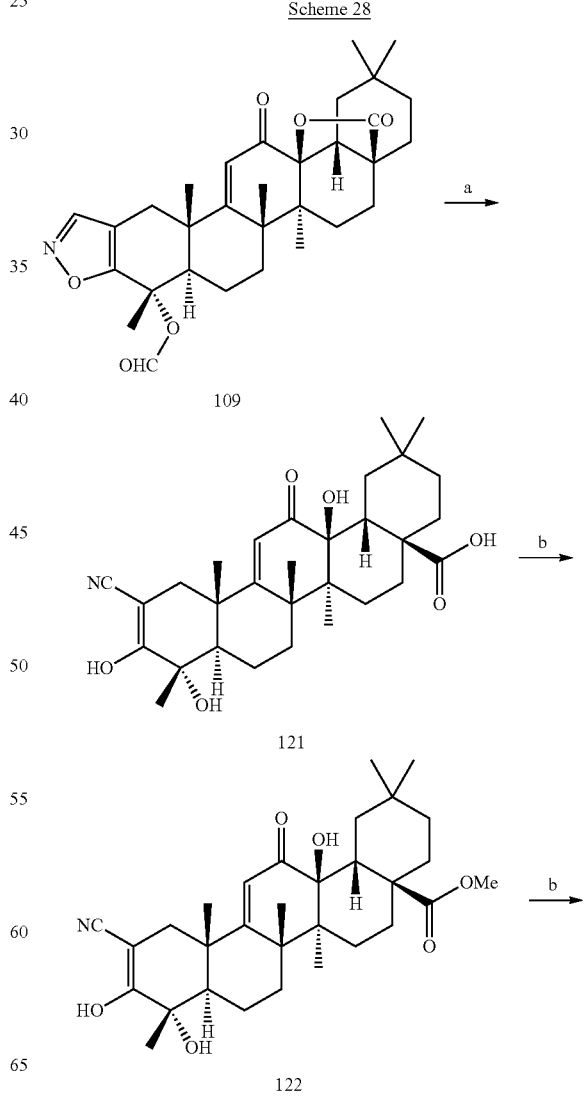
109
121
122

131
-continued
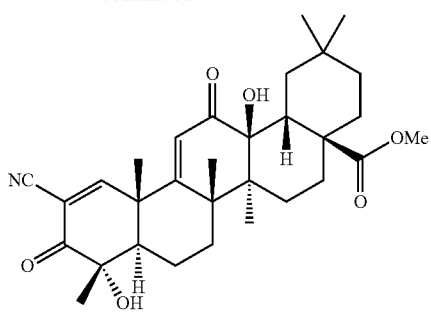
T38
Reagents and conditions: a) aq. NaOH, THF, EtOH, 0° C.; b) TMSCHN₂, Et₂O, toluene, MeOH, 0° C., 67% from 109; c) DBDMH, DMF, 0° C.; Py, 55° C., 74%.
132
-continued
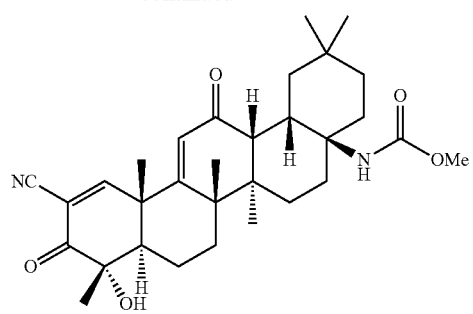
T39
Reagents and conditions: a) NaOMe, MeOH, rt-55° C., 66%; b) DBDMH, DMF, 0° C.; Py, 55° C., 88%.
Scheme 29
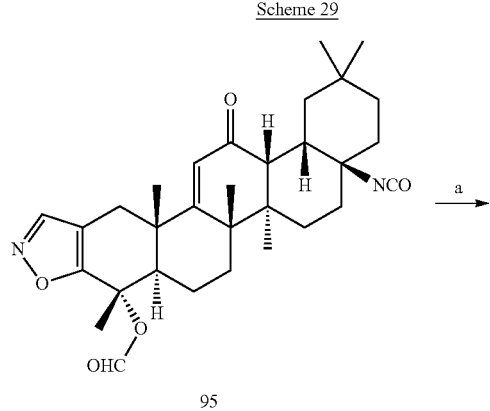
Scheme 30
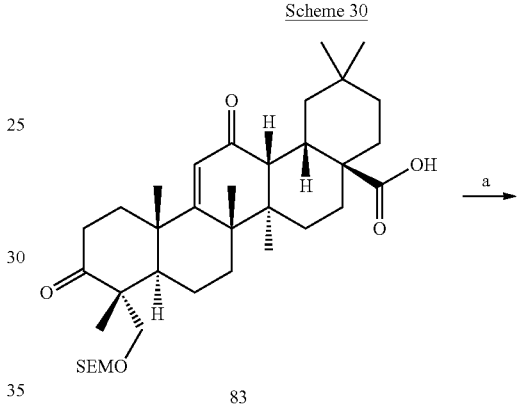
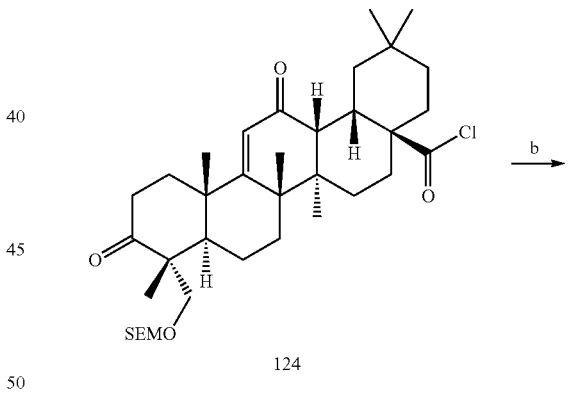
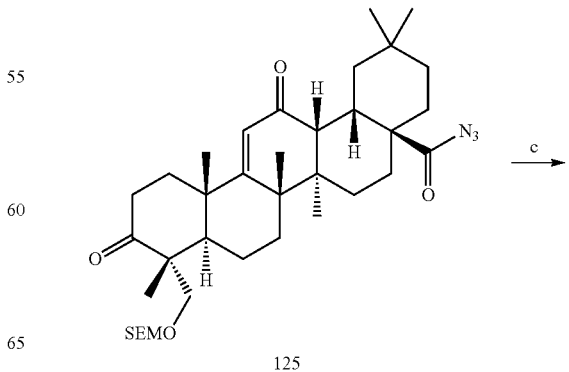

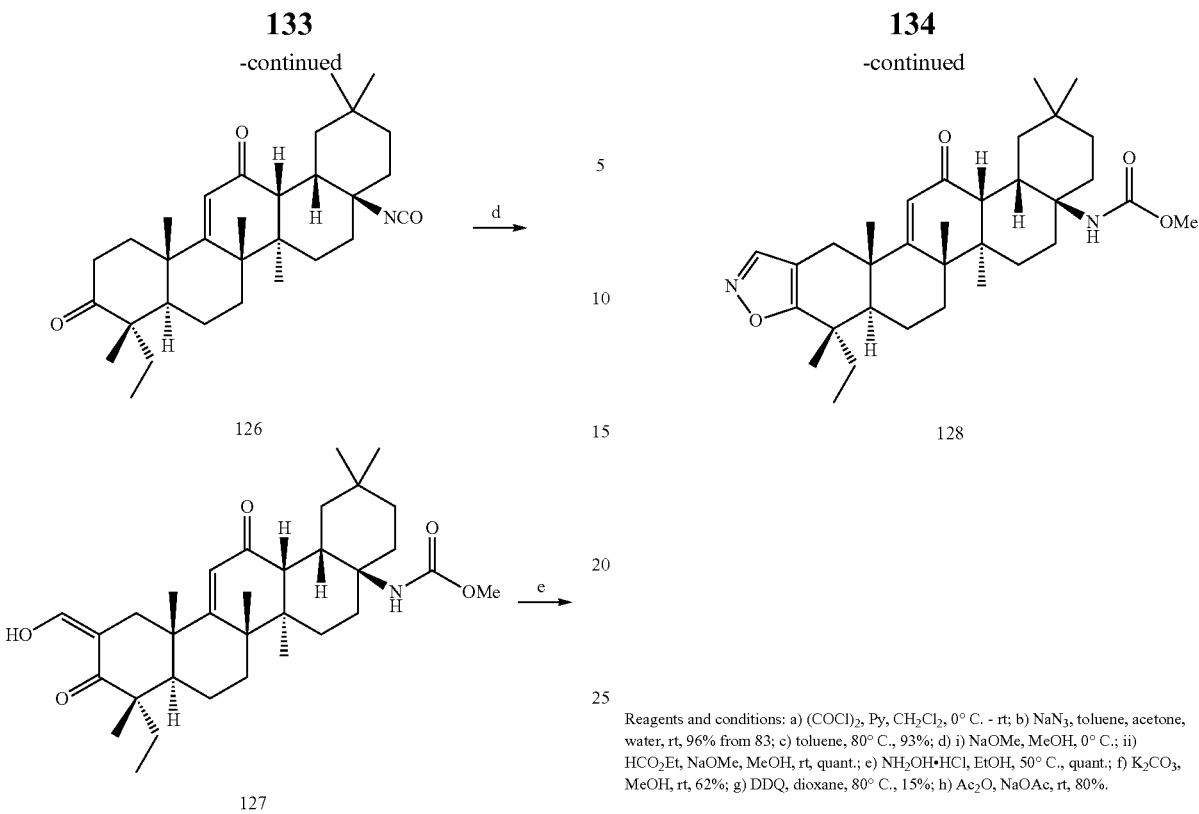
Reagents and conditions: a) (COCl)$_2$, Py, CH$_2$Cl$_2$, 0° C. - rt; b) NaN$_3$, toluene, acetone, water, rt, 96% from 83; c) toluene, 80° C., 93%; d) i) NaOMe, MeOH, 0° C.; ii) HCO$_2$Et, NaOMe, MeOH, rt, quant.; e) NH$_2$OH•HCl, EtOH, 50° C., quant.; f) K$_2$CO$_3$, MeOH, rt, 62%; g) DDQ, dioxane, 80° C., 15%; h) Ac$_2$O, NaOAc, rt, 80%.
Scheme 31
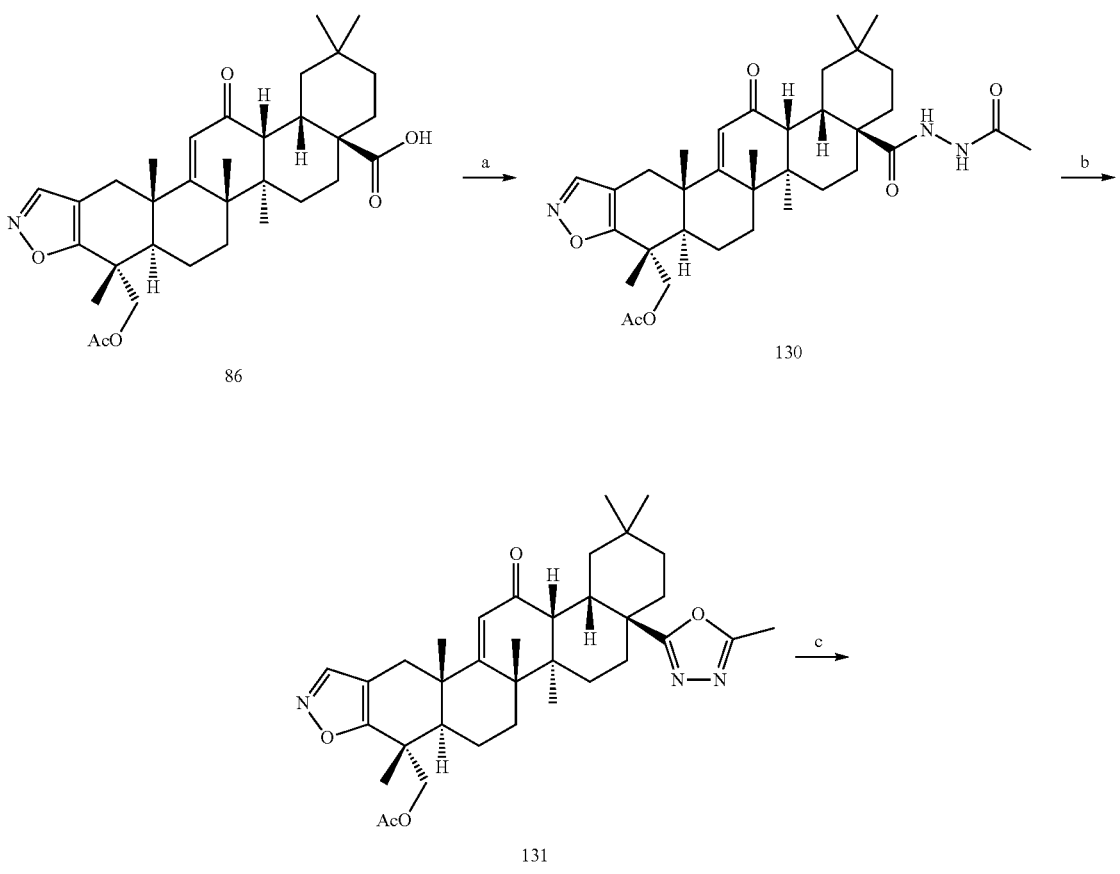

-continued
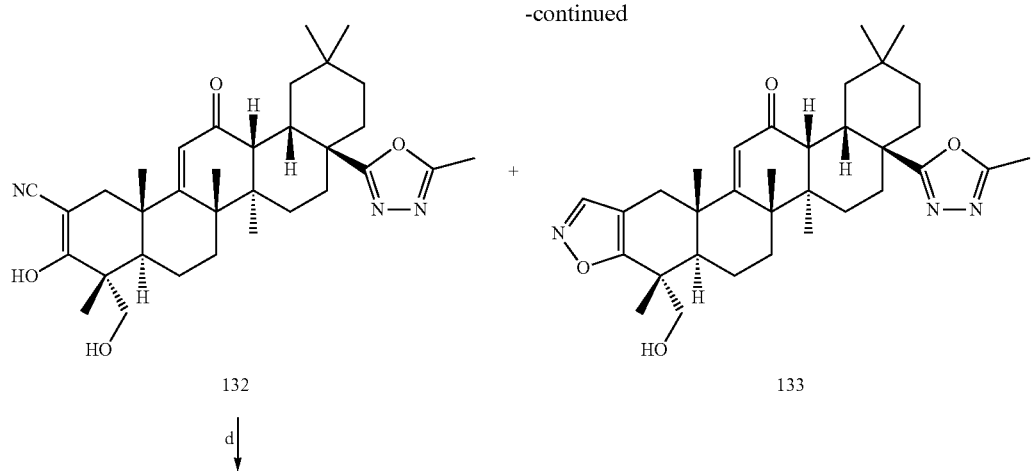
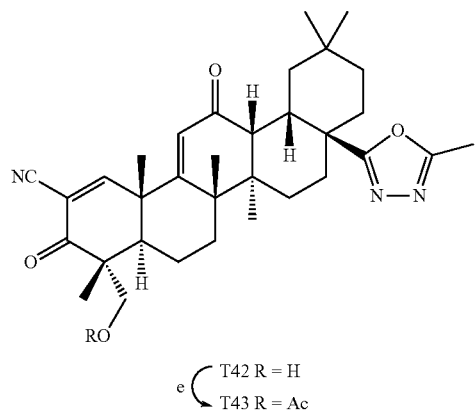
Reagents and conditions: a) i) (COCl)$_2$, DMF, CH$_2$Cl$_2$, rt: ii) AcNHNH$_2$, Et$_3$N, Et$_2$O, CH$_2$Cl$_2$, rt, quant.; b) TsOH•H$_2$O, toluene, reflux, 81%; c) K$_2$CO$_3$, MeOH, rt, 44% for 132; 31% for 133; d) DDQ, benzene, reflux, 47%; e) Ac$_2$O, DMAP, Py, rt, 34%.
Scheme 32
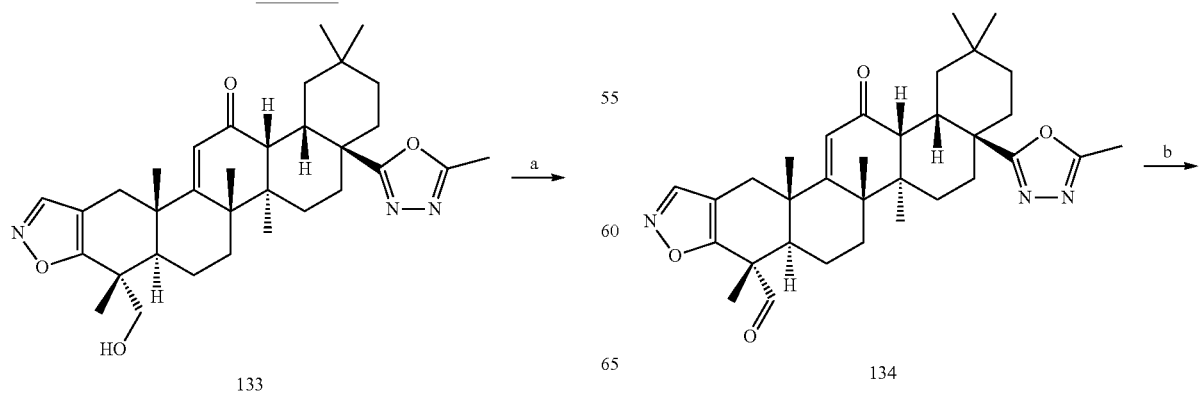

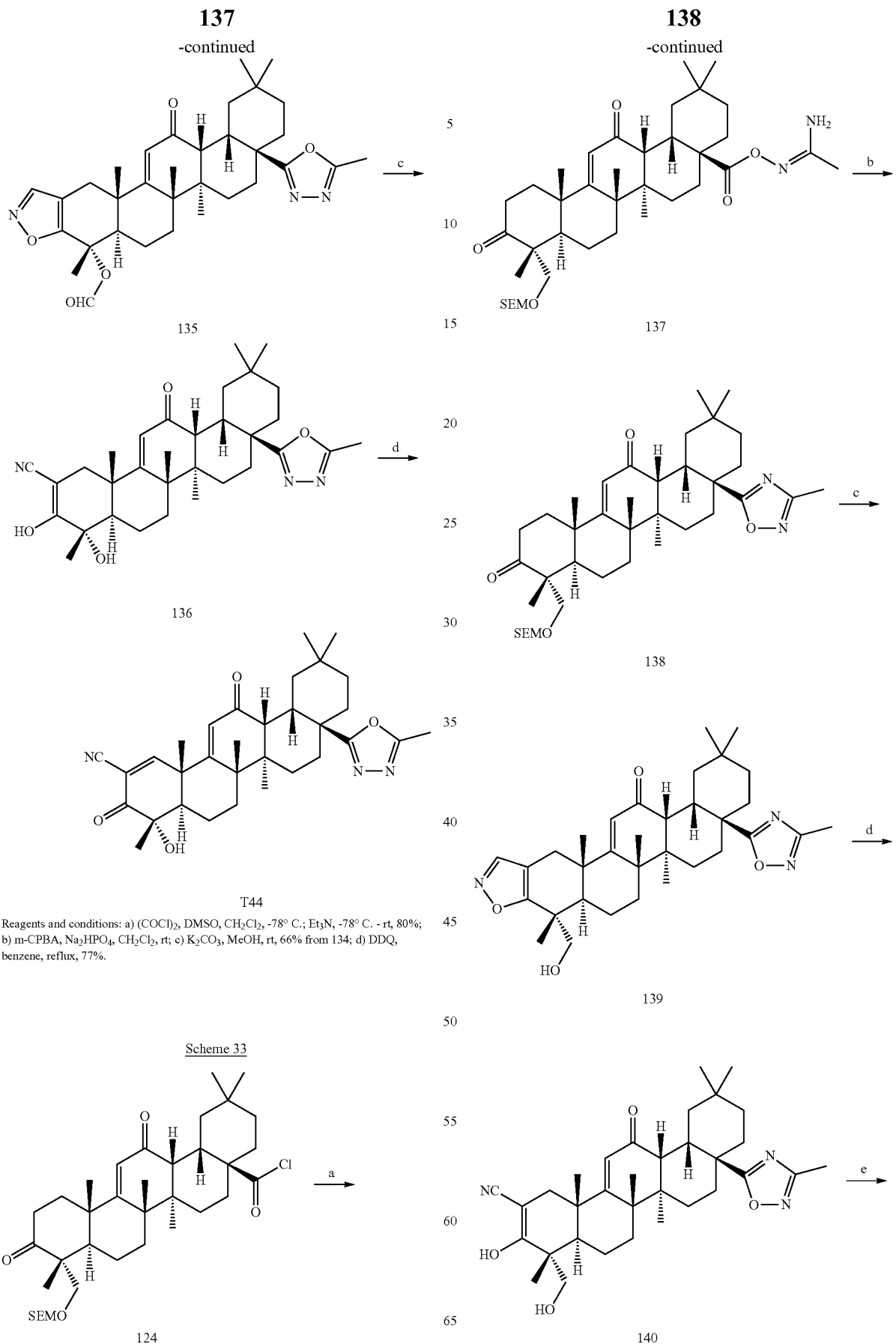
Reagents and conditions: a) (COCl)₂, DMSO, CH₂Cl₂, -78° C.; Et₃N, -78° C. - rt, 80%; b) m-CPBA, Na₂HPO₄, CH₂Cl₂, rt; c) K₂CO₃, MeOH, rt, 66% from 134; d) DDQ, benzene, reflux, 77%.
Scheme 33

139 -continued
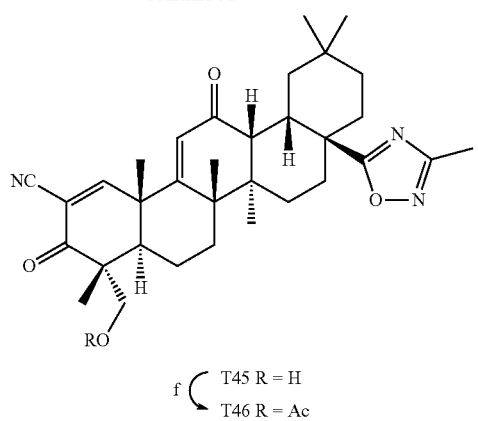
T45 R = H
T46 R = Ac
Reagents and conditions: a) acetamide oxime, Et₃N, CH₂Cl₂, 0° C., 83%; b) Bu₄NOH, THF, rt, 71%; c) i) HCO₂Et, NaOMe, MeOH, 0° C. - rt; ii) NH₂OH·H₂O, aq. EtOH, 55° C., 76%; d) K₂CO₃, MeOH, rt, quant.; e) DBDMH, DMF, 0° C.; Py, 55° C., 64%; f) AcCl, Et₃N, CH₂Cl₂, 82%.
Scheme 34
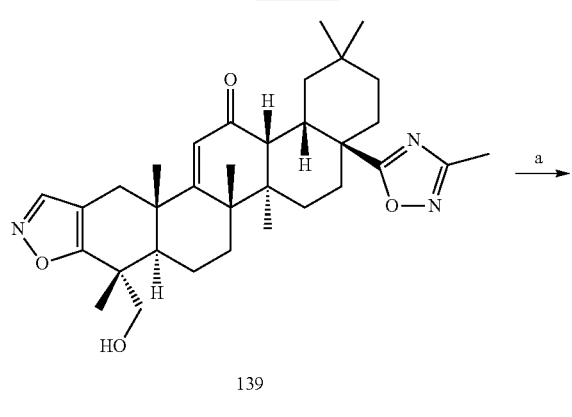
140 -continued
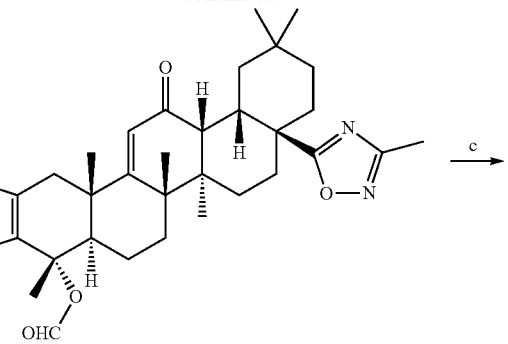
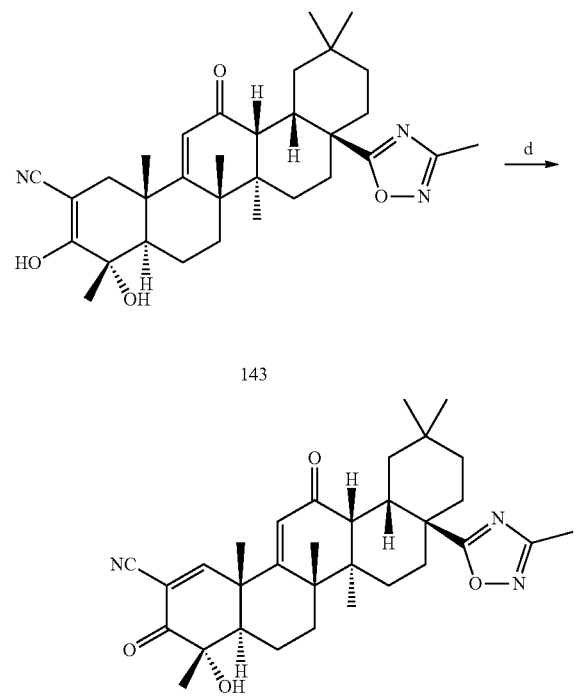
Reagents and conditions: a) Dess-Martin periodinane, CH₂Cl₂, rt; b) m-CPBA, Na₂HPO₄, CH₂Cl₂, rt, 51% from 139; c) K₂CO₃, MeOH, rt, 99%; d) DBDMH, DMF, 0° C.; Py, 55° C., 65%.
Scheme 35
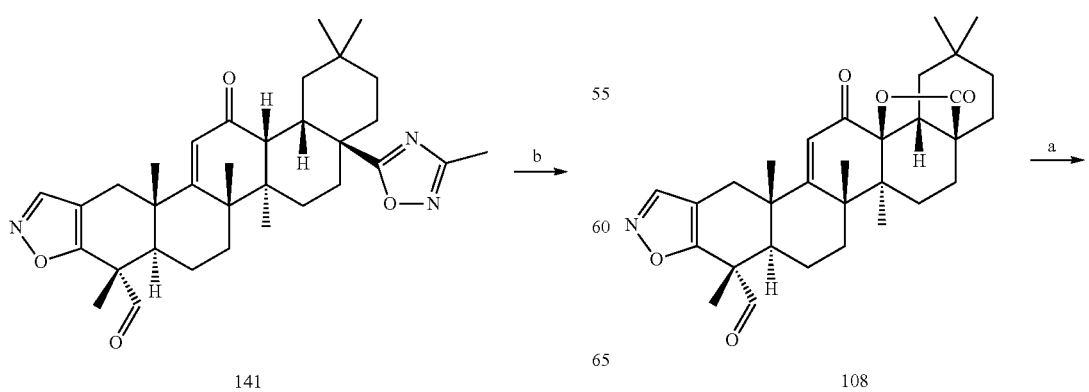

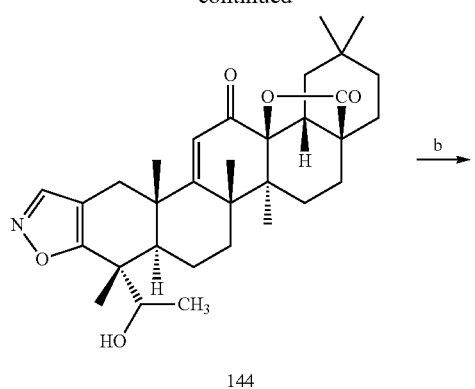
144
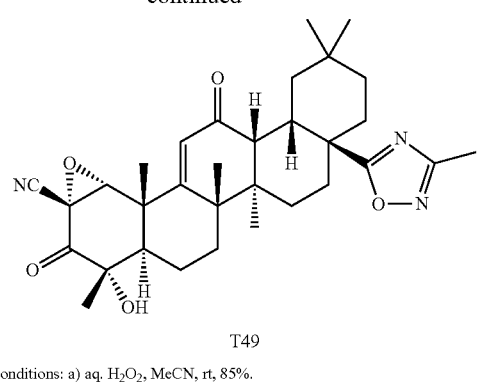
T49
Reagents and conditions: a) aq. H₂O₂, MeCN, rt, 85%.
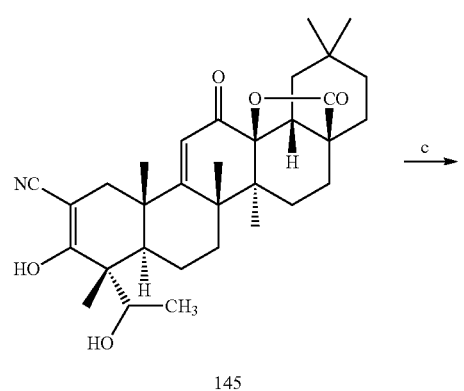
145
Scheme 37
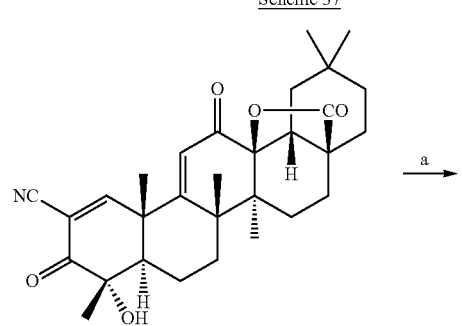
T33
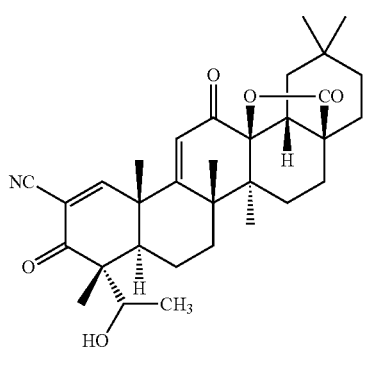
T48
Reagents and conditiond: a) MeMgCl, THF, -78° C., 60%; b) K₂CO₃, MeOH, rt, 40%; c) DBDMH, DMF, 0° C.; Py, 55° C., 28%.
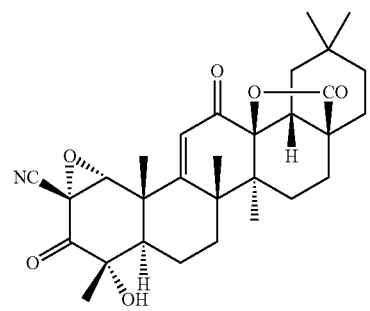
T50
Reagents and conditions: a) aq. H₂O₂, MeCN, rt, 26%.
Scheme 36
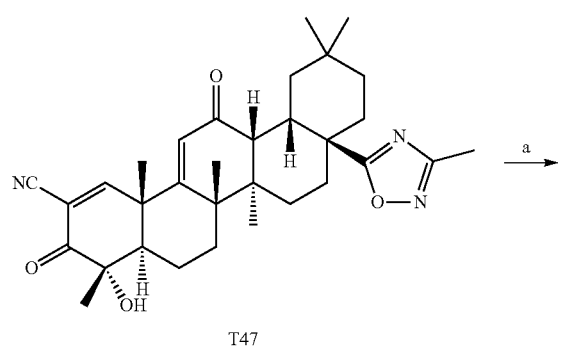
T47
Scheme 38
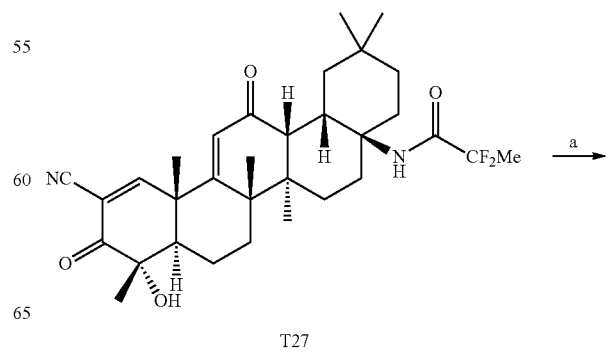
T27

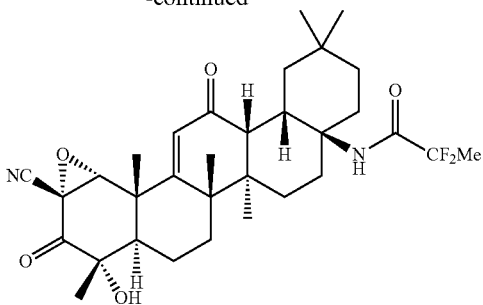

T51

Reagents and conditions: a) aq. H$_2$O$_2$, MeCN, rt, 49%.

Experimental Procedure

Compound 2:

A mixture of compound 1 (1.16 g, 2.48 mmol), NaOAc (466 mg, 5.68 mmol) and NH$_2$OH.HCl (398 mg, 5.73 mmol) in CH$_2$Cl$_2$ (12 mL) and MeOH (12 mL) were heated at 60° C. for 1.5 h. EtOAc was added. The mixture was washed with water. The organic extract was dried over Na$_2$SO$_4$, filtered and concentrated to give oxime 2 as a white foam. m/z=484.3 (M+1).

Compound 3:

Compound 2 (all obtained from the last step) was dissolved in AcOH (2.9 mL). Ac$_2$O (0.35 mL, 3.71 mmol) was added. After the reaction was stirred at room temperature for 1 h, ClCH$_2$CH$_2$Cl (5.8 mL), PhI(OAc)$_2$ (1.195 g, 3.71 mmol) and Pd(OAc)$_2$ (28 mg, 0.13 mmol) were added. The mixture was stirred at 60° C. for 15 h, and at 80° C. for 3 h. Additional amount of Pd(OAc)$_2$ (28 mg, 0.13 mmol) was added. The mixture was at stirred 80° C. for another 3 h, and was cooled to room temperature. The solvent was removed. Aq. NaHCO$_3$ was added. The product was extracted with EtOAc. The organic extract was dried over Na$_2$SO$_4$, filtered and concentrated. The residue was purified by column chromatography (Silica gel, 0-50% EtOAc in hexanes) to give compound 3 (629 mg, 43% yield from 1) as a light orange foam. m/z=584.3 (M+1).

Compound 4:

To a mixture of compound 3 (627 mg, 1.07 mmol) in MeOH (22 mL) was added K$_2$CO$_3$ (742 mg, 5.37 mmol) at 0° C. The reaction was stirred at room temperature for 1.5 h. CH$_2$Cl$_2$ and 12 N aq. HCl (0.90 mL, 1.08 mmol) were added. The mixture was washed with water, and the aq. wash was extracted with CH$_2$Cl$_2$. The combined organic extract was dried over Na$_2$SO$_4$, filtered and concentrated to give compound 4 as a light yellow foam. m/z=500.2 (M+1).

Compound 5:

To a mixture of compound 4 (all obtained from the last step) in EtOH (7.5 mL) and water (2.5 mL) was added sodium bisulfite (mixture of NaHSO$_3$ and Na$_2$S$_2$O$_5$, ≥58.5% SO$_2$, 410 mg, 3.75 mmol). The reaction was heated at 80° C. for 1 h. Additional amount of sodium bisulfite (mixture of NaHSO$_3$ and Na$_2$S$_2$O$_5$, ≥58.5% SO$_2$, 100 mg, 0.91 mmol) was added. The mixture was heated at 80° C. for another 3 h, and cooled to room temperature. EtOAc was added. The mixture was washed with water. The organic extract was dried over Na$_2$SO$_4$, filtered and concentrated. The residue was purified by column chromatography (Silica gel, 0-100% EtOAc in hexanes) to give compound 5 (380 mg, 73% yield from 3) as a white solid. m/z=485.2 (M+1).

Compound 6:

Compound 5 (51.6 mg, 0.11 mmol) was dissolved in acetone (1 mL), and cooled to 0° C. Jones reagent (2.5 M) was added until the orange color persisted. The mixture was stirred until compound 5 was completely consumed. During the reaction, if the mixture turned green, additional amount of Jones reagent (2.5 M) was added until the orange color persisted. i-PrOH was added to quench the reaction. EtOAc was added. The mixture was washed with water. The organic extract was dried over Na$_2$SO$_4$, filtered and concentrated to give a mixture of compound 6 (m/z=455.2 (m+1)) and the C$_4$-acid (m/z=499.2 (m+1)) as a white solid. The mixture was heated under vacuum at 80° C. for 2 h, and 120° C. for 3 h. The residue was purified by column chromatography (Silica gel, 0-40% EtOAc in hexanes and then, 15% EtOAc in CH$_2$Cl$_2$) to give compound 6 (39 mg, 81% yield) as a white solid. m/z=455.2 (M+1).

Compound 7:

To a mixture of compound 6 (39 mg, 0.086 mmol) in HCO$_2$Et (196 L, 2.44 mmol) was added NaOMe (25% w/w in MeOH, 279 µL, 1.21 mmol) at 0° C. The mixture was stirred at room temperature for 10 min. THF (0.3 mL) was added. The reaction was stirred at room temperature for another 5 h. MTBE was added, followed by 6 N aq. HCl (0.22 mL, 1.32 mmol). EtOAc was added. The mixture was washed with water. The organic extract was dried with Na$_2$SO$_4$, filtered and concentrated. The residue was dissolved in EtOH (4 mL) and water (0.2 mL). NH$_2$OH.HCl (9 mg, 0.13 mmol) was added. The mixture was heated at 55° C. for 18 h, and cooled to room temperature. EtOAc was added. The mixture was washed with water. The organic extract was dried over Na$_2$SO$_4$, filtered and concentrated. The residue was purified by column chromatography (Silica gel, 0-10% EtOAc in CH$_2$Cl$_2$) to give compound 7 (18 mg, 44% yield) as a white solid. m/z=480.2 (M+1).

Compound 8:

To a mixture of compound 7 (17 mg, 0.035 mmol) in MeOH (0.70 mL) was added NaOMe (25% w/w in MeOH, 12 µL, 0.052 mmol) at room temperature. The mixture was heated at 55° C. for 30 min. THF (0.35 mL) was added. The mixture was heated at 55° C. for another 2 h. Additional amount of MeOH (0.70 mL) and NaOMe (25% w/w in MeOH, 12 µL, 0.052 mmol) were added. The reaction was heated at 55° C. for an additional 1 h, and cooled to room temperature. MTBE and CH$_2$Cl$_2$ were added. The mixture was washed with water. The organic extract was dried over Na$_2$SO$_4$, filtered and concentrated. The residue was purified by column chromatography (Silica gel, 0-70% EtOAc in hexanes) to give compound 8 (8.7 mg, 51% yield) as a white foam. m/z=480.2 (M+1).

Compound T1:

To a solution of compound 8 (8.7 mg, 0.018 mmol) in DMF (0.1 mL) was added a solution of 1,3-dibromo-5,5-dimethylhydantoin (2.6 mg, 0.009 mmol) in DMF (21 µL) at 0° C. After the reaction was stirred at 0° C. for 1 h, pyridine (5 µL, 0.062 mmol) was added. The reaction was heated at 55° C. for 3 h, and cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-50% EtOAc in hexanes) to give compound T1 (7 mg, 80% yield) as a white solid. m/z=478.2 (M+1); $^1$H NMR (500 MHz, CDCl$_3$) δ 8.06 (s, 1H), 6.03 (s, 1H), 3.70 (s, 3H), 3.05 (m, 1H), 2.96 (d, 1H, 4.7 Hz), 2.50-2.55 (m, 2H), 2.12 (m, 1H), 1.42 (s, 3H), 1.33 (s, 3H), 1.16-1.95 (m, 14H), 1.03 (s, 3H), 1.01 (s, 3H), 0.90 (s, 3H).

Compound 11 and 12:

To a mixture of compound 9 and 10 (2.9/1, 500 mg, 1.00 mmol) in HCO$_2$Et (2.42 mL, 30.18 mmol) was added NaOMe (25% w/w in MeOH, 3.43 mL, 14.85 mmol) at 0° C. The reaction was stirred at 0° C. for 30 min. MTBE was added, followed by 6 N aq. HCl (2.70 mL, 16.20 mmol). EtOAc was added. The mixture was washed with water. The organic extract was dried with MgSO$_4$, filtered and concentrated. The residue was dissolved in EtOH (10 mL) and water (1 mL). NH$_2$OH.HCl (105 mg, 1.51 mmol) was added. The mixture was heated at 55° C. for 2 h, and cooled to room temperature. EtOH was removed by evaporation. EtOAc was added. The mixture was washed with water and brine. The organic extract was dried over MgSO$_4$, filtered and concentrated. The residue was purified by column chromatography (Silica gel, 0-100% EtOAc in hexanes) to give compound 11 (280 mg, 53% yield) as a white foam. m/z=524.2 (M+1). From the column, also get compound 12 (35 mg, 6.7% yield) as a white solid. m/z=524.2 (M+1).

Compound 13:

Compound 11 (80 mg, 0.15 mmol) was dissolved in acetone (1.5 mL), and cooled to 0° C. Jones reagent (2.5 M) was added until the orange color persisted. The mixture was stirred at 0° C. for 2 h, and at room temperature for 1 h. During the reaction, additional small amount of Jones reagent was added to maintain the orange color of the mixture. i-PrOH was added to quench the reaction. EtOAc was added. The mixture was washed with water. The organic extract was dried over Na$_2$SO$_4$, filtered and concentrated to give compound 13 (72 mg, 88% yield) as an off-white solid. m/z=538.2 (M+1). Compound 13 was used in the next step without further purification.

Compound 14:

Compound 13 (72 mg, 0.13 mmol) was dissolved in toluene (1.2 mL) and MeOH (0.4 mL), and was cooled to 0° C. Trimethylsilyldiazomethane (2 M in Et$_2$O, 0.15 mL, 0.30 mmol) was added at 0° C., and stirred for 10 min. AcOH was added to quench the reaction. EtOAc was added. The mixture was washed with aq. NaHCO$_3$, and water. The organic extract was dried over MgSO$_4$, filtered and concentrated. The residue was purified by column chromatography (Silica gel, 0-25% EtOAc in hexanes) to give compound 14 (62 mg, 84% yield) as a white foam. m/z=552.2 (M+1).

Compound 15:

To a mixture of compound 14 (60 mg, 0.11 mmol) in MeOH (1.1 mL) was added NaOMe (25% w/w in MeOH, 37 μL, 0.16 mmol) at room temperature. The mixture was heated at 55° C. for 1 h, and was cooled to room temperature. MTBE was added. The mixture was washed with 1 N aq. HCl and water. The organic extract was dried over Na$_2$SO$_4$, filtered and concentrated to give compound 15 (60 mg, quantitative yield) as a white foam. m/z=552.2 (M+1). Compound 15 was used in the next step without further purification.

Compound T2:

To a solution of compound 15 (60 mg, 0.11 mmol) in DMF (0.54 mL) was added 1,3-dibromo-5,5-dimethylhydantoin (16 mg, 0.056 mmol) at 0° C. After the reaction was stirred at 0° C. for 1 h, pyridine (26 μL, 0.32 mmol) was added. The reaction was heated at 55° C. for 2 h, and was cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-30% EtOAc in hexanes) to give compound T2 (46 mg, 77% yield) as a white solid. m/z=550.2 (M+1); $^1$H NMR (500 MHz, CDCl$_3$) δ 8.07 (s, 1H), 5.97 (s, 1H), 3.75 (s, 3H), 3.69 (s, 3H), 3.03 (m, 1H), 2.94 (d, 1H, J=4.6 Hz), 2.55 (dd, 1H, J=2.0, 12.4 Hz), 1.52 (s, 3H), 1.44 (s, 3H), 1.31 (s, 3H), 1.15-1.95 (m, 14H), 1.03 (s, 3H), 1.00 (s, 3H), 0.90 (s, 3H).

Compound 16:

Compound 12 (35 mg, 0.067 mmol) was dissolved in acetone (0.7 mL), and cooled to 0° C. Jones reagent (2.5 M) was added until the orange color persisted. The mixture was stirred at 0° C. for 1 h, and at room temperature for 2 h. During the reaction, additional small amount of Jones reagent was added to maintain the orange color of the mixture. i-PrOH was added to quench the reaction. EtOAc was added. The mixture was washed with water. The organic extract was dried over Na$_2$SO$_4$, filtered and concentrated to give the crude acid, which was dissolved in toluene (0.6 mL) and MeOH (0.2 mL), and was cooled to 0° C. Trimethylsilyldiazomethane (2 M in Et$_2$O, 70 μL, 0.14 mmol) was added at 0° C., and stirred for 10 min. AcOH was added to quench the reaction. EtOAc was added. The mixture was washed with aq. NaHCO$_3$, and water. The organic extract was dried over MgSO$_4$, filtered and concentrated. The residue was purified by column chromatography (Silica gel, 0-100% EtOAc in hexanes) to give compound 16 (18 mg, 49% yield from 12) as a white foam. m/z=552.2 (M+1).

Compound 17:

To a mixture of compound 16 (18 mg, 0.033 mmol) in MeOH (0.33 mL) was added NaOMe (25% w/w in MeOH, 11 μL, 0.048 mmol) at room temperature. The mixture was heated at 55° C. for 40 min, and was cooled to room temperature. MTBE was added. The mixture was washed with 1 N aq. HCl and water. The organic extract was dried over Na$_2$SO$_4$, filtered and concentrated. The residue was purified by column chromatography (Silica gel, 0-100% EtOAc in hexanes). The product was purified again by column chromatography (Silica gel, 0-5% MeOH in CH$_2$Cl$_2$) to give compound 17 (13.5 mg, 75% yield) as a white foam. m/z=552.2 (M+1).

Compound T3:

To a solution of compound 17 (13.5 mg, 0.024 mmol) in DMF (0.12 mL) was added 1,3-dibromo-5,5-dimethylhydantoin (3.5 mg, 0.012 mmol) at 0° C. After the reaction was stirred at 0° C. for 1 h, pyridine (6 μL, 0.074 mmol) was added. The reaction was heated at 55° C. for 3.5 h, and was cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-30% EtOAc in hexanes) to give compound T3 (10 mg, 74% yield) as a white solid. m/z=550.2 (M+1); $^1$H NMR (500 MHz, CDCl$_3$) δ 7.91 (s, 1H), 5.94 (s, 1H), 3.69 (s, 3H), 3.67 (s, 3H), 3.02 (m, 1H), 2.94 (m, 1H), 1.56 (s, 3H), 1.34 (s, 3H), 1.32 (s, 3H), 1.12-2.13 (m, 15H), 0.99 (s, 3H), 0.98 (s, 3H), 0.89 (s, 3H).

Compound 18:

To a solution of (COCl)$_2$ (0.121 mL, 1.43 mmol) in CH$_2$Cl$_2$ (1.5 mL) was added DMSO (0.203 mL, 2.86 mmol) dropwise at −78° C., and stirred for 30 min. Compound 11 (312 mg, 0.60 mmol) in CH$_2$Cl$_2$ (3 mL) was added at −78° C., and stirred for another 1 h. Et$_3$N (0.60 mL, 4.31 mmol) was added. The cold bath was removed, and the reaction was stirred at ambient temperature for 30 min. Water was added. The product was extracted with CH$_2$Cl$_2$. The combined organic extract was washed with aq. NaHCO$_3$ and water, dried with MgSO$_4$, and concentrated. The residue was purified by column chromatography (Silica gel, 0-100% EtOAc in hexanes) to give compound 18 (268 mg, 86% yield) as a white foam. m/z=522.3 (M+1).

Compound 19:

To a solution of compound 18 (60 mg, 0.11 mmol) in $CH_2Cl_2$ (2.3 mL) was added DAST (0.40 mL, 3.03 mmol) at room temperature. The reaction was stirred for 60 h at room temperature. EtOAc was added. The mixture was washed with aq. $CaCl_2$. The organic extract was dried with $MgSO_4$, and concentrated. The residue was purified by column chromatography (Silica gel, 0-35% EtOAc in hexanes) to give a mixture of compound 18 and 19 (51 mg, 18/19=1.5/1). The mixture of compound 18 and 19 was dissolved in MeOH (3.5 mL), and was cooled to 0° C. $NaBH_4$ (20 mg, 0.53 mmol) was added. The reaction was stirred at 0° C. for 10 min. EtOAc was added. The mixture was washed with aq. 1N HCl, and water. The organic extract was dried with $MgSO_4$, and concentrated. The residue was purified by column chromatography (Silica gel, 0-90% EtOAc in hexanes) to give compound 19 (20 mg, 32% yield) as a white foam. m/z=544.3 (M+1).

Compound 20:

To a mixture of compound 19 (22 mg, 0.040 mmol) in MeOH (0.40 mL) was added NaOMe (25% w/w in MeOH, 14 µL, 0.061 mmol) at room temperature. The mixture was heated at 55° C. for 40 min, and was cooled to room temperature. MTBE was added. The mixture was washed with 1 N aq. HCl and water. The organic extract was dried over $Na_2SO_4$, filtered and concentrated. The residue was purified by column chromatography (Silica gel, 0-100% EtOAc in hexanes) to give compound 20 (18 mg, 82% yield) as a white foam. m/z=544.2 (M+1).

Compound T4:

To a solution of compound 20 (17 mg, 0.031 mmol) in DMF (0.16 mL) was added 1,3-dibromo-5,5-dimethylhydantoin (4.5 mg, 0.016 mmol) at 0° C. After the reaction was stirred at 0° C. for 1 h, pyridine (8 µL, 0.099 mmol) was added. The reaction was heated at 55° C. for 4.5 h, and was cooled to room temperature. EtOAc was added. The mixture was washed with 1 N aq. HCl and water. The organic extract was dried over $Na_2SO_4$, filtered and concentrated. The residue was purified by column chromatography (Silica gel, 0-35% EtOAc in hexanes) to give compound T4 (14.5 mg, 86% yield) as a white foam. m/z=542.3 (M+1); $^1H$ NMR (500 MHz, $CDCl_3$) δ 8.14 (s, 1H), 5.99 (s, 1H), 5.93 (t, 1H, J=55.8 Hz), 3.70 (s, 3H), 3.05 (m, 1H), 2.96 (d, 1H, J=4.7 Hz), 2.46 (d, 1H, J=10.4 Hz) 1.50 (s, 3H), 1.37 (s, 3H), 1.32 (s, 3H), 1.17-2.11 (m, 14H), 1.05 (s, 3H), 1.00 (s, 3H), 0.91 (s, 3H).

Compound 21:

$Na_2HPO_4$ (49 mg, 0.35 mmol) and m-CPBA (≤77%, 65 mg, 0.29 mmol) were added to a solution of compound 18 (100 mg, 0.19 mmol) in $CH_2Cl_2$ (3.8 mL). After stirring at room temperature for 6 h, aq. $Na_2SO_3$ was added. The mixture was extracted with $CH_2Cl_2$. The organic extract was washed with aq. $NaHCO_3$, dried with $MgSO_4$, and concentrated. The residue was purified by column chromatography (Silica gel, 0-40% EtOAc in hexanes) to give compound 21 (89 mg, 86% yield) as a white solid. m/z=538.3 (M+1).

Compound 22:

To a solution of compound 21 (89 mg, 0.17 mmol) in MeOH (1.8 mL) was added NaOMe (25% w/w in MeOH, 60 µL, 0.26 mmol). The reaction was heated at 55° C. for 1 h, and was cooled to room temperature. MTBE was added. The mixture was washed with 1N aq. HCl, and water. The organic extract was dried with $MgSO_4$, and concentrated to give compound 22 (83 mg, 98% yield) as a white foam. m/z=510.3 (M+1). Compound 22 was used in the next step without further purification.

Compound T5:

To a solution of compound 22 (83 mg, 0.16 mmol) in DMF (0.8 mL) was added 1,3-dibromo-5,5-dimethylhydantoin (23 mg, 0.080 mmol) at 0° C. After stirring at 0° C. for 1 h, pyridine (40 µL, 0.50 mmol) was added. The reaction was heated at 55° C. for 2.5 h. EtOAc was added. The mixture was washed with 1 N aq. HCl and water. Organic extract was dried with $Na_2SO_4$, filtered and concentrated. The residue was purified by column chromatography (Silica gel, 0-60% EtOAc in hexanes) to give T5 (66 mg, 80% yield) as a white foam. m/z=508.3 (M+1); $^1H$ NMR (500 MHz, $CDCl_3$) δ 8.01 (s, 1H), 5.90 (s, 1H), 3.70 (s, 3H), 3.24 (s, 1H), 3.03 (m, 1H), 2.94 (d, 1H, J=4.7 Hz), 2.13 (m, 1H), 2.02 (d, 1H, J=10.5 Hz), 1.54 (s, 3H), 1.34 (s, 3H), 1.32 (s, 3H), 1.16-1.95 (m, 13H), 1.01 (s, 3H), 1.00 (s, 3H), 0.90 (s, 3H).

Compound 23:

To a solution of $(COCl)_2$ (24 µL, 0.28 mmol) in $CH_2Cl_2$ (1 mL) was added DMSO (41 µL, 0.57 mmol) dropwise at −78° C. The reaction was stirred for 30 min. Compound 12 (60 mg, 0.11 mmol) in $CH_2Cl_2$ (2 mL) was added at −78° C., and stirred for another 1 h. $Et_3N$ (0.239 mL, 1.72 mmol) was added. The cold bath was removed, and the reaction was stirred at ambient temperature for 30 min. Water was added. The product was extracted with $CH_2Cl_2$. The combined organic extract was washed with aq. $NaHCO_3$ and water, dried with $MgSO_4$, and concentrated. The residue was purified by column chromatography (Silica gel, 0-40% EtOAc in hexanes) to give compound 23 (43 mg, 72% yield) as a white foam. m/z=522.3 (M+1).

Compound 24: $Na_2HPO_4$ (21 mg, 0.15 mmol) and m-CPBA (≤77%, 28 mg, 0.12 mmol) were added to a solution of compound 23 (43 mg, 0.082 mmol) in $CH_2Cl_2$ (1.6 mL). After the reaction was stirred at room temperature for 5 h, additional amount of $Na_2HPO_4$ (10 mg, 0.070 mmol) and m-CPBA (≤77%, 14 mg, 0.062 mmol) were added. The reaction was stirred at room temperature overnight. Aq. $Na_2SO_3$ was added. The mixture was extracted with EtOAc. The organic extract was washed with aq. $NaHCO_3$, dried with $MgSO_4$, and concentrated. The residue was purified by column chromatography (Silica gel, 0-40% EtOAc in hexanes) to give compound 24 (28 mg, 63% yield) as a white solid. m/z=538.3 (M+1).

Compound 25:

To a solution of compound 24 (28 mg, 0.052 mmol) in MeOH (0.52 mL) was added NaOMe (25% w/w in MeOH, 24 µL, 0.10 mmol). The reaction was heated at 55° C. for 1.5 h, and was cooled to room temperature. MTBE was added. The mixture was washed with 1N aq. HCl, and water. The organic extract was dried with $MgSO_4$, and concentrated. The residue was purified by column chromatography (Silica gel, 0-100% EtOAc in hexanes) to give compound 25 (18 mg, 68% yield) as a white foam. m/z=510.3 (M+1).

Compound T6:

To a solution of compound 25 (17.5 mg, 0.034 mmol) in DMF (0.17 mL) was added 1,3-dibromo-5,5-dimethylhydantoin (4.9 mg, 0.017 mmol) at 0° C. After stirring at 0° C. for 1 h, pyridine (9 µL, 0.11 mmol) was added. The reaction was heated at 55° C. for 11 h. EtOAc was added. The mixture was washed with 1 N aq. HCl and water. Organic extract was dried with $Na_2SO_4$, filtered and concentrated. The residue was purified by column chromatography (Silica gel, 0-40% EtOAc in hexanes) to give T6 (11 mg, 63% yield) as a white foam. m/z=508.3 (M+1); $^1H$ NMR (500 MHz, $CDCl_3$) δ 8.17 (s, 1H), 5.98 (s, 1H), 3.70 (s, 3H), 3.05 (m, 1H), 2.96 (d, 1H, J=4.6 Hz), 2.20 (s, 1H), 1.52 (s, 3H), 1.45 (s, 3H), 1.34 (s, 3H), 1.00 (s, 6H), 1.17-2.02 (m, 15H), 0.90 (s, 3H).

Compound 26:

To a solution of compound 9 (1.00 g, 2.00 mmol) in CH$_2$Cl$_2$ (8 mL) was added chloromethyl methyl ether (0.46 mL, 6.05 mmol) at 0° C. The mixture was stirred at room temperature for 16 h, and then concentrated. The residue was purified by column chromatography (Silica gel, 0-30% EtOAc in hexanes) to give compound 26 (0.98 g, 90% yield) as a white foam. m/z=543.4 (M+1).

Compound 27:

To a mixture of compound 26 (955 mg, 1.76 mmol) in HCO$_2$Et (4.3 mL, 53.5 mmol) was added NaOMe (25% w/w in MeOH, 6.1 mL, 26.4 mmol) at 0° C. The mixture was stirred at room temperature for 1 h. MTBE was added, followed by 3 N aq. HCl. The mixture was extracted with EtOAc. The organic extract was washed with water, dried with Na$_2$SO$_4$, filtered and concentrated. The residue was dissolved in EtOH (18 mL) and water (2 mL). NH$_2$OH.HCl (185 mg, 2.66 mmol) was added. The mixture was heated at 55° C. for 6 h, then cooled to room temperature and concentrated. EtOAc was added. The mixture was washed with water. The organic extract was dried over Na$_2$SO$_4$, filtered and concentrated. The residue was purified by column chromatography (Silica gel, 0-70% EtOAc in hexanes) to give compound 27 (615 mg, 61% yield) as a white foam. m/z=568.4 (M+1).

Compound 28:

To a mixture of compound 27 (200 mg, 0.35 mmol) in MeOH (3.5 mL) and THF (1 mL) was added NaOMe (25% w/w in MeOH, 0.16 mL, 0.69 mmol) at room temperature. The mixture was heated at 55° C. for 2 h. MTBE was added. The mixture was washed with aq. NaH$_2$PO$_4$. The aqueous wash was back extracted with MTBE. The organic extract was dried over Na$_2$SO$_4$, filtered and concentrated to give compound 28 (210 mg, quantitative yield) as a light yellow foam. m/z=568.4 (M+1).

Compound T7:

To a solution of compound 28 (all obtained from the last step) in DMF (1 mL) was added a solution of 1,3-dibromo-5,5-dimethylhydantoin (53 mg, 0.19 mmol) in DMF (0.8 mL) at 0° C. After the reaction was stirred at 0° C. for 1 h, pyridine (90 µL, 1.12 mmol) was added. The reaction was heated at 55° C. for 20 h, and cooled to room temperature. EtOAc was added. The mixture was washed with aq. Na$_2$SO$_3$, 1 N aq. HCl and water. The organic extract was dried over Na$_2$SO$_4$, filtered and concentrated. The residue was purified by column chromatography (Silica gel, 0-45% EtOAc in hexanes) to give compound T7 (170 mg, 85% yield) as a white foam. m/z=566.2 (M+1); $^1$H NMR (400 MHz, CDCl$_3$) δ 8.02 (s, 1H), 5.98 (s, 1H), 4.49 (AB, 2H), 3.72 (d, 1H, J=9.2 Hz), 3.68 (s, 3H), 3.43 (d, 1H, J=9.2 Hz), 3.26 (s, 3H), 3.03 (m, 1H), 2.92 (d, 1H, J=4.4 Hz), 2.45 (dd, 1H, J=1.2, 10.8 Hz), 1.47 (s, 3H), 1.31 (s, 3H), 1.14-1.94 (m, 14H), 1.05 (s, 3H), 1.02 (s, 3H), 0.99 (s, 3H), 0.88 (s, 3H).

Compound T8:

To a solution of compound 29 (32 mg, 0.061 mmol) in pyridine (0.3 mL) was added Ac$_2$O (30 µL, 0.32 mmol) and catalytic amount of DMAP at room temperature. The reaction was stirred for 30 min. Aq. NaHCO$_3$ was added, and the mixture was stirred for 5 min. The product was extracted with EtOAc. The organic extract was washed with aq. NaHCO$_3$, aq. 1 N HCl and water, dried with Na$_2$SO$_4$, and concentrated. The residue was purified by column chromatography (Silica gel, 0-40% EtOAc in hexanes) to give compound T8 (11 mg, 32% yield) as a white foam. m/z=564.3 (M+1); $^1$H NMR (400 MHz, CDCl$_3$) δ 8.06 (s, 1H), 5.98 (s, 1H), 4.30 (d, 1H, J=10.8 Hz), 4.14 (d, 1H, J=11.6 Hz), 3.70 (s, 3H), 3.05 (m, 1H), 2.94 (d, 1H, J=4.4 Hz), 2.07 (dd, 1H, J=2.0, 11.6 Hz), 1.99 (s, 3H), 1.51 (s, 3H), 1.32 (s, 3H), 1.18-1.95 (m, 14H), 1.12 (s, 3H), 1.01 (s, 3H), 1.00 (s, 3H), 0.89 (s, 3H).

Compound T9:

To a solution of compound 29 (37 mg, 0.071 mmol) and pyridine (57 µL, 0.71 mmol) in CH$_2$Cl$_2$ (0.35 mL) was added BzCl (13 µL, 0.11 mmol) and catalytic amount of DMAP at room temperature. The reaction was stirred for 1 h. EtOAc was added. The mixture was washed with aq. 1 N HCl and water, dried with Na$_2$SO$_4$, and concentrated. The residue was purified by column chromatography (Silica gel, 0-50% EtOAc in hexanes) to give compound T9 (31 mg, 70% yield) as a white foam. m/z=626.3 (M+1); $^1$H NMR (400 MHz, CDCl$_3$) δ 8.08 (s, 1H), 7.88 (m, 2H), 7.57 (m, 1H), 7.43 (m, 2H), 5.97 (s, 1H), 4.58 (d, 1H, J=11.2 Hz), 4.39 (d, 1H, J=11.2 Hz), 3.69 (s, 3H), 3.01 (m, 1H), 2.92 (d, 1H, J=4.4 Hz), 2.20 (m, 1H), 1.54 (s, 3H), 1.31 (s, 3H), 1.21 (s, 3H), 1.10-1.87 (m, 14H), 0.98 (s, 3H), 0.87 (s, 3H), 0.85 (s, 3H).

Compound 30:

To a solution of compound 13 (112 mg, 0.21 mmol) in CH$_2$Cl$_2$ (2 mL) was added (COCl)$_2$ (53 µL, 0.62 mmol) and catalytic amount of DMF at 0° C. The reaction was stirred at room temperature for 2 h, and concentrated. The residue was dissolved in toluene, and concentrated again to give compound 30 as a yellow solid. Compound 30 was used in the next step without further purification.

Compound 31:

Compound 30 (all obtained in the last step) was dissolved in toluene (1 mL). NaN$_3$ (17 mg, 0.26 mmol), acetone (2 mL) and water (0.5 mL) were added at room temperature. The reaction was stirred at room temperature for 1 h. Toluene was added. The mixture was washed with water. The organic extract was dried with Na$_2$SO$_4$, filtered, and concentrated to give compound 31 as w white foam. m/z=563.3 (M+1).

Compound 32:

Compound 31 (all obtained in the last step) was dissolved in toluene (2 mL), and heated at 85° C. for 2 h. The solution was cooled, and concentrated to give compound 32 (92 mg, 83% yield from 13) as a yellow foam. m/z=535.3 (M+1).

Compound 33:

Compound 32 (92 mg, 0.17 mmol) was dissolved in MeCN (1.7 mL) at room temperature. 12 N aq. HCl (0.34 mL, 4.08 mmol) was added. The reaction was stirred at room temperature for 2 h, and was cooled to 0° C. 3 N aq. NaOH (1.36 mL, 4.08 mmol), EtOAc, and aq. NaHCO$_3$ were added. The mixture was stirred until a clear two phase solution was obtained. The organic extract was separated, dried with Na$_2$SO$_4$, and concentrated to give compound 33 (90 mg, quantitative yield) as a white foam.

Compound 34:

Compound 33 (90 mg, 0.18 mmol) and (Boc)$_2$O (82 mg, 0.38 mmol) were dissolved in THF (2 mL), and heated at 55° C. for 16 h. After concentration, the residue was purified by column chromatography (Silica gel, 0-40% EtOAc in hexanes) to give compound 34 (74 mg, 69% yield) as a white foam. m/z=609.4 (M+1).

Compound 35:

Compound 34 (74 mg, 0.12 mmol) and K$_2$CO$_3$ (50 mg, 0.36 mmol) in MeOH (1.2 mL) were stirred at room temperature for 5 h. EtOAc was added. The mixture was washed with 1N aq. HCl and water. The organic extract was dried with Na$_2$SO$_4$, filtered, and concentrated to give compound 35 (66 mg, 89% yield) as a white foam. m/z=609.3 (M+1). Compound 35 was used in the next step without further purification.

Compound T10:

DDQ (30 mg, 0.13 mmol) was added to a solution of compound 35 (66 mg, 0.11 mmol) in toluene (1.1 mL). The reaction was heated at 85° C. for 2.5 h, and was cooled to room temperature. CH$_2$Cl$_2$ was added. The mixture was washed with aq. NaHCO$_3$. The aq. washes were extracted again with CH$_2$Cl$_2$. The combined organic extract was dried with Na$_2$SO$_4$, filtered and concentrated. The residue was purified by column chromatography (Silica gel, 0-10% EtOAc in CH$_2$Cl$_2$) to give compound T10 (40 mg, 61% yield) as a white foam. m/z=551.3 (M-C$_4$H$_8$); $^1$H NMR (400 MHz, CDCl$_3$) δ 7.97 (s, 1H), 5.96 (s, 1H), 4.76 (b, 1H), 3.69 (s, 3H), 3.02 (m, 1H), 2.91 (d, 1H, J=4.4 Hz), 2.90 (m, 1H), 1.50 (s, 3H), 1.38 (s, 9H), 1.31 (s, 3H), 1.25 (s, 3H), 1.16-1.94 (m, 14H), 1.01 (s, 3H), 1.00 (s, 3H), 0.90 (s, 3H).

Compound T11:

Compound T10 (40 mg, 0.066 mmol) was dissolved in CH$_2$Cl$_2$ (1 mL). CF$_3$CO$_2$H (0.1 mL) was added. The reaction was stirred at room temperature for 2 h. EtOAc was added. The mixture was washed with aq. NaHCO$_3$. The organic extract was dried with Na$_2$SO$_4$, filtered and concentrated. The residue was purified by column chromatography (Silica gel, 0-10% MeOH in CH$_2$Cl$_2$) to give compound T11 (11 mg, 33% yield) as a white foam. m/z=507.3 (M+1); $^1$H NMR (400 MHz, CDCl$_3$) δ 8.03 (s, 1H), 5.93 (s, 1H), 3.69 (s, 3H), 3.03 (m, 1H), 2.93 (d, 1H, J=4.4 Hz), 2.18 (m, 1H), 1.33 (s, 3H), 1.21 (s, 3H), 1.18-1.85 (m, 16H), 1.00 (s, 6H), 1.00 (s, 3H), 0.90 (s, 3H).

Compound T12:

To a solution of compound T11 (16 mg, 0.031 mmol) in CH$_2$Cl$_2$ (0.6 mL) were added Et$_3$N (13 µL, 0.093 mmol) and AcCl (4 µL, 0.056 mmol) at room temperature. The reaction was stirred for 30 min. EtOAc was added. The mixture was washed with 1N aq. HCl and aq. NaHCO$_3$. The organic extract was dried with Na$_2$SO$_4$, filtered and concentrated. The residue was purified by column chromatography (Silica gel, 0-40% acetone in hexanes) to give compound T12 (7 mg, 40% yield) as a white foam. m/z=549.3 (M+1); $^1$H NMR (400 MHz, CDCl$_3$) δ 7.95 (s, 1H), 5.98 (s, 1H), 5.76 (s, 1H), 3.69 (s, 3H), 3.03 (m, 1H), 2.90 (d, 1H, J=4.4 Hz), 2.86 (dd, 1H, J=4.0, 10.3 Hz), 1.97 (s, 3H), 1.49 (s, 3H), 1.33 (s, 3H), 1.30 (s, 3H), 1.12-1.95 (m, 14H), 0.99 (s, 3H), 0.99 (s, 3H), 0.90 (s, 3H).

Compound 36:

To the suspension of MeNH$_2$.HCl (25 mg, 0.37 mmol) in CH$_2$Cl$_2$ (0.8 mL) was added Et$_3$N (100 µL, 0.72 mmol) at 0° C. After the reaction was stirred for 10 min, compound 30 (100 mg, 0.18 mmol) in CH$_2$Cl$_2$ (1 mL) was added. The reaction was stirred at 0° C. for 30 min. The solvent was removed. The residue was purified by column chromatography (Silica gel, 0-70% EtOAc in hexanes) to give compound 36 (83 mg, 84% yield) as a white solid. m/z=551.3 (M+1).

Compound 37:

To the suspension of Me$_2$NH.HCl (30 mg, 0.37 mmol) in CH$_2$Cl$_2$ (0.8 mL) was added Et$_3$N (100 µL, 0.72 mmol) at 0° C. After the reaction was stirred for 10 min, compound 30 (100 mg, 0.18 mmol) in CH$_2$Cl$_2$ (1 mL) was added. The reaction was stirred at 0° C. for 30 min. The solvent was removed. The residue was purified by column chromatography (Silica gel, 0-50% EtOAc in hexanes) to give compound 37 (89 mg, 88% yield). m/z=565.3 (M+1).

Compound 38:

Compound 36 (83 mg, 0.15 mmol) and K$_2$CO$_3$ (63 mg, 0.46 mmol) in MeOH (1.5 mL) were stirred at room temperature for 16 h. EtOAc was added. The mixture was washed with 1N aq. HCl. The organic extract was dried with Na$_2$SO$_4$, filtered, and concentrated to give compound 38 as a white foam. m/z=551.3 (M+1). Compound 38 was used in the next step without further purification.

Compound T13:

DDQ (38 mg, 0.17 mmol) was added to a solution of compound 38 (all obtained from the last step) in benzene (1.5 mL). The reaction was heated at reflux for 2.5 h and was cooled to room temperature. CH$_2$Cl$_2$ was added. The mixture was washed with aq. NaHCO$_3$. The organic extract was dried with Na$_2$SO$_4$, filtered and concentrated. The residue was purified by column chromatography (Silica gel, 0-40% acetone in hexanes) to give compound T13 (42 mg, 51% yield from 36) as a white foam. m/z=549.3 (M+1); $^1$H NMR (400 MHz, CDCl$_3$) δ 8.16 (s, 1H), 6.35 (q, 1H, J=4.4 Hz), 5.99 (s, 1H), 3.69 (s, 3H), 3.04 (m, 1H), 2.95 (d, 1H, J=4.8 Hz), 2.92 (dd, 1H, J=3.2, 10.4 Hz), 2.81 (d, 3H, J=4.8 Hz), 1.54 (s, 3H), 1.47 (s, 3H), 1.31 (s, 3H), 1.16-1.96 (m, 14H), 1.05 (s, 3H), 1.00 (s, 3H), 0.90 (s, 3H).

Compound 39:

Compound 37 (86 mg, 0.15 mmol) and K$_2$CO$_3$ (63 mg, 0.46 mmol) in MeOH (1.5 mL) were stirred at room temperature for 16 h. EtOAc was added. The mixture was washed with 1N aq. HCl. The organic extract was dried with Na$_2$SO$_4$, filtered, and concentrated to give compound 39 as a white foam. m/z=565.3 (M+1). Compound 39 was used in the next step without further purification.

Compound T14:

DDQ (38 mg, 0.17 mmol) was added to a solution of compound 39 (all obtained from the last step) in benzene (1.5 mL). The reaction was heated at reflux for 2.5 h, and was cooled to room temperature. CH$_2$Cl$_2$ was added. The mixture was washed with aq. NaHCO$_3$. The organic extract was dried with Na$_2$SO$_4$, filtered and concentrated. The residue was purified by column chromatography (Silica gel, 0-40% acetone in hexanes) to give partially purified compound T14, which was purified again by column chromatography (Silica gel, 0-60% EtOAc in hexanes) to give compound T14 (17 mg, 20% yield from 37) as a white foam. m/z=563.3 (M+1); $^1$H NMR (400 MHz, CDCl$_3$) δ 8.06 (s, 1H), 5.95 (s, 1H), 3.69 (s, 3H), 3.03 (m, 1H), 2.94 (d, 1H, J=4.8 Hz), 2.84 (bs, 6H), 2.19 (d, 1H, J=12.2 Hz), 1.56 (s, 3H), 1.41 (s, 3H), 1.33 (s, 3H), 1.14-1.94 (m, 14H), 1.01 (s, 3H), 1.00 (s, 3H), 0.89 (s, 3H).

Compound 40:

Compound 30 (70 mg, 0.13 mmol) was dissolved in CH$_2$Cl$_2$ (1.3 mL). NH$_3$ (2 M in MeOH, 0.13 mL, 0.26 mmol) was added at room temperature. After stirring for 1 h, additional amount of NH$_3$ (2 M in MeOH, 0.13 mL, 0.26 mmol) was added, and the reaction was stirred for another 2 h. EtOAc was added. The mixture was washed with 1 N aq. HCl. The organic extract was dried with Na$_2$SO$_4$, filtered and concentrated. The residue was purified by column chromatography (Silica gel, 0-80% EtOAc in hexanes) to give compound 40 (35 mg, 52% yield) as a white foam. m/z=537.2 (M+1).

Compound 41:

Compound 40 (35 mg, 0.10 mmol) and K$_2$CO$_3$ (35 mg, 0.25 mmol) in MeOH (1.3 mL) were stirred at room temperature overnight. EtOAc was added. The mixture was washed with 1N aq. HCl and water. The organic extract was dried with Na$_2$SO$_4$, filtered, and concentrated. The residue was purified by column chromatography (Silica gel, 0-100% acetone in hexanes) to give compound 41 (23 mg, 66% yield) as a white solid. m/z=537.3 (M+1).

Compound T15:

To a solution of compound 41 (23 mg, 0.043 mmol) in DMF (0.4 mL) was added a solution of 1,3-dibromo-5,5- dimethylhydantoin (6 mg, 0.021 mmol) at 0° C. After the reaction was stirred at 0° C. for 1 h, pyridine (10 µL, 0.12 mmol) was added. The reaction was heated at 55° C. for 5 h, and cooled to room temperature. EtOAc was added. The mixture was washed with 1 N aq. HCl and water. The organic extract was dried over $Na_2SO_4$, filtered and concentrated. The residue was purified by column chromatography (Silica gel, 0-50% acetone in hexanes) to give compound T15 (15 mg, 65% yield) as a white foam. m/z=535.3 (M+1); $^1$H NMR (400 MHz, $CDCl_3$) δ 8.17 (s, 1H), 6.29 (b, 1H), 6.00 (s, 1H), 5.43 (b, 1H), 3.69 (s, 3H), 3.03 (m, 1H), 2.96 (d, 1H, J=4.6 Hz), 2.85 (dd, 1H, J=3.6, 10.3 Hz), 1.58 (s, 3H), 1.48 (s, 3H), 1.31 (s, 3H), 1.16-1.96 (m, 14H), 1.05 (s, 3H), 1.00 (s, 3H), 0.90 (s, 3H).

Compound 42:

To a suspension of compound 30 (30 mg, 0.054 mmol) in $Et_2O$ (0.5 mL) was added a solution of acethydrazide (12 mg, 0.16 mmol) and $Et_3N$ (15 µL, 0.11 mmol) in $CH_2Cl_2$ (0.5 mL) at room temperature. The reaction was stirred at room temperature for 30 min. Aq. $NaHCO_3$ was added. The product was extracted with EtOAc. The organic extract was washed with water, dried with $Na_2SO_4$, filtered and concentrated. The residue was purified by column chromatography (Silica gel, 0-100% EtOAc in hexanes) to give compound 42 (26 mg, 78% yield) as a white foam. m/z=594.2 (M+1).

Compound 43:

Compound 42 (24 mg, 0.040 mmol) and $TsOH.H_2O$ (5 mg, 0.026 mmol) in toluene (3 mL) were heated at reflux with a Dean-Stark apparatus for 1 h. After cooled to room temperature, the reaction mixture was purified by column chromatography (Silica gel, 0-60% EtOAc in hexanes) to give compound 43 (20 mg, 86% yield) as a white foam. m/z=576.2 (M+1).

Compound 44:

Compound 43 (20 mg, 0.035 mmol) and $K_2CO_3$ (17 mg, 0.12 mmol) in MeOH (0.8 mL) were stirred at room temperature for 16 h. EtOAc was added. The mixture was washed with 1N aq. HCl. The organic extract was dried with $Na_2SO_4$, filtered, and concentrated to give compound 44 (21 mg, quantitative yield) as a white foam. m/z=576.3 (M+1). Compound 44 was used in the next step without further purification.

Compound T16:

A mixture of DDQ (9.1 mg, 0.040 mmol) and compound 44 (21 mg, 0.036 mmol) in benzene (1.6 mL) was heated at reflux for 1 h, and was cooled to room temperature. $CH_2Cl_2$ and aq. $NaHCO_3$ were added. The product was extracted with $CH_2Cl_2$. The organic extract was washed with aq. $NaHCO_3$, dried with $Na_2SO_4$, filtered and concentrated. The residue was purified by column chromatography (Silica gel, 0-35% acetone in hexanes) to give compound T16 (12.6 mg, 60% yield) as a yellow foam. m/z=574.3 (M+1); $^1$H NMR (400 MHz, $CDCl_3$) δ 8.16 (s, 1H), 5.99 (s, 1H), 3.69 (s, 3H), 3.03 (m, 1H), 2.95 (d, 1H, J=4.8 Hz), 2.55 (s, 3H), 2.72 (dd, 1H, J=1.9, 12.2 Hz), 1.80-1.98 (m, 3H), 1.72 (s, 3H), 1.62 (s, 3H), 1.33 (s, 3H), 1.04 (s, 3H), 1.13-1.77 (m, 11H), 1.00 (s, 3H), 0.91 (s, 3H).

Compound 45:

A mixture of compound 9 (0.30 g, 0.60 mmol), ethylene glycol (0.3 mL, 5.39 mmol), and PPTS (25 mg, 0.10 mmol) in benzene (70 mL) was heated to reflux employing a Dean-Stark trap for 6 h. The mixture was cooled, and diluted with EtOAc. The mixture was washed with sat. $NaHCO_3$ solution (30 mL), brine (30 mL), dried over $MgSO_4$, filtered, concentrated, and dried under vacuum to give compound 45 (239 mg, 73% yield) as a white solid. m/z=543.5 (M+1).

Compound 46:

A mixture of compound 45 (0.77 g, 1.42 mmol) and Dess-Martin periodinane (0.78 g, 1.84 mmol) in $CH_2Cl_2$ (100 mL) was stirred overnight. The reaction mixture was poured into a flask containing a solution of $Na_2S_2O_3$ (2.2 g) in water (25 mL) and sat. aq. $NaHCO_3$ (50 mL). The mixture was stirred until the phases cleared. The organic layer was collected, and the aqueous layer was extracted with additional $CH_2Cl_2$ (100 mL). The combined organic extracts were dried over $MgSO_4$, filtered, concentrated, and dried under vacuum to give compound 46 (0.73 g, 95% yield) as a white solid. m/z=541.3 (M+1).

Compound 47:

(Methoxymethyl)triphenylphosphonium chloride (3.72 g, 10.86 mmol) was suspended in THF (30 mL) and cooled in an ice bath. n-BuLi (1.6 M solution in hexane, 5.66 mL, 9.05 mmol) was added dropwise. The orange-red mixture was stirred for 20 min. A solution of compound 46 (0.98 g, 1.81 mmol) in THF (10 mL) was added dropwise over 5 min. The flask was rinsed with THF (3 mL) and the solution was added to the reaction mixture. The mixture was allowed to slowly warm to room temperature and stirred for 3 h. The mixture was cooled again in an ice bath and quenched by the rapid addition of sat. aq. $KH_2PO_4$ (50 mL). The mixture was extracted with EtOAc (2×50 mL). The combined organic extracts were washed with brine (25 mL), dried over $MgSO_4$, and concentrated to give a light yellow-brown oil. Flash chromatography (Silica gel, 25% EtOAc in hexanes) gave compound 47 (0.80 g, 78% yield) as a white solid. m/z=569.4 (M+1). $^1$H NMR spectrum confirms cis-olefin stereochemistry.

Compound 48:

10% Pd/C (17 mg) was added to a solution of compound 47 (114 mg, 0.20 mmol) in EtOAc (5 mL). The flask was evacuated and purged three times with $H_2$. The mixture was stirred overnight under a $H_2$ balloon. Additional 10% Pd/C (28 mg) was added and the flask was evacuated and purged three times with $H_2$. The flask was stirred under $H_2$ for 3 d. The mixture was filtered, and the filtrate was concentrated to give compound 48 (127 mg, quantitative yield) as an oil. m/z=571.5 (M+1).

Compound 49:

A mixture of compound 48 (127 mg, 0.20 mmol) in MeOH (15 mL) and 1N aq. HCl (3 mL) was stirred overnight. Additional 1N aq. HCl (1 mL) was added and the mixture was slowly concentrated via rotary evaporation (T<35° C.). The mixture was diluted with brine. The product was extracted with EtOAc. The organic extract was dried over $MgSO_4$, filtered, and concentrated to give compound 49 (100 mg, 95% yield) as a glass. m/z=527.5 (M+1).

Compound 50:

Compound 49 (100 mg, 0.19 mmol) was taken up in $HCO_2Et$ (10 mL), and NaOMe (5.4 M solution in MeOH, 0.2, 1.08 mmol) was added. The mixture was stirred overnight, and then quenched with sat. aq. $KH_2PO_4$ solution (20 mL). The product was extracted with EtOAc (100 mL). The organic extract was dried over $MgSO_4$, filtered, and concentrated to give compound 50 (85 mg, 81% yield) as a glass. m/z=555.5 (M+1).

Compound 51:

Compound 50 (85 mg, 0.15 mmol) was mixed with $NH_2OH.HCl$ (25 mg, 0.36 mmol) in EtOH (10 mL). The mixture was briefly heated at 50° C., then stirred at room temperature, monitoring by TLC. The EtOH was repeatedly removed via rotary evaporation at 50° C. and added back to the reaction mixture until the reaction appeared to be complete by TLC. The mixture was stirred overnight, concentrated, and diluted with sat. aq. $NaHCO_3$ (20 mL). The product was extracted with EtOAc (100 mL). The organic extract was dried over MgSO$_4$, filtered, and concentrated to give compound 51 (81 mg, 96% yield) as a glass. m/z=552.5 (M+1).

Compound 52: Compound 51 (81 mg, 0.15 mmol) was taken up in THF (10 mL). MeOH (1 mL) and NaOMe (5.4 M solution in MeOH, 0.2 mL, 1.08 mmol) were added. After stirring for 4.5 h, the mixture was quenched with sat. aq. KH$_2$PO$_4$ (20 mL). The product was extracted with EtOAc (100 mL). The organic extract was dried over MgSO$_4$, filtered, and concentrated to compound 52 (78 mg, 96% yield) as a glass. m/z=552.5 (M+1).

Compound T17:

A mixture of compound 52 (78 mg, 0.14 mmol) and DDQ (42 mg, 0.18 mmol) in benzene (20 mL) was stirred at room temperature for 3 d. The mixture was diluted with EtOAc (100 mL), and washed with sat. aq. NaHCO$_3$ (2×20 mL). The organic extract was dried over MgSO$_4$, filtered, and concentrated to a glass. Flash chromatography (Silica gel, 25% EtOAc in hexanes) gave compound T17 (11.6 mg, 15% yield) as a glass/foam. m/z=550.5 (M+1); $^1$H NMR (400 MHz, CDCl$_3$) δ 7.95 (s, 1H), 5.98 (s, 1H), 3.70 (s, 3H), 3.34 (m, 1H), 3.24 (m, 1H), 3.18 (s, 3H), 3.05 (m, 1H), 2.93 (d, 1H, J=4.0 Hz), 1.47 (s, 3H), 1.32 (s, 3H), 1.15 (s, 3H), 1.04 (s, 3H), 1.00 (s, 3H), 0.97-2.35 (m, 17H), 0.90 (s, 3H).

Compound 53:

Compound 47 (234 mg, 0.41 mmol) was taken up in THF (6 mL) and water (1 mL). 1N aq. HCl (0.6 mL) was added and the solution was stirred for 2 d. The solution was diluted with sat. aq. NaHCO$_3$ (20 mL) and extracted with EtOAc (2×50 mL). The combined organic extracts were washed with brine (20 mL), dried over MgSO$_4$, and concentrated to give a white foam. Flash chromatography (Silica gel, 33% EtOAc in hexanes) gave compound 53 (210 mg, 92% yield) as a white solid. m/z=555.5 (M+1).

Compound 54:

Compound 53 (205 mg, 0.37 mmol) was taken up in THF (4 mL) and EtOH (1 mL), and cooled in an ice bath. NaBH$_4$ (4 mg, 0.11 mmol) was added and the mixture was stirred for 20 min. Additional NaBH$_4$ (14 mg, 0.37 mmol) was added in portions over 90 min. After stirring for an additional 30 min, the mixture was carefully quenched with sat. aq. KH$_2$PO$_4$ (20 mL) and extracted with EtOAc (2×50 mL). The combined organic extracts were washed with brine (20 mL), dried over MgSO$_4$, concentrated, and dried under vacuum to give compound 54 (208 mg, quantitative yield) as a white solid. m/z=557.5 (M+1).

Compound 55:

Compound 54 (207 mg, 0.37 mmol) was taken up in THF (7 mL) and 3 N aq. HCl (1.5 mL) was added. The solution was stirred for 3 h, then carefully neutralized with sat. aq. NaHCO$_3$ (20 mL) and extracted with EtOAc (2×50 mL). The combined organic extracts were washed with brine (20 mL), dried over MgSO$_4$, concentrated, and dried under vacuum to give compound 55 (208 mg, quantitative yield) as a white solid. m/z=513.5 (M+1).

Compound 56:

Compound 55 (150 mg, 0.29 mmol) was taken up in HCO$_2$Et (5 mL) and cooled in an ice bath. NaOMe (30 wt. % solution in MeOH, 0.53 g, 2.95 mmol) was added. The mixture was allowed to warm to room temperature and stirred overnight, and cooled again in an ice bath. Sat. aq. KH$_2$PO$_4$ (20 mL) was added. The mixture was extracted with EtOAc (2×50 mL). The combined organic extracts were washed with brine (20 mL), dried over MgSO$_4$, concentrated, and dried under vacuum to give compound 56 (170 mg, quantitative yield) as a light yellow foam. m/z=541.4 (M+1).

Compound 57:

Compound 56 (0.29 mmol) was taken up in EtOH (5 mL) and water (0.5 mL). NH$_2$OH.HCl (60 mg, 0.87 mmol) was added and the mixture was heated at 50° C. overnight. The solution was cooled and concentrated, then diluted with sat. aq. NaHCO$_3$ (20 mL), and extracted with EtOAc (2×50 mL). The combined organic extracts were washed with brine (20 mL), dried over MgSO$_{04}$, concentrated, and dried under vacuum to give compound 57 (160 mg, quantitative yield) as a light yellow foamy solid. m/z=538.5 (M+1).

Compound 58:

Compound 57 (0.29 mmol) was taken up in MeOH (8 mL) and K$_2$CO$_3$ (160 mg, 1.16 mmol) was added. The mixture was stirred overnight, and then concentrated. The residue was diluted with sat. aq. KH$_2$PO$_4$ (20 mL), and extracted with EtOAc (2×50 mL). The combined organic extracts were washed with brine (20 mL), dried over MgSO$_4$, concentrated, and dried under vacuum to give a light yellow glass. Flash chromatography (Silica gel, 33% EtOAc in hexanes) gave compound 58 (102 mg, 65% yield) as a white solid. m/z=538.5 (M+1). $^1$H NMR (500 MHz, CDCl$_3$) δ 5.74 (s, 1H), 4.06 (dt, 1H, J=3.2, 9.2 Hz), 3.89 (q, 1H, J=8.8 Hz), 3.69 (s, 3H), 3.12 (dd, 1H, J=3.6, 13.2 Hz), 3.02 (m, 1H), 2.84 (d, 1H, J=4.4 Hz), 2.54 (s, 1H), 2.18 (dd, 1H, J=3.9, 13.0 Hz), 1.26 (s, 3H), 1.23 (s, 3H), 1.10-2.08 (m, 18H), 1.09 (s, 3H), 1.00 (s, 3H), 0.98 (s, 3H), 0.90 (s, 3H).

Compound 59:

Compound 58 (43 mg, 0.080 mmol) was taken up in CH$_2$Cl$_2$ (2 mL). Et$_3$N (0.056 mL, 0.40 mmol) was added, followed by TBSCl (24 mg, 0.16 mmol) and DMAP (1 mg). The solution was stirred for 4 h, then diluted with sat. aq. NaHCO$_3$ (20 mL) and extracted with EtOAc (2×50 mL). The combined organic extracts were washed with brine (20 mL), dried over MgSO$_4$, concentrated, and dried under vacuum to give compound 59 (60 mg, 98% yield) as a white foam. m/z=766.5 (M+1).

Compound T18:

Compound 59 (60 mg, 0.078 mmol) was taken up in DMF (2 mE) and cooled in an ice bath. 1,3-dibromo-5,5-dimethylhydantoin (11 mg, 0.039 mmol) was added and the solution was allowed to warm to room temperature and stirred for 1 h. Pyridine (0.2 mL) was added and the solution was heated at 60° C. for 3 h. The solution was cooled, diluted with sat. aq. NaHCO$_3$ (20 mL), and extracted with EtOAc (2×50 mL). The combined organic extracts were washed with brine (20 mL), dried over MgSO$_4$, concentrated, and dried under vacuum to give a yellow oil. Flash chromatography (Silica gel, 5% EtOAc in CH$_2$Cl$_2$) gave compound T18 (24 mg, 47% yield) as a white solid. m/z=650.5 (M+1); $^1$H NMR (400 MHz, CDCl$_3$) δ 7.95 (s, 1H), 5.98 (s, 1H), 3.69 (s, 3H), 3.59 (m, 2H), 3.04 (m, 1H), 2.94 (d, 1H, J=4.4 Hz), 2.41 (m, 1H), 2.34 (d, 1H, J=10.6 Hz), 1.49 (s, 3H), 1.32 (s, 3H), 1.12 (s, 3H), 1.10-1.95 (m, 15H), 1.01 (s, 6H), 0.91 (s, 3H), 0.82 (s, 9H), 0.01 (s, 3H), 0.01 (s, 3H).

Compound T19:

Compound T18 (17 mg, 0.026 mmol) was taken up in MeCN (2 mL). Water (3 drops) and HF-pyridine (70% solution, 3 drops) were added. The solution was stirred overnight, then diluted with sat. aq. NaHCO$_3$ (20 mL), and extracted with EtOAc (2×50 mL). The combined organic extracts were washed with brine (20 mL), dried over MgSO$_4$, concentrated, and dried under vacuum to give a white foam. Flash chromatography (Silica gel, 10% EtOAc in CH$_2$Cl$_2$) gave compound T19 (8 mg, 57% yield) as a white foam; m/z=536.4 (M+1). In CDCl$_3$, compound T19 exist as a mixture with compound 60. $^1$H NMR (400 MHz, CDCl$_3$) δ 7.99 (s, 0.5H), 7.00 (s, 0.5H), 5.97 (s, 0.5H), 5.84 (s, 0.5H), 3.70 (s, 1.5H), 3.69 (s, 1.5H), 1.49 (s, 1.5H), 1.39 (s, 1.5H), 1.32 (s, 1.5H), 1.29 (s, 1.5H), 1.25 (s, 1.5H), 1.16 (s, 1.5H), 1.14 (s, 1.5H), 1.00 (s, 1.5H), 0.99 (s, 1.5H), 0.97 (s, 1.5H), 0.90 (s, 1.5H), 0.89 (s, 1.5H).

Compound 61:

To a stirring solution of NaH (0.049 g, 1.22 mmol) in THF (3.0 mL) at 0° C. was added dropwise a solution of compound 45 (0.49 g, 0.902 mmol) in THF (4.0 mL). The mixture was stirred at 0° C. for 30 min. MeI (0.124 mL, 1.99 mmol) was added. The mixture was warmed to room temperature, stirred for 4 h, and then warmed to 45° C., stirred for 18 h. The reaction was cooled to 0° C., quenched with sat. aq. NH$_4$Cl, and extracted with EtOAc (3×15 mL). The combined organic extracts were washed with water, dried over MgSO$_4$ and concentrated. Flash chromatography (Silica gel, 50% EtOAc in hexanes) gave compound 61 (0.143 g, 28% yield) as a white solid. m/z=557.5 (M+1).

Compound 62:

A mixture of compound 61 (0.143 g, 0.257 mmol), 3 N aq. HCl (1.2 mL, 3.6 mmol) and THF (5.0 mL) was stirred at room temperature for 20 h. The mixture was neutralized with sat. aq. NaHCO$_3$, and extracted with EtOAc (3×20 mL). The organic extracts were washed with brine, dried over MgSO$_4$ and concentrated. The residue was dried under high vacuum to afford compound 62 (0.130 g, 99% yield) as a colorless, sticky solid. m/z=513.5 (M+1).

Compound 63:

Compound 62 (0.130 g, 0.254 mmol) was taken up in HCO$_2$Et (6.0 mL) and cooled to 0° C. NaOMe (30 wt. % solution in MeOH, 0.46 g, 2.55 mmol) was added dropwise. The mixture was warmed to room temperature and stirred for 18 h. The mixture was diluted with sat. aq. KH$_2$PO$_4$, and extracted with EtOAc (3×20 mL). The organic extracts were washed with brine, dried over MgSO$_4$ and concentrated. The residue was dried under high vacuum to afford compound 63 (0.135 g, 98%) as a light orange foam. m/z=541.5 (M+1).

Compound 64:

Compound 63 (0.135 g, 0.249 mmol) was taken up in EtOH (5 mL) and H$_2$O (0.5 mL). NH$_2$OH.HCl (0.052 g, 0.748 mmol) was added and the mixture stirred at 50° C. for 18 h. The mixture was cooled, concentrated, diluted with sat. aq. NaHCO$_3$, and extracted with EtOAc (3×15 mL). The organic extracts were washed with brine, dried over MgSO$_4$ and concentrated. The residue was dried under high vacuum to afford compound 64 (0.134 g, quantitative yield) as a light yellow foam. m/z=538.4 (M+1).

Compound 65:

A mixture of compound 64 (0.134 g, 0.249 mmol) and K$_2$CO$_3$ (0.139 g, 1.00 mmol) in MeOH (6 mL) was stirred at room temperature for 20 h. The mixture was concentrated, diluted with sat. aq. KH$_2$PO$_4$, and extracted with EtOAc (3×15 mL). The organic extracts were washed with brine, dried over MgSO$_4$ and concentrated. Flash chromatography (Silica gel, 25% EtOAc in hexanes) gave compound 65 (0.082 g, 62% yield) as a light yellow foam. m/z=538.4 (M+1).

Compound T20:

To a stirring solution of compound 65 (0.080 g, 0.148 mmol) in DMF (1.5 mL) at 0° C. was added 1,3-dibromo-5,5-dimethylhydantoin (0.022 g, 0.073 mmol). The mixture stirred at 0° C. for 1 h. Pyridine (0.08 mL, 0.993 mmol) was added. The reaction was heated to 55° C., stirred for 3 h, and cooled to room temperature. EtOAc was added. The mixture was washed with 1 N aq. HCl and water. The aq. wash was back-extracted with EtOAc (3×20 mL). The combined organic extracts were washed with water, dried over Na$_2$SO$_4$, and concentrated. Flash chromatography (Silica gel, 25% EtOAc in hexanes) gave compound T20 (0.048 g, 61%) as white solid. m/z=536.4 (M+1); $^1$H NMR (400 MHz, CDCl$_3$) δ 8.01 (s, 1H), 5.97 (s, 1H), 3.68 (s, 3H), 3.53 (d, 1H, J=9.0 Hz), 3.32 (d, 1H, J=9.0 Hz), 3.22 (s, 3H), 3.04 (m, 1H), 2.92 (d, 1H, J=4.7 Hz), 2.42 (d, 1H, J=9.5 Hz), 1.46 (s, 3H), 1.30 (s, 3H), 1.15-1.95 (m, 14H), 1.02 (s, 6H), 0.99 (s, 3H), 0.89 (s, 3H).

Compound 66:

A solution of compound 57 (109 mg, 0.20 mmol) in acetone (2 mL) was cooled in an ice bath. Jones reagent (2.5 M) was added dropwise until the orange color persisted. The mixture was allowed to warm to room temperature and stirred 15 min. Additional small amounts of Jones reagent were added over 30 minutes to maintain the orange color of the reaction mixture. After stirring another 20 min., the mixture was cooled again in an ice bath and i-PrOH was added to quench the reaction. Most of the solvent was removed via concentration. The mixture was diluted with water (20 mL) and extracted with EtOAc (2×50 mL). The combined organic extracts were washed with brine (20 mL), dried over MgSO$_4$, concentrated, and dried under vacuum to give compound 66 (103 mg, 92% yield) as a white foam. m/z=552.4 (M+1).

Compound 67:

Crude compound 66 (100 mg, 0.20 mmol) was taken up in THF (3 mL) and MeOH (1 mL) and cooled in an ice bath. Trimethylsilyldiazomethane (2M solution in hexane, 0.5 mL, 1.0 mmol) was added dropwise and the solution was stirred for 30 min. The solution was allowed to warm to room temperature and stirred 2 h. The solution was concentrated to give a light yellow solid. Flash chromatography (Silica gel, 33% EtOAc in hexane) gave compound 67 (64 mg, 62% yield) as a white solid. m/z=566.4 (M+1).

Compound 68:

Compound 67 (61 mg, 0.11 mmol) was suspended in MeCN (2 mL) and Et$_3$N (1 mL) was added. The mixture was heated at 70° C. overnight and then concentrated. The mixture was diluted with sat. aq. KH$_2$PO$_4$ (20 mL), and extracted with EtOAc (2×50 mL). The combined organic extracts were washed with brine (20 mL), dried over MgSO$_4$, concentrated, and dried under vacuum to give compound 68 (65 mg, quantitative yield) as an off-white solid. m/z=566.4 (M+1).

Compound T21:

To a stirring solution of compound 68 (0.058 g, 0.102 mmol) in DMF (2 mL) was added dropwise a solution of 1,3-dibromo-5,5-dimethylhydantoin (0.015 g, 0.052 mmol) in DMF (1 mL) at 0° C. under N$_2$. After 30 min, pyridine (0.1 mL, 1.2 mmol) was added. The reaction was heated to 60° C., and stirred under N$_2$ for 4 h. The sample was cooled, concentrated, and then partitioned between sat. aq. KH$_2$PO$_4$ (20 mL) and EtOAc (20 mL). The organic extract was washed with brine (20 mL), dried over MgSO$_4$, filtered, and concentrated. The residue was purified by column chromatography (Silica gel, 50% EtOAc in hexanes) to give compound T21 (0.036 g, 63% yield) as an off-white foamy solid. m/z=564.4 (M+1); $^1$H NMR (400 MHz, CDCl$_3$) δ 7.99 (s, 1H), 5.97 (s, 1H), 3.69 (s, 3H), 3.60 (s, 3H), 3.07 (d, 1H, J=6.5 Hz), 3.04 (m, 1H), 2.91 (d, 1H, J=4.7 Hz), 2.62 (d, 1H, J=6.5 Hz), 2.21 (dd, 1H, J=1.8, 11.9 Hz), 1.50 (s, 3H), 1.31 (s, 3H), 1.17 (s, 3H), 1.15-1.94 (m, 14H), 1.00 (s, 3H), 0.99 (s, 3H), 0.89 (s, 3H).

Compound 70:

To a stirring solution of compound 69 (2.00 g, 4.27 mmol) and DMF (5 drops) in $CH_2Cl_2$ (43 mL) was added $(COCl)_2$ (1.1 ml, 12.8 mmol) dropwise at room temperature under $N_2$. The mixture was stirred for 3 h, concentrated, and then vacuum dried for 30 min. The resultant yellow solid was dissolved in $CH_2Cl_2$ (40 mL), and was added dropwise to a stirring suspension of trifluoroethylamine hydrochloride (1.16 g, 8.56 mmol) and $Et_3N$ (3.0 mL, 21.5 mmol) in $CH_2Cl_2$ (40 mL) at room temperature under $N_2$. After addition, the solution was stirred for 1 h, concentrated, and then partitioned between sat. aq. $KH_2PO_4$ (100 mL) and EtOAc (100 mL). The organic extract was washed with brine (100 mL), dried over $MgSO_4$, filtered, and concentrated. The residue was purified by column chromatography (Silica gel, 50% EtOAc in hexanes) to give compound 70 (1.90 g, 81% yield) as a light yellow foamy solid. m/z=550 (M+1).

Compound 71:

A mixture of compound 70 (1.90 g, 3.46 mmol), $NH_2OH·HCl$ (0.48 g, 6.91 mmol) and NaOAc (0.57 g, 6.94 mmol) in $CH_2Cl_2$ (8.5 mL) and EtOH (8.5 mL) was heated at 60° C. under $N_2$ for 2 h, and then filtered hot. The filtrate was concentrated, and partitioned between sat. aq. $NaHCO_3$ (50 mL) and EtOAc (50 mL). The organic extract was washed with brine (50 mL), dried over $MgSO_4$, filtered and concentrated to give compound 71 (2.52 g, quantitative yield) as an off-white solid. m/z=565 (M+1).

Compound 72:

To a stirring suspension of compound 71 (all obtained from the last step) in AcOH (10 mL) was added $Ac_2O$ (0.50 mL, 5.30 mmol) dropwise at room temperature under $N_2$. After stirring at room temperature overnight, the solution was treated with 1,2-dichloroethane (25 mL), iodosobenzene diacetate (1.67 g, 5.18 mmol) and $Pd(OAc)_2$ (0.039 g, 0.17 mmol). The sample was degassed, and then heated at 70° C. under $N_2$ overnight. The sample was cooled, concentrated, and then partitioned between brine (50 mL) and EtOAc (50 mL). The organic extract was washed with brine (50 mL), dried over $MgSO_4$, filtered, and concentrated. The residue was purified by column chromatography (Silica gel, 50% EtOAc in hexanes) to give compound 72 (0.89 g, 38% yield) as a light yellow foamy solid. m/z=665 (M+1). $^1H$ NMR indicates compound 72 is a mixture of $C_4$ diastereomers (C4α-$CH_2OAc$/C4β—$CH_2OAc$=4/1).

Compound 73:

To a stirring solution compound 72 (0.89 g, 1.33 mmol) in MeOH (20 mL) was added $K_2CO_3$ (0.92 g, 6.66 mmol) in one portion at 0° C. under $N_2$. After stirring at 0° C. for 1.5 h, the mixture was filtered. The filtrate was concentrated, and then partitioned between sat. aq. $KH_2PO_4$ (50 mL) and EtOAc (50 mL). The organic extract was washed with brine (50 mL), dried over $MgSO_4$, filtered, and concentrated. The residue was purified by column chromatography (Silica gel, 50% EtOAc in $CH_2Cl_2$) to give compound 73 (0.52 g, 67% yield) as a yellow foamy solid. m/z=581 (M+1).

Compound 74:

To a stirring solution of compound 73 (0.49 g, 0.85 mmol) in EtOH (20 mL) and water (5 mL) was added sodium bisulfite (0.31 g, 2.98 mmol) in one portion at room temperature under $N_2$. The mixture was heated at 80° C. for 2.5 h, cooled, concentrated, and partitioned between brine (50 mL) and $CHCl_3$ (50 mL). The organic extract was dried over $MgSO_4$, filtered and concentrated to give compound 74 (0.41 g, 85% yield) as an off-white solid. m/z=536 (M-$CH_2O$+1).

Compound 75:

To a stirring solution of compound 74 (0.41 g, 0.72 mmol) and N,N-diisopropylethylamine (0.44 mL, 2.53 mmol) in $CH_2Cl_2$ (10 mL) was added 2-(trimethylsilyl)ethoxymethyl chloride (0.26 mL, 1.47 mmol) dropwise at 0° C. under $N_2$. After slowly warming to room temperature overnight, the sample was concentrated, and then partitioned between sat. aq. $KH_2PO_4$ (50 mL) and EtOAc (50 mL). The organic extract was washed with brine (50 mL), dried over $MgSO_4$, filtered, and concentrated. The residue was purified by column chromatography (Silica gel, 50% EtOAc in hexanes) to give compound 75 (0.25 g, 51% yield) as a white solid. m/z=696 (M+1).

Compound 76:

To a stirring solution of compound 75 (0.25 g, 0.36 mmol) in $HCO_2Et$ (5 mL) was added NaOMe (30 wt. % solution in methanol, 0.34 mL, 1.81 mmol) at room temperature under $N_2$. The mixture was stirred for 2 h, and then partitioned between sat. aq. $KH_2PO_4$ (50 mL) and EtOAc (50 mL). The organic extract was washed with brine (50 mL), dried over $MgSO_4$, filtered and concentrated to give compound 76 (0.26 g, 97% yield) as a tan foamy solid. m/z=724 (M+1).

Compound 77:

A mixture of compound 76 (0.26 g, 0.36 mmol) and $NH_2OH·HCl$ (0.061 g, 0.88 mmol) in ethanol (20 mL) was heated at 50° C. under $N_2$ overnight. The sample was cooled, concentrated, and partitioned between sat. aq. $NaHCO_3$ (25 mL) and EtOAc (25 mL). The organic extract was washed with brine (50 mL), dried over $MgSO_4$, filtered and concentrated to give compound 77 (0.19 g, 92% yield) as a light yellow foamy solid. m/z=591 (M+1). Compound 77 is contaminated with 2-(trimethylsilyl)ethanol, and was used in the next step without further purification.

Compound 78:

A solution of compound 77 (0.19 g, 0.33 mmol) in methanol (20 mL) was treated with $K_2CO_3$ (0.23 g, 1.66 mmol) at room temperature. After stirring for 6.5 h, the reaction mixture was filtered through a pad of Celite®. The filtrate was concentrated and partitioned between sat. aq. $KH_2PO_4$ (15 mL) and EtOAc (25 mL). The organic extract was washed with brine (25 mL), dried over $MgSO_4$, filtered and concentrated to give compound 78 (0.18 g, 92% yield) as a light yellow foamy solid. m/z=591 (M+1). Compound 78 is contaminated with 2-(trimethylsilyl)ethanol, and was used in the next step without further purification.

Compound T22:

A suspension of compound 78 (0.16 g, 0.26 mmol) and DDQ (0.073 g, 0.32 mmol) in benzene (20 mL) and dioxane (10 mL) was heated at 85° C. under $N_2$ for 1 h. The reaction mixture was cooled, concentrated and partitioned between sat. aq. $NaHCO_3$ (50 mL) and EtOAc (50 mL). The organic extract was washed with brine (50 mL), dried over $MgSO_4$, filtered, and concentrated. The residue was purified by column chromatography (Silica gel, 50% EtOAc in hexanes) to give compound T22 (0.050 g, 32% yield) as a tan foamy solid. m/z=589 (M+1); $^1H$ NMR (400 MHz, $CDCl_3$) δ 8.09 (s, 1H), 6.10 (b, 1H), 6.00 (s, 1H), 3.95 (m, 2H), 3.93 (d, 1H, J=11.5 Hz), 3.51 (d, 1H, J=10.9 Hz), 3.05 (d, 1H, J=4.6 Hz), 2.93 (m, 1H), 2.37 (d, 1H, J=9.6 Hz), 1.52 (s, 3H), 1.31 (s, 3H), 1.15-2.09 (m, 15H), 1.06 (s, 3H), 1.04 (s, 3H), 1.00 (s, 3H), 0.91 (s, 3H).

Compound T23:

A mixture of compound T22 (0.028 g, 0.049 mmol) and NaOAc (0.020 g, 0.24 mmol) in $Ac_2O$ (1.0 mL, 10.6 mmol) was stirred at room temperature under $N_2$ overnight. The reaction mixture was concentrated, suspended into $CH_2Cl_2$ (1 mL) and purified by column chromatography (Silica gel, 50% EtOAc in hexanes) to give compound T23 (0.016 g, 52% yield) as an off-white foamy solid. m/z=631 (M+1); $^1H$ NMR (400 MHz, $CDCl_3$) δ 8.06 (s, 1H), 6.02 (t, 1H, J=6.5

Hz), 5.99 (s, 1H), 4.31 (d, 1H, J=11.0 Hz), 4.15 (d, 1H, J=11.0 Hz), 3.96 (m, 2H), 3.05 (d, 1H, J=4.5 Hz), 2.94 (m, 1H), 2.06 (m, 2H), 1.99 (s, 3H), 1.51 (s, 3H), 1.31 (s, 3H), 1.17-1.86 (m, 13H), 1.12 (s, 3H), 1.02 (s, 3H), 1.00 (s, 3H), 0.91 (s, 3H).

Compound 79:

To a stirring solution of compound 77 (0.31 g, 0.52 mmol) in $CH_2Cl_2$ (25 mL) was added Dess-Martin periodinane (0.28 g, 0.66 mmol) at room temperature under $N_2$. The mixture was stirred at room temperature overnight. 5% aq. $Na_2S_2O_3$ (20 mL) and sat. aq. $NaHCO_3$ (25 mL) were added, and the mixture was stirred for 1 h. The organic extract was separated, washed with brine (25 mL), dried over $MgSO_4$, filtered and concentrated to give compound 79 (0.31 g, quantitative yield) an off-white foamy solid. m/z=589 (M+1).

Compound 80:

To a stirring solution of compound 79 (0.31 g, 0.52 mmol) in $CH_2Cl_2$ (10 mL) was added $Na_2HPO_4$ (0.15 g, 1.06 mmol) and m-CPBA (≤77%, 0.18 g, 0.80 mmol) at room temperature under $N_2$. After stirring for 1 h, the mixture was treated with an aqueous solution of $Na_2SO_3$ (0.66 g in water (10 mL)), and stirred for 30 min. The organic extract was washed with sat. aq. $NaHCO_3$ (25 mL) and brine (25 mL), dried over $MgSO_4$, filtered and concentrated to give compound 80 (0.26 g, 81% yield) as an off-white foamy solid. m/z=605 (M+1).

Compound 81:

To a solution of compound 80 (0.26 g, 0.43 mmol) in methanol (10 mL) was added NaOMe (30 wt % solution in methanol, 0.24 mL, 1.30 mmol) at room temperature under $N_2$. The mixture was stirred for 1 h, concentrated, and then partitioned between sat. aq. $KH_2PO_4$ (25 mL) and EtOAc (25 mL). The organic extract was washed with brine (25 mL), dried over $MgSO_4$, filtered and concentrated to give compound 81 (0.22 g, 89% yield) as a tan foamy solid. m/z=577 (M+1).

Compound T24:

To a stirring solution of compound 81 (0.22 g, 0.38 mmol) in DMF (8 mL) was added a solution of 1,3-dibromo-5,5-dimethylhydantoin (0.054 g, 0.19 mmol) in DMF (2 mL) dropwise at 0° C. under $N_2$. After 30 min, pyridine (0.31 mL, 3.83 mmol) was added. The reaction was heated to 60° C. and stirred for 4 h under $N_2$. The mixture was cooled, concentrated, and then partitioned between sat. aq. $KH_2PO_4$ (25 mL) and EtOAc (25 mL). The organic extract was washed with brine (25 mL), dried over $MgSO_4$, filtered, and concentrated. The residue was purified by column chromatography (Silica gel, 50% EtOAc in hexanes) to give compound T24 (0.129 g, 59% yield) as light yellow solid. m/z=575 (M+1); $^1H$ NMR (400 MHz, $CDCl_3$) δ 8.03 (s, 1H), 6.04 (t, 1H, J=6.5 Hz), 5.92 (s, 1H), 4.02 (m, 1H), 3.90 (m, 1H), 3.24 (s, 1H), 3.04 (d, 1H, J=4.6 Hz), 2.93 (m, 1H), 1.54 (s, 3H), 1.32 (s, 3H), 1.32 (s, 3H), 1.17-2.15 (m, 15H), 1.02 (s, 3H), 0.99 (s, 3H), 0.90 (s, 3H).

Compound 82:

To a stirring solution of compound 9 (5.3 g, 10.64 mmol) and N,N-diisopropylethylamine (6.49 mL, 37.24 mmol) in $CH_2Cl_2$ (80 mL) was added 2-(trimethylsilyl)ethoxymethyl chloride (3.77 mL, 21.28 mmol) dropwise at 0° C. The reaction was stirred at room temperature overnight. Aq. $NaHCO_3$ was added. The mixture was stirred for 5 min, and extracted with $CH_2Cl_2$. The organic extract was dried over $Na_2SO_4$, filtered and concentrated. The residue was purified by column chromatography (Silica gel, 0-30% EtOAc in hexanes) to give compound 82 (6.4 g, 96% yield) as a white foam. m/z=629.4 (M+1).

Compound 83:

A mixture of compound 82 (7.43 g, 11.81 mmol), LiBr (10.27 g, 118.2 mmol) and NaOAc (2.42 g, 29.6 mmol) in N,N-dimethylacetamide (120 mL) was heated at 150° C. with $N_2$ bubbled through the reaction mixture for 6 h, and then cooled to room temperature. EtOAc was added. The mixture was washed with 1 N aq. HCl and water. The organic extract was dried over $Na_2SO_4$, filtered and concentrated. The residue was purified by column chromatography (Silica gel, 0-40% acetone in hexanes) to give compound 83 (3.85 g, 53% yield) as a white foam. m/z=615.4 (M+1).

Compound 84 and 85:

To a mixture of compound 83 (5.5 g, 8.94 mmol) in $HCO_2Et$ (37 mL, 447 mmol) was added NaOMe (25% w/w in MeOH, 20.5 mL, 89.4 mmol) at 0° C. The mixture was stirred at room temperature for 2 h, and was cooled to 0° C. MTBE was added, followed by 1 N aq. HCl (89 mL, 89 mmol). EtOAc was added. The mixture was washed with water. The organic extract was dried with $Na_2SO_4$, filtered and concentrated. The residue was dissolved in EtOH (90 mL) and water (9 mL). $NH_2OH\cdot HCl$ (804 mg, 11.6 mmol) was added. The mixture was heated at 55° C. for 3 h, cooled to room temperature, and concentrated. EtOAc was added. The mixture was washed with water. The organic extract was dried over $Na_2SO_4$, filtered and concentrated. The residue was purified by column chromatography (Silica gel, 0-50% acetone in hexanes) to give compound 84 (1.22 g, 26% yield) and 85 (1.77 g, 30% yield). Compound 84: white solid, m/z=510.3 (M+1); Compound 85: white solid, m/z=640.4 (M+1).

Compound 86:

A mixture of compound 84 (105 mg, 0.206 mmol), pyridine (0.5 mE, 6.18 mmol), acetic anhydride (0.250 mL, 2.68 mmol) and DMAP (2.5 mg, 0.02 mmol) was stirred at room temperature for 30 minutes. Aq. $NaHCO_3$ and EtOAc were added. The mixture was stirred for 60 min, and extracted with EtOAc. The organic extract was washed with 1N aq. HCl solution and water. The organic extract was dried over $Na_2SO_4$, filtered and concentrated to give compound 86 (110 mg, 97% yield) as a white foam. m/z=552.3 (M+1).

Compound 87:

To a stirring solution of compound 86 (110 mg, 0.199 mmol) in $CH_2Cl_2$ (2 mL) was added $(COCl)_2$ (51 μL, 0.60 mmol) at room temperature followed by one drop of DMF. The reaction was stirred at room temperature for 2 h, and concentrated. The residue was dissolved in toluene, and concentrated again to give the acid chloride as a yellow foam. The acid chloride was suspended in $Et_2O$ (2 mL). $EtNH_2$ (2M in THF, 0.3 mL, 0.6 mmol) and $Et_3N$ (55 μL, 0.40 mmol) in $CH_2Cl_2$ (2 mL) were added. The reaction was stirred at room temperature for 30 min. Aq. $NaHCO_3$ and EtOAc were added. The mixture was extracted with EtOAc. The organic extracts were washed with water, dried over $Na_2SO_4$, filtered and concentrated. The residue was purified by column chromatography (Silica gel, 0-60% EtOAc in hexanes) to give compound 87 (65 mg, 56% yield) as a white foam. m/z=579.4 (M+1).

Compound 88:

To a solution of compound 87 (64 mg, 0.110 mmol) in MeOH (2 mL), was added $K_2CO_3$ (61 mg, 0.44 mmol). The mixture was stirred for 14 h, and concentrated. The residue was diluted with water, and extracted with EtOAc. The organic extract was dried over $Na_2SO_4$, filtered and concentrated to give compound 88 (32 mg, 54% yield) as a white foam. m/z=537.3 (M+1).

Compound T25:

To a solution of compound 88 (32 mg, 0.06 mmol) in benzene (2 mL), was added DDQ (16.2 mg, 0.07 mmol). The mixture was stirred for 30 min at reflux, and cooled to room temperature. $CH_2Cl_2$ was added. The mixture was washed with water, dried over $Na_2SO_4$, filtered and concentrated to give T25 (10 mg, 31% yield) as a white foam. m/z=535.3 (M+1); $^1$H NMR (400 MHz, $CDCl_3$) δ 8.07 (s, 1H), 5.98 (s, 1H), 5.79 (t, 1H, J=5.9 Hz), 3.92 (d, 1H, J=10.9 Hz), 3.51 (d, 1H, J=10.9 Hz), 3.32 (m, 2H), 3.06 (d, 1H, J=4.6 Hz), 2.85 (m, 1H), 2.37 (m, 1H), 1.52 (s, 3H), 1.34 (s, 3H), 1.15-2.01 (m, 15H), 1.13 (t, 3H, J=7.2 Hz), 1.06 (s, 3H), 1.03 (s, 3H), 1.00 (s, 3H), 0.90 (s, 3H).

Compound 89:

A mixture of compound 84 (445 mg, 0.87 mmol), $Na_2HPO_4$ (495 mg, 3.49 mmol) and Dess-Martin periodinane (740 mg, 1.75 mmol) in $CH_2Cl_2$ (10 mL) was stirred at room temperature overnight. 10% aq. $Na_2S_2O_3$ (50 mL) was added. The mixture was stirred for 10 min, and was extracted with $CH_2Cl_2$ (4×20 mL). The combined organic extracts were dried over $Na_2SO_4$, filtered, concentrated to give compound 89 (500 mg) as an off-white foam. m/z=508.3 (M+1). Compound 89 was used in the next step without further purification.

Compound 90:

$Na_2HPO_4$ (495 mg, 3.49 mmol) and m-CPBA (≤77%, 292 mg, 1.31 mmol) were added to a solution of compound 89 (all obtained from the last step) in $CH_2Cl_2$ (10 mL). After stirring at room temperature for 1 h, aq. $Na_2SO_3$ was added. The mixture was stirred for 5 min, and was extracted with $CH_2Cl_2$. The organic extract was dried with $Na_2SO_4$, filtered, and concentrated. The residue was purified by column chromatography (C18, 10-100% MeCN in water) to give compound 90 (227 mg, 50% yield from 84) as a white solid. m/z=524.3 (M+1).

Compound 91:

To a solution of compound 90 (70 mg, 0.13 mmol) in $CH_2Cl_2$ (2.6 mL) was added $(COCl)_2$ (34 μL, 0.40 mmol) and catalytic amount of DMF at 0° C. The reaction was stirred at room temperature for 2 h, and concentrated. The residue was dissolved in toluene, and concentrated again to give compound 91 (70 mg) as a yellow foam.

Compound 92:

Compound 91 (60 mg, 0.11 mmol) was dissolved in $CH_2Cl_2$ (1.1 mL). $EtNH_2$ (2 M in THF, 0.12 mL, 0.24 mmol) was added at room temperature. After stirring for 30 min, the mixture was concentrated. The residue was purified by column chromatography (Silica gel, 0-50% EtOAc in hexanes) to give compound 92 (38 mg, 60% yield from 90) as a light yellow foam. m/z=551.3 (M+1).

Compound 93:

A mixture of compound 92 (36 mg, 0.065 mmol) and $K_2CO_3$ (36 mg, 0.26 mmol) in MeOH (1.3 mL) was stirred at room temperature for 16 h. EtOAc was added. The mixture was washed with 1 N aq. HCl and water. The organic extract was dried with $Na_2SO_4$, filtered, and concentrated. The residue was purified by column chromatography (Silica gel, 0-50% acetone in hexanes) to give compound 93 (30 mg, 83% yield) as a white solid. m/z=523.3 (M+1).

Compound T26:

To a solution of compound 93 (30 mg, 0.057 mmol) in DMF (0.4 mL) was added 1,3-dibromo-5,5-dimethylhydantoin (8.2 mg, 0.029 mmol) at 0° C. After the reaction was stirred at 0° C. for 1 h, pyridine (14 μL, 0.17 mmol) was added. The reaction was heated at 55° C. for 2 h, and cooled to room temperature. EtOAc was added. The mixture was washed with 1 N aq. HCl and water. The organic extract was dried over $Na_2SO_4$, filtered and concentrated. The residue was purified by column chromatography (Silica gel, 0-50% acetone in hexanes) to give compound T26 (23 mg, 77% yield) as a white foam. m/z=521.3 (M+1); $^1$H NMR (400 MHz, $CDCl_3$) δ 8.03 (s, 1H), 5.91 (s, 1H), 5.77 (t, 1H, J=5.7 Hz), 3.31 (m, 2H), 3.26 (s, 1H), 3.06 (d, 1H, J=4.6 Hz), 2.86 (m, 1H), 1.92-2.14 (m, 3H), 1.72-1.85 (m, 4H), 1.60 (s, 3H), 1.35 (s, 3H), 1.31 (s, 3H), 1.13 (t, 3H, J=7.2 Hz), 1.10-1.60 (m, 8H), 1.01 (s, 3H), 0.99 (s, 3H), 0.89 (s, 3H).

Compound 94:

Compound 91 (123 mg, 0.23 mmol) was dissolved in toluene (1.2 mL) and acetone (2.4 mL), and cooled to 0° C. The solution of $NaN_3$ (19 mg, 0.29 mmol) in water (0.6 mL) was added. The reaction was stirred at room temperature for 3 h. EtOAc was added. The mixture was washed with sat. aq. $NaHCO_3$ and water. The organic extract was dried with $Na_2SO_4$, filtered, and concentrated. The residue was purified by column chromatography (Silica gel, 0-35% EtOAc in hexanes) to give compound 94 (72 mg, 60% yield) as a white foam. m/z=549.3 (M+1).

Compound 95:

A solution of compound 94 (100 mg, 0.18 mmol) in toluene (2 mL) was heated at 85° C. for 2 h. The solution was concentrated to give compound 95, which was used in the next step without further purification. m/z=521.3 (M+1).

Compound 96:

To a solution of compound 95 (all obtained from the last step) in $CH_2Cl_2$ (1.7 mL) was added 12 N aq. HCl (0.34 mL, 4.08 mmol) at 0° C. After stirring at room temperature for 2 h, the mixture was treated with sat. aq. $NaHCO_3$ to adjust pH>7, and was extracted with EtOAc. The organic extract was dried with $Na_2SO_4$, and concentrated to give the crude compound 96 (85 mg) as a yellow foam. m/z=467.3. The crude product was contaminated with a major impurity, and was carried on to the next step without further purification.

Compound 97:

To a solution of compound 96 (all obtained from the last step) and 2,2-difluoropropionic acid (25 mg, 0.23 mmol) in $CH_2Cl_2$ (2 mL) was added propylphosphonic anhydride (≥50 wt. % in EtOAc, 224 μL, 0.38 mmol) and $Et_3N$ (79 μL, 0.56 mmol) at room temperature. The mixture was stirred at room temperature for 2 h. Sat. aq. $NaHCO_3$ was added. The mixture was stirred for 30 min, and then extracted with EtOAc. The organic extract was dried over $Na_2SO_4$, filtered and concentrated. The residue was purified by column chromatography (Silica gel, 0-40% EtOAc in hexanes) to give compound 97 (20 mg, 20% yield from 94) as a white foam. m/z=559.3 (M+1).

Compound 98:

A mixture of compound 97 (20 mg, 0.036 mmol) and $K_2CO_3$ (30 mg, 0.22 mmol) in MeOH (1.4 mL) was stirred at room temperature for 16 h. EtOAc was added. The mixture was washed with 1 N aq. HCl and water. The organic extract was dried with $Na_2SO_4$, filtered, and concentrated to give compound 98 (19 mg, 95% yield) as a white foam. m/z=559.4 (M+1).

Compound T27:

To a solution of compound 98 (19 mg, 0.034 mmol) in DMF (0.4 mL) was added 1,3-dibromo-5,5-dimethylhydantoin (5 mg, 0.017 mmol) at 0° C. After the reaction was stirred at 0° C. for 1 h, pyridine (8 μL, 0.099 mmol) was added. The reaction was heated at 55° C. for 2 h, and cooled to room temperature. EtOAc was added. The mixture was washed with 1 N aq. HCl and water. The organic extract was dried over $Na_2SO_4$, filtered and concentrated. The residue was purified by column chromatography (Silica gel, 0-50% EtOAc in hexanes) to give compound T27 (13 mg, 68% yield) as a white solid. m/z=557.3 (M+1); $^1$H NMR (400 MHz, CDCl$_3$) δ 8.00 (s, 1H), 5.93 (s, 1H), 5.91 (bs, 1H), 3.24 (s, 1H), 2.98 (d, 1H, J=4.6 Hz), 2.81 (m, 1H), 1.78 (t, 3H, J=19.3 Hz), 1.55 (s, 3H), 1.44 (s, 3H), 1.32 (s, 3H), 1.16-2.18 (m, 15H), 1.05 (s, 3H), 1.03 (s, 3H), 0.90 (s, 3H).

Compound 99:

To a stirring solution of compound 85 (0.65 g, 1.02 mmol) and Et$_3$N (0.42 mL, 3.01 mmol) in benzene (25 mL) was added dropwise diphenylphosphorylazide (0.33 mL, 1.53 mmol) at 0° C. After slowly warming to room temperature overnight, the mixture was concentrated, and then partitioned between sat. aq. KH$_2$PO$_4$ (50 mL) and EtOAc (50 mL). The organic extract was washed with brine (50 mL), dried over MgSO$_4$, filtered and concentrated. The resultant light yellow oil (0.92 g) was dissolved into benzene (50 mL), and heated at reflux for 2 h. The sample was cooled, and concentrated. The residue was purified by column chromatography (Silica gel, 25% EtOAc in hexanes) to give compound 99 (0.72 g, quantitative yield). m/z=637 (M+1). Compound 99 was contaminated with diphenylphosphorylazide, and was used in the next step without further purification.

Compound 100:

A solution of compound 99 (all obtained from the last step) in CH$_3$CN (20 mL) was treated with 12 N aq. HCl (2.1 mL, 25.2 mmol) at 0° C. The mixture was stirred at room temperature for 2 h, concentrated, and then vacuum dried overnight. The resultant gummy oil was carefully partitioned between sat. aq. NaHCO$_3$ (50 mL) and EtOAc (50 mL). The organic extract was washed with brine (50 mL), dried over MgSO$_4$, filtered and concentrated to give compound 100 (0.52 g, quantitative yield) as a tan foamy solid. m/z=481 (M+1). Compound 100 was contaminated with diphenylphosphorylazide, and was used in the next step without further purification.

Compound 101 and 102:

To a stirring solution of compound 100 (0.27 g, 0.56 mmol), 2,2-difluoropropionic acid (0.094 g, 0.85 mmol) and Et$_3$N (0.24 mL, 1.72 mmol) in CH$_2$Cl$_2$ (50 mL) was added propylphosphonic anhydride (50 wt. % solution in EtOAc, 0.34 mL, 0.57 mmol) dropwise at room temperature. After stirring overnight, the mixture was concentrated, and then partitioned between sat. aq. KH$_2$PO$_4$ (25 mL) and EtOAc (25 mL). The organic extract was washed with brine (25 mL), dried over MgSO$_4$, filtered and concentrated to give a mixture of compound 101 and compound 102 (0.12 g) as an off-white foamy solid. 101: m/z=573 (M+1); 102: m/z=665 (M+1). The mixture was carried on to the next step without separation.

Compound 103:

To a solution of compound 101 and 102 (0.12 g, all obtained from the last step) in methanol (20 mL) was added K$_2$CO$_3$ (0.13 g, 0.94 mmol). The mixture was stirred at room temperature for 4 h, and then filtered through a pad of Celite®. The filtrate was concentrated, and partitioned between sat. aq. KH$_2$PO$_4$ (50 mL) and EtOAc (50 mL). The organic extract was washed with brine (50 mL), dried over MgSO$_4$, filtered and concentrated to give compound 103 (100 mg, 31% yield from 100) as a light yellow foamy solid. m/z=573 (M+1).

Compound T28:

To a stirring solution of compound 103 (0.100 g, 0.174 mmol) in DMF (5 mL) was added a solution of 1,3-dibromo-5,5-dimethylhydantoin (0.025 g, 0.087 mmol) in DMF (1 mL) dropwise at 0° C. After 30 min, pyridine (0.14 mL, 1.73 mmol) was added. The mixture was heated to 60° C., stirred for 4 h, cooled, and concentrated. The residue was partitioned between sat. aq. KH$_2$PO$_4$ (25 mL) and EtOAc (25 mL). The organic extract was washed with brine (25 mL), dried over MgSO$_4$, filtered, and concentrated. The residue was purified by column chromatography (Silica gel, 20% EtOAc in CH$_2$Cl$_2$) to give compound T28 (0.043 g, 43% yield) as an off-white foamy solid. m/z=571.3; $^1$H NMR (400 MHz, CDCl$_3$) δ 8.06 (s, 1H), 6.01 (s, 1H), 5.93 (bs, 1H), 3.93 (dd, 1H, J=5.5, 10.6 Hz), 3.51 (dd, 1H, J=5.4, 11.0 Hz), 3.02 (d, 1H, J=4.0 Hz), 2.79 (m, 1H), 2.39 (d, 1H, J=7.9 Hz), 1.78 (t, 3H, J=19.5 Hz), 1.53 (s, 3H), 1.43 (s, 3H), 1.15-2.15 (m, 15H), 1.07 (s, 3H), 1.06 (s, 6H), 0.91 (s, 3H).

Compound T29:

A mixture of compound T28 (0.038 g, 0.066 mmol) and NaOAc (0.027 g, 0.33 mmol) in Ac$_2$O (1.0 mL, 10.6 mmol) was stirred at room temperature overnight. The sample was filtered and the solid was washed with CH$_2$Cl$_2$. The filtrate was concentrated and purified by column chromatography (Silica gel, 10% EtOAc in CH$_2$Cl$_2$) to give compound T29 (0.024 g, 58% yield) as an off-white solid. m/z=613 (M+1, 30%); $^1$H NMR (400 MHz, CDCl$_3$) δ 8.06 (s, 1H), 6.01 (s, 1H), 5.91 (bs, 1H), 4.31 (d, 1H, J=11.1 Hz), 4.16 (d, 1H, J=11.0 Hz), 3.01 (d, 1H, J=4.8 Hz), 2.81 (m, 1H), 1.99 (s, 3H), 1.78 (t, 3H, J=19.5 Hz), 1.53 (s, 3H), 1.42 (s, 3H), 1.17-2.13 (m, 15H), 1.13 (s, 3H), 1.06 (s, 3H), 1.04 (s, 3H), 0.90 (s, 3H).

Compound 104:

Compound 91 (33 mg, 0.061 mmol) was dissolved in CH$_2$Cl$_2$ (1 mL). Et$_3$N (27 μL, 0.19 mmol) and Me$_2$NH.HCl (10 mg, 0.122 mmol) were added at room temperature. After stirring for 30 min, the mixture was concentrated. The residue was purified by column chromatography (Silica gel, 0-100% EtOAc in hexanes) to give compound 104 (29 mg, 86% yield) as a white foam. m/z=551.3 (M+1).

Compound 105:

A mixture of compound 104 (29 mg, 0.053 mmol) and K$_2$CO$_3$ (29 mg, 0.21 mmol) in MeOH (1 mL) was stirred at room temperature for 16 h. EtOAc was added. The mixture was washed with 1 N aq. HCl and water. The organic extract was dried with Na$_2$SO$_4$, filtered, and concentrated to give compound 105 (30 mg, quantitative yield). m/z=523.3 (M+1). Compound 105 was used in the next step without further purification.

Compound T30:

DDQ (14 mg, 0.062 mmol) was added to a solution of compound 105 (all obtained from the last step) in benzene (1.1 mL). The reaction was heated at reflux for 1 h, and cooled to room temperature. CH$_2$Cl$_2$ was added. The mixture was washed with aq. NaHCO$_3$. Organic extract was dried with Na$_2$SO$_4$, filtered and concentrated. The residue was purified by column chromatography to give compound T30 (9 mg, 31% yield) as a white solid. m/z=521.2 (M+1); $^1$H NMR (400 MHz, CDCl$_3$) δ 8.02 (s, 1H), 5.86 (s, 1H), 3.27 (d, 1H, J=4.7 Hz), 3.25 (s, 1H), 3.18 (m, 1H), 3.08 (s, 6H), 1.95-2.04 (m, 3H), 1.53 (s, 3H), 1.33 (s, 3H), 1.31 (s, 3H), 1.16-1.90 (m, 12H), 1.01 (s, 3H), 1.01 (s, 3H), 0.90 (s, 3H).

Compound 106:

Compound 84 (125 mg, 0.25 mmol) and [hydroxy(tosyloxy)iodo]benzene (125 mg, 0.32 mmol) and CH$_2$Cl$_2$ (4 mL) in a sealed vial was heated at 55° C. for 2 h, and then cooled to room temperature. The mixture was purified by column chromatography (Silica gel, 0-100% EtOAc in hexanes). The mixed fractions were concentrated, and purified again by column chromatography (Silica gel, 0-40% acetone in hexanes). The purified fractions were combined and concentrated to give compound 106 (43 mg, 35% yield) as a white solid. m/z=508.3 (M+1).

Compound 107:

To a solution of compound 106 (38 mg, 0.075 mmol) in MeOH (1.5 mL) was added K$_2$CO$_3$ (31 mg, 0.22 mmol) at room temperature. After stirring for 16 h, the mixture was diluted with EtOAc, washed with 1 N aq. HCl and water. The organic extract was dried with Na$_2$SO$_4$, filtered, and concentrated. The residue was purified by column chromatography (Silica gel, 0-40% acetone in hexanes) to give compound 107 (33 mg, 87% yield) as a white solid. m/z=508.3 (M+1).

Compound T31:

DDQ (18 mg, 0.079 mmol) was added to a solution of compound 107 (33 mg, 0.065 mmol) in benzene (1.3 mL). The reaction was heated at reflux for 1 h, and at room temperature for 1 h. Sat. aq. NaHCO$_3$ was added. The mixture was extracted with CH$_2$Cl$_2$. The organic extract was dried with Na$_2$SO$_4$, filtered and concentrated. The residue was purified by column chromatography (Silica gel, 0-40% acetone in hexanes) to give compound T31 (17 mg, 52% yield) as a white foam. m/z=506.2 (M+1); $^1$H NMR (400 MHz, CDCl$_3$) δ 8.04 (s, 1H), 6.22 (s, 1H), 3.94 (dd, 1H, J=5.9, 10.9 Hz), 3.52 (dd, 1H, J=5.6, 10.8 Hz), 2.97 (dd, 1H, J=3.4, 13.7 Hz), 2.45 (dd, 1H, J=2.1, 11.8 Hz), 2.10 (dt, 1H, J=6.0, 13.4 Hz), 1.60 (s, 3H), 1.54 (s, 3H), 1.22-1.93 (m, 14H), 1.08 (s, 3H), 1.05 (s, 3H), 0.97 (s, 6H).

Compound T32:

To the solution of compound T31 (11 mg, 0.022 mmol) in CH$_2$Cl$_2$ (0.4 mL) was added Et$_3$N (9 μL, 0.065 mmol) and AcCl (10 vol. % solution in CH$_2$Cl$_2$, 23 μL, 0.033 mmol) sequentially at room temperature. After stirring for 30 min, the mixture was diluted with EtOAc and sat. aq. NaHCO$_3$, and then stirred for another 5 min. The organic extract was washed with 1 N aq. HCl and water, dried with Na$_2$SO$_4$, filtered and concentrated. The residue was purified by column chromatography (Silica gel, 0-40% EtOAc in hexanes) to give compound T32 (12 mg, 99% yield) as a white foam. m/z=548.2 (M+1); $^1$H NMR (400 MHz, CDCl$_3$) δ 8.03 (s, 1H), 6.23 (s, 1H), 4.33 (d, 1H, J=11.0 Hz), 4.13 (d, 1H, J=11.0 Hz), 2.97 (dd, 1H, J=3.4, 13.7 Hz), 1.99 (s, 3H), 1.59 (s, 3H), 1.54 (s, 3H), 1.24-2.16 (m, 15H), 1.16 (s, 3H), 1.02 (s, 3H), 0.97 (s, 3H), 0.96 (s, 3H).

Compound 108:

To a solution of (COCl)$_2$ (18 μL, 0.22 mmol) in CH$_2$Cl$_2$ (0.6 mL) was added DMSO (28 μL, 0.39 mmol) dropwise at −78° C., and stirred for 30 min. Compound 106 (42 mg, 0.082 mmol) in CH$_2$Cl$_2$ (1 mL) was added at −78° C., and stirred for another 1 h. Et$_3$N (81 μL, 0.58 mmol) was added. The cold bath was removed, and the reaction was stirred at ambient temperature for 30 min. EtOAc was added, and the mixture was washed with sat. aq. NaHCO$_3$ and water. The organic extract was dried with Na$_2$SO$_4$, and concentrated to give compound 108 as an off-white solid. m/z=506.3 (M+1). Compound 108 was used in the next step without further purification.

Compound 109:

Na$_2$HPO$_4$ (22 mg, 0.15 mmol) and m-CPBA (≤77%, 28 mg, 0.12 mmol) were added to a solution of compound 108 (all obtained from the last step) in CH$_2$Cl$_2$ (1.7 mL). After stirring at room temperature for 16 h, aq. Na$_2$SO$_3$ was added. The mixture was stirred for 5 min, and was extracted with CH$_2$Cl$_2$. The organic extract was dried with Na$_2$SO$_4$, filtered, and concentrated. The residue was purified by column chromatography (Silica gel, 0-35% EtOAc in hexanes) to give compound 109 (28 mg, 65% yield from 106) as a white solid. m/z=522.3 (M+1).

Compound 110:

A mixture of compound 109 (28 mg, 0.053 mmol) and K$_2$CO$_3$ (30 mg, 0.22 mmol) in MeOH (1 mL) was stirred at room temperature for 16 h. EtOAc was added. The mixture was washed with 1 N aq. HCl and water. The organic extract was dried with Na$_2$SO$_4$, filtered, and concentrated to give compound 110 (29 mg, quantitative yield) as a white foam. m/z=494.2 (M+1).

Compound T33:

To a solution of compound 110 (29 mg, 0.059 mmol) in DMF (0.2 mL) was added the solution of 1,3-dibromo-5,5-dimethylhydantoin (8.4 mg, 0.029 mmol) in DMF (0.2 mL) at 0° C. After the reaction was stirred at 0° C. for 1 h, pyridine (14 L, 0.17 mmol) was added. The reaction was heated at 55° C. for 2 h, and cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-50% acetone in hexanes) to give compound T33 (19 mg, 66% yield) as a white solid. m/z=492.3 (M+1); $^1$H NMR (400 MHz, CDCl$_3$) δ 8.01 (s, 1H), 6.16 (s, 1H), 3.23 (s, 1H), 2.96 (dd, 1H, J=3.4, 13.8 Hz), 1.62 (s, 3H), 1.56 (s, 3H), 1.35 (s, 3H), 1.23-2.17 (m, 15H), 1.02 (s, 3H), 0.97 (s, 6H).

Compound 111:

Compound 106 (226 mg, 0.52 mmol) was dissolved in acetone (5 mL), and cooled to 0° C. Jones reagent (2.5 M) was added until the orange color persisted. The mixture was stirred at 0° C. for 2 h, and at room temperature for 1 h. During the reaction, additional small amount of Jones reagent was added to maintain the orange color of the mixture. i-PrOH was added to quench the reaction. The solvent was removed, and EtOAc was added. The mixture was washed with water. The organic extract was dried over Na$_2$SO$_4$, filtered and concentrated. The residue was purified by column chromatography (Silica gel, 0-100% acetone in hexanes) to give compound 111 (167 mg, 61% yield) as a white solid. m/z=522.3 (M+1).

Compound 112:

Compound 111 (38 mg, 0.073 mmol) was dissolved in toluene (1 mL) and MeOH (0.3 mL), and was cooled to 0° C. Trimethylsilyldiazomethane (2 M in Et$_2$O, 73 μL, 0.14 mmol) was added at 0° C., and stirred for 15 min. AcOH was added to quench the reaction. The mixture was concentrated. The residue was purified by column chromatography (Silica gel, 0-50% EtOAc in hexanes) to give compound 112 (30 mg, 77% yield) as a white solid. m/z=536.2 (M+1).

Compound 113:

A mixture of compound 112 (30 mg, 0.056 mmol) and K$_2$CO$_3$ (46 mg, 0.33 mmol) in MeOH (2 mL) was stirred at room temperature for 16 h. EtOAc was added. The mixture was washed with 1 N aq. HCl and water. The organic extract was dried with Na$_2$SO$_4$, filtered, and concentrated to give compound 113 (35 mg, quantitative yield) as a white foam. m/z=536.3 (M+1).

Compound T34:

To a solution of compound 113 (all obtained from the last step) in DMF (0.6 mL) was added 1,3-dibromo-5,5-dimethylhydantoin (9 mg, 0.031 mmol) at 0° C. After the reaction was stirred at 0° C. for 1 h, pyridine (16 μL, 0.20 mmol) was added. The reaction was heated at 55° C. for 4 h, and was cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-35% acetone in hexanes) to give compound T34 (25 mg, 83% yield) as a white foam. m/z=534.3 (M+1); $^1$H NMR (400 MHz, CDCl$_3$) δ 8.04 (s, 1H), 6.22 (s, 1H), 3.76 (s, 3H), 2.97 (dd, 1H, J=3.4, 13.1 Hz), 2.61 (dd, 1H, J=1.9, 12.5 Hz), 2.11 (dt, 1H, J=6.0, 13.2 Hz), 1.60 (s, 3H), 1.55 (s, 3H), 1.47 (s, 3H), 1.25-2.01 (m, 13H), 1.05 (s, 3H), 0.97 (s, 6H).

Compound 114:

To a solution of compound 111 (124 mg, 0.24 mmol) in $CH_2Cl_2$ (2.4 mL) was added $(COCl)_2$ (60 µL, 0.71 mmol) and catalytic amount of DMF at 0° C. The reaction was stirred at room temperature for 2 h, and concentrated. The residue was dissolved in toluene, and concentrated again to give compound 114 (131 mg, quantitative yield) as a yellow solid. m/z=540.2, 542.2 (M+1). Compound 114 was used in the next step without further purification.

Compound 115:

To the suspension of $MeNH_2 \cdot HCl$ (11 mg, 0.16 mmol) in $CH_2Cl_2$ (0.8 mL) was added $Et_3N$ (44 µL, 0.32 mmol) at room temperature. After the reaction was stirred for 5 min, compound 114 (43 mg, 0.079 mmol) in $CH_2Cl_2$ (0.8 mL) was added. The reaction was stirred at room temperature for 1 h. The solvent was removed. The residue was purified by column chromatography (Silica gel, 0-100% EtOAc in hexanes) to give compound 115 (32 mg, 75% yield) as a white solid. m/z=535.3 (M+1).

Compound 116:

Compound 115 (31 mg, 0.058 mmol) and $K_2CO_3$ (48 mg, 0.35 mmol) in MeOH (1.2 mL) were stirred at room temperature for 18 h. EtOAc was added. The mixture was washed with 1N aq. HCl and water. The organic extract was dried with $Na_2SO_4$, filtered, and concentrated to give compound 116 (30 mg, 97% yield) as a white foam. m/z=535.4 (M+1). Compound 116 was used in the next step without further purification.

Compound T35:

To a solution of compound 116 (30 mg, 0.056 mmol) in DMF (0.5 mL) was added 1,3-dibromo-5,5-dimethylhydantoin (8 mg, 0.028 mmol) at 0° C. After the reaction was stirred at 0° C. for 30 min, and then, at room temperature for 30 min, pyridine (14 µL, 0.17 mmol) was added. The reaction was heated at 55° C. for 4 h, and was cooled to room temperature. EtOAc was added. The mixture was washed with 1 N aq. HCl and water. The organic extract was dried over $Na_2SO_4$, filtered and concentrated. The residue was purified by column chromatography (Silica gel, 0-60% acetone in hexanes) to give compound T35 (21 mg, 70% yield) as a white foam. m/z=533.3 (M+1); $^1$H NMR (400 MHz, $CDCl_3$) δ 8.12 (s, 1H), 6.39 (q, 1H, J=5.5 Hz), 6.23 (s, 1H), 2.94-3.03 (m, 2H), 2.83 (d, 3H, J=4.7 Hz), 2.11 (dt, 1H, J=6.0, 13.4 Hz), 1.57 (s, 3H), 1.54 (s, 3H), 1.52 (s, 3H), 1.25-1.95 (m, 13H), 1.07 (s, 3H), 0.98 (s, 3H), 0.97 (s, 3H).

Compound 117:

To the suspension of $Me_2NH \cdot HCl$ (14 mg, 0.17 mmol) in $CH_2Cl_2$ (0.8 mL) was added $Et_3N$ (44 µL, 0.32 mmol) at room temperature. After the reaction was stirred for 5 min, compound 114 (43 mg, 0.079 mmol) in $CH_2Cl_2$ (0.8 mL) was added. The reaction was stirred at room temperature for 1 h. The solvent was removed. The residue was purified by column chromatography (Silica gel, 0-100% EtOAc in hexanes) to give compound 117 (32 mg, 73% yield) as a white foam. m/z=549.3 (M+1).

Compound 118:

Compound 117 (31 mg, 0.056 mmol) and $K_2CO_3$ (47 mg, 0.34 mmol) in MeOH (1.2 mL) were stirred at room temperature for 18 h. EtOAc was added. The mixture was washed with 1N aq. HCl and water. The organic extract was dried with $Na_2SO_4$, filtered, and concentrated to give compound 118 (31 mg, quantitative yield) as a white foam. m/z=549.3 (M+1). Compound 118 was used in the next step without further purification.

Compound T36:

To a solution of compound 118 (31 mg, 0.056 mmol) in DMF (0.5 mL) was added 1,3-dibromo-5,5-dimethylhydantoin (8 mg, 0.028 mmol) at 0° C. After the reaction was stirred at 0° C. for 1 h, pyridine (14 µL, 0.17 mmol) was added. The reaction was heated at 55° C. for 3 h, and was cooled to room temperature. EtOAc was added. The mixture was washed with 1 N aq. HCl and water. The organic extract was dried over $Na_2SO_4$, filtered and concentrated. The residue was purified by column chromatography (Silica gel, 0-80% EtOAc in hexanes) to give compound T36 (20 mg, 65% yield) as a white foam. m/z=547.3 (M+1); $^1$H NMR (400 MHz, $CDCl_3$) δ 8.06 (s, 1H), 6.21 (s, 1H), 2.97 (dd, 1H, J=3.4, 13.7 Hz), 2.85 (bs, 6H), 2.25 (dd, 1H, J=1.5, 11.8 Hz), 2.09 (dt, 1H, J=5.6, 13.2 Hz), 1.65 (s, 3H), 1.55 (s, 3H), 1.44 (s, 3H), 1.24-2.00 (m, 13H), 1.03 (s, 3H), 0.97 (s, 3H), 0.96 (s, 3H).

Compound 119:

To the solution of compound 114 (45 mg, 0.083 mmol) in $CH_2Cl_2$ (0.9 mL) was added $NH_3$ (2 M solution in MeOH, 0.17 mL, 0.34 mmol) at 0° C. After the reaction was stirred for 30 min, additional amount of $NH_3$ (2 M solution in MeOH, 0.04 mL, 0.08 mmol) was added. The reaction was stirred at 0° C. for another 20 min. EtOAc was added. The mixture was washed with 1 N aq. HCl and water. The organic extract was dried over $Na_2SO_4$, filtered and concentrated. The residue was purified by column chromatography (Silica gel, 0-60% acetones in hexanes) to give compound 119 (32 mg, 74% yield) as a white solid. m/z=521.3 (M+1).

Compound 120:

A mixture of compound 119 (32 mg, 0.061 mmol) and $K_2CO_3$ (48 mg, 0.35 mmol) in MeOH (2.4 mL) was stirred at room temperature for 16 h, and concentrated. EtOAc was added. The mixture was washed with 1N aq. HCl. The organic extract was dried with $Na_2SO_4$, filtered, and concentrated to give compound 120 (34 mg, quantitative yield) as a white foam. m/z=521.3 (M+1). Compound 120 was used in the next step without further purification.

Compound T37:

To a solution of compound 120 (all obtained from the last step) in DMF (0.5 mL) was added 1,3-dibromo-5,5-dimethylhydantoin (9 mg, 0.031 mmol) at 0° C. After the reaction was stirred at 0° C. for 1 h, pyridine (16 µL, 0.20 mmol) was added. The reaction was heated at 55° C. for 3 h, and was cooled to room temperature. EtOAc was added. The mixture was washed with 1 N aq. HCl and water. The organic extract was dried over $Na_2SO_4$, filtered and concentrated. The residue was purified by column chromatography (Silica gel, 0-60% acetone in hexanes) to give compound T37 (21 mg, 66% yield) as a white foam. m/z=519.3 (M+1); $^1$H NMR (400 MHz, $CDCl_3$) δ 8.13 (s, 1H), 6.34 (bs, 1H), 6.24 (s, 1H), 5.42 (bs, 1H), 2.91-2.98 (m, 2H), 2.13 (dt, 1H, J=5.9, 13.3 Hz), 1.61 (s, 3H), 1.56 (s, 3H), 1.53 (s, 3H), 1.25-1.95 (m, 13H), 1.07 (s, 3H), 0.98 (s, 3H), 0.97 (s, 3H).

Compound 121:

Compound 109 (122 mg, 0.23 mmol) was dissolved in EtOH (3 mL) and THF (1.5 mL), and was cooled to 0° C. 10% aq. NaOH (0.69 mL, 1.73 mmol) was added. The mixture was stirred at room temperature for 5 h. MTBE and 1 N aq. HCl (4 mL) were added. The mixture was extracted with EtOAc. The organic extract was washed with water, dried with $Na_2SO_4$, and concentrated to give compound 121 as a white foam. m/z=494.3 (M−17). Compound 121 was used in the next step without further purification.

Compound 122:

Compound 121 (all obtained from the last step) was dissolved in toluene (6 mL) and MeOH (2 mL), and was cooled to 0° C. Trimethylsilyldiazomethane (2 M in Et$_2$O, 0.13 mL, 0.26 mmol) was added dropwise at 0° C. After stirring for 15 min, the reaction mixture was treated with additional amount of trimethylsilyldiazomethane (2 M in Et$_2$O, 0.20 mL, 0.40 mmol) dropwise at 0° C. During the addition, the reaction was monitored by TLC. When compound 121 was completely consumed, the reaction was quenched with AcOH, and concentrated. The residue was purified by column chromatography (Silica gel, 0-60% EtOAc in hexanes) to give compound 122 (82 mg, 67% yield from 109) as a white foam. m/z=508.3 (M−17).

Compound T38:

To a solution of compound 122 (80 mg, 0.15 mmol) in DMF (0.8 mL) was added 1,3-dibromo-5,5-dimethylhydantoin (22 mg, 0.077 mmol) at 0° C. After the reaction was stirred at 0° C. for 1 h, pyridine (37 μL, 0.46 mmol) was added. The reaction was heated at 55° C. for 3 h, and was cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-50% EtOAc in hexanes) to give compound T38 (59 mg, 74% yield) as a white foam. m/z=506.3 (M−17); $^1$H NMR (400 MHz, CDCl$_3$) δ 8.03 (s, 1H), 5.90 (s, 1H), 3.69 (s, 3H), 3.28 (s, 1H), 2.86 (m, 1H), 2.25 (dt, 1H, J=4.1, 13.3 Hz), 1.56 (s, 3H), 1.50 (s, 3H), 1.31 (s, 3H), 1.07-2.13 (m, 14H), 1.02 (s, 3H), 0.97 (s, 3H), 0.88 (s, 3H).

Compound 123:

To a mixture of compound 95 (50 mg, 0.096 mmol) in MeOH (1 mL) was added NaOMe (25% w/w in MeOH, 90 μL, 0.39 mmol) at room temperature. The mixture was stirred at room temperature for 2 h, heated at 55° C. for 1 h, and then, cooled to room temperature. EtOAc and 1 N aq. HCl were added. The organic extract was washed with water, dried over Na$_2$SO$_4$, filtered and concentrated. The residue was purified by column chromatography (Silica gel, 0-50% acetone in hexanes) to give compound 123 (33 mg, 66% yield) as a white foam. m/z=525.3 (M+1).

Compound T39:

To a solution of compound 123 (32 mg, 0.061 mmol) in DMF (0.4 mL) was added 1,3-dibromo-5,5-dimethylhydantoin (9 mg, 0.031 mmol) at 0° C. After the reaction was stirred at 0° C. for 1 h, pyridine (15 μL, 0.19 mmol) was added. The reaction was heated at 55° C. for 2 h, and cooled to room temperature. EtOAc was added. The mixture was washed with 1 N aq. HCl and water. The organic extract was dried over Na$_2$SO$_4$, filtered and concentrated. The residue was purified by column chromatography (Silica gel, 0-55% EtOAc in hexanes) to give compound T39 (28 mg, 88% yield) as a white foam. m/z=523.3 (M+1); $^1$H NMR (400 MHz, CDCl$_3$) δ 8.01 (s, 1H), 5.91 (s, 1H), 4.38 (s, 1H), 3.62 (s, 3H), 3.24 (s, 1H), 3.08 (d, 1H, J=4.7 Hz), 2.72 (m, 1H), 1.55 (s, 3H), 1.46 (s, 3H), 1.33 (s, 3H), 1.10-2.19 (m, 15H), 1.03 (s, 3H), 1.01 (s, 3H), 0.89 (s, 3H).

Compound 124:

To a solution of compound 83 (100 mg, 0.16 mmol) and pyridine (26 μL, 0.32 mmol) in CH$_2$Cl$_2$ (1.6 mL) was added (COCl)$_2$ (41 μL, 0.49 mmol) at 0° C. The reaction was stirred at 0° C. for 10 min, and then at room temperature for 2 h, and concentrated. The residue was mixed with toluene, and concentrated again to give compound 124 as a light yellow foam. m/z=633.4 (M+1). Compound 124 was used in the next step without further purification.

Compound 125:

To a solution of compound 124 (all obtained in the last step) in toluene (1 mL) was added NaN$_3$ (12.6 mg, 0.19 mmol), acetone (2 mL) and water (0.5 mL) at room temperature. The reaction was stirred at room temperature for 1 h. EtOAc was added. The mixture was washed with water and aq. NaHCO$_3$. The organic extract was dried with Na$_2$SO$_4$, filtered, and concentrated to give compound 125 (100 mg, 96% yield from 83) as a light yellow foam. m/z=640.4 (M+1). Compound 125 was used in the next step without further purification.

Compound 126:

Compound 125 (100 mg, 0.16 mmol) was dissolved in toluene (2 mL), and heated at 80° C. for 2 h. The solution was cooled, and concentrated to give compound 126 (90 mg, 93% yield) as a light yellow foam. m/z=612.4 (M+1). Compound 126 was used in the next step without further purification.

Compound 127:

Compound 126 (330 mg, 0.54 mmol) was dissolved in MeOH (2 mL) at 0° C., and NaOMe (30 wt. % in methanol, 150 mg, 0.83 mmol) was added. The reaction mixture was stirred for 1 h, and the solvent was removed under vacuum. The crude reaction mixture was dissolved in HCO$_2$Et (5 mL), and NaOMe (30 wt. % in methanol, 500 mg, 2.78 mmol) was added. After stirring at room temperature for 2 h, the reaction mixture was neutralized by the addition of sat. aq. KH$_2$PO$_4$, and was extracted with EtOAc. The organic extract was washed with brine, then dried with MgSO$_4$, and concentrated to give compound 127 (360 mg, quantitative yield). m/z=672 (M+1).

Compound 128:

Compound 127 (355 mg, 0.53 mmol) was dissolved in EtOH. NH$_2$OH.HCl (75 mg, 1.1 mmol) was added. The reaction mixture was stirred overnight at 50° C. After cooling to room temperature, the reaction mixture was concentrated. The residue was diluted with EtOAc, and the mixture was washed with aq. NaHCO$_3$. The organic extract was dried with MgSO$_4$, and concentrated to give compound 128 (285 mg, quantitative yield). m/z=539 (M+1).

Compound 129:

Compound 128 (160 mg, 0.30 mmol) was dissolved in MeOH (5 mL), and K$_2$CO$_3$ (165 mg, 1.2 mmol) was added. The reaction mixture was stirred at room temperature for 4 h. The reaction was neutralized by the addition of sat. aq. KH$_2$PO$_4$, and was extracted with EtOAc. The organic extract was washed with brine, dried with MgSO$_4$, and concentrated. The crude product was purified by column chromatography (Silica gel, 10-50% EtOAc in hexanes) to give compound 129 (100 mg, 62% yield) as a foam. m/z=539 (M+1).

Compound T40:

To a solution of compound 129 (80 mg, 0.15 mmol) in dioxane (2 mL) was added DDQ (70 mg, 0.31 mmol), and the solution was heated at 80° C. for 1 h. After cooling, the mixture was diluted with EtOAc (25 mL), washed with sat. aq. NaHCO$_3$ and brine, dried over MgSO$_4$, and concentrated. The crude product was purified by column chromatography (Silica gel, 15-50% EtOAc in hexanes) to give compound T40 (12 mg, 15% yield) as an off-white solid. m/z=537 (M+1); $^1$H NMR (400 MHz, CDCl$_3$) δ 8.06 (s, 1H), 5.99 (s, 1H), 4.39 (s, 1H), 3.92 (dd, 1H, J=4.7, 10.9 Hz), 3.62 (s, 3H), 3.51 (dd, 1H, J=4.3, 10.9 Hz), 3.11 (d, 1H, J=4.7 Hz), 2.70 (m, 1H), 2.38 (dd, 1H, J=3.1, 10.2 Hz), 1.53 (s, 3H), 1.45 (s, 3H), 1.10-2.08 (m, 15H), 1.08 (s, 3H), 1.04 (s, 6H), 0.89 (s, 3H).

Compound T41:

A mixture of compound T40 (37 mg, 0.069 mmol), Ac$_2$O (3 mL), and NaOAc (30 mg, 0.37 mmol) was stirred at room temperature for 16 h. The reaction was quenched with sat. aq. KH$_2$PO$_4$, and was extracted with EtOAc. The organic phase was dried over Mg$_2$SO$_4$ and concentrated to give compound T41 (32 mg, 80% yield) as an off-white solid. m/z=579 (M+1); $^1$H NMR (400 MHz, CDCl$_3$) δ 8.06 (s, 1H), 5.99 (s, 1H), 4.38 (s, 1H), 4.31 (d, 1H, J=11.0 Hz), 4.15 (d, 1H, J=11.0 Hz), 3.62 (s, 3H), 3.11 (d, 1H, J=4.7 Hz), 2.72 (m, 1H), 2.08 (dd, 1H, J=2.4, 11.5 Hz), 1.99 (s, 3H), 1.53 (s, 3H), 1.45 (s, 3H), 1.13 (s, 3H), 1.10-2.05 (m, 14H), 1.04 (s, 3H), 1.02 (s, 3H), 0.89 (s, 3H).

Compound 130:

To a solution of compound 86 (102 mg, 0.18 mmol) in CH$_2$Cl$_2$ (1.8 mL) was added (COCl)$_2$ (47 µL, 0.56 mmol) and catalytic amount of DMF at 0° C. The reaction was stirred at room temperature for 2 h, and concentrated. The residue was dissolved in toluene, and concentrated again to give the acid chloride as a brown foam. The acid chloride was dissolved in CH$_2$Cl$_2$ (1 mL). Et$_3$N (52 µL, 0.37 mmol) and acethydrazide (41 mg, 0.56 mmol) in CH$_2$Cl$_2$ (1 mL) were added at room temperature. The reaction was stirred at room temperature for 30 min. Aq. NaHCO$_3$ was added. The product was extracted with EtOAc. The organic extract was washed with water, dried with Na$_2$SO$_4$, filtered and concentrated to give compound 130 (114 mg, quantitative yield) as an off-white foam. m/z=608.4 (M+1).

Compound 131:

Compound 130 (114 mg, 0.18 mmol) and TsOH.H$_2$O (23 mg, 0.12 mmol) in toluene (5 mL) were heated at reflux with a Dean-Stark apparatus for 1 h. After cooling to room temperature, the mixture was washed with sat. aq. NaHCO$_3$, dried with Na$_2$SO$_4$, filtered and concentrated. The residue was purified by column chromatography (Silica gel, 0-30% acetone in hexanes) to give compound 131 (90 mg, 81% yield) as a white foam. m/z=590.3 (M+1).

Compound 132 and 133:

Compound 131 (88 mg, 0.15 mmol) and K$_2$CO$_3$ (63 mg, 0.46 mmol) in MeOH (1.5 mL) were stirred at room temperature for 1 h. EtOAc was added. The mixture was washed with 1N aq. HCl. The organic extract was dried with Na$_2$SO$_4$, filtered, and concentrated. The residue was purified by column chromatography (Silica gel, 0-35% acetone in hexanes) to give compound 132 (36 mg, 44% yield) and compound 133 (25 mg, 31% yield). Compound 132: white foam, m/z=548.3; Compound 133: white foam, m/z=548.3.

Compound T42:

DDQ (18 mg, 0.079 mmol) was added to a solution of compound 132 (36 mg, 0.066 mmol) in benzene (0.6 mL) at room temperature. The mixture was refluxed for 1 h, and cooled to room temperature. The mixture was diluted with CH$_2$Cl$_2$, and washed with sat. aq. NaHCO$_3$. The aqueous wash was back extracted with CH$_2$Cl$_2$. The combined organic extract was washed with aq. NaHCO$_3$, dried with Na$_2$SO$_4$, filtered and concentrated. The residue was purified by column chromatography (Silica gel, 0-40% acetone in hexanes) to give compound T42 (20 mg, 47% yield) as a white foam. m/z=546.3 (M+1); $^1$H NMR (400 MHz, CDCl$_3$) δ 8.05 (s, 1H), 5.96 (s, 1H), 3.92 (dd, 1H, J=6.1, 10.9 Hz), 3.50 (dd, 1H, J=5.8, 10.9 Hz), 3.12 (m, 1H), 2.94 (d, 1H, J=4.6 Hz), 2.52 (s, 3H), 2.36 (m, 1H), 2.19 (dt, 1H, J=4.1, 13.3 Hz), 1.49 (s, 3H), 1.20-2.03 (m, 14H), 1.19 (s, 3H), 1.06 (s, 3H), 1.05 (s, 6H), 0.94 (s, 3H).

Compound T43:

To a solution of compound T42 (15 mg, 0.027 mmol) in pyridine (0.1 mL) was added Ac$_2$O (50 µL, 0.53 mmol) and catalytic amount of DMAP at room temperature. The reaction was stirred for 10 min, and was quenched with sat. aq. NaHCO$_3$. After stirring for 5 min, the mixture was extracted with EtOAc. The organic extract was washed with 1 N aq. HCl and water, dried with Na$_2$SO$_4$, and concentrated. The residue was purified by column chromatography (Silica gel, 0-100% EtOAc in hexanes) to give compound T43 (5.5 mg, 34% yield) as a white foam. m/z=588.3 (M+1); $^1$H NMR (400 MHz, CDCl$_3$) δ 8.04 (s, 1H), 5.97 (s, 1H), 4.30 (d, 1H, J=11.0 Hz), 4.14 (d, 1H, J=11.0 Hz), 3.12 (m, 1H), 2.97 (d, 1H, J=4.6 Hz), 2.52 (s, 3H), 1.99 (s, 3H), 1.48 (s, 3H), 1.20-2.25 (m, 15H), 1.19 (s, 3H), 1.11 (s, 3H), 1.05 (s, 3H), 1.04 (s, 3H), 0.94 (s, 3H).

Compound 134:

To a solution of (COCl)$_2$ (10 µL, 0.12 mmol) in CH$_2$Cl$_2$ (0.5 mL) was added DMSO (16 µL, 0.23 mmol) dropwise at −78° C., and stirred for 30 min. Compound 133 (25 mg, 0.046 mmol) in CH$_2$Cl$_2$ (0.5 mL) was added at −78° C., and stirred for another 1 h. Et$_3$N (45 µL, 0.32 mmol) was added. The cold bath was removed, and the reaction was stirred at ambient temperature for 30 min. EtOAc was added, and the mixture was washed with sat. aq. NaHCO$_3$ and water. The organic extract was dried with Na$_2$SO$_4$, and concentrated. The residue was purified by column chromatography (Silica gel, 0-25% acetone in hexanes) to give compound 134 (20 mg, 80% yield) as a white foam. m/z=546.3 (M+1).

Compound 135:

Na$_2$HPO$_4$ (10 mg, 0.070 mmol) and m-CPBA (≤77%, 13 mg, 0.58 mmol) were added to a solution of compound 134 (20 mg, 0.037 mmol) in CH$_2$Cl$_2$ (0.8 mL). After stirring at room temperature for 3 h, aq. Na$_2$SO$_3$ was added. The mixture was stirred for 5 min, and was extracted with EtOAc. The organic extract was washed with sat. aq. NaHCO$_3$, dried with Na$_2$SO$_4$, filtered, and concentrated to give compound 135. m/z=562.3 (M+1). Compound 135 was used in the next step without further purification.

Compound 136:

A mixture of compound 135 (all obtained from the last step) and K$_2$CO$_3$ (15 mg, 0.11 mmol) in MeOH (0.8 mL) was stirred at room temperature for 16 h. EtOAc was added. The mixture was washed with 1 N aq. HCl and water. The organic extract was dried with Na$_2$SO$_4$, filtered, and concentrated. The residue was purified by column chromatography to give compound 136 (13 mg, 66% yield from 134) as a white foam. m/z=534.3 (M+1).

Compound T44:

DDQ (7 mg, 0.031 mmol) was added to a solution of compound 136 (13 mg, 0.024 mmol) in benzene (0.5 mL) at room temperature. The mixture was refluxed for 1.5 h, and cooled to room temperature. The mixture was diluted with CH$_2$Cl$_2$, and washed with sat. aq. NaHCO$_3$. The aqueous wash was back extracted with CH$_2$Cl$_2$. The combined organic extract was washed with aq. NaHCO$_3$, dried with Na$_2$SO$_4$, filtered and concentrated. The residue was purified by column chromatography (Silica gel, 0-100% EtOAc in hexanes) to give compound T44 (10 mg, 77% yield) as a white foam. m/z=532.3 (M+1); $^1$H NMR (400 MHz, CDCl$_3$) δ 7.99 (s, 1H), 5.89 (s, 1H), 3.23 (s, 1H), 3.11 (m, 1H), 2.97 (d, 1H, J=4.6 Hz), 2.52 (s, 3H), 1.50 (s, 3H), 1.31 (s, 3H), 1.21-2.22 (m, 15H), 1.20 (s, 3H), 1.04 (s, 3H), 1.04 (s, 3H), 0.94 (s, 3H).

Compound 137:

To a solution of compound 124 (300 mg, 0.47 mmol) in CH$_2$Cl$_2$ (5 mL) was added Et$_3$N (0.27 mL, 1.94 mmol) and acetamide oxime (54 mg, 0.73 mmol) at 0° C. The mixture was stirred at room temperature for 30 min. Water was added. The mixture was extracted with CH$_2$Cl$_2$. The combined organic extract was dried with Na$_2$SO$_4$, filtered and concentrated. The residue was purified by column chromatography (Silica gel, 0-100% EtOAc in hexanes) to give compound 137 (263 mg, 83% yield) as a white foam. m/z=671.4 (M+1).

Compound 138:

To a solution of compound 137 (200 mg, 0.30 mmol) in THF (0.8 mL) was added tetrabutylammonium hydroxide (40% aq. solution, 0.2 mL) at room temperature. After stirring for 2 h, the reaction was diluted with EtOAc, and was washed with water. The aqueous wash was back extracted with EtOAc. The combined organic extract was dried with $Na_2SO_4$, filtered and concentrated. The residue was purified by column chromatography (Silica gel, 0-20% acetone in hexanes) to give compound 138 (140 mg, 71% yield) as a white foam. m/z=653.4 (M+1).

Compound 139:

To a mixture of compound 138 (160 mg, 0.25 mmol) in $HCO_2Et$ (0.59 mL, 7.34 mmol) was added NaOMe (25% w/w in MeOH, 0.84 mL, 3.63 mmol) at 0° C. The mixture was stirred at room temperature for 1 h. MTBE was added, followed by 6 N aq. HCl (0.61 mL, 3.66 mmol). EtOAc was added. The mixture was washed with water. The organic extract was dried with $Na_2SO_4$, filtered and concentrated. The residue was dissolved in EtOH (2 mL) and water (0.2 mL). $NH_2OH \cdot HCl$ (26 mg, 0.38 mmol) was added. The mixture was heated at 55° C. for 18 h, and cooled to room temperature. EtOAc was added. The mixture was washed with water. The organic extract was dried over $Na_2SO_4$, filtered and concentrated. The residue was purified by column chromatography (Silica gel, 0-100% EtOAc in hexanes) to give compound 139 (102 mg, 76% yield) as a white foam. m/z=548.3 (M+1).

Compound 140:

Compound 139 (50 mg, 0.091 mmol) and $K_2CO_3$ (75 mg, 0.54 mmol) in MeOH (1 mL) were stirred at room temperature for 16 h. EtOAc was added. The mixture was washed with 1N aq. HCl. The organic extract was dried with $Na_2SO_4$, filtered, and concentrated to give compound 140 (50 mg, quantitative yield) as a white foam, m/z=548.3.

Compound T45:

To a solution of compound 140 (50 mg, 0.091 mmol) in DMF (0.5 mL) was added 1,3-dibromo-5,5-dimethylhydantoin (13 mg, 0.045 mmol) at 0° C. After the reaction was stirred at 0° C. for 1 h, pyridine (22 μL, 0.27 mmol) was added. The reaction was heated at 55° C. for 5 h, and cooled to room temperature. EtOAc was added. The mixture was washed with 1 N aq. HCl and water. The organic extract was dried over $Na_2SO_4$, filtered and concentrated. The residue was purified by column chromatography (Silica gel, 0-45% EtOAc in hexanes) to give compound T45 (32 mg, 64% yield) as a yellow foam. m/z=546.3 (M+1); $^1$H NMR (400 MHz, $CDCl_3$) δ 8.05 (s, 1H), 5.97 (s, 1H), 3.92 (dd, 1H, J=6.1, 10.9 Hz), 3.50 (dd, 1H, J=5.7, 10.9 Hz), 3.24 (m, 1H), 3.03 (dd, 1H, J=4.6 Hz), 2.37 (s, 3H), 2.19 (dt, 1H, J=4.1, 13.8 Hz), 1.48 (s, 3H), 1.19-1.97 (m, 15H), 1.12 (s, 3H), 1.06 (s, 3H), 1.05 (s, 3H), 1.05 (s, 3H), 0.94 (s, 3H).

Compound T46:

To the solution of compound T45 (17 mg, 0.031 mmol) in $CH_2Cl_2$ (0.6 mL) was added $Et_3N$ (13 μL, 0.093 mmol) and AcCl (3.5 μL, 0.049 mmol) sequentially at room temperature. After stirring for 30 min, the mixture was diluted with EtOAc and sat. aq. $NaHCO_3$, and then stirred for another 5 min. The organic extract was washed with water, dried with $Na_2SO_4$, filtered and concentrated. The residue was purified by column chromatography (Silica gel, 0-30% acetone in hexanes) to give compound T46 (15 mg, 82% yield) as a white solid. m/z=588.4 (M+1); $^1$H NMR (400 MHz, $CDCl_3$) δ 8.04 (s, 1H), 5.98 (s, 1H), 4.30 (d, 1H, J=11.0 Hz), 4.14 (d, 1H, J=11.0 Hz), 3.24 (m, 1H), 3.03 (d, 1H, J=4.6 Hz), 2.37 (s, 3H), 2.19 (dt, 1H, J=4.1, 13.8 Hz), 2.05 (dd, 1H, J=3.2, 10.8 Hz), 1.99 (s, 3H), 1.48 (s, 3H), 1.20-1.98 (m, 13H), 1.12 (s, 3H), 1.11 (s, 3H), 1.05 (s, 3H), 1.04 (s, 3H), 0.93 (s, 3H).

Compound 141:

To a solution of compound 139 (40 mg, 0.073 mmol) in $CH_2Cl_2$ (1.5 mL) was added Dess-Martin periodinane (64 mg, 0.15 mmol) at room temperature. After the reaction mixture was stirred for 2 h, aq. $Na_2SO_3$ was added. The mixture was stirred for 10 min, and was extracted with MTBE. The combined organic extracts were washed with sat. aq. $NaHCO_3$, dried over $Na_2SO_4$, filtered, and concentrated to give compound 141. Compound 141 was used in the next step without further purification.

Compound 142:

$Na_2HPO_4$ (22 mg, 0.15 mmol) and m-CPBA (≤77%, 28 mg, 0.13 mmol) were added to a solution of compound 141 (all obtained from the last step) in $CH_2Cl_2$ (1.7 mL). After stirring at room temperature for 2 h, aq. $Na_2SO_3$ was added. The mixture was stirred for 10 min, and was extracted with EtOAc. The organic extract was washed with sat. aq. $NaHCO_3$, dried with $Na_2SO_4$, filtered, and concentrated to give compound 142 (21 mg, 51% yield from 139) as a white foam. m/z=562.4 (M+1).

Compound 143:

A mixture of compound 142 (21 mg, 0.037 mmol) and $K_2CO_3$ (31 mg, 0.22 mmol) in MeOH (0.75 mL) was stirred at room temperature for 16 h. EtOAc was added. The mixture was washed with 1 N aq. HCl and water. The organic extract was dried with $Na_2SO_4$, filtered, and concentrated to give compound 143 (20 mg, 99% yield) as a glass. m/z=534.3 (M+1).

Compound T47:

To a solution of compound 143 (20 mg, 0.037 mmol) in DMF (0.2 mL) was added the solution of 1,3-dibromo-5,5-dimethylhydantoin (5.4 mg, 0.019 mmol) in DMF (0.2 mL) at 0° C. After the reaction was stirred at 0° C. for 1 h, pyridine (9 μL, 0.11 mmol) was added. The reaction was heated at 55° C. for 4 h, and cooled to room temperature. EtOAc was added. The mixture was washed with 1 N aq. HCl and water. The organic extract was dried over $Na_2SO_4$, filtered and concentrated. The residue was purified by column chromatography (Silica gel, 0-40% EtOAc in hexanes) to give compound T47 (13 mg, 65% yield) as a white foam. m/z=532.3 (M+1); $^1$H NMR (400 MHz, $CDCl_3$) δ 7.99 (s, 1H), 5.89 (s, 1H), 3.23 (s, 1H), 3.22 (m, 1H), 3.02 (d, 1H, J=4.7 Hz), 2.38 (s, 3H), 2.20 (dt, 1H, J=4.1, 13.8 Hz), 1.50 (s, 3H), 1.30 (s, 3H), 1.19-2.13 (m, 14H), 1.13 (s, 3H), 1.04 (s, 3H), 1.04 (s, 3H), 0.94 (s, 3H).

Compound 144:

Compound 108 (110 mg, 0.22 mmol) was dissolved in THF (2.2 mL), and was cooled to −78° C. Methylmagnesium chloride (3 M in THF, 0.29 mL, 0.87 mmol) was added, and the mixture was stirred at −78° C. for 2 h. The reaction was quenched with aq. $NH_4Cl$. The mixture was extracted with EtOAc. The organic extract was washed with 1 N aq. HCl, and water, dried with $Na_2SO_4$, filtered and concentrated. The residue was purified by column chromatography (Silica gel, 0-45% EtOAc in hexanes) to give compound 144 (68 mg, 60% yield) as a white foam. m/z=522.3 (M+1).

Compound 145:

A mixture of compound 144 (91 mg, 0.17 mmol) and $K_2CO_3$ (144 mg, 1.04 mmol) in MeOH (2 mL) was stirred at room temperature for 16 h. EtOAc was added. The mixture was washed with 1 N aq. HCl and water. The organic extract was dried with $Na_2SO_4$, filtered, and concentrated. The residue was purified by column chromatography (Silica gel, 0-50% EtOAc in hexanes) to give compound 145 (36 mg, 40% yield) as a glass. m/z=522.3 (M+1).

Compound T48:

To a solution of compound 145 (36 mg, 0.069 mmol) in DMF (0.6 mL) was added 1,3-dibromo-5,5-dimethylhydantoin (10 mg, 0.035 mmol) at 0° C. After the reaction was stirred at 0° C. for 1 h, pyridine (66 µL, 0.82 mmol) was added. The reaction was heated at 55° C. for 16 h, and cooled to room temperature. EtOAc was added. The mixture was washed with 1 N aq. HCl and water. The organic extract was dried over $Na_2SO_4$, filtered and concentrated. The residue was purified by column chromatography (Silica gel, 0-60% EtOAc in hexanes) to give compound T48 (10 mg, 28% yield) as a white solid. T48 is a 3:1 mixture of diastereomers. m/z=520.3 (M+1); $^1$H NMR (400 MHz, $CDCl_3$) δ 8.00 (s, 0.25H), 7.93 (s, 0.75H), 6.23 (s, 0.75H), 6.21 (s, 0.25H), 3.80-3.92 (m, 1H), 2.98 (m, 1H), 1.54 (s, 0.75H), 1.53 (s, 0.75H), 1.52 (s, 2.25H), 1.49 (s, 2.25H), 1.34 (s, 0.75H), 1.31 (d, 2.25H, J=6.2 Hz), 1.22 (d, 0.75H, J=6.6 Hz), 1.19 (s, 2.25H), 1.17-2.60 (m, 16H), 1.07 (s, 2.25H), 1.06 (s, 0.75H), 0.97 (s, 6H).

Compound T49:

To a solution of compound T47 (100 mg, 0.19 mmol) in MeCN (2 mL) was added 30% aq. $H_2O_2$ (28 µL, 0.28 mmol) at room temperature. After stirring for 5 h, additional amount of 30% aq. $H_2O_2$ (300 µL, 3 mmol) was added. The reaction was stirred at room temperature overnight. EtOAc was added. The mixture was washed with water and 10% aq. $Na_2SO_3$. The organic extract was dried over $Na_2SO_4$, filtered and concentrated. The residue was purified by column chromatography (Silica gel, 0-50% EtOAc in hexanes) to give compound T49 (88 mg, 85% yield) as a white foamy solid. m/z=548.3 (M+1); $^1$H NMR (400 MHz, $CDCl_3$) δ 6.05 (s, 1H), 4.26 (s, 1H), 3.24 (m, 1H), 3.04 (d, 1H, J=4.8 Hz), 2.61 (s, 1H), 2.38 (s, 3H), 2.21 (ddd, 1H, J=4.0, 14.0, 14.0 Hz), 1.41 (s, 3H), 1.30 (s, 3H), 1.21-2.02 (m, 14H), 1.10 (s, 3H), 1.08 (s, 3H), 1.05 (s, 3H), 0.95 (s, 3H).

Compound T50:

To a solution of compound T33 (100 mg, 0.19 mmol) in MeCN (2 mL) was added 30% aq. $H_2O_2$ ((300 µL, 3 mmol) at room temperature. After stirring overnight, additional amount of MeCN (10 mL) and 30% aq. $H_2O_2$ ((300 µL, 3 mmol) were added. The reaction was stirred at room temperature for another 6 h. EtOAc was added. The mixture was washed with water and 10% aq. $Na_2SO_3$. The organic extract was dried over $Na_2SO_4$, filtered and concentrated. The residue was purified by column chromatography (Silica gel, 0-60% EtOAc in hexanes) to give compound T50 (27 mg, 26% yield) as a white solid. m/z=508.3 (M+1); $^1$H NMR (400 MHz, $CDCl_3$) δ 6.28 (s, 1H), 4.30 (s, 1H), 2.97 (dd, 1H, J=2.8, 13.6 Hz), 2.61 (s, 1H), 1.52 (s, 3H), 1.51 (s, 3H), 1.34 (s, 3H), 1.24-2.16 (m, 15H), 1.07 (s, 3H), 0.98 (s, 6H).

Compound T51:

To a solution of compound T27 (2 mg, 3.76 µmol) in MeCN (0.3 mL) was added 30% aq. $H_2O_2$ (30 µL, 0.3 mmol) at room temperature. After stirring for 3 h, $CH_2Cl_2$ and 10% aq. $Na_2SO_3$ were added. The mixture was extracted with $CH_2Cl_2$. The organic extract was dried over $Na_2SO_4$, filtered and concentrated. The residue was purified by preparative TLC (Silica gel, 50% EtOAc in hexanes) to give compound T51 (1 mg, 49% yield) as a white solid. m/z=573.3 (M+1); $^1$H NMR (400 MHz, $CDCl_3$) δ 6.09 (s, 1H), 5.90 (b, 1H), 4.28 (s, 1H), 2.99 (d, 1H, J=5.2 Hz), 2.80 (m, 1H), 2.60 (s, 1H), 1.78 (t, 3H, J=19.2 Hz), 1.46 (s, 3H), 1.38 (s, 3H), 1.32 (s, 3H), 1.16-2.09 (m, 15H), 1.09 (s, 3H), 1.06 (s, 3H), 0.91 (s, 3H).

Example 2: Biological Activity Methods and Materials

A. Nitric Oxide Production Assay and Cell Viability

RAW 264.7 mouse macrophages were plated in 96-well plates at a density of 30,000 cells per well in triplicate in RPMI 1640+0.5% FBS and incubated at 37° C. with 5% $CO_2$ in a humidified atmosphere. The next day, cells were pre-treated with DMSO (vehicle) or test compound (concentration ranges of 0.4-200 nM or 2-1000 nM) for 2 hours and then treated with recombinant mouse IFNγ (R&D Systems) for 24 hours. Nitric oxide concentration in media was determined using the Griess reagent system (Promega). Cell viability was determined using WST-1 reagent (Roche). Values from test compound samples were normalized to those from DMSO/IFNγ-treated samples. $IC_{50}$ values were determined based on the suppression of IFNγ-induced Nitric Oxide production normalized to cell viability.

B. AREc32 Luciferase Reporter Assay

The AREc32 luciferase reporter assay allows for quantitative assessment of the endogenous activity of the Nrf2 transcription factor in cultured mammalian cells. AREc32 cells are derived from MCF-7 human breast carcinoma cells that were stably transfected with a reporter construct that contains the firefly luciferase gene located downstream of eight copies of the rat GSTA2 antioxidant response element (ARE) sequence (Wang et al., 2006; CXR Biosciences). Active NRF2 binds to the ARE sequences and increases expression of the firefly luciferase gene. To assess the NRF2-activating potential of the test compounds, AREc32 cells were plated in black 96-well plates at a density of 20,000 cells per well in triplicate in DMEM+10% FBS+0.8 mg/mL Geneticin and incubated at 37° C. with 5% $CO_2$ in a humidified atmosphere. The next day, cells were treated with DMSO (vehicle) or test compound (concentration ranges of 0.4-200 nM or 2-1000 nM) for 19 hours. Luciferase activity was determined using the ONE-Glo Luciferase assay (Promega). The luminescence signal was measured on a BMG Pherastar microplate reader. The mean luminescence value from test compound-treated wells was normalized to that from DMSO-treated wells and was represented as fold-induction. Data were analyzed using GraphPad Prism version 6.00 for Windows, GraphPad Software, La Jolla Calif. USA. A non-linear regression curve with log (agonist) vs. response using a variable slope was used to fit the data. Where applicable, a maximum threshold value of 50-fold over DMSO was set. $EC_{2x}$ values were interpolated from the curve. $EC_{2x}$ corresponds to the concentration of test compound required to increase GST ARE Luciferase reporter activity by 2-fold.

C. RORγ Assay and Cell Viability

The RORγ assay system was purchased from Indigo Biosciences. This nuclear receptor assay utilizes a human cell line that has been engineered to express a hybrid form of the Human RAR-related Orphan Receptor Gamma (RORγ) at high levels. The N-terminal DNA binding domain (DBD) of the native RORγ receptor was substituted with the yeast GAL4-DBD to generate the GAL4-RORγ hybrid nuclear receptor. The reporter cell line is transfected with a plasmid that encodes the beetle luciferase gene under the control of the GAL4 upstream activating sequence (UAS). GAL4 binds to the UAS and increases transcription of downstream target genes. The GAL4-RORγ hybrid is constitutively active; therefore, the principle application of this reporter assay system is to screen test compounds to quantify inverse-agonist activities against human RORγ. To assess the RORγ inverse-agonist activity of the test compounds, reporter cells were plated in white 96-well plates in triplicate and were treated with DMSO (vehicle) or test compound (concentration ranges of 0.4-200 nM or 2-1000 nM) at 37° C. with 5% $CO_2$ in a humidified atmosphere for 23 hours. After this incubation, luciferin was added to the wells and luciferase activity was determined by measuring the luminescence signal using a BMG Pherastar microplate reader. Viability was determined using the Live Cell Multiplex Assay (Indigo Biosciences). Values from test compound samples were normalized to those from DMSO-treated samples. Data were analyzed using GraphPad Prism version 6.00 for Windows (GraphPad Software, La Jolla Calif. USA). A non-linear regression analysis with log (inhibitor) vs. normalized response using a variable slope was applied to fit the data and determine the $IC_{50}$ values for inhibition of RORγ and cell viability.

D. IL-17 Release from Differentiated Primary Human T-Cells and Cell Viability

Primary human cryopreserved CD4+ T Cells (Lonza, donor #0000402103) were plated in Lymphocyte Growth Medium-3 (LGM-3, Lonza) according to the manufacturer's recommendations, and allowed to recover for approximately 3 hours at 37° C. with 5% $CO_2$ in a humidified atmosphere. After the recovery step, cells were collected by centrifugation and re-plated in 96-well plates at a density of ~140,000 cells per well in LGM-3 medium that contained DMSO (vehicle) or test compound (2-500 nM or 4-1000 nM concentration range). Triplicate wells were plated for each test condition. DMSO (final concentration ≤0.1%) was used as the vehicle. Immediately after plating, CD4+ T cells were activated by adding Dynabeads Human T-Activator CD3/CD28 (Life Technologies; bead-to-cell ratio of 1:2.5) and differentiated into Th17 cells by adding a mixture of the following cytokines: transforming growth factor-β (TGF-β, 5 ng/mL), IL-6 (20 ng/mL), IL-23 (20 ng/mL), and IL-113 (10 ng/mL). Undifferentiated control cells received only cytokine IL-2 (50 ng/mL). All human recombinant cytokines were purchased from R&D Systems. Following a 46-hour incubation at 37° C. with 5% $CO_2$ in a humidified atmosphere, the plates were centrifuged for 3 minutes at 250×g, and half of the supernatant was transferred to a new plate to be used in the IL-17A assay (see below). Cell viability was assessed in the original plate using the CyQuant Direct Assay (Life Technologies). CyQuant values from test compound samples were normalized to those from DMSO-treated samples. The concentration of IL-17A in the supernatant was measured using the Homogeneous Time-Resolved Fluorescence (HTRF) assay (Cisbio Bioassays) according to the manufacturer's protocol. The assay was performed at room temperature in low volume, solid white 384-well plates (Greiner Bio-One). Samples and standards (serially-diluted human recombinant IL-17A (0 to 5,000 pg/mL concentration range; Cisbio Bioassays) were incubated with the anti-human IL-17A antibody conjugate for 16 hours and fluorescence was measured using a Pherastar FS microplate reader (BMG Labtech) in the HTRF mode (excitation at 337 nm and emission at 665 nm and 620 nm). IL-17A concentrations were assessed in duplicate aliquots of supernatant from each well resulting in a total of six readings per test condition. The 665 nm/620 nm signal ratio was calculated and the concentration of IL-17A in each sample was determined by interpolation from the standard curve. IL-17A values from test compound samples were normalized to those from DMSO-treated samples. Data were analyzed using GraphPad Prism version 6.00 for Windows (GraphPad Software, La Jolla Calif. USA). A non-linear regression analysis with log (inhibitor) vs. normalized response using a variable slope was applied to fit the data and determine the $IC_{50}$ values for inhibition of IL-17A levels and cell viability.

TABLE 1

Inhibition of hIL17, RORγ, and NO production and NRF2 Activation of the Compounds

| Compound ID | Structure | hIL17 $IC_{50}$ (nM) | RORγ $IC_{50}$ (nM) | NRF2 ARE 2X (nM) | NO $IC_{50}$ (nM) |
|---|---|---|---|---|---|
| Comparison Compound #1 | 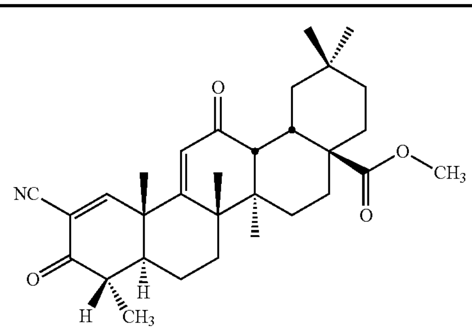 | 25 | 127 | 11 | 1.2 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
| --- | --- | --- | --- | --- | --- |
| Comparison Compound #300 | 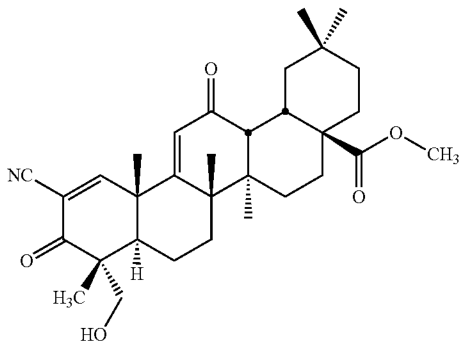 | 18 | 152 | 34 | 7.4 |
| Comparison Compound #301 | 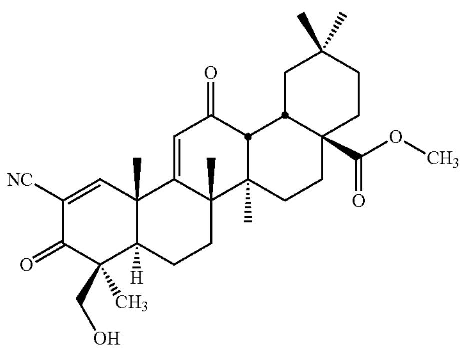 | 17 | 144 | 8 | 1.8 |
| Comparison Compound #302 | 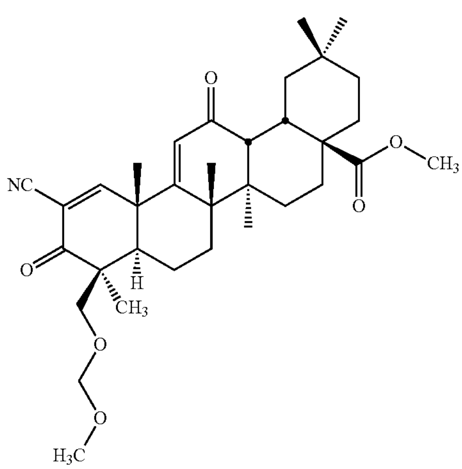 | 24 | 91 | 78 | 13.1 |
| T1 | 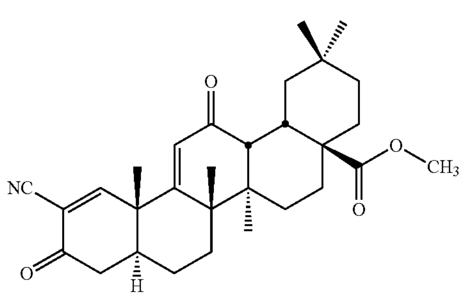 | 40 | 144 | 50 | 8.1 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T2 | 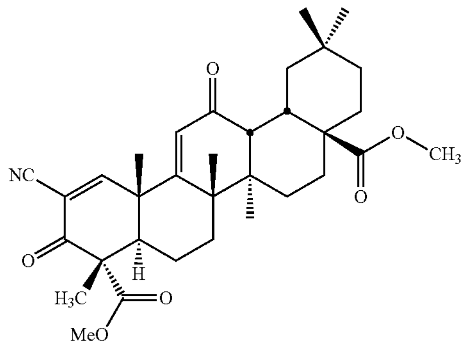 | 19 | 216 | 204 | 92.0 |
| T3 | 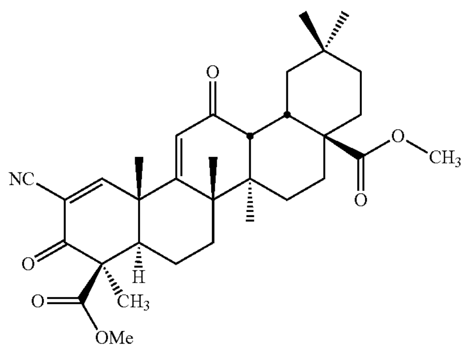 | 18 | 169 | 48 | 22.3 |
| T4 | 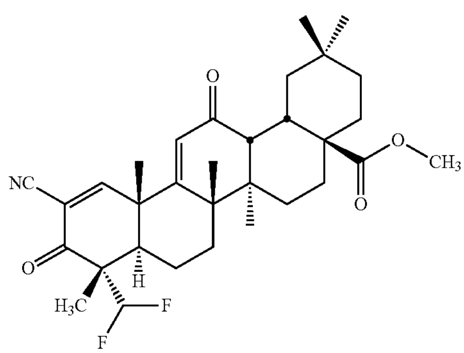 | 29 | 234 | 36 | 19.6 |
| T5 | 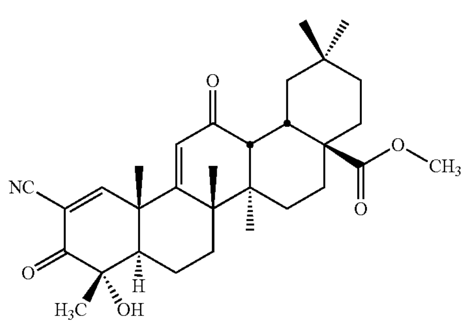 | 18 | 115 | 56 | 22.6 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T6 | 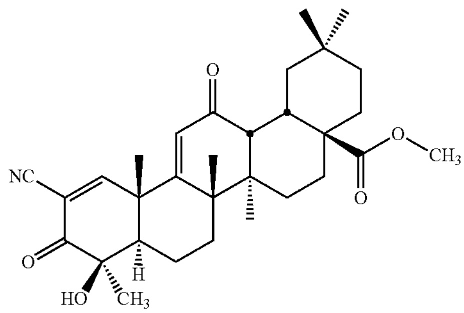 | 32 | 115 | 30 | 9.2 |
| T7 | 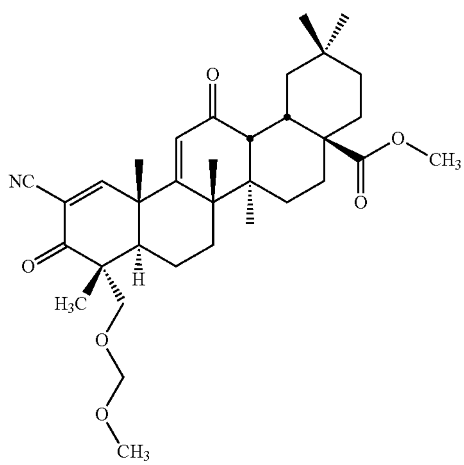 | 27 | 251 | 270 | 95.1 |
| T8 | 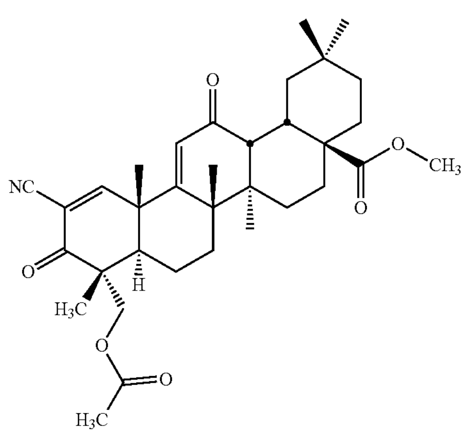 | 24 | 109 | 276 | 74.6 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
| --- | --- | --- | --- | --- | --- |
| T9 | 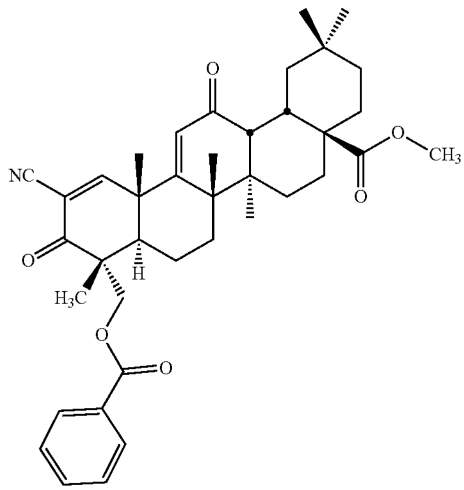 | 37 | 361 | 962 | 191.2 |
| T10 | 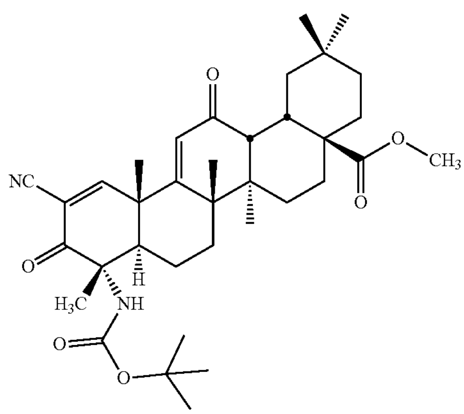 | 204 | 1075 | >1000 | 414.0 |
| T11 | 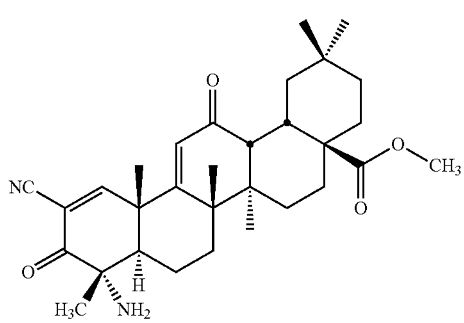 | 75 | 146 | 477 | 601.0 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T12 | 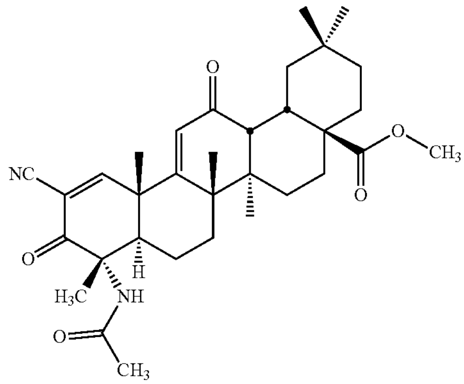 | 81 | 419 | >1000 | >1000 |
| T13 | 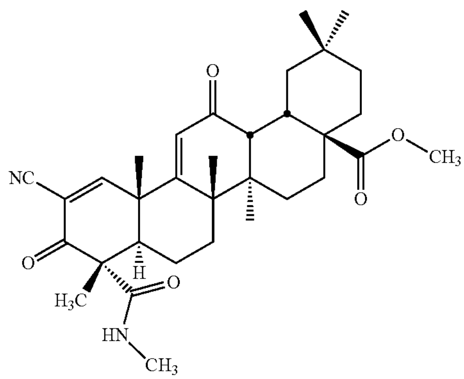 | 49 | 161 | 567 | 295.2 |
| T14 | 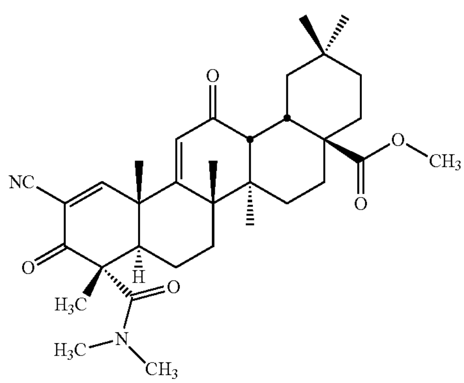 | 46 | 139 | >1000 | 164.5 |
| T16 | 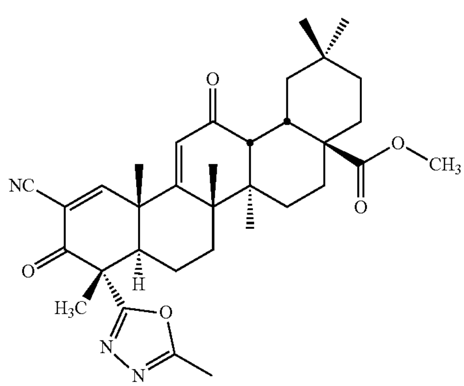 | 92 | 406 | >1000 | 614.7 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T17 | 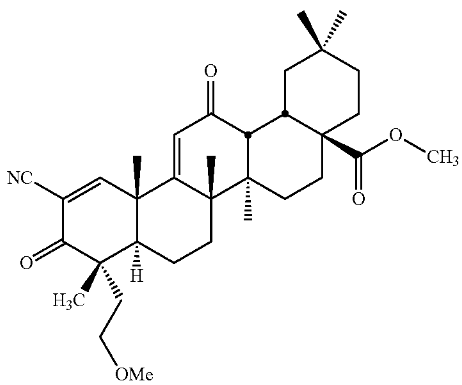 | 30 | 250 | 64 | 19.5 |
| T15 | 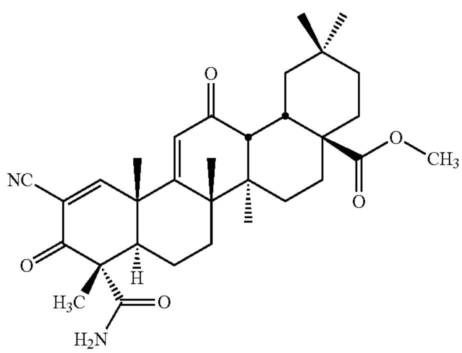 | 65 | 206 | 612 | 714.4 |
| T18 | 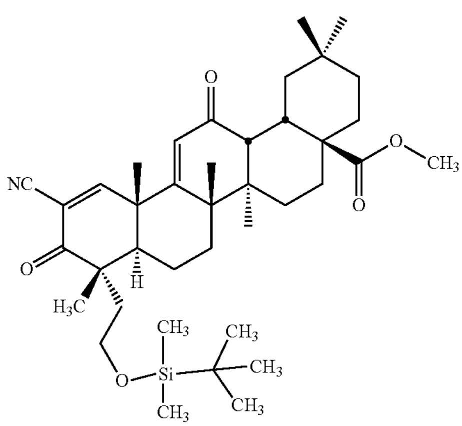 | 24 | 583 | 585 | 78.5 |
| T20 | 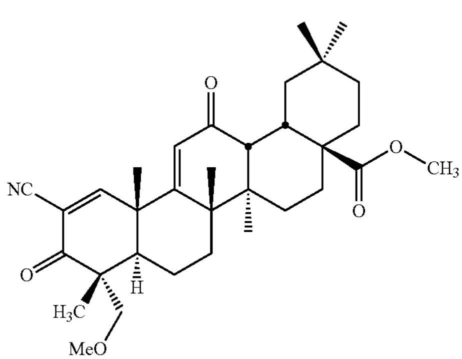 | 21 | 223 | 175 | 15.6 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T19 | 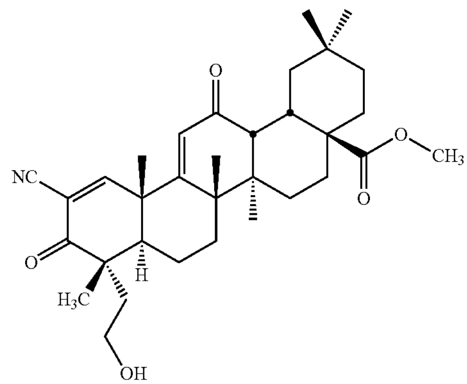 | 15 | 233 | 76 | 17.4 |
| T21 | 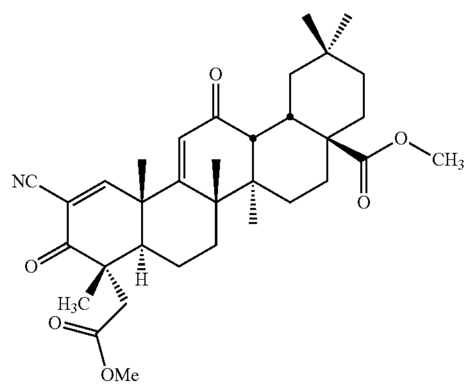 | 33 | 203 | 269 | 104.6 |
| Comparison Compound #2 | 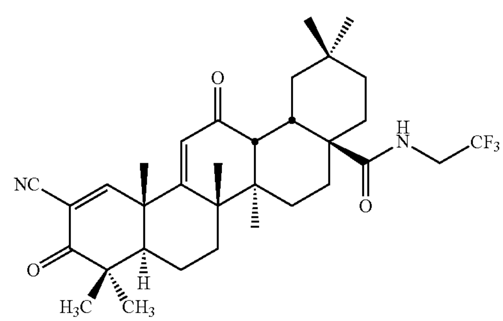 | 40 | 104 | 53 | 4.5 |
| T22 | 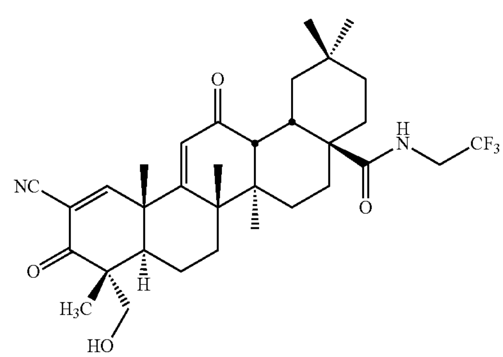 | 50 | 256 | 103 | 13.5 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T23 | 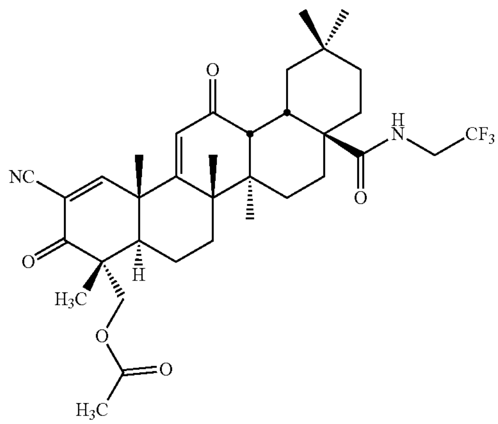 | 68 | 145 | 484 | 150.3 |
| T24 | 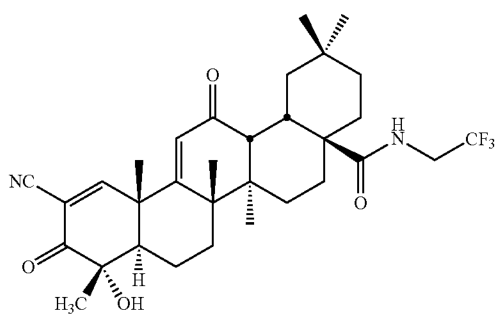 | 37 | 197 | 406 | 184.4 |
| Comparison Compound #3 | 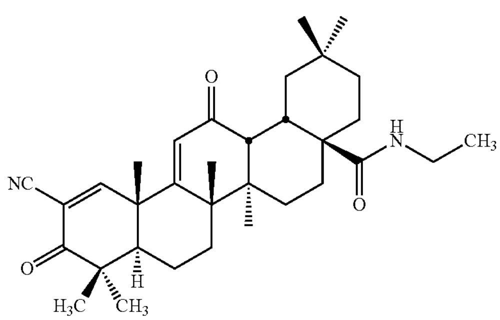 | 81 | 204 | 32 | 3.4 |
| T25 | 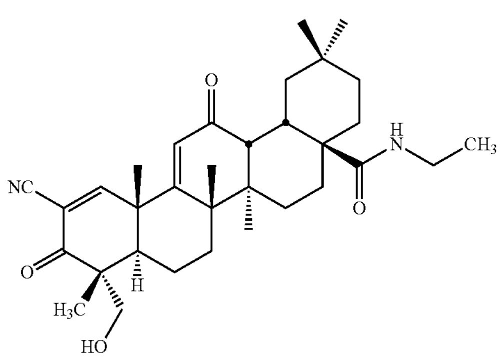 | 67 | 536 | 131 | 16.0 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T26 | 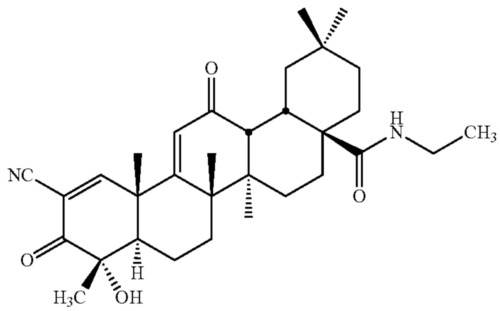 | 132 | 292 | 463 | 370.0 |
| Comparison Compound #4 | 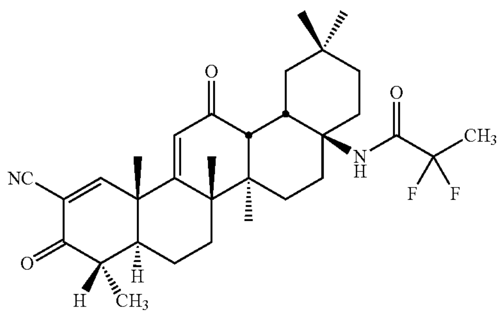 | 38 | 177 | 11 | 0.6 |
| T27 | 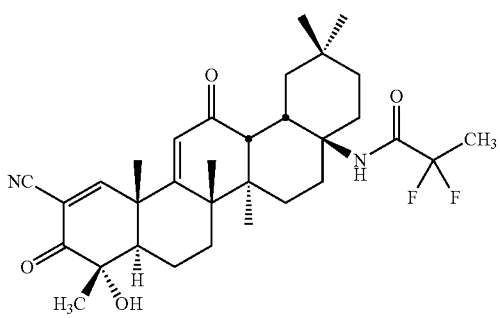 | 62 | 410 | 396 | 145.8 |
| T28 | 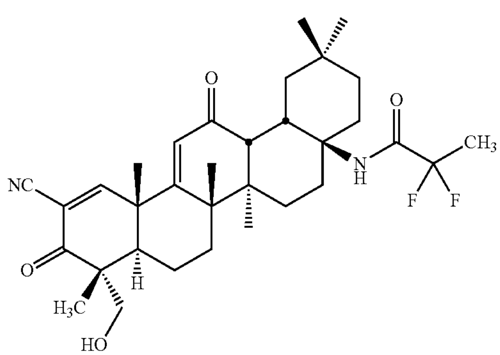 | 67 | 463 | 117 | 21.1 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T29 | 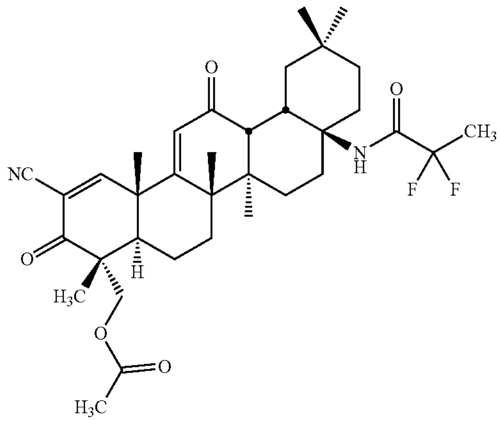 | 37 | 141 | 360 | 118.3 |
| Comparison Compound #5 | 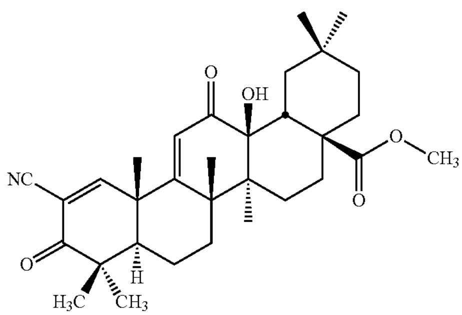 | 15 | 135 | 2 | 1.6 |
| T38 | 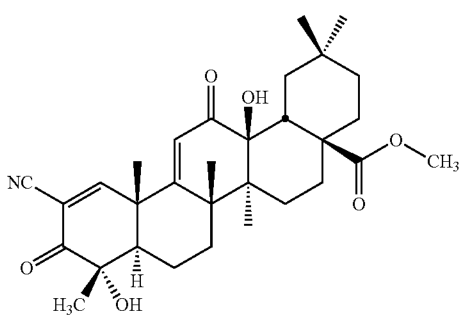 | 16 | 177 | 80 | 57.2 |
| T30 | 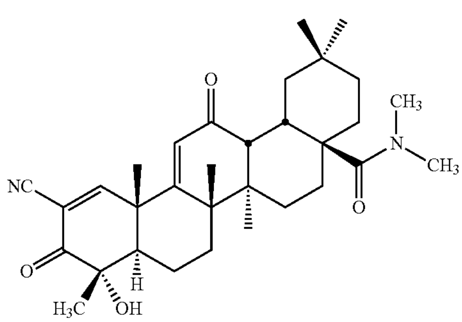 | 59 | 164 | 448 | 173.0 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| Comparison Compound #6 | 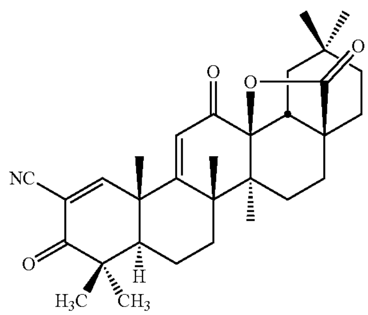 | 15 | 159 | 2 | 0.7 |
| T31 | 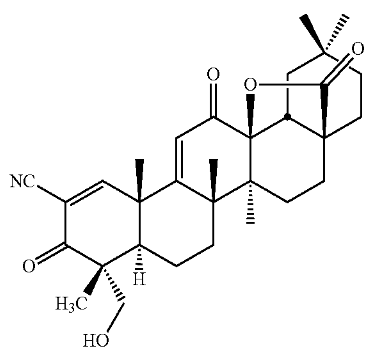 | 20 | 177 | 21 | 10.5 |
| T32 | 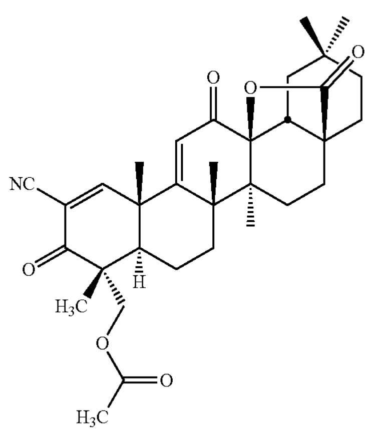 | 28 | 118 | 243 | 114.6 |
| T33 | 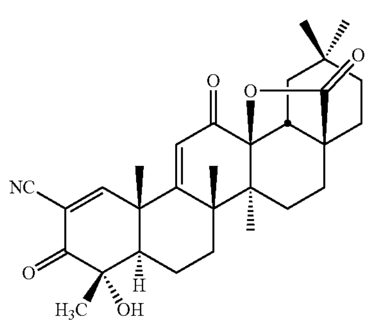 | 25 | 220 | 120 | 79.9 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T34 | 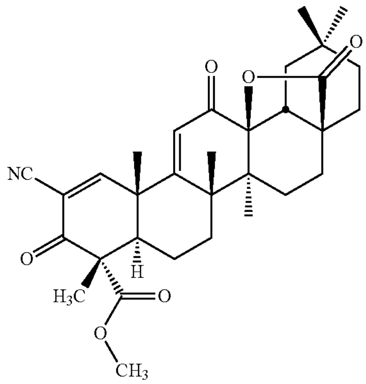 | 46 | 268 | 377 | 382.9 |
| T35 | 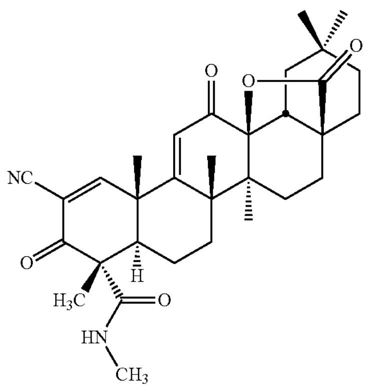 | 68 | 413 | >1000 | >1000 |
| T36 | 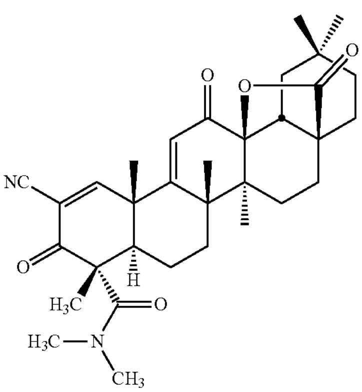 | 126 | 533 | >1000 | >1000 |
| T37 | 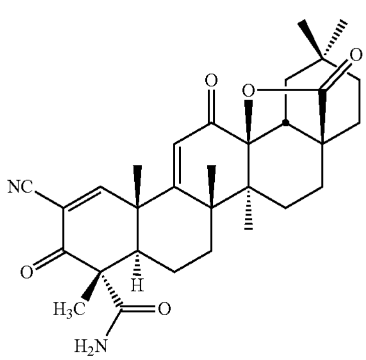 | 336 | 1354 | >1000 | >1000 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T48 | 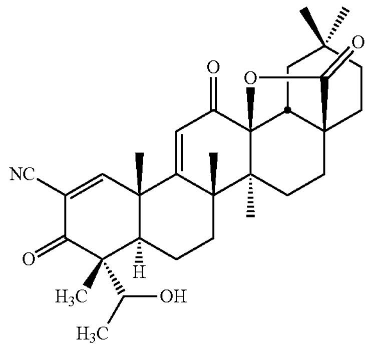 | 13 | 162 | 3 | 1.2 |
| Comparison Compound #7 | 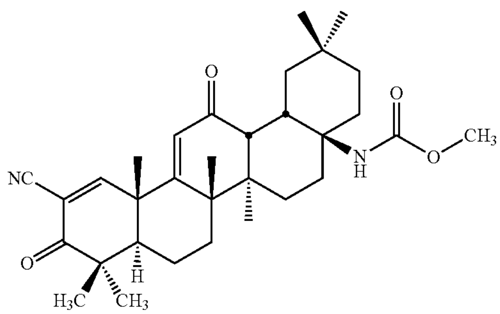 | 27 | 371 | 20 | 2.4 |
| T39 | 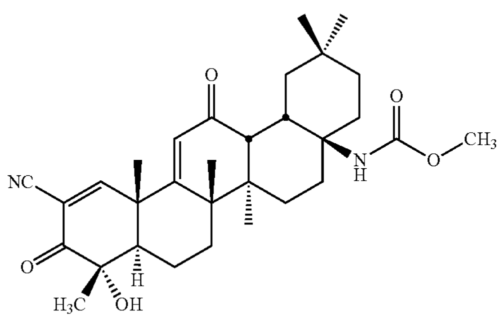 | 47 | 364 | 218 | 91.2 |
| T40 | 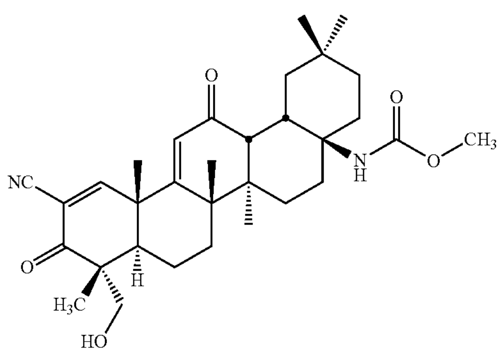 | 37 | 698 | 130 | 24.6 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T41 | 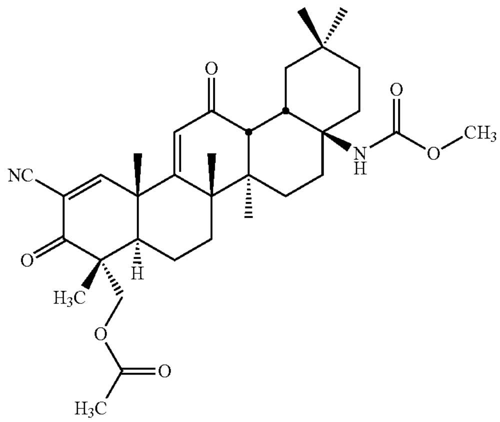 | 35 | 135 | 330 | 151.4 |
| Comparison Compound #8 | 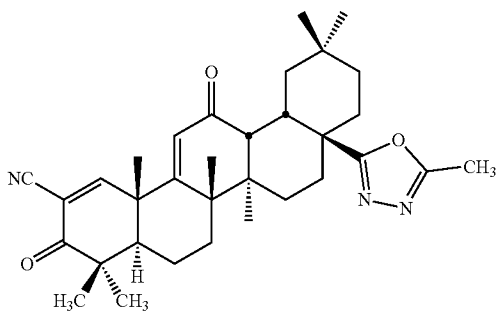 | 32 | 222 | 15 | 2.0 |
| T42 | 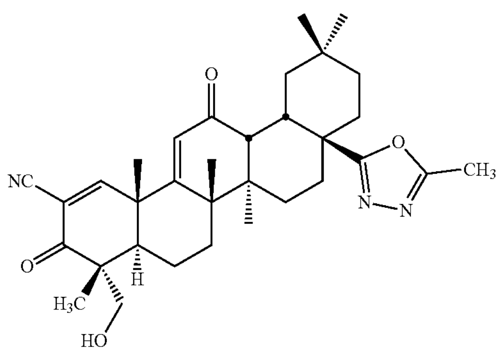 | 101 | 389 | 97 | 10.4 |
| T43 | 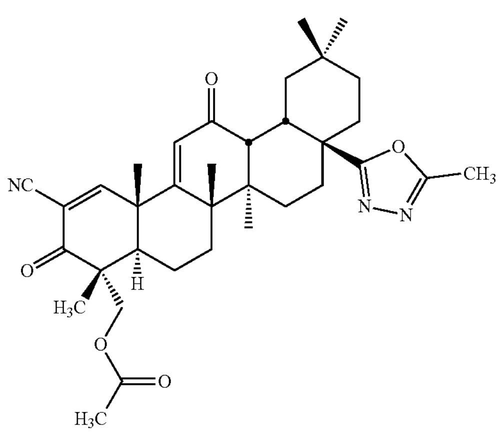 | 46 | 146 | 369 | 109.6 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T44 | 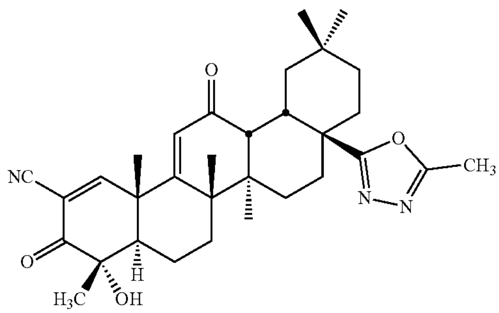 | 50 | 236 | 156 | 72.8 |
| Comparison Compound #9 | 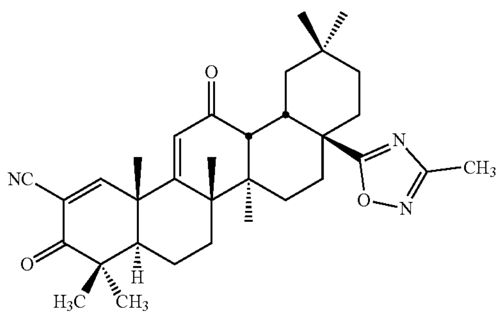 | 18 | 176 | 12 | 1.2 |
| T45 | 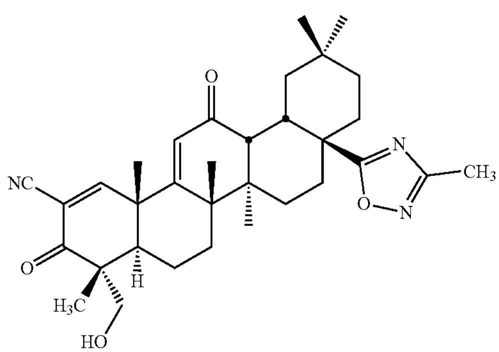 | 17 | 165 | 47 | 6.9 |
| T46 | 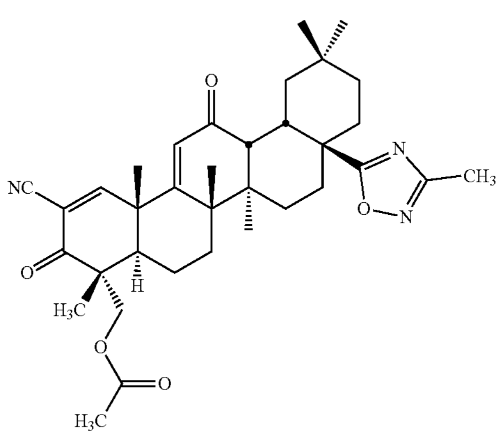 | 13 | 115 | 366 | 100.7 |

TABLE 1-continued

Inhibition of hIL17, RORγ, and NO production and NRF2 Activation of the Compounds

| Compound ID | Structure | hIL17 IC$_{50}$ (nM) | RORγ IC$_{50}$ (nM) | NRF2 ARE 2X (nM) | NO IC$_{50}$ (nM) |
|---|---|---|---|---|---|
| T47 | 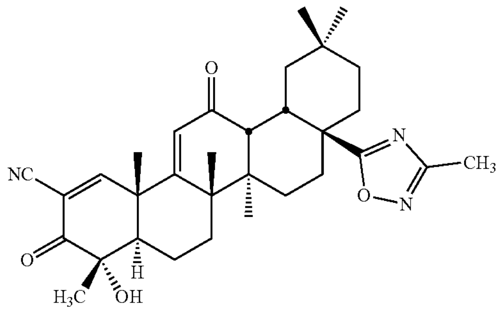 | 17 | 139 | 79 | 35.8 |
| T49 | 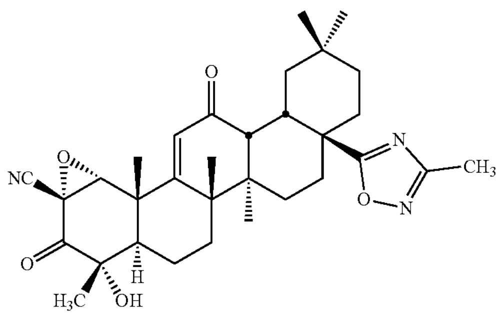 | 18 | 608 | 244 | 37.5 |
| T50 | 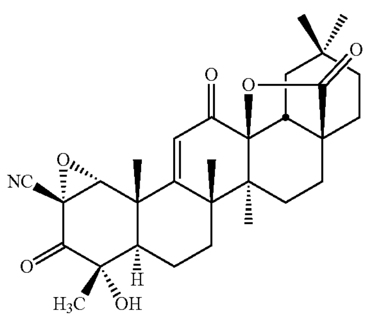 | 11 | 1042 | 162 | 65.4 |
| T51 | 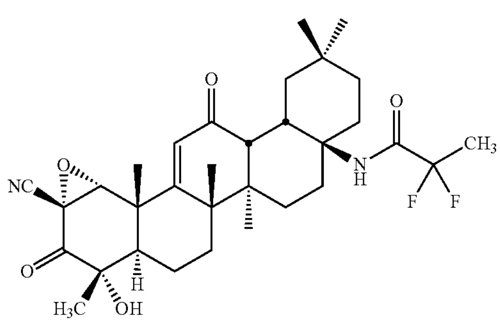 | 139 | 1686 | 840 | 118.6 |

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references to the extent that they provide exemplary procedural or other details supplementary to those set forth herein, are specifically incorporated herein by reference.
U.S. Pat. No. 7,915,402
U.S. Pat. No. 7,943,778
U.S. Pat. No. 8,124,799
U.S. Pat. No. 8,129,429
PCT Application WO 2008/064133
PCT Application WO 2012/083306
PCT Application WO 2013/163344
Abraham and Kappas, *Free Radical Biol. Med.*, 39:1-25, 2005.
Ahmad et al., *Cancer Res.*, 68:2920-2926, 2008.
Ahmad et al., *J. Biol. Chem.*, 281:35764-9, 2006.
Araujo et al., *J. Immunol.*, 171(3):1572-1580, 2003.
Bach, *Hum. Immunol.*, 67(6):430-432, 2006.
Bronner, et al., *Expert Opin. Ther. Pat.*, 2016, Published Online Ahead of Print
Chauhan and Chauhan, *Pathophysiology*, 13(3): 171-181 2006.
Dickerson et al., *Prog Neuropsychopharmacol Biol. Psychiatry*, Mar. 6, 2007.
Dinkova-Kostova et al., *Proc. Natl. Acad. Sci. USA*, 102 (12):4584-4589, 2005.
Dudhgaonkar et al., *Eur. J. Pain*, 10(7):573-9, 2006.
Favaloro, et al., *J. Med. Chem.*, 45:4801-4805, 2002.
Forstermann, *Biol. Chem.*, 387:1521, 2006.
Fujiwara, et al., *J Immunol.*, 193(5):2565-73, 2014.
*Handbook of Pharmaceutical Salts: Properties, and Use*, Stahl and Wermuth Eds.), Verlag Helvetica Chimica Acta, 2002.
Hanson et al., *BMC Medical Genetics*, 6(7), 2005.
Honda et al. *Bioorg. Med. Chem. Lett.*, 12:1027-1030, 2002.
Honda et al., *J. Med. Chem.*, 43:4233-4246, 2000a.
Honda, et al., *J. Med. Chem.*, 43:1866-1877, 2000b.
Honda et al., *Bioorg. Med. Chem. Lett.*, 7:1623-1628, 1997.
Honda et al., *Bioorg. Med. Chem. Lett.*, 9(24):3429-3434, 1999.
Honda et al., *Bioorg. Med. Chem. Lett.*, 8(19):2711-2714, 1998.
Honda et al., *Bioorg. Med. Chem. Lett.*, 16(24):6306-6309, 2006.
Honda et al., *Org. Biomol. Chem.*, 1:4384-4391, 2003.
Honda, et al., *J. Med. Chem.*, 54(6):1762-1778, 2011.
Hong, et al., 2012.
Ishikawa et al., *Circulation*, 104(15):1831-1836, 2001.
Kawakami et al., *Brain Dev.*, 28(4):243-246, 2006.
Kendall-Tackett, Trauma Violence Abuse, 8(2): 117-126, 2007.
Kruger et al., *J. Pharmacol. Exp. Ther.*, 319(3):1144-1152, 2006.
Lee et al., *Glia.*, 55(7):712-22, 2007.
Lencz et al., *Mol. Psychiatry*, 12(6):572-80, 2007.
Liby et al., *Cancer Res.*, 65(11):4789-4798, 2005.
Liby et al., *Nat. Rev. Cancer*, 7(5):357-356, 2007a.
Liby et al., *Mol. Cancer Ther.*, 6(7):2113-9, 2007b.
Liu et al., *FASEB J.*, 20(2):207-216, 2006.
Lu et al., *J. Clin. Invest.*, 121(10):4015-29, 2011.
*March's Advanced Organic Chemistry*: Reactions, Mechanisms, and Structure, 2007.
McIver et al., *Pain*, 120(1-2): 161-9, 2005.
Morris et al., *J. Mol. Med.*, 80(2):96-104, 2002.
Morse and Choi, *Am. J. Respir. Crit. Care Med.*, 172(6): 660-670, 2005.
Morse and Choi, *Am. J. Respir. Crit. Care Med.*, 27(1):8-16, 2002.
Pall, *Med. Hypoth.*, 69:821-825, 2007.
Pergola et al., 2011.
Place et al., *Clin. Cancer Res.*, 9(7):2798-806, 2003.
Rajakariar et al., *Proc. Natl. Acad. Sci. USA*, 104(52):20979-84, 2007.
Reagan-Shaw et al., *FASEB J.*, 22(3):659-661, 2008
Reisman et al., *Arch. Dermatol. Res.*, 306(5):447-454, 2014.
Ross et al., *Am. J. Clin. Pathol.*, 120(Suppl):S53-71, 2003.
Ross et al., *Expert Rev. Mol. Diagn.*, 3(5):573-585, 2003.
Ruster et al., *Scand. J. Rheumatol.*, 34(6):460-3, 2005.
Sacerdoti et al., *Curr Neurovasc Res.* 2(2): 103-111, 2005.
Salvemini et al., *J. Clin. Invest.*, 93(5):1940-1947, 1994.
Sarchielli et al., *Cephalalgia*, 26(9):1071-1079, 2006.
Satoh et al., *Proc. Natl. Acad. Sci. USA*, 103(3):768-773, 2006.
Schulz et al., *Antioxid. Redox. Sig.*, 10:115, 2008.
Suh et al., *Cancer Res.*, 58:717-723, 1998.
Suh et al., *Cancer Res.*, 59(2):336-341, 1999.
Szabo et al., *Nature Rev. Drug Disc.*, 6:662-680, 2007.
Takahashi et al., *Cancer Res.*, 57:1233-1237, 1997.
Tamir and Tannebaum, *Biochim. Biophys. Acta*, 1288:F31-F36, 1996.
Wang et al., *Cancer Res.* 66(22):10983-94, 2006.
Xie T et al., *J Biol Chem.* 270(12):6894-6900, 1995.
Zhou et al., *Am. J. Pathol.*, 166(1):27-37, 2005.

What is claimed is:
1. A compound of the formula:

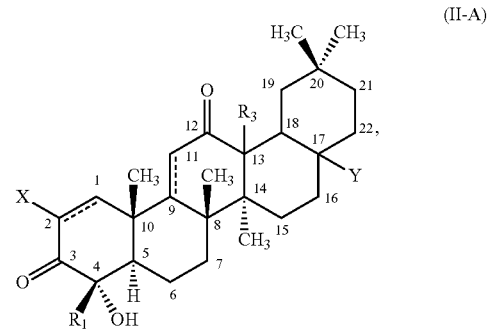

wherein:
$R_1$ is alkyl$_{(C \leq 8)}$;
$R_3$ is hydrogen or hydroxy, or $R_3$ is taken together with Y as described below;
Y is heteroaryl$_{(C \leq 8)}$ or substituted versions thereof;
—C(O)$R_c$, wherein $R_c$ is hydroxy, alkoxy$_{(C \leq 8)}$, alkylamino$_{(C \leq 8)}$, dialkyl-amino$_{(C \leq 8)}$, or a substituted version of any of these groups;
—NR$_d$C(O)R$_e$, wherein: $R_d$ is hydrogen; and $R_e$ is alkyl$_{(C \leq 8)}$, alkoxy$_{(C \leq 8)}$, or a substituted version of any of these groups; or
Y is taken together with $R_3$ and is —C(O)O—;

wherein when the terms alkyl, alkoxy, alkylamino, dialkylamino, and heteroaryl are used with the substituted modifier, one or more hydrogen atom has been independently replaced by —F;

or a pharmaceutically acceptable salt thereof.

2. The compound of claim 1, wherein $R_1$ is methyl.

3. The compound of claim 1, wherein Y is heteroaryl$_{(C\leq 8)}$ or substituted heteroaryl$_{(C\leq 8)}$.

4. The compound of claim 1, wherein Y is taken together with $R_3$ and is —C(O)O—.

5. The compound of claim 1, wherein Y is —C(O)$R_c$, wherein $R_c$ is hydroxy or alkoxy$_{(C\leq 8)}$.

6. The compound of claim 1, wherein R3 is hydrogen.

7. The compound of claim 1, wherein the compound is further defined as:

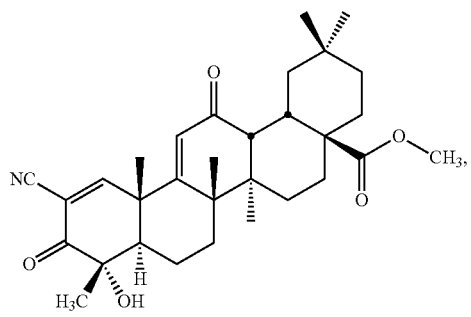

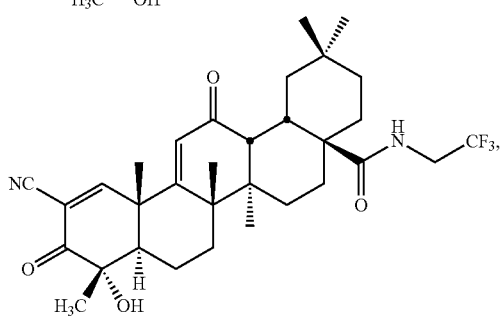

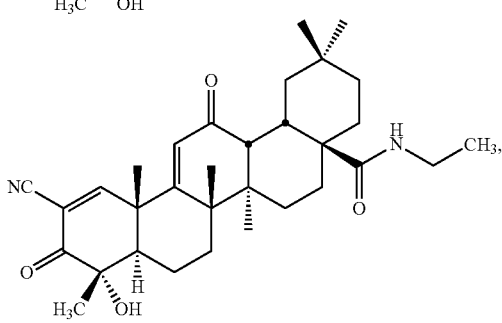

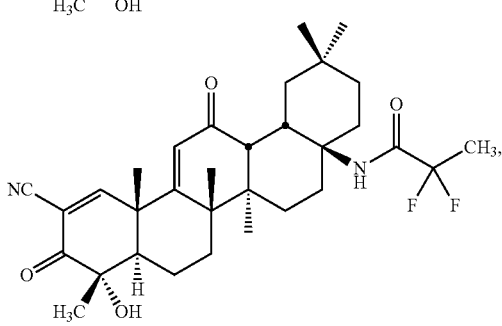

-continued

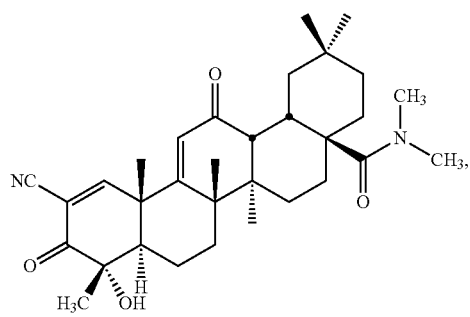

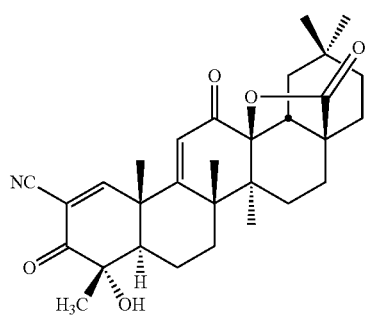

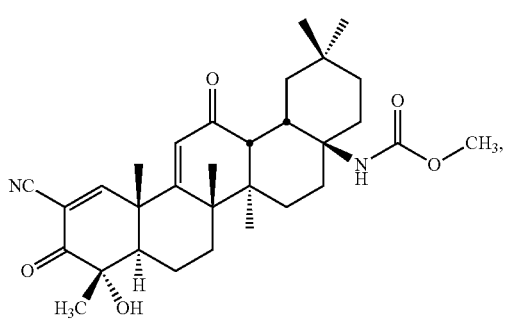

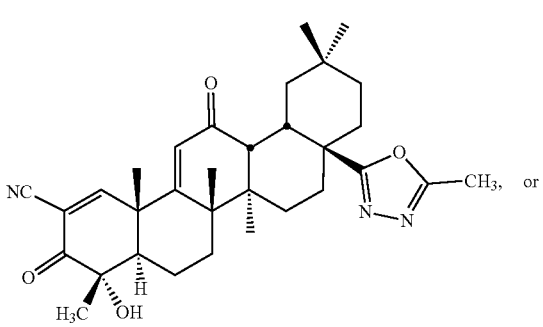

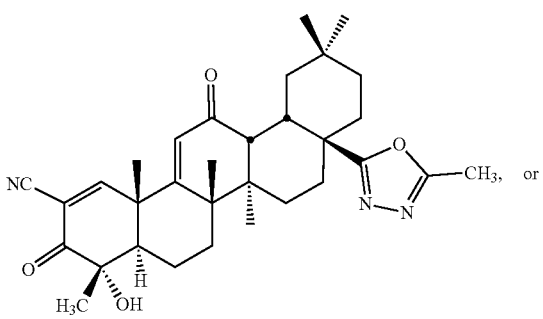, or or a pharmaceutically acceptable salt thereof.

8. A pharmaceutical composition comprising:
(A) a compound of claim 1; and
(B) an excipient or a pharmaceutically acceptable carrier.

9. The compound of claim 1, further defined as:

or a pharmaceutically acceptable salt thereof.

10. A pharmaceutical composition comprising:
(A) a compound of claim 9; and
(B) an excipient or a pharmaceutically acceptable carrier.

* * * * *

UNITED STATES PATENT AND TRADEMARK OFFICE
CERTIFICATE OF CORRECTION

PATENT NO. : 11,584,775 B2
APPLICATION NO. : 15/760662
DATED : February 21, 2023
INVENTOR(S) : Melean Visnick et al.

It is certified that error appears in the above-identified patent and that said Letters Patent is hereby corrected as shown below:

On the Title Page

Item (56) References Cited Foreign Patent Documents, delete "WO 2002/092768 06/2006" and insert -- WO 2002/092768 06/2002 -- therefor.

In the Claims

In Claim 6, Column 215, Line 15, delete "R3" and insert -- $R_3$ -- therefor.

Signed and Sealed this
Twenty-seventh Day of June, 2023

Katherine Kelly Vidal
*Director of the United States Patent and Trademark Office*